United States Patent
Yen et al.

(10) Patent No.: US 10,807,972 B2
(45) Date of Patent: Oct. 20, 2020

(54) INDENOTRIPHENYLENE-BASED AMINE DERIVATIVE AND ORGANIC ELECTROLUMINESCENCE DEVICE USING THE SAME

(71) Applicants: Feng-Wen Yen, Taipei (TW); Wen-Feng Hsiao, Nantou (TW)

(72) Inventors: Feng-Wen Yen, Taipei (TW); Wen-Feng Hsiao, Nantou (TW)

(*) Notice: Subject to any disclaimer, the term of this patent is extended or adjusted under 35 U.S.C. 154(b) by 261 days.

(21) Appl. No.: 16/159,725

(22) Filed: Oct. 15, 2018

(65) Prior Publication Data

US 2020/0115369 A1    Apr. 16, 2020

(51) Int. Cl.
*H01L 51/50* (2006.01)
*C07D 409/14* (2006.01)
*H01L 51/00* (2006.01)

(52) U.S. Cl.
CPC ........ *C07D 409/14* (2013.01); *H01L 51/0061* (2013.01); *H01L 51/0067* (2013.01); *H01L 51/0072* (2013.01); *H01L 51/0073* (2013.01); *H01L 51/0074* (2013.01); *H01L 51/5004* (2013.01); *H01L 51/5016* (2013.01); *H01L 51/5024* (2013.01); *H01L 2251/552* (2013.01)

(58) Field of Classification Search
None
See application file for complete search history.

(56) References Cited

U.S. PATENT DOCUMENTS 9,172,046 B1   10/2015   Kim et al.

FOREIGN PATENT DOCUMENTS

| CN | 108129380 | * | 6/2018 | ............. H01L 51/50 |
| WO | 2013009079 A1 | | 1/2013 | |

* cited by examiner

*Primary Examiner* — Gregory D Clark

(57) ABSTRACT

The present invention discloses an indenotriphenylene-based amine derivative and an organic electroluminescence device employing the indenotriphenylene-based amine derivative as the dopant material, the hole transporting material, or the electron blocking material of the organic electroluminescence device. The organic electroluminescence device of the present invention exhibits improved performance, such as reduced power consumption, increased current efficiency, and longer half-life time.

11 Claims, 1 Drawing Sheet

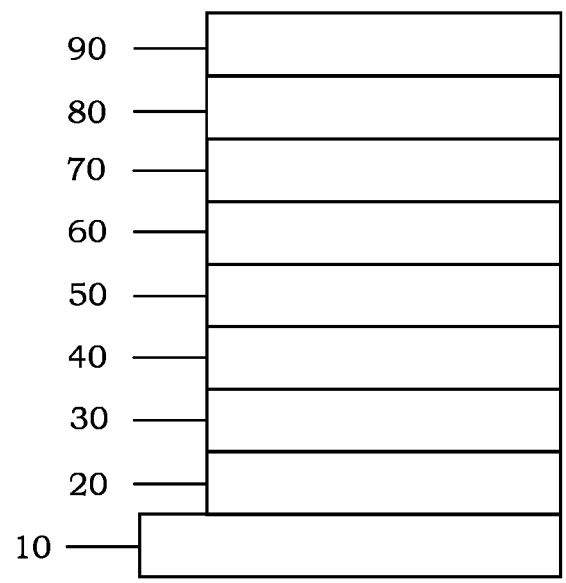

INDENOTRIPHENYLENE-BASED AMINE DERIVATIVE AND ORGANIC ELECTROLUMINESCENCE DEVICE USING THE SAME

FIELD OF INVENTION

The present invention relates generally to an indenotriphenylene-based amine derivative, and, more specifically, to an organic electroluminescence (hereinafter referred to as organic EL) device using the indenotriphenylene-based amine derivative.

BACKGROUND OF THE INVENTION

An organic EL device is a light-emitting diode (LED) in which the light emitting layer is a film made from organic compounds, which emits light in response to an electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

The first observation of electroluminescence in organic materials was in the early 1950s by Andre Bernanose and his co-workers at the Nancy-University in France. Martin Pope and his co-workers at New York University first observed direct current (DC) electroluminescence on a single pure crystal of anthracene and on anthracene crystals doped with tetracene under vacuum in 1963. The first diode device was created by Ching W. Tang and Steven Van Slyke at Eastman Kodak in 1987. The diode device used a two-layer structure with separate hole transporting and electron transporting layers, resulting in reduction of operating voltage and improvement of the efficiency, thereby leading to the current era of organic EL research and device production.

Typically, organic EL device is composed of organic material layers sandwiched between two electrodes. The organic material layers include the hole transporting layer, the light emitting layer, and the electron transporting layer. The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from a cathode into a LUMO (lowest unoccupied molecular orbital) and holes will be injected from an anode into a HOMO (highest occupied molecular orbital). Subsequently, the electrons recombine with holes in the light emitting layer to form excitons and then emit light. When luminescent molecules absorb energy to achieve an excited state, the exciton may either be in a singlet state or a triplet state, depending on how the spins of the electrons and holes have been combined. 75% of the excitons is formed by recombination of electrons and holes to achieve the triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is achieved by certain heavy atoms, such as iridium, rhodium, platinum, and palladium, and the phosphorescent transition may be observed from an excited MLCT (metal to ligand charge transfer) state of organic metallic complexes.

The phosphorescent organic EL device utilizes both triplet and singlet excitons. Cause of longer lifetime and diffusion length of triplet excitions compared to those of singlet excitions, the phosphorescent organic EL device generally need an additional hole blocking layer (HBL) between the emitting layer (EML) and the electron transporting layer (ETL) or an electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or the electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting field, the conventional materials used for the phosphorescent guest in light emitting layer, such as the metallic complexes, are still unsatisfactory in driving voltage, current efficiency and half-life time, and still have disadvantages for industrial practice use.

SUMMARY OF THE INVENTION

According to the reasons described above, the present invention has the objective of resolving the problems of prior arts and offering a novel indenotriphenylene-based amine derivative. Another object of the invention is to provide an organic EL device using the indenotriphenylene-based amine derivative. The organic EL device of the present invention can operate under reduced voltage and exhibit higher current efficiency and longer half-life time. The present invention discloses an indenotriphenylene-based amine derivative of formula (1):

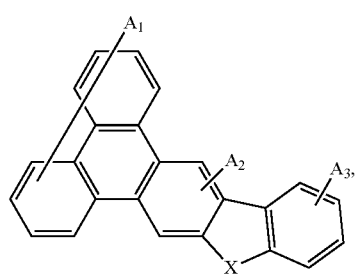

formula (1)

wherein at least one of $A_1$, $A_2$ and $A_3$ exists and represents formula (2) below:

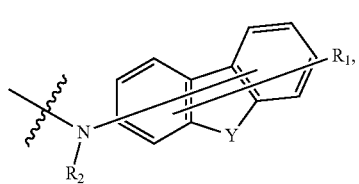

formula (2)

wherein X is a divalent bridge selected from the group consisting of O and S; Y is a divalent bridge selected from the group consisting of O and S; $R_1$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_2$ is a hydrogen atom, a halogen, a substituted or unsubstituted aralkyl group having 5 to 30 ring atoms, a substituted or unsubstituted aryl group having 5 to 30 ring atoms, or a substituted or unsubstituted heteroaryl group having 5 to 30 ring atoms.

The present invention further discloses an organic electroluminescence device. The organic electroluminescence device comprises a pair of electrodes composed of a cathode and an anode, and a light emitting layer and one or more organic thin film layers between the pair of electrodes. At least one of the light emitting layer and the organic thin film layer comprises the indenotriphenylene-based amine derivative of formula (1).

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an indenotriphenylene-based amine derivative which can be used as the dopant material, hole transporting material, or electron blocking material of the organic EL device is disclosed. The indenotriphenylene-based amine derivative is represented by the following formula (1):

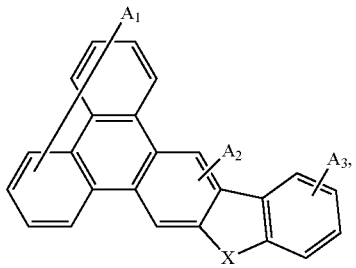

formula (1)

wherein at least one of $A_1$, $A_2$ and $A_3$ exists and represents formula (2) below:

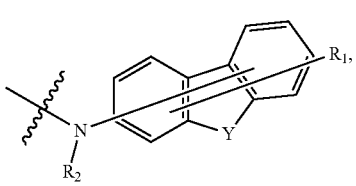

formula (2)

wherein X is a divalent bridge selected from the group consisting of O and S; Y is a divalent bridge selected from the group consisting of O and S; $R_1$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_2$ is a hydrogen atom, a halogen, a substituted or unsubstituted aralkyl group having 5 to 30 ring atoms, a substituted or unsubstituted aryl group having 5 to 30 ring atoms, or a substituted or unsubstituted heteroaryl group having 5 to 30 ring atoms.

In some embodiments, the indenotriphenylene-based amine derivative can be represented by one of the following formula (3) to formula (22):

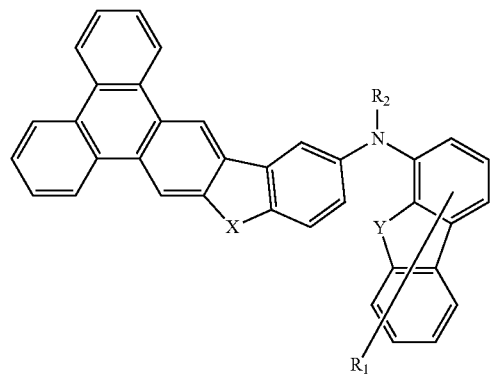

formula (3)

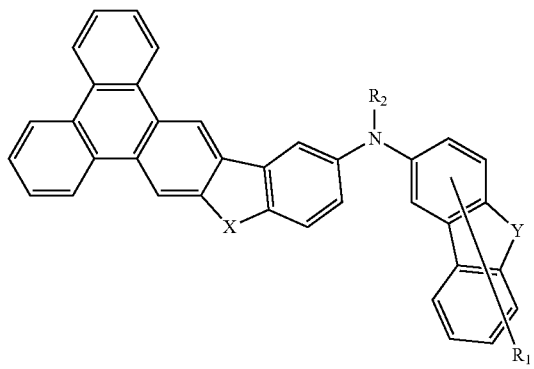

formula (4)

-continued
formula (5)
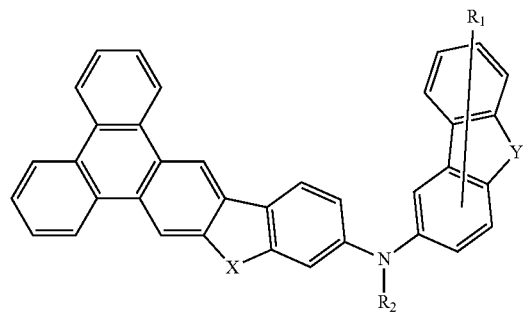
formula (6)
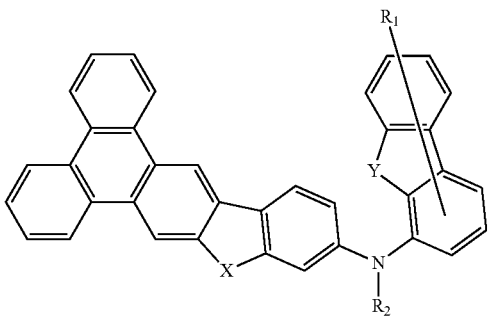
formula (7)
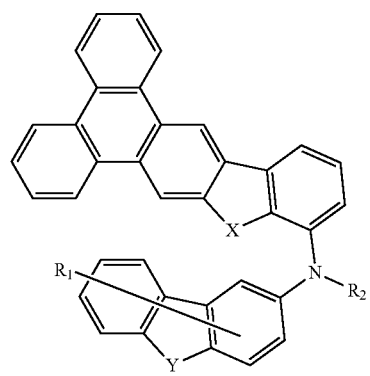
formula (8)
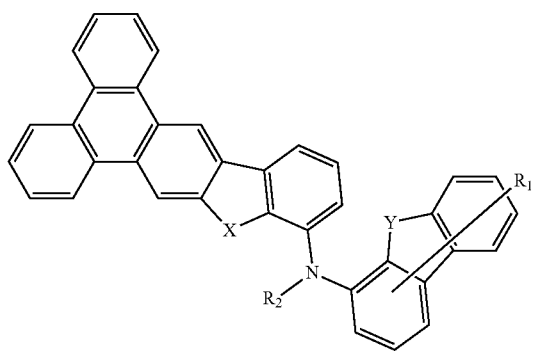
formula (9)
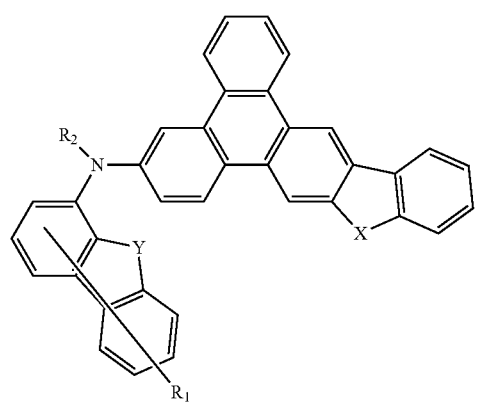
formula (10)
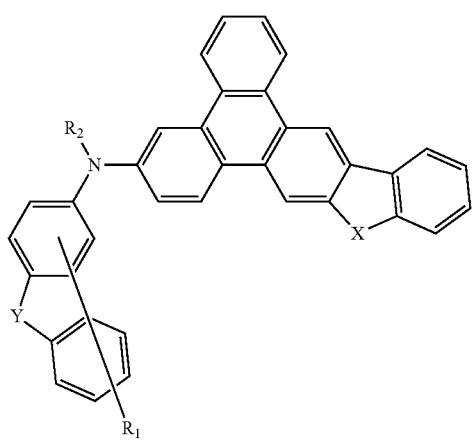
formula (11)
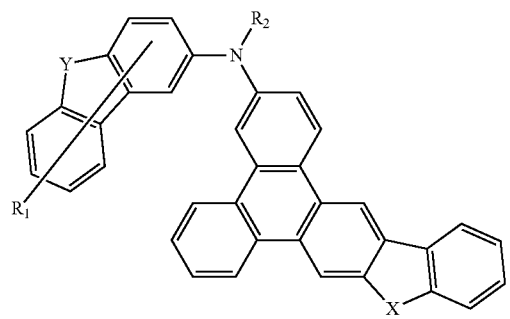
formula (12)
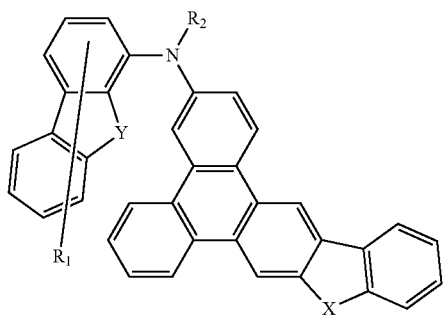

-continued
formula (13)
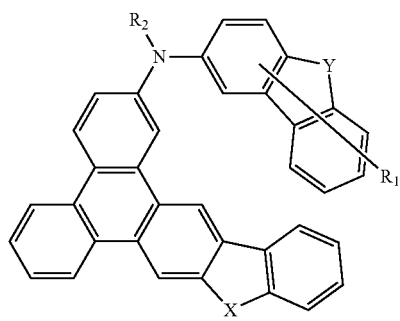
formula (14)
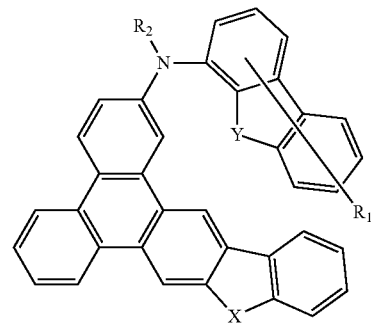
formula (15)
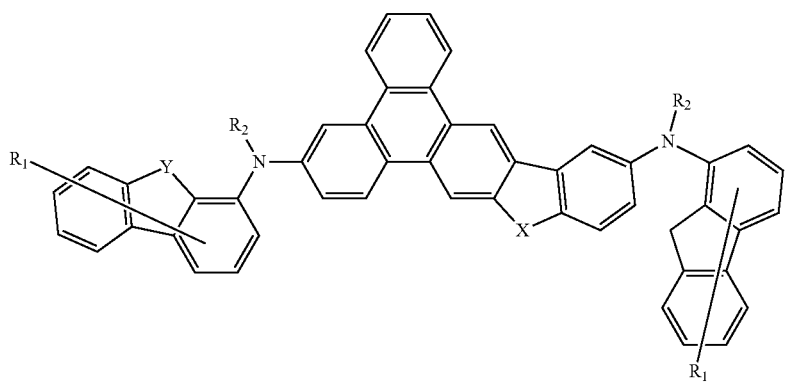
formula (16)
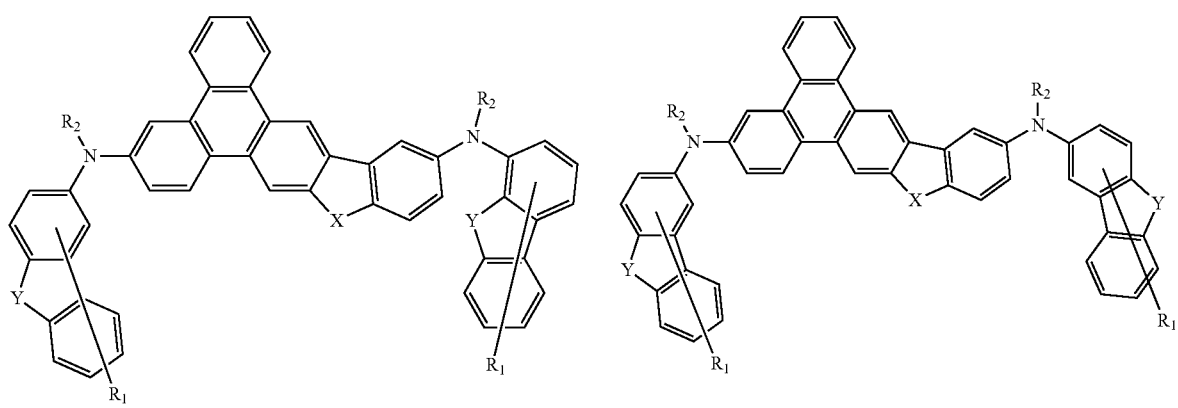
formula (17)
formula (18)
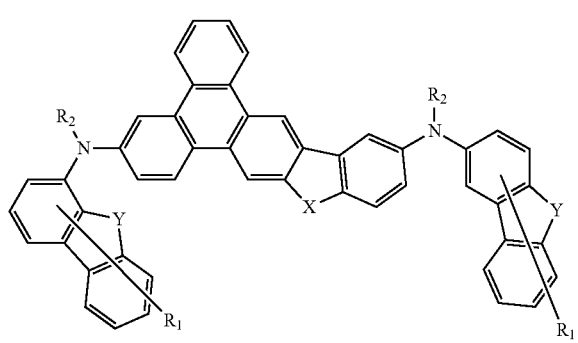

-continued
formula (19)
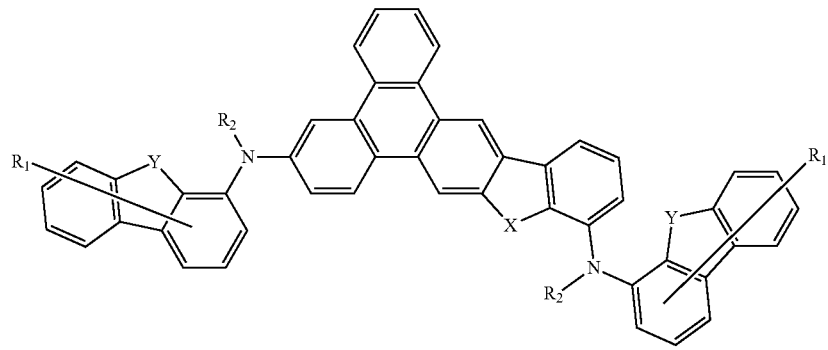
formula (20)
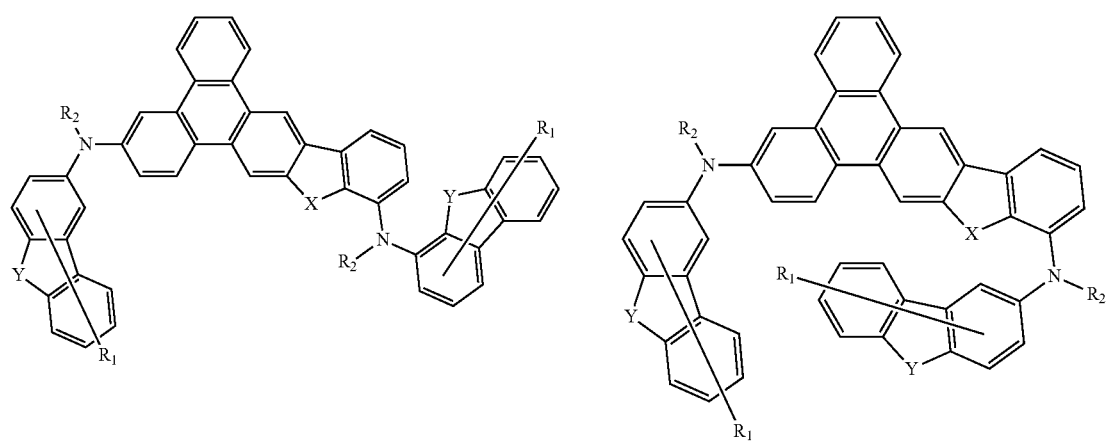
formula (21)
formula (22)
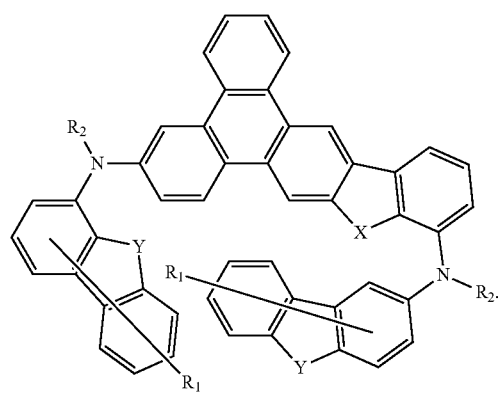

In some embodiments, R$_2$ can be a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, or a substituted or unsubstituted pyridinyl group.

In some embodiments, R$_2$ may represent one of the following substituents:

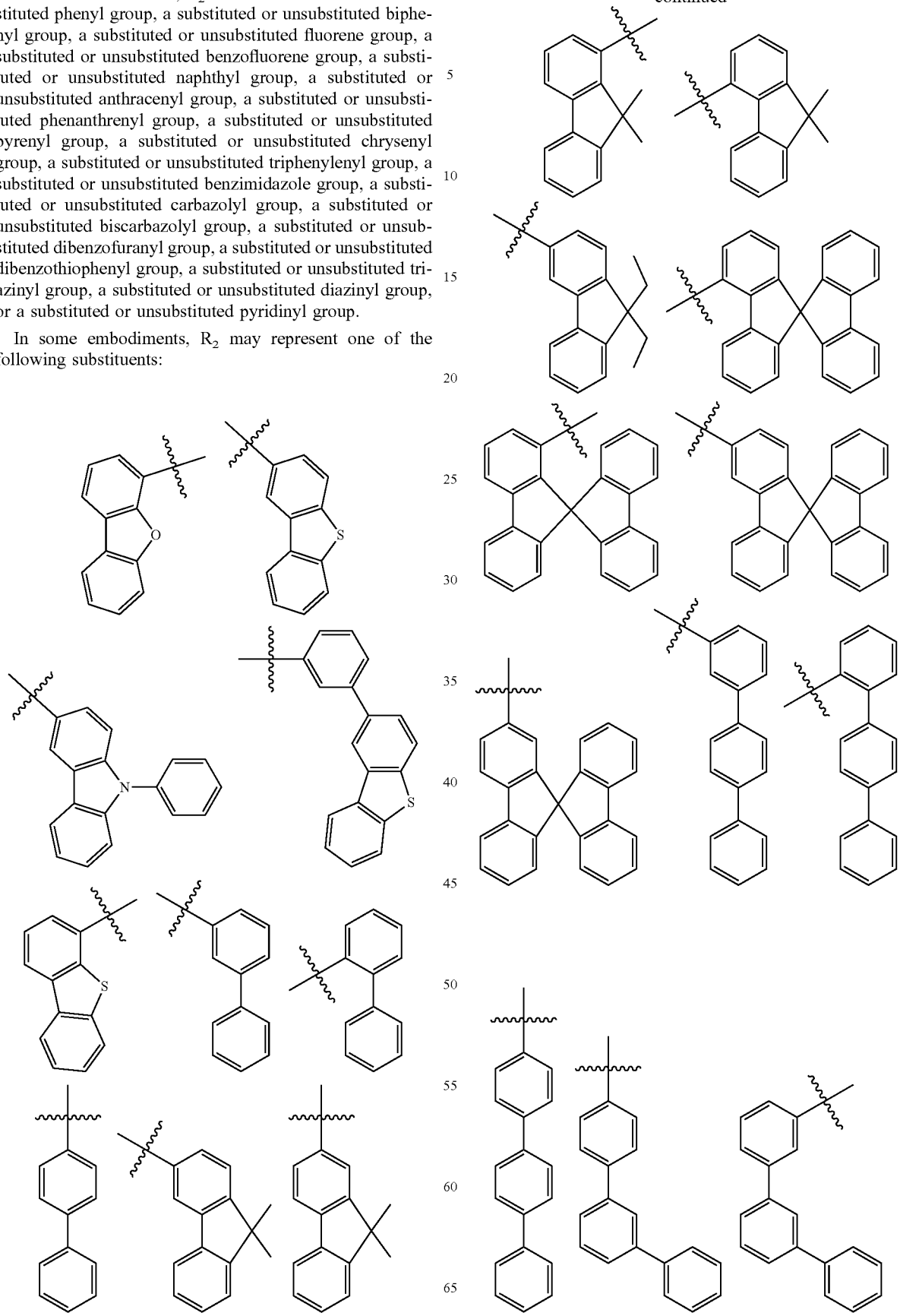

-continued
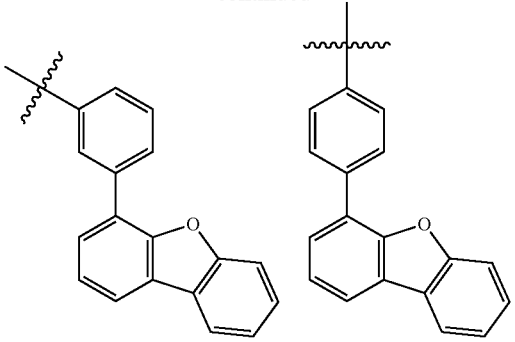
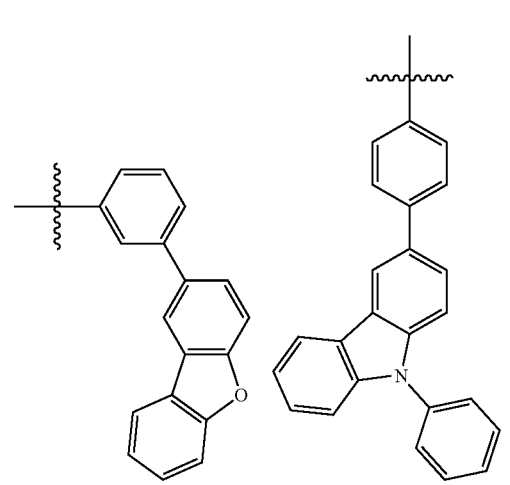
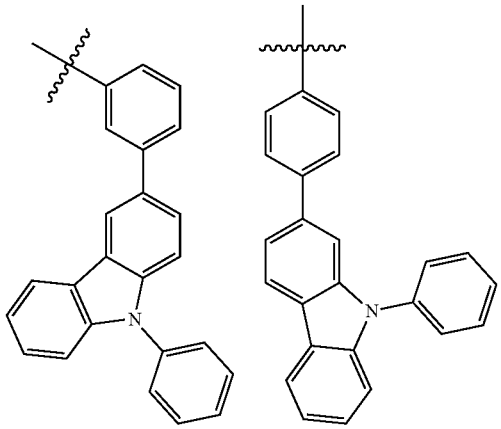
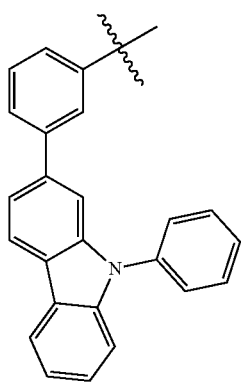
In some embodiments, the indenotriphenylene-based amine derivative is one of the following compounds:
C1
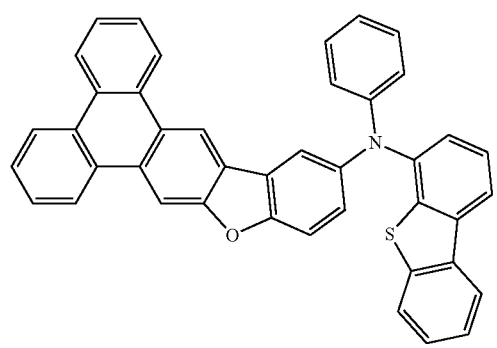
C2
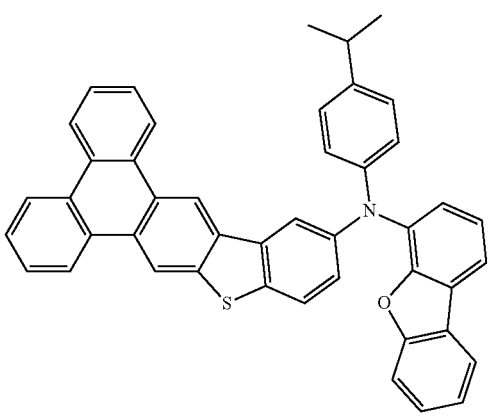

-continued
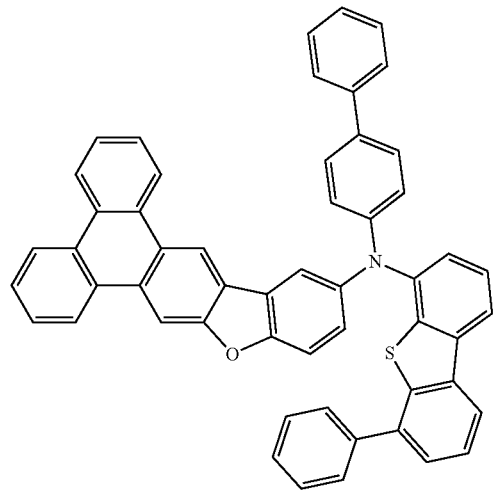
C3
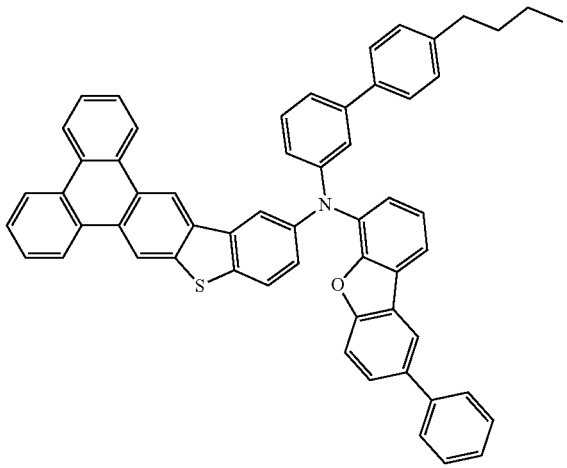
C4
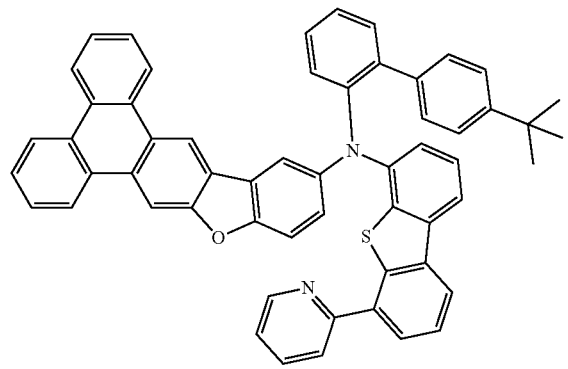
C5
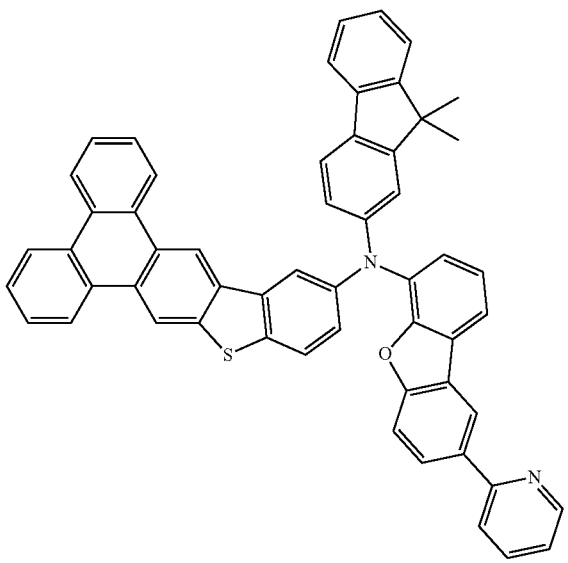
C6
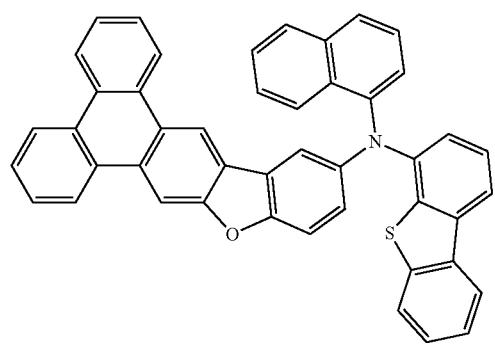
C7
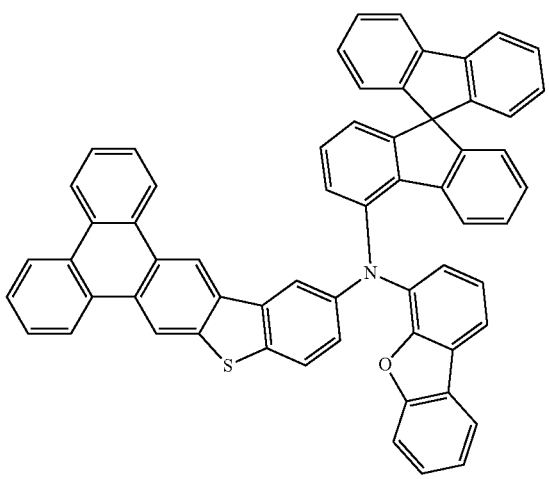
C8

-continued
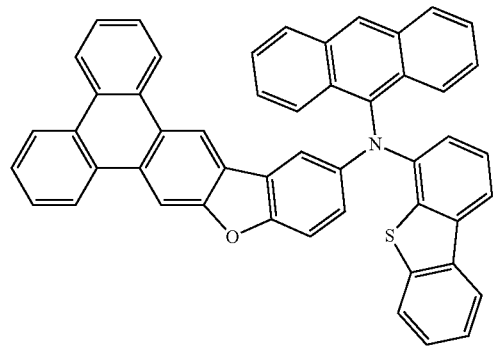
C9
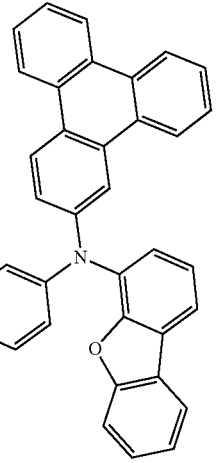
C10
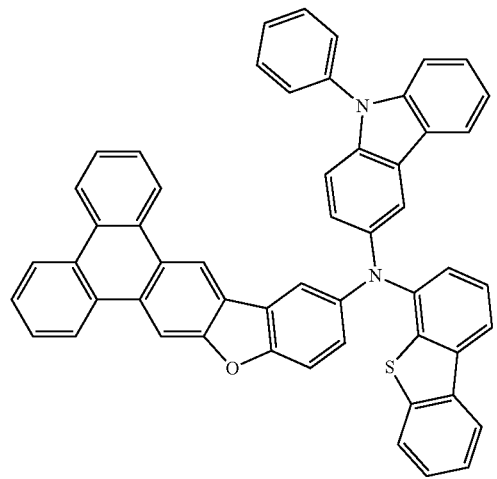
C11
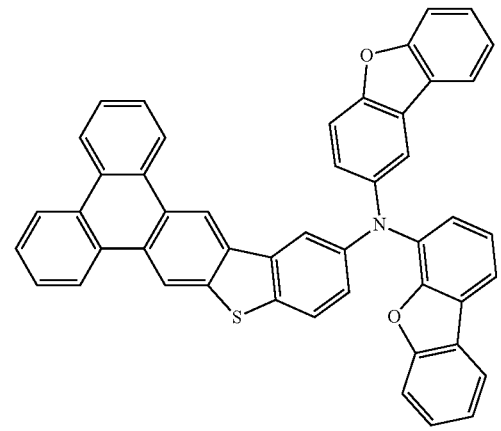
C12
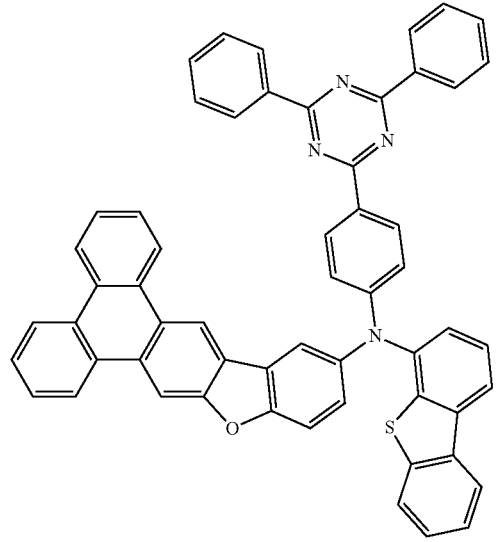
C13
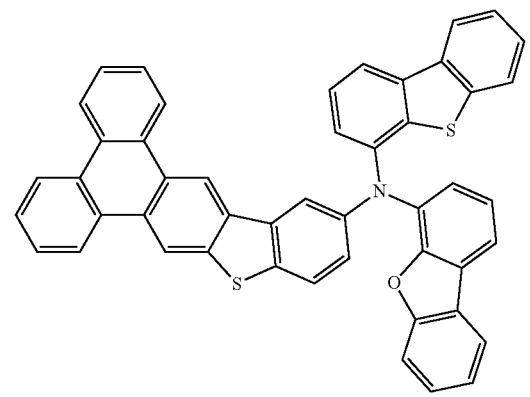
C14

-continued
C15
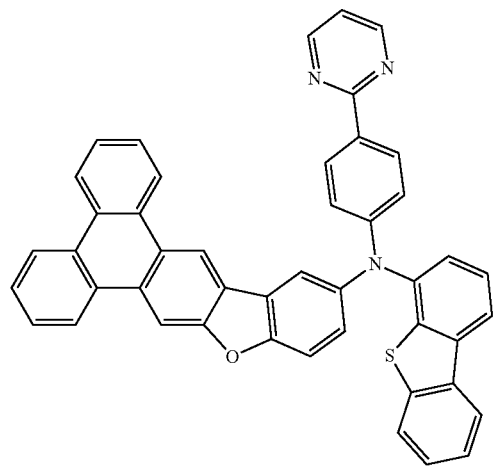
C16
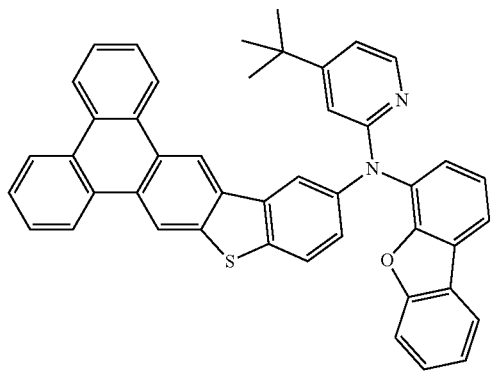
C17
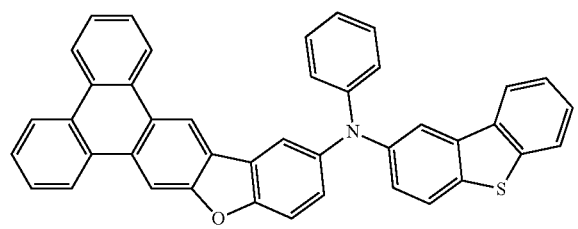
C18
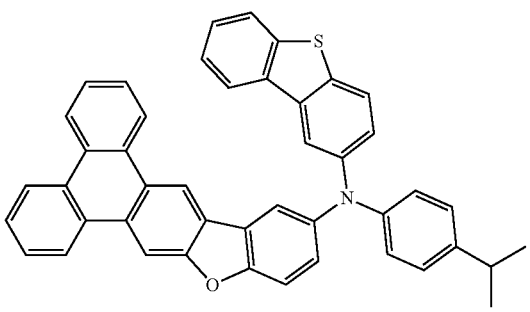
C19
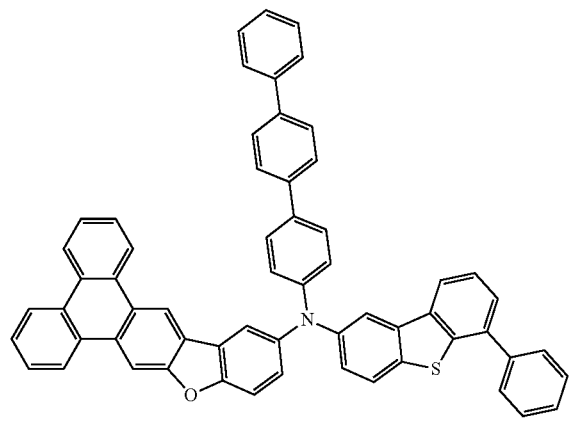
C20
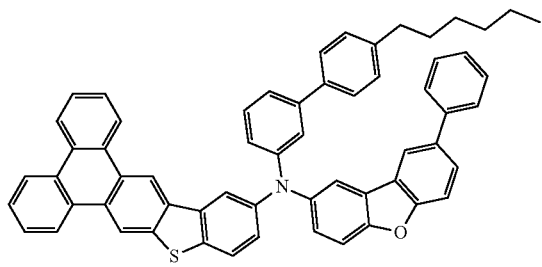
C21
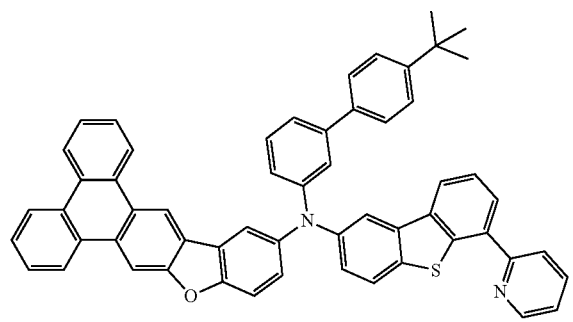
C22
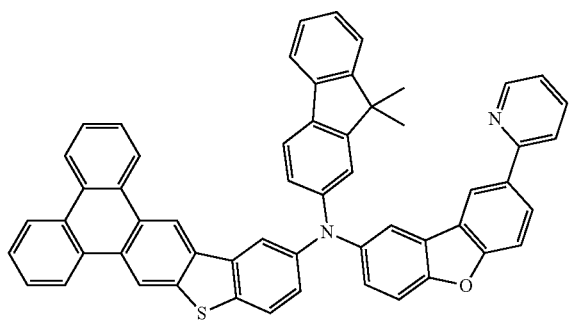

-continued
C23
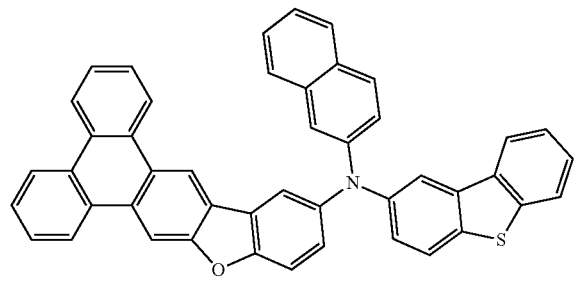
C24
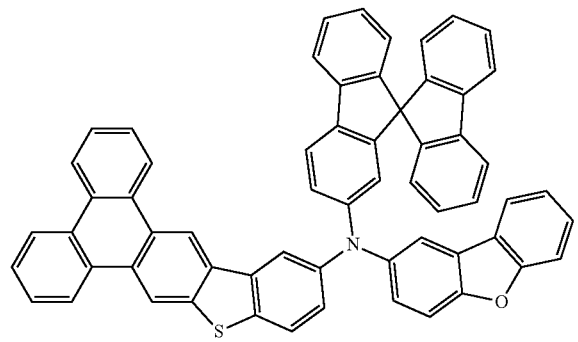
C25
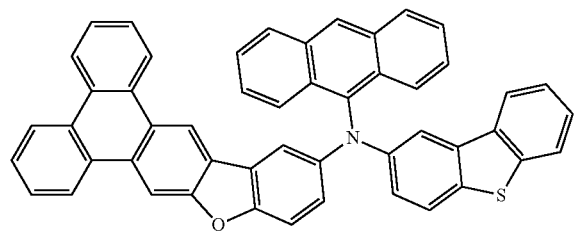
C26
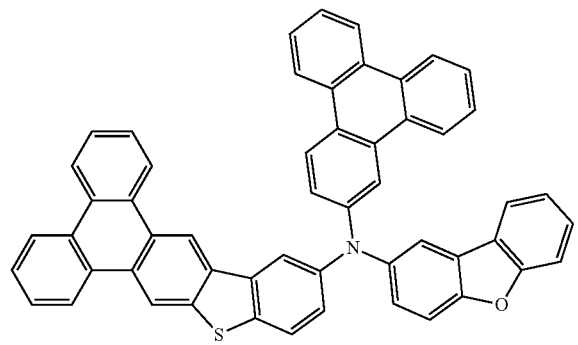
C27
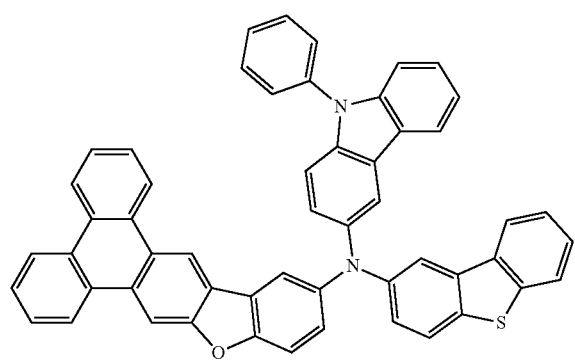
C28
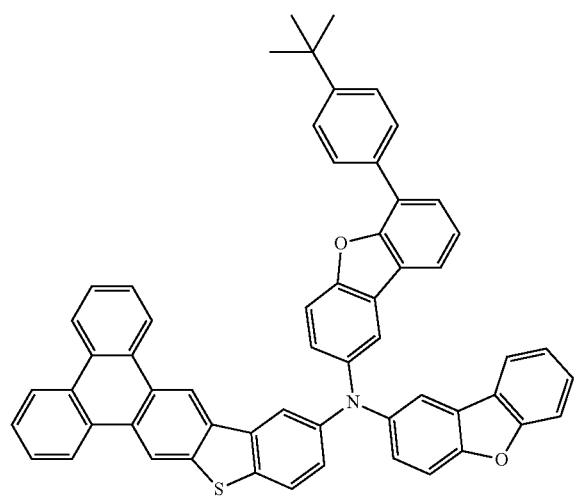

-continued
C29
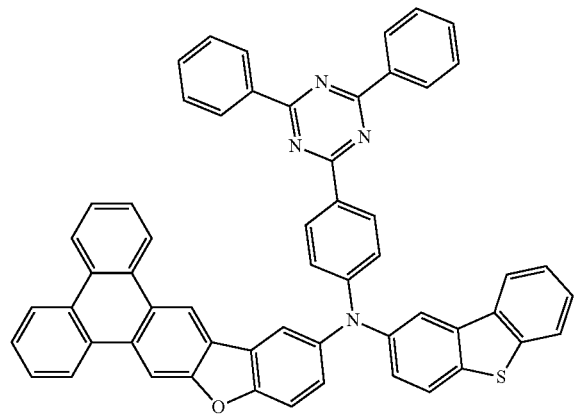
C30
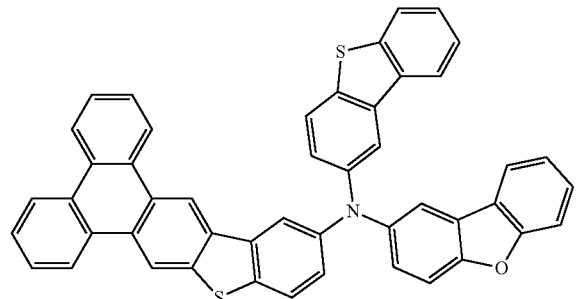
C31
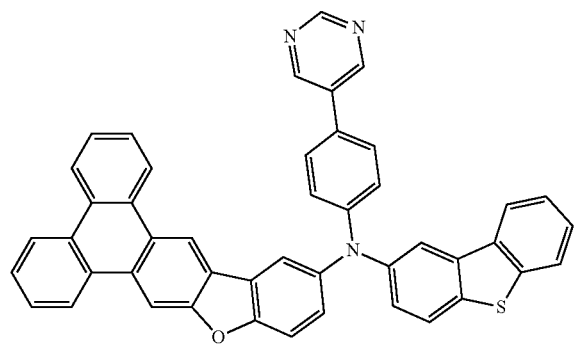
C32
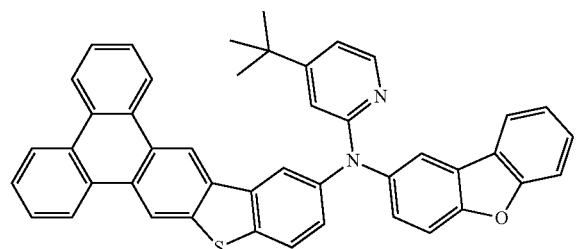
C33
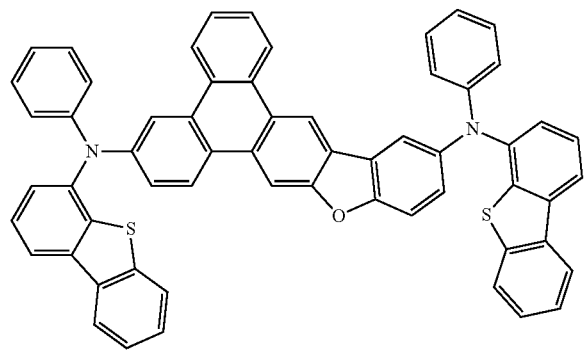
C34
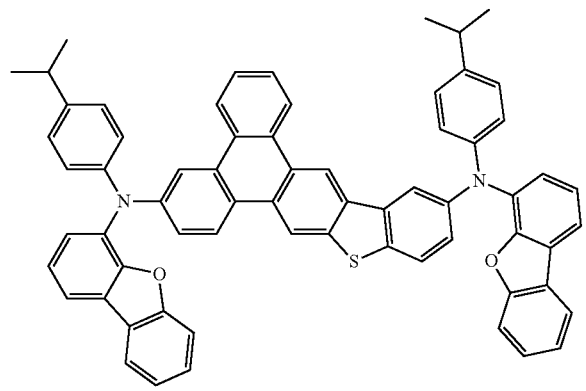

-continued
C35
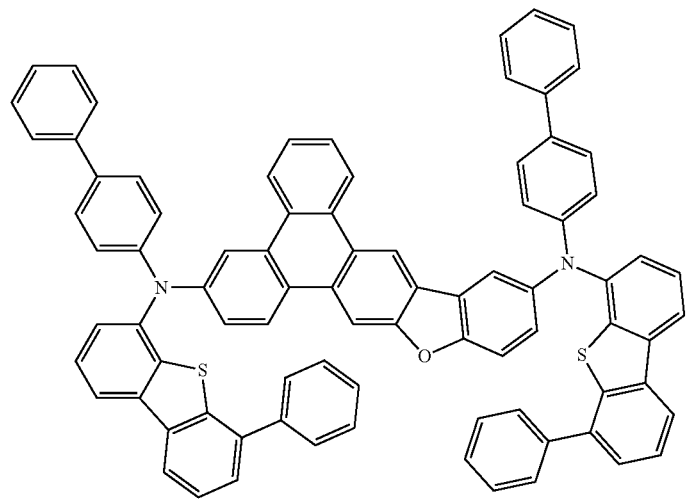
C36
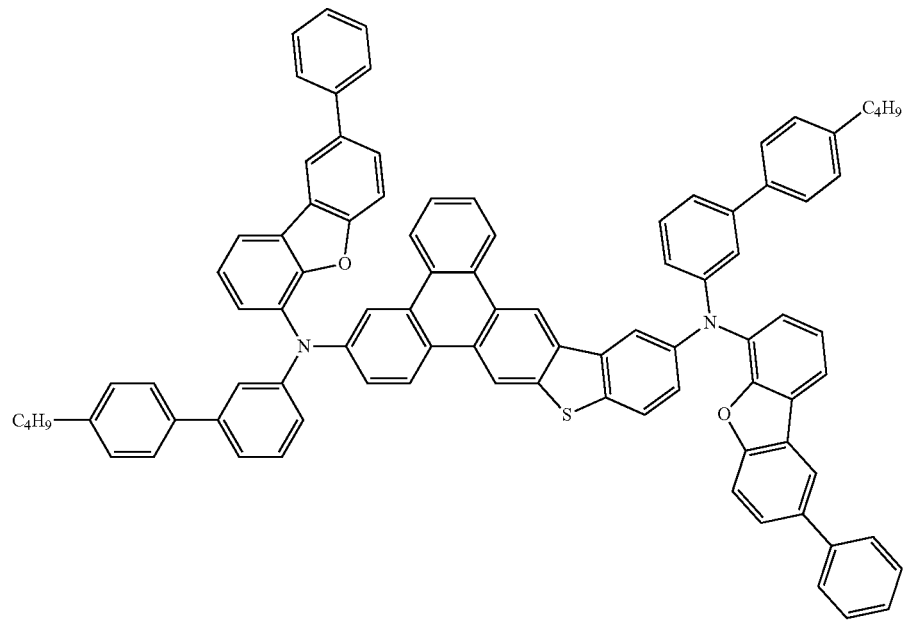
C37
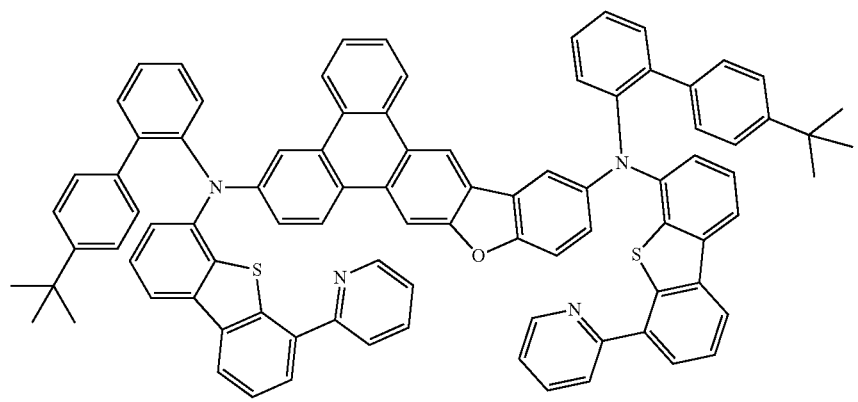

-continued
C38
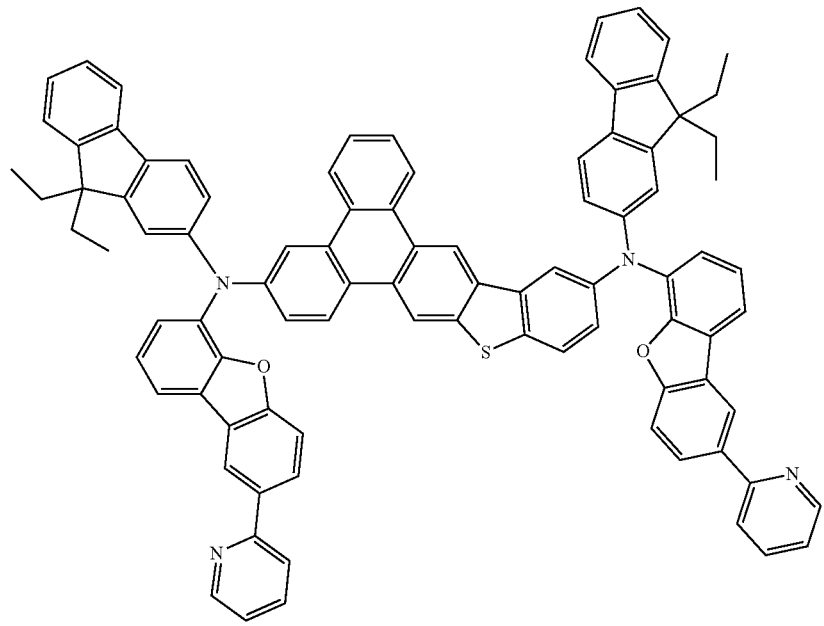
C39
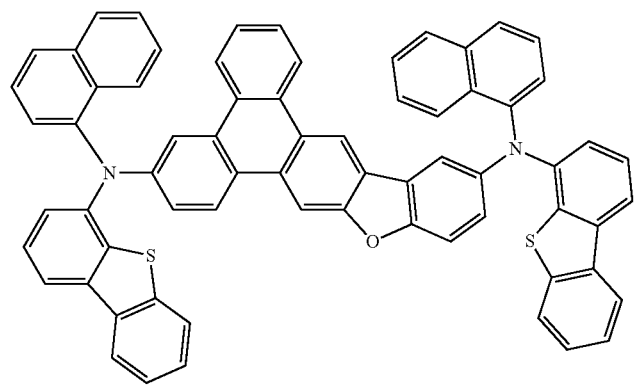
C40
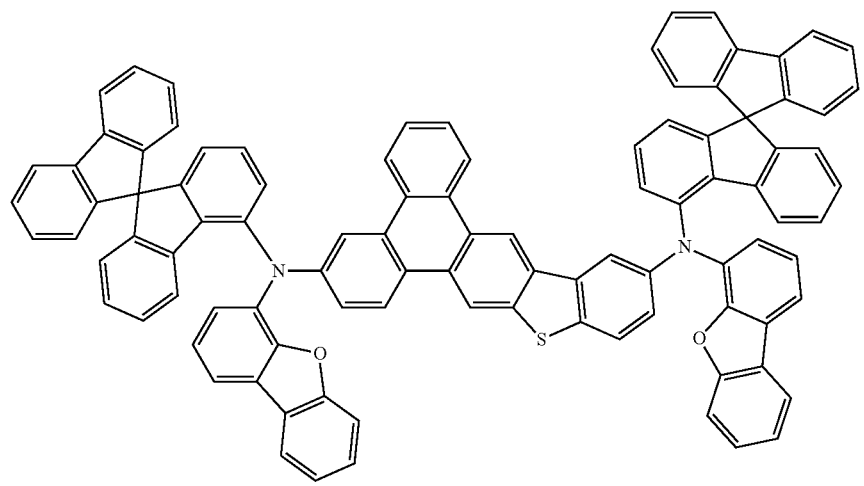

-continued
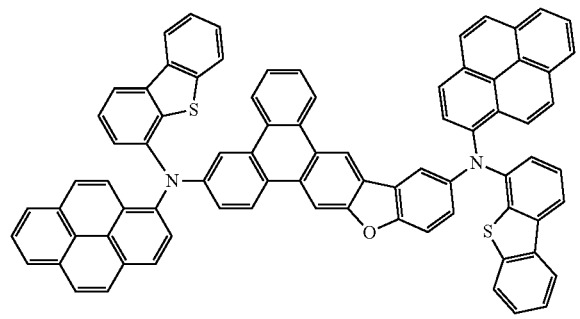
C41
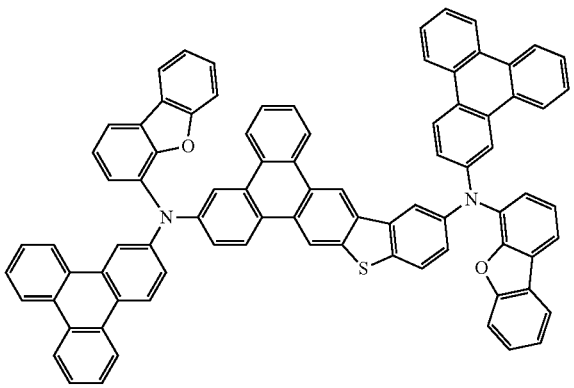
C42
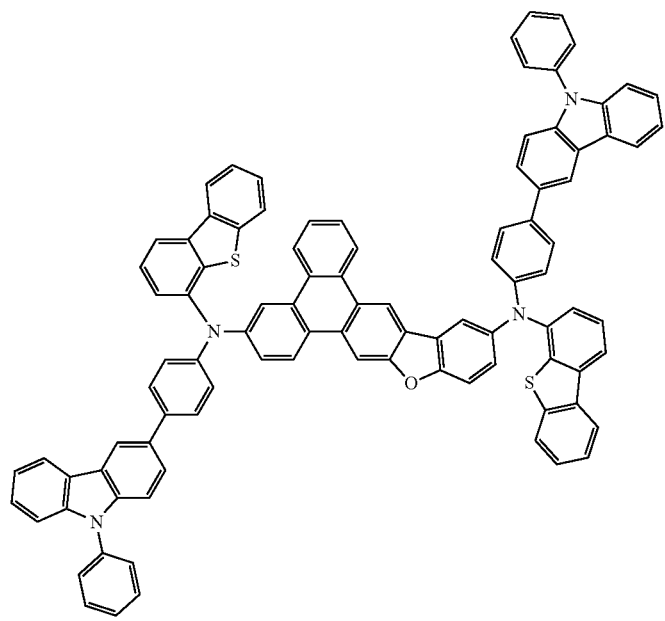
C43
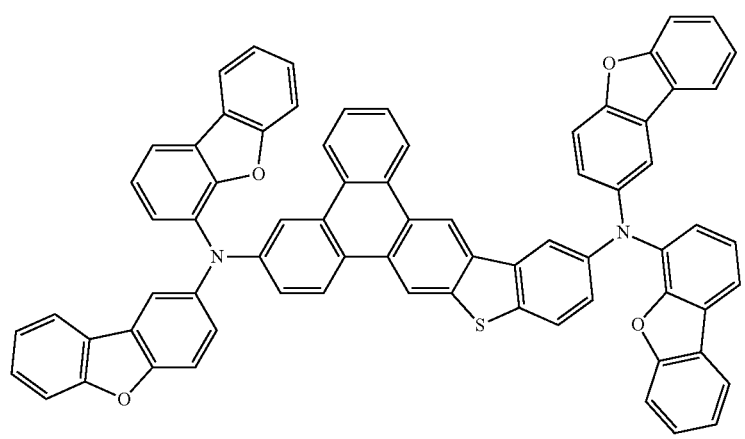
C44

-continued
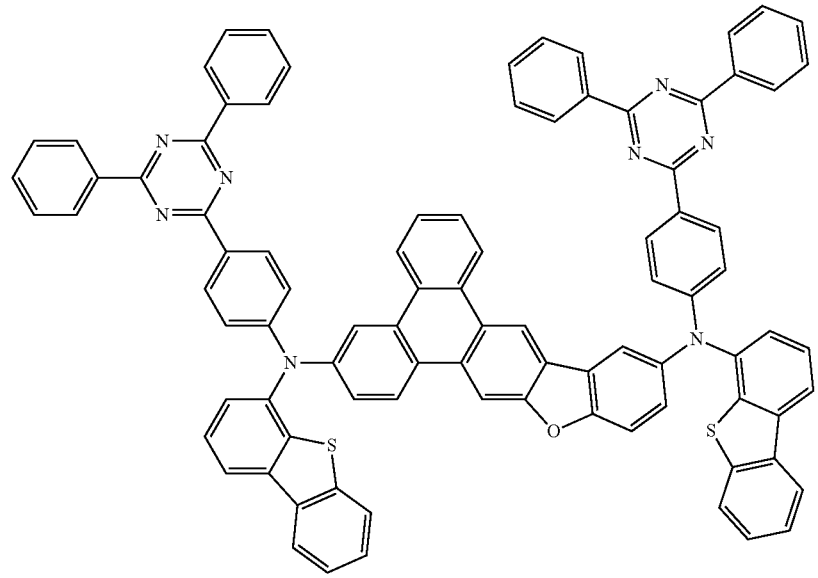
C45
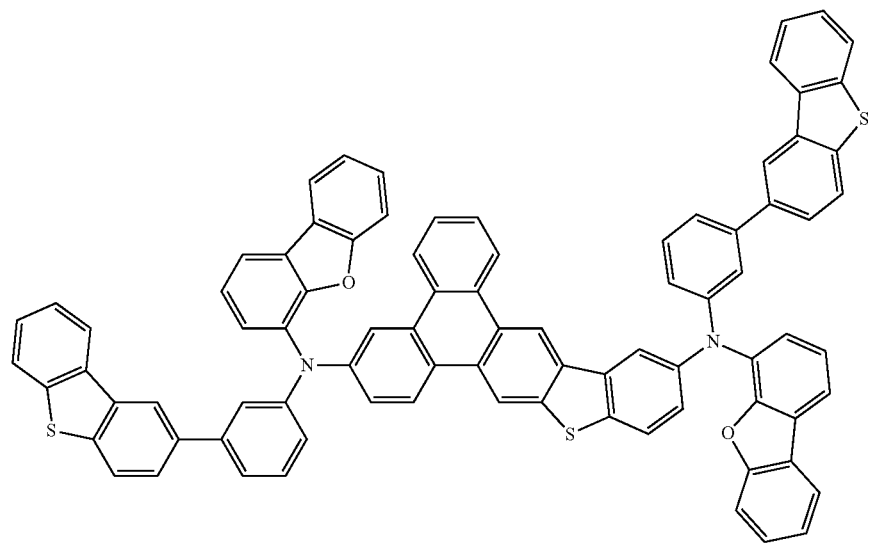
C46
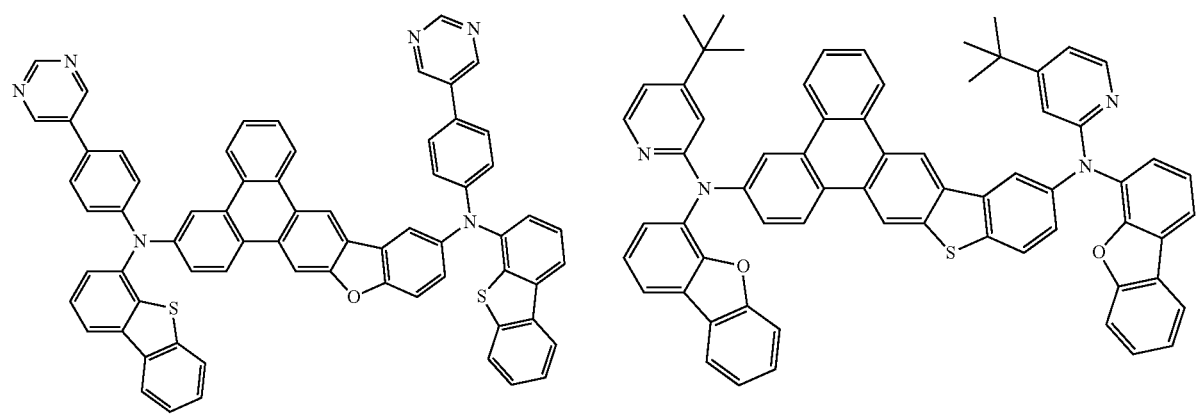
C47 C48

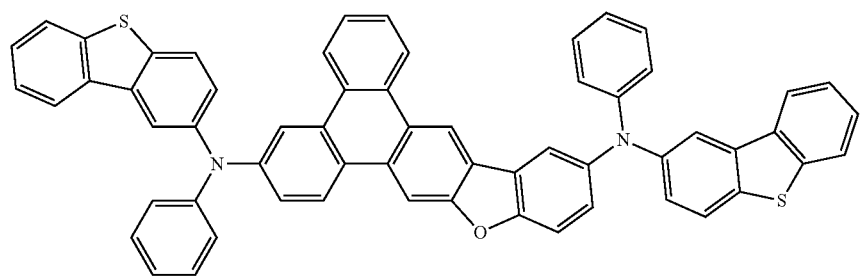
C49
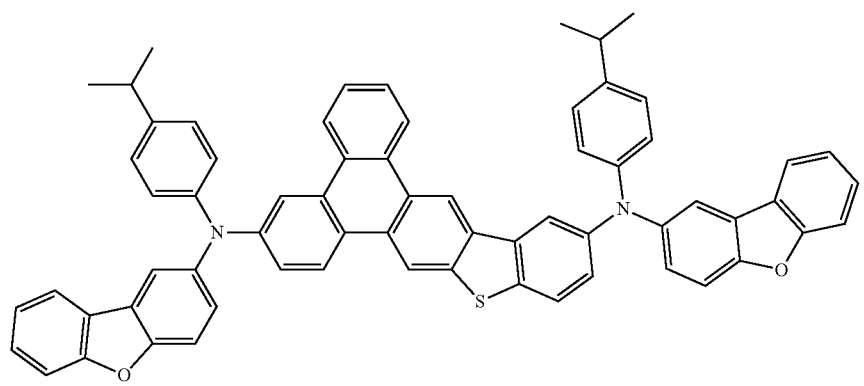
C50
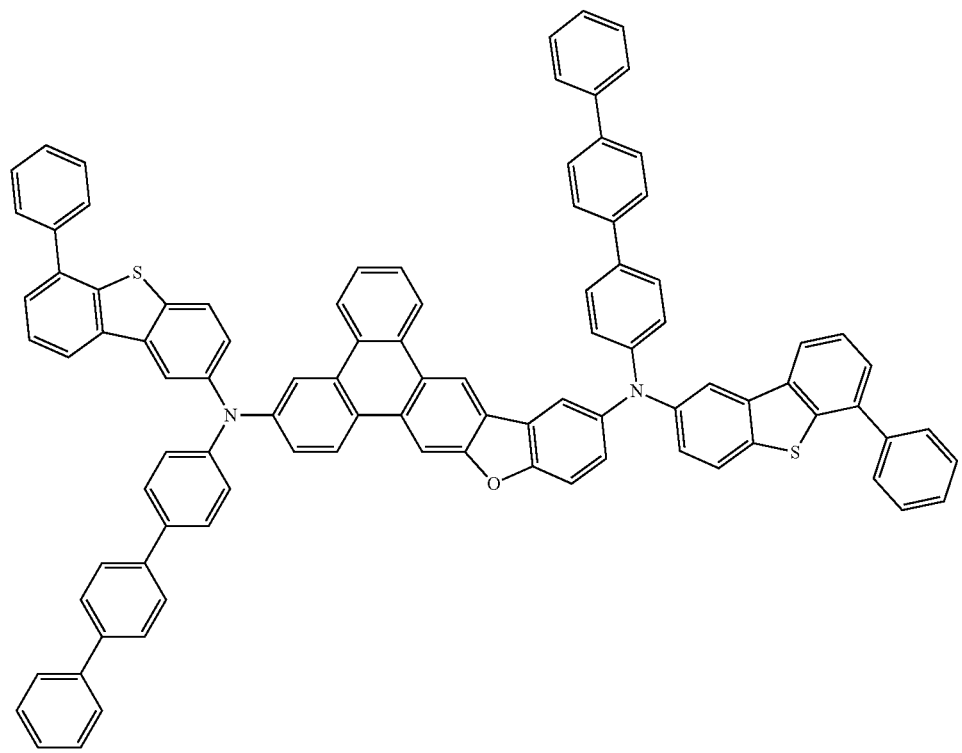
C51

-continued
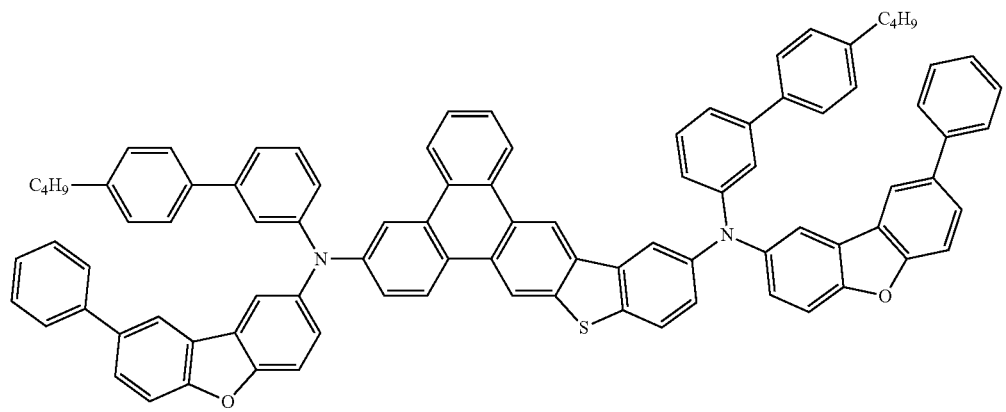
C52
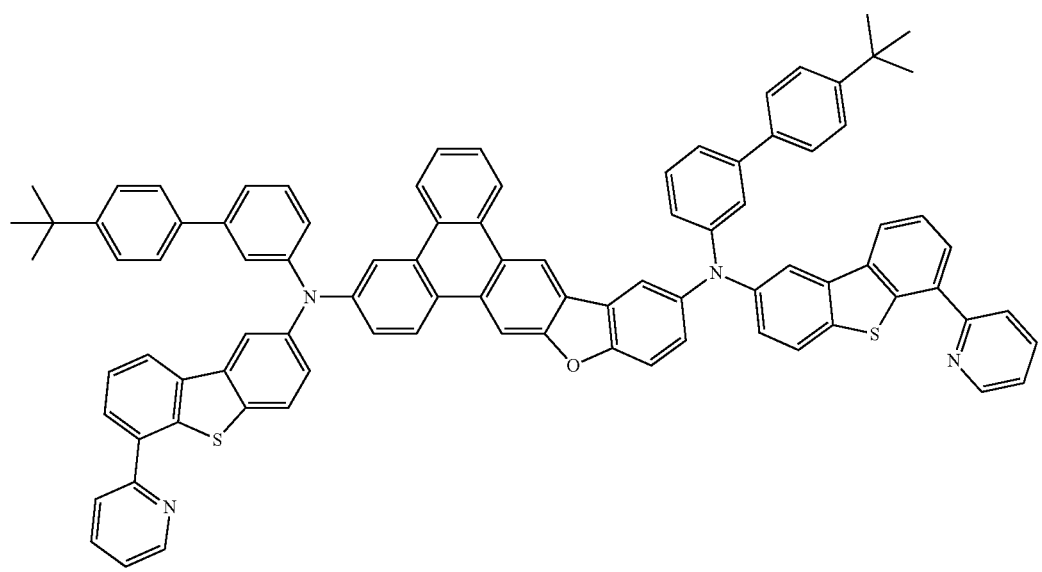
C53
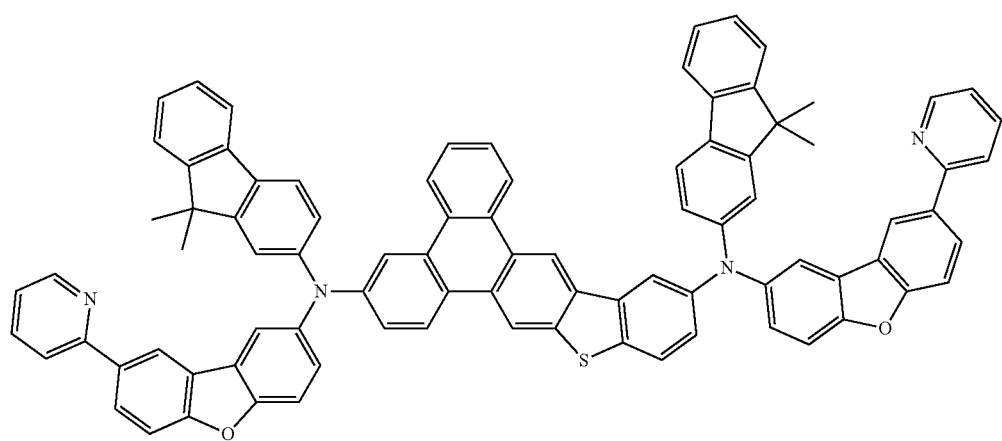
C54

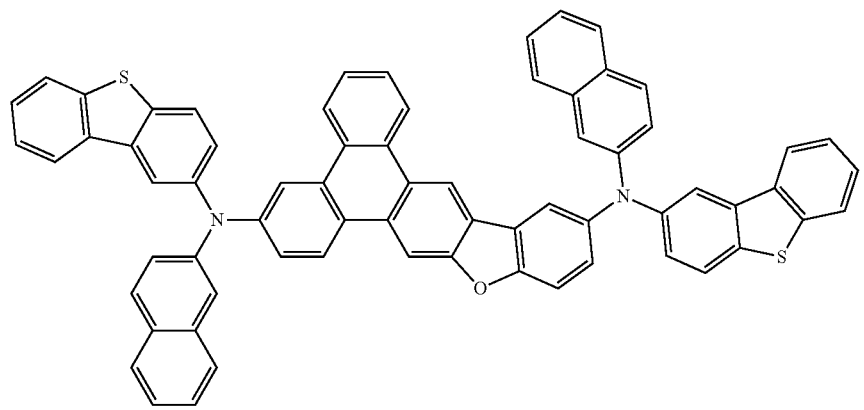
C55
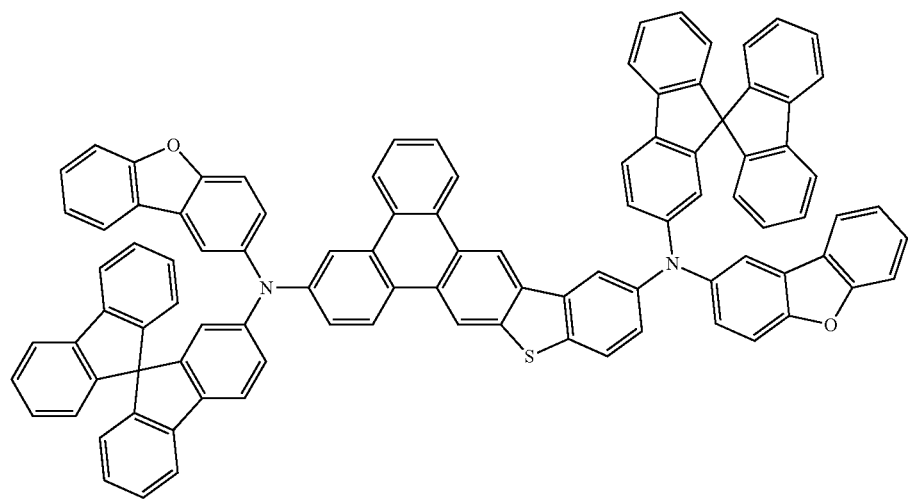
C56
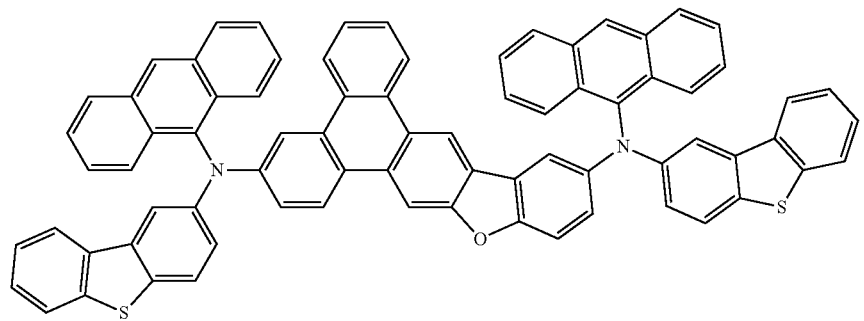
C57

-continued
C58
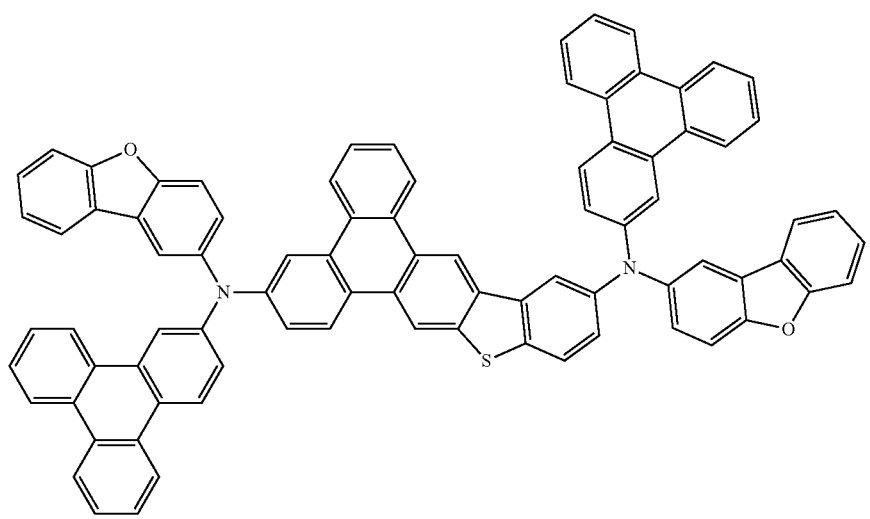
C59
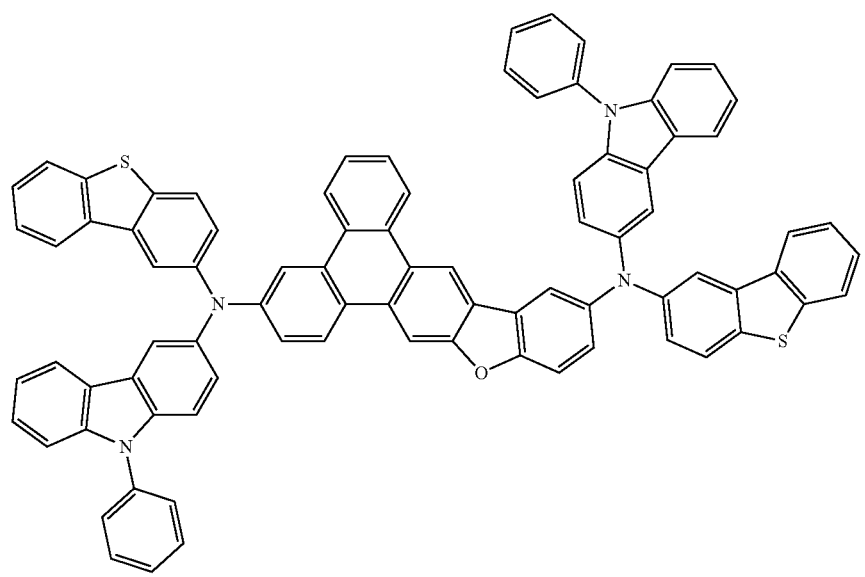

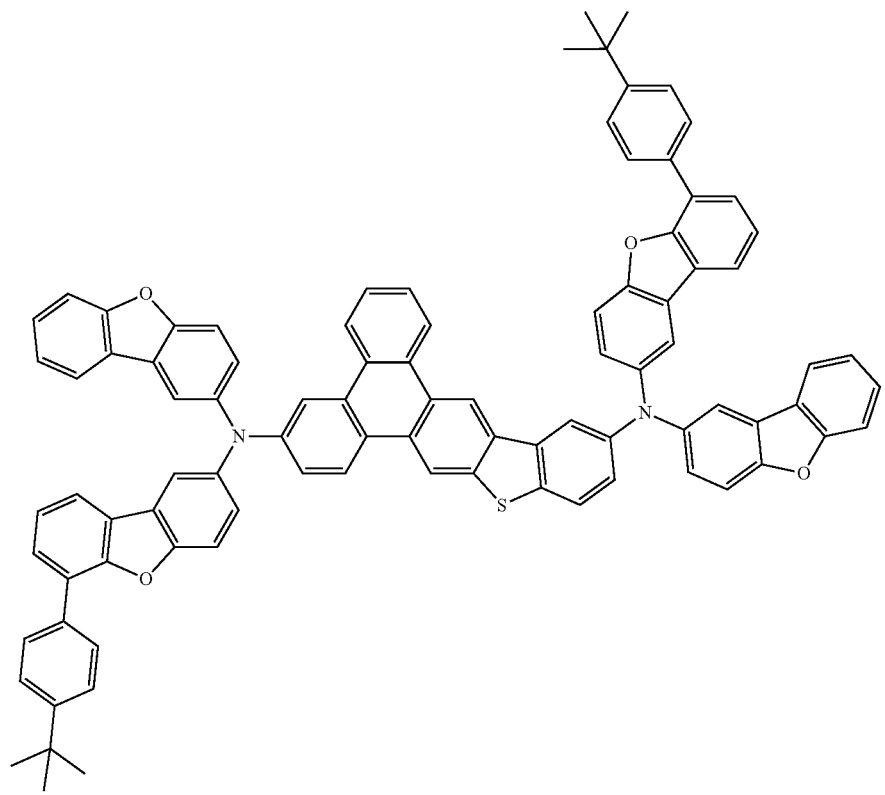
C60
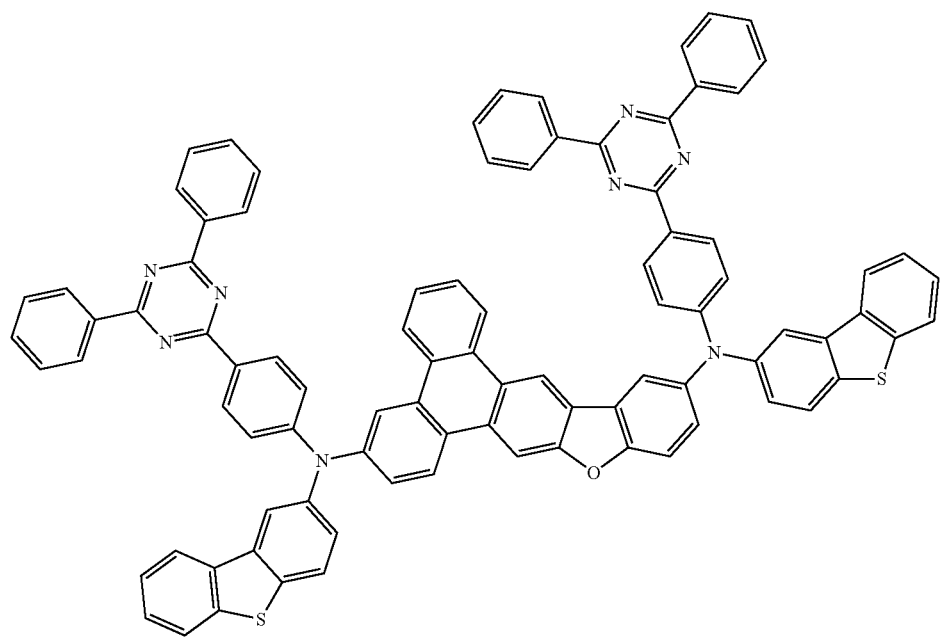
C61

-continued
C62
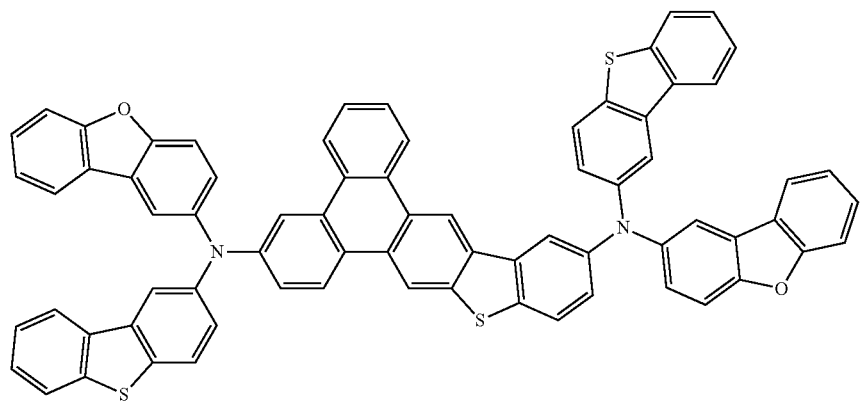
C63
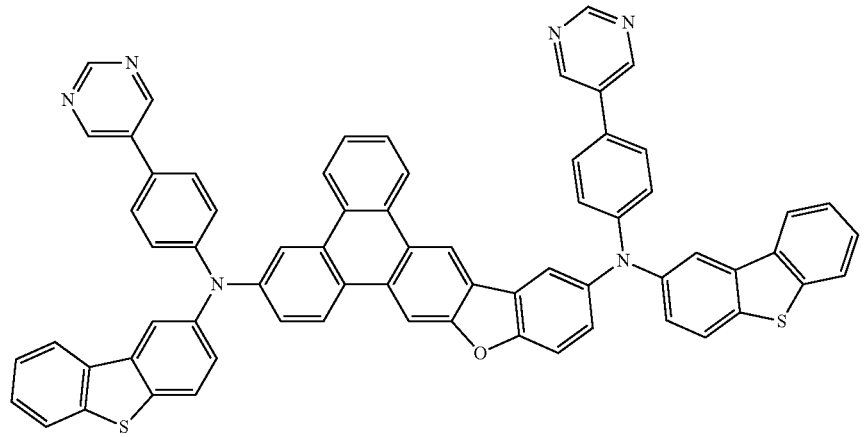
C64
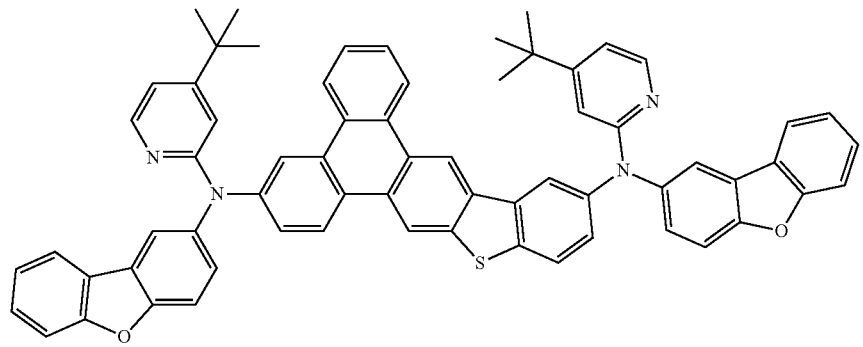
C65 C66
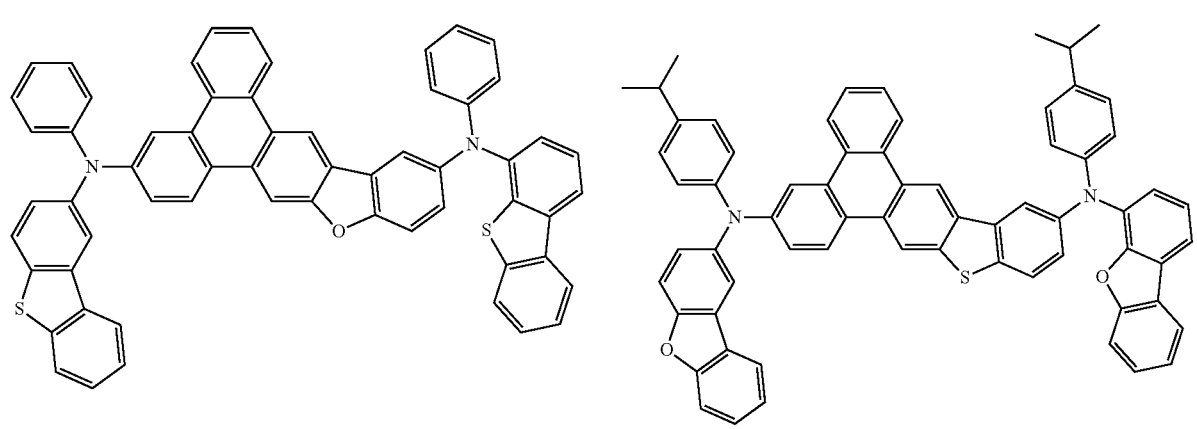

C67
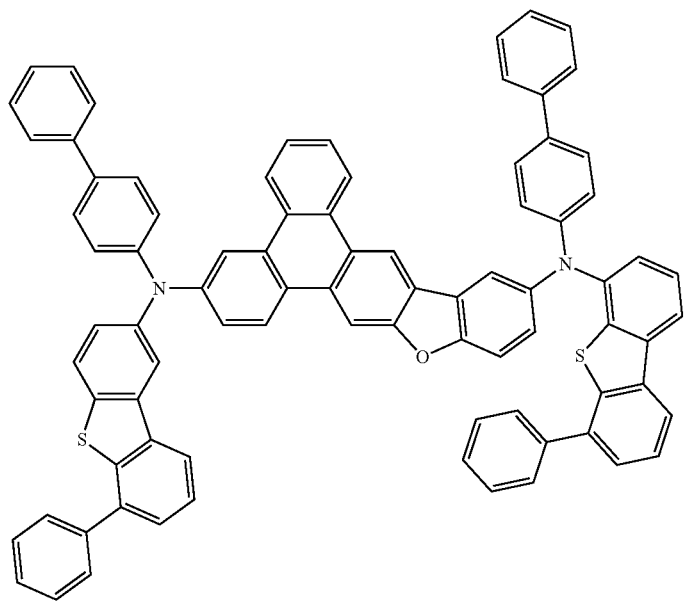
C68
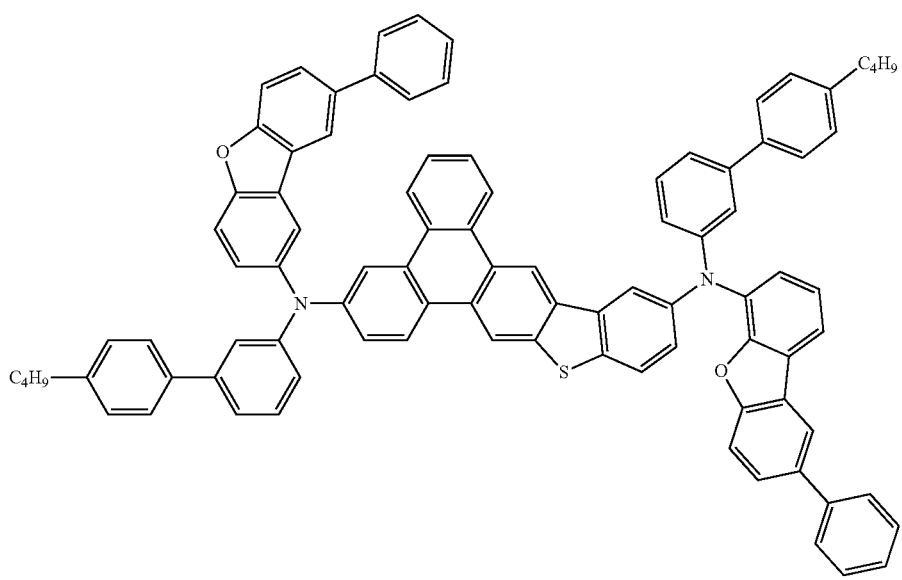
C69
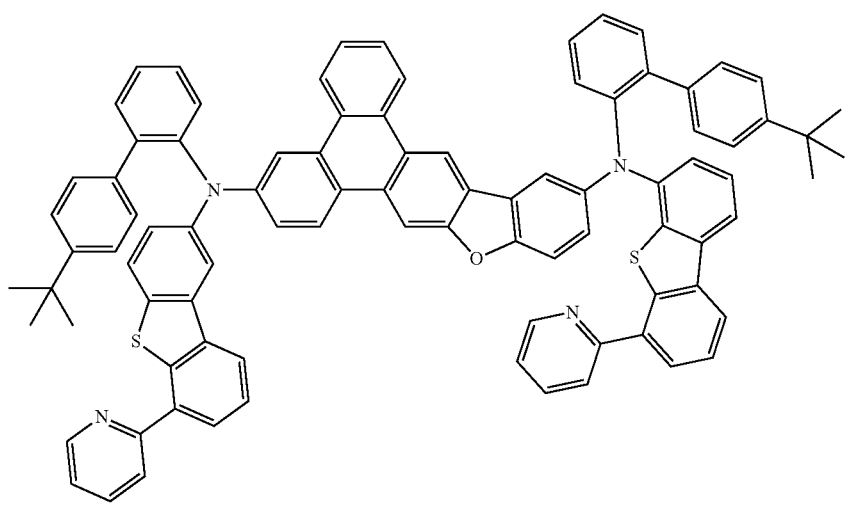

-continued
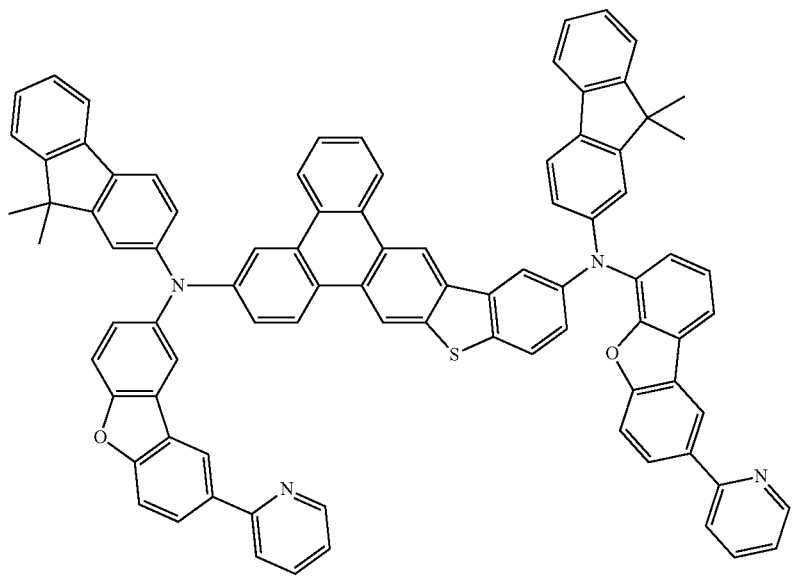
C70
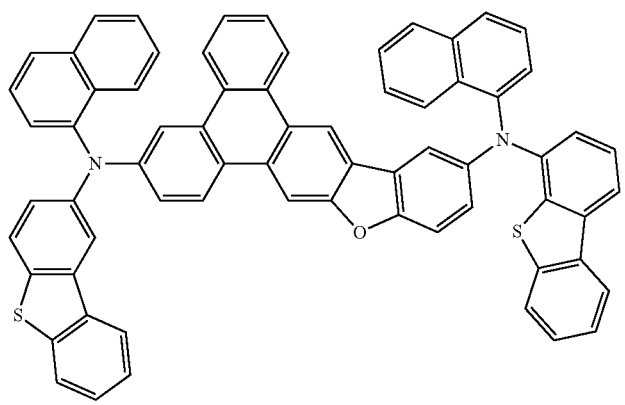
C71
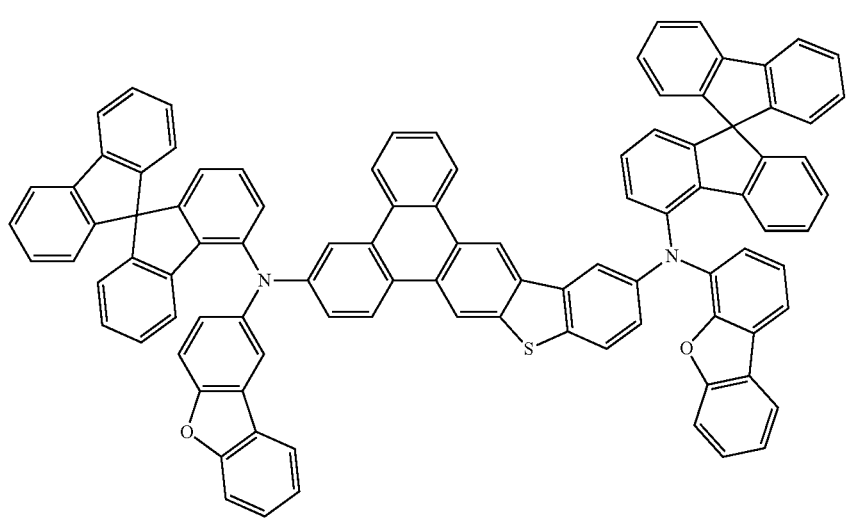
C72

-continued
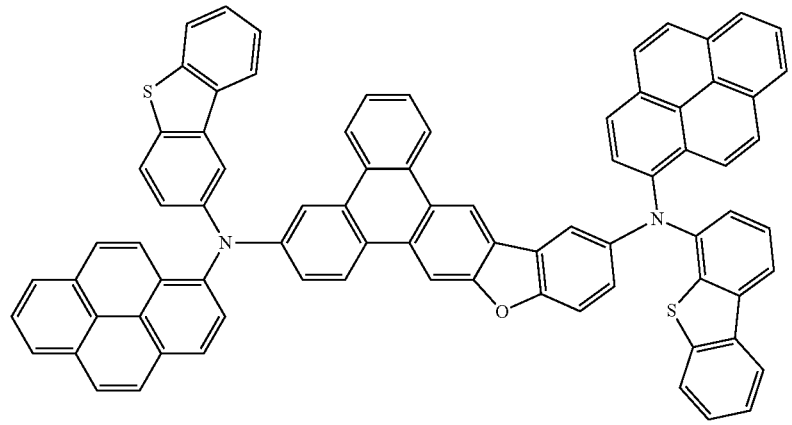
C73
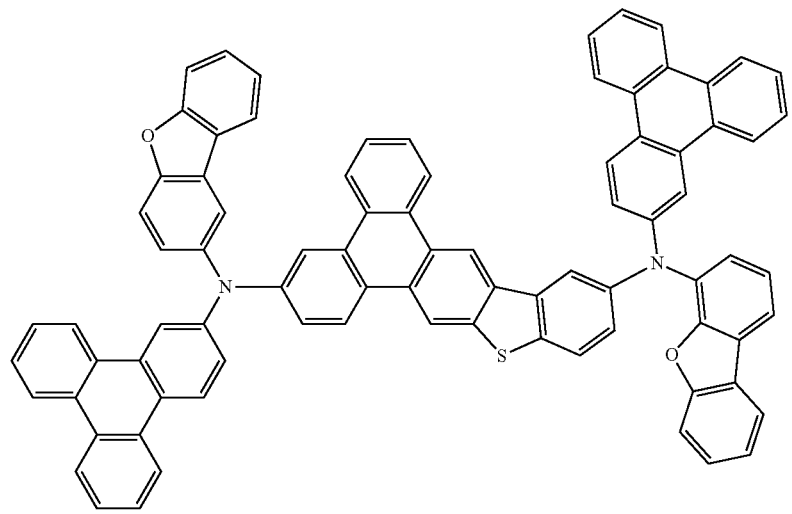
C74
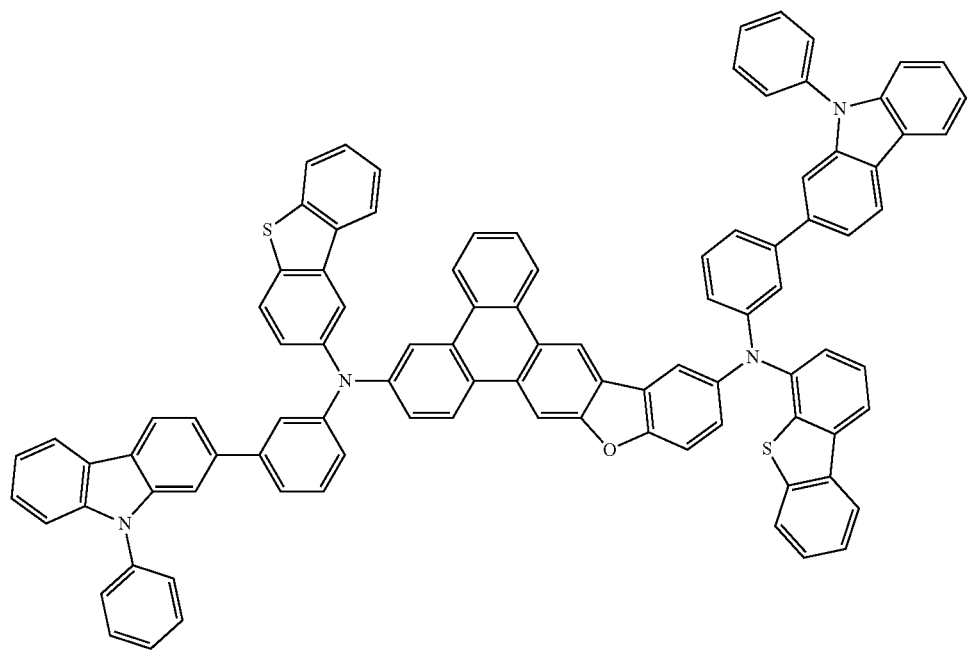
C75

C76
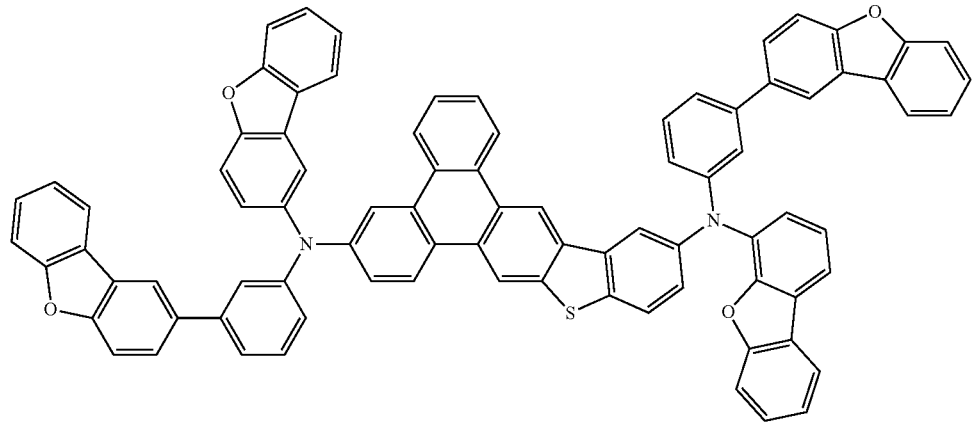
C77
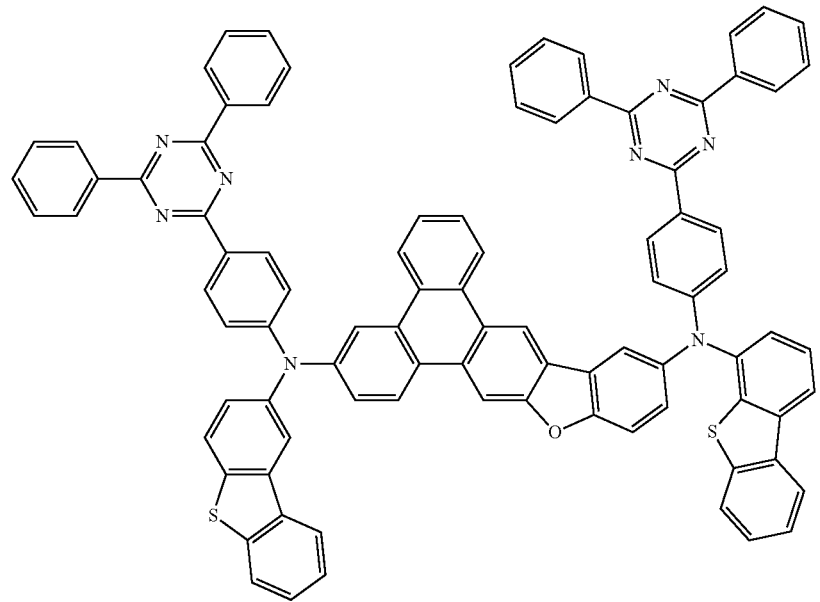
C78
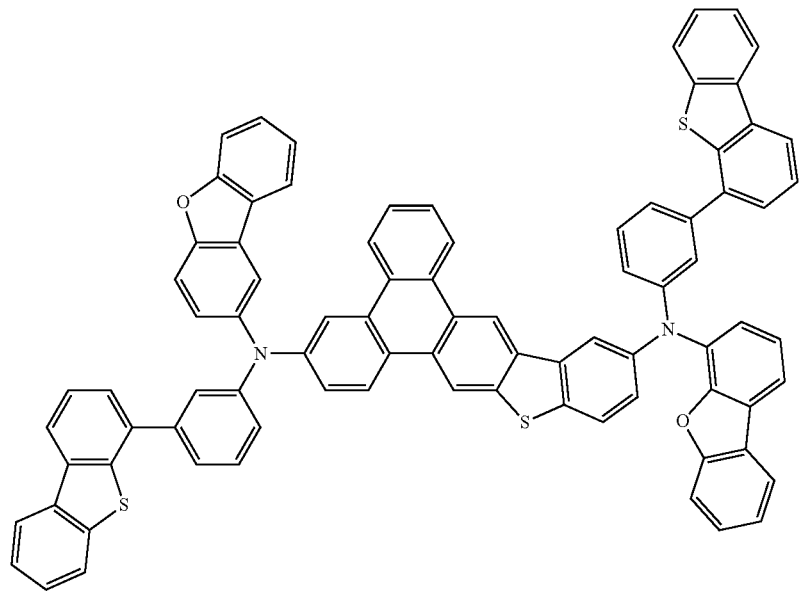

-continued
C79
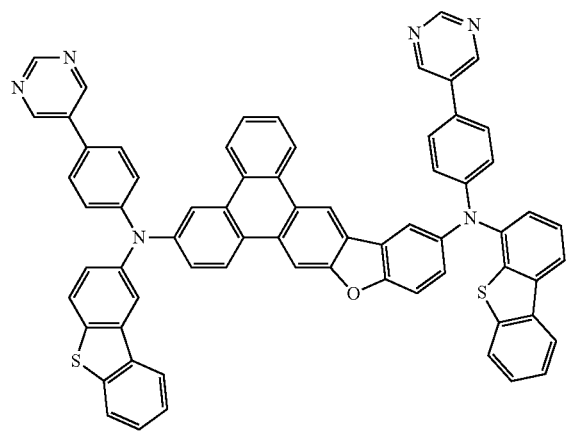
C80
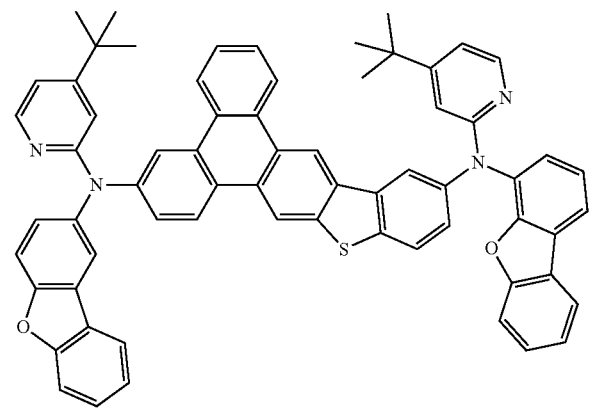
C81
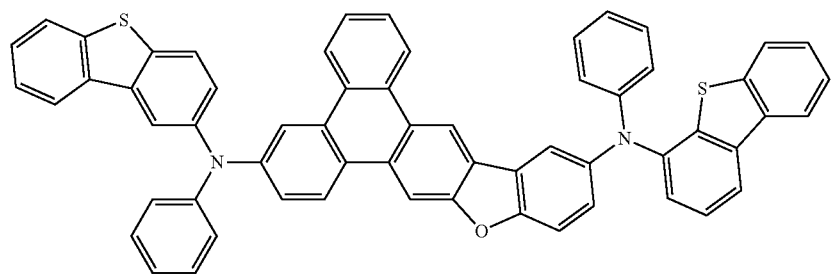
C82
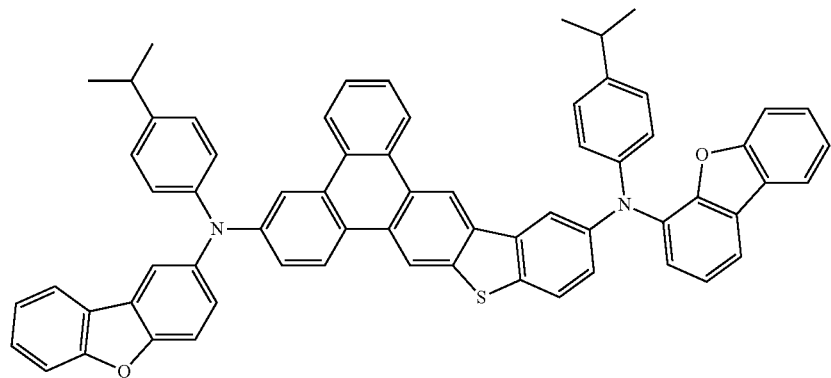
C83
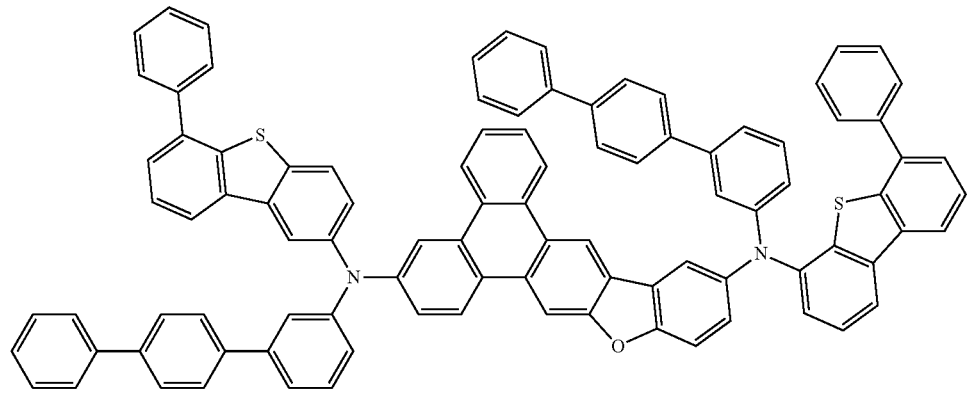

-continued
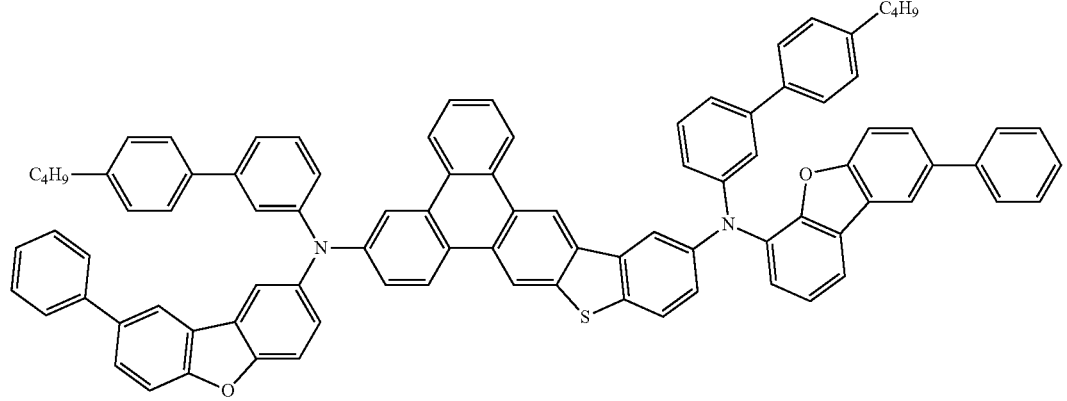
C84
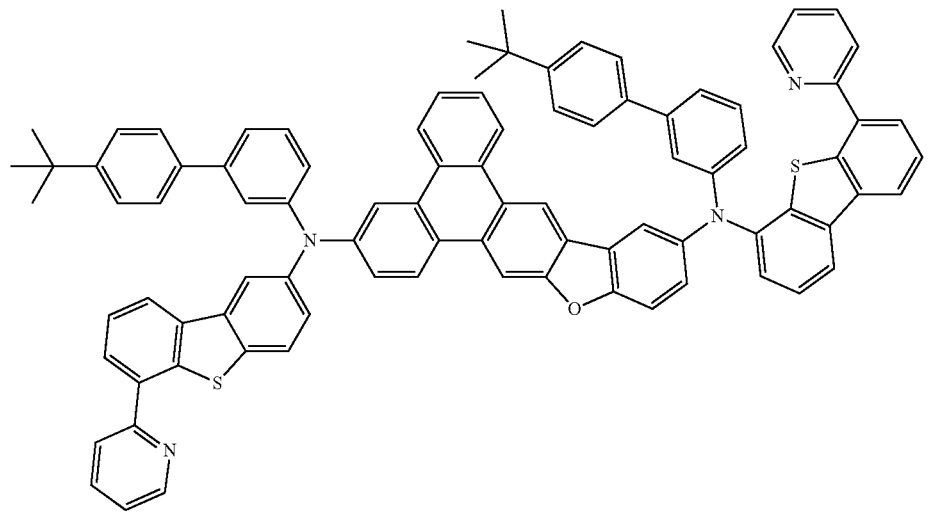
C85
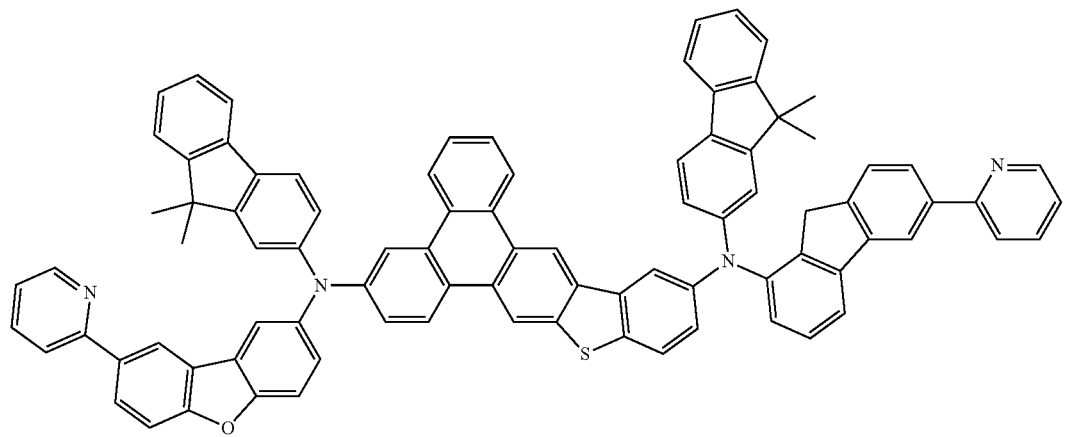
C86

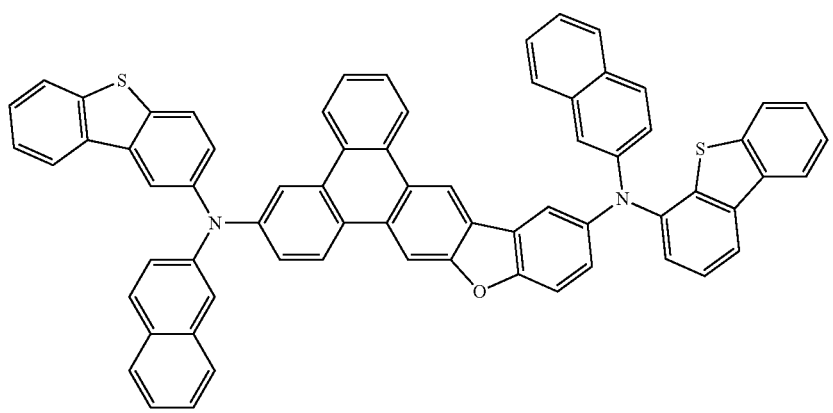
C87
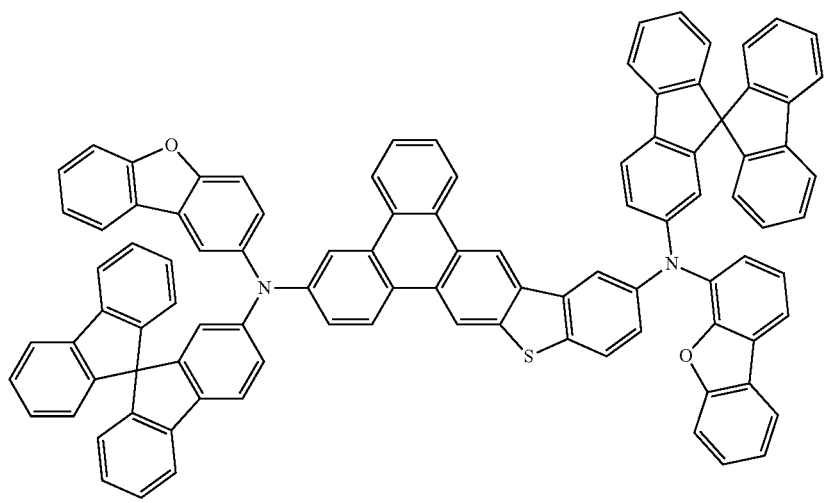
C88
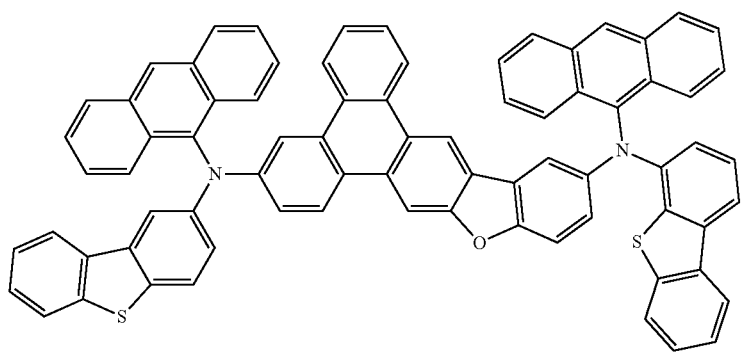
C89

-continued
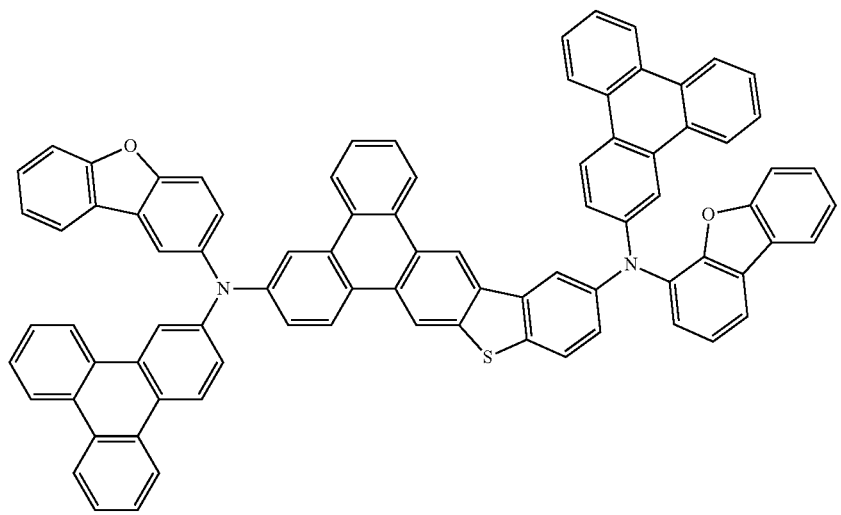
C90
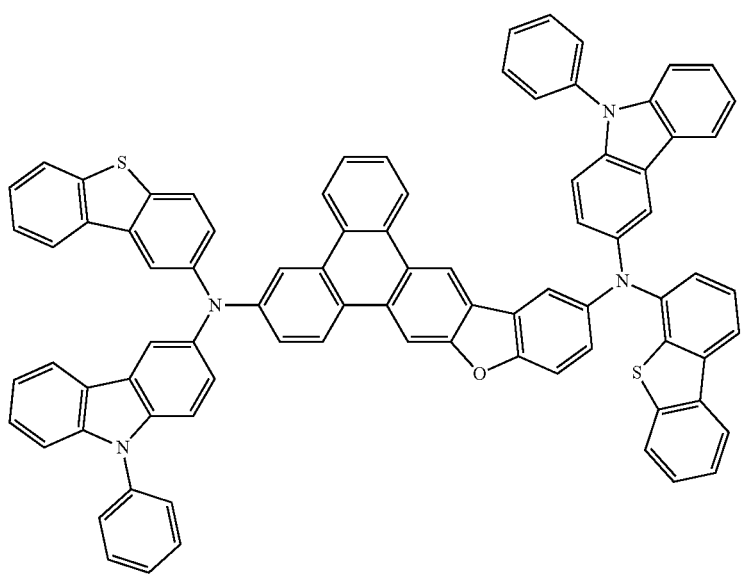
C91

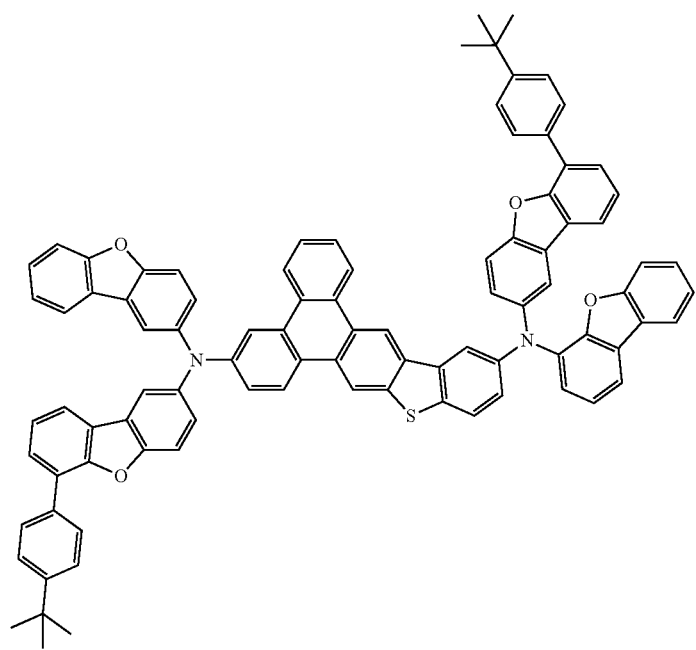
C92
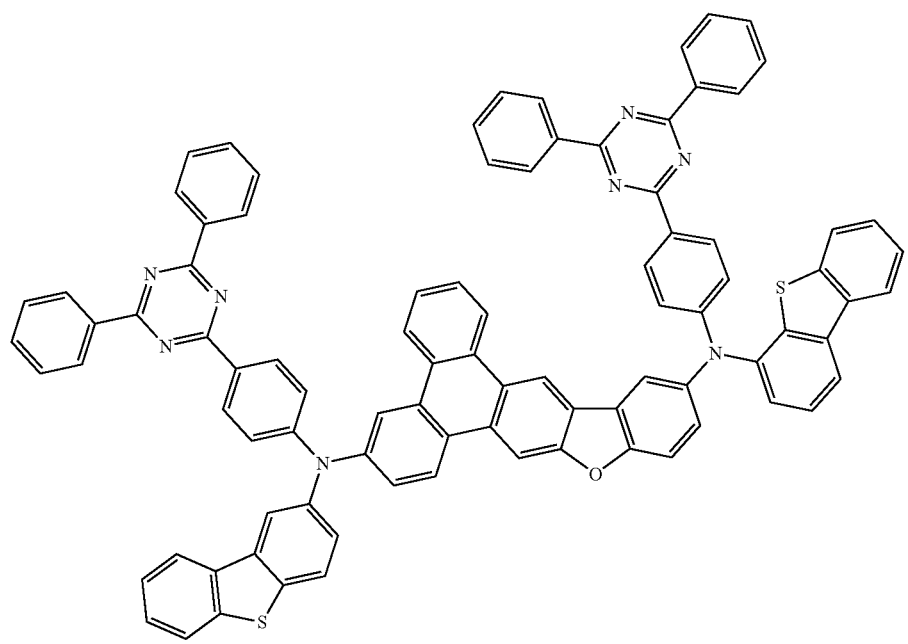
C93

-continued
C94
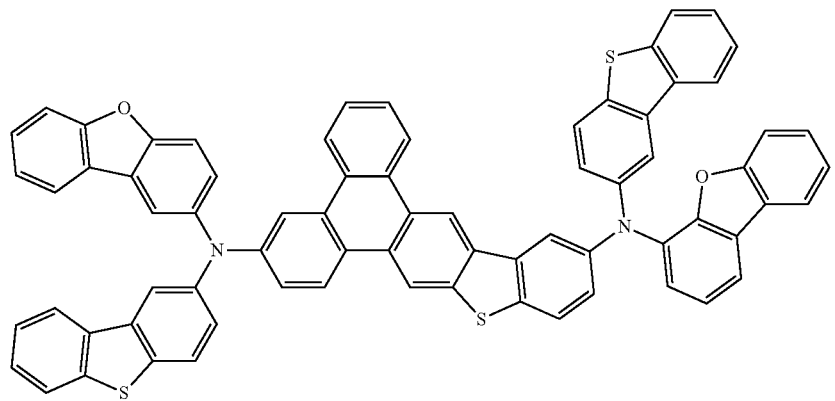
C95
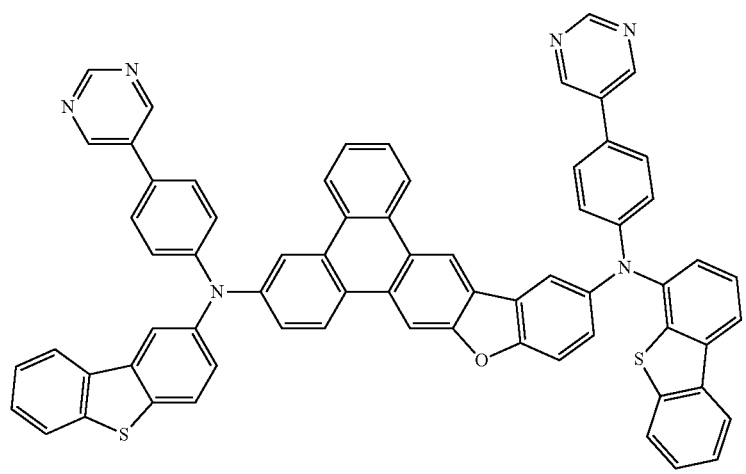
C96
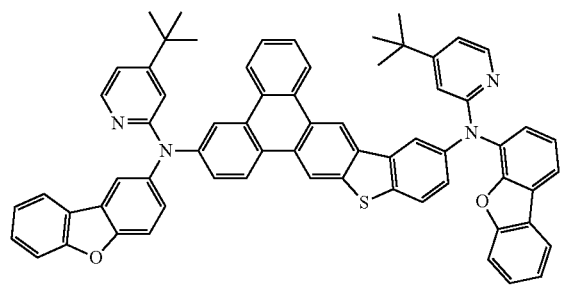
C97
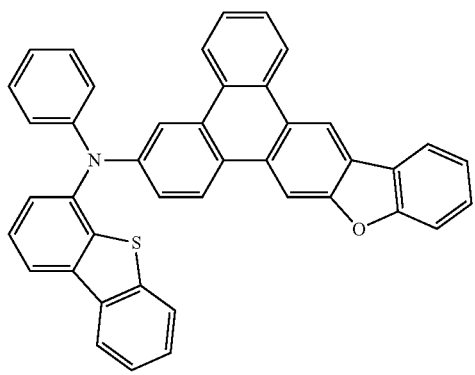

-continued
C98
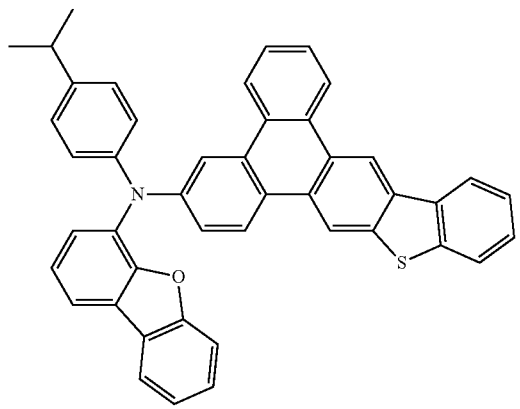
C99
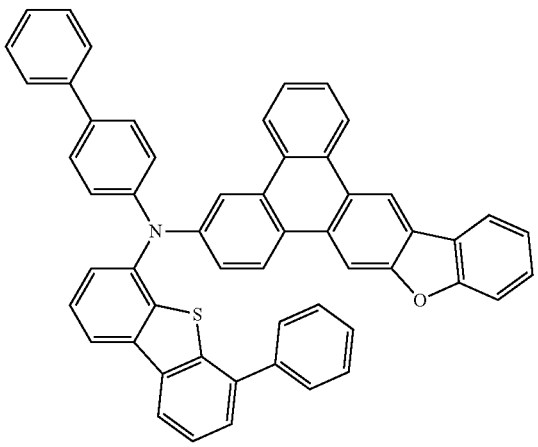
C100
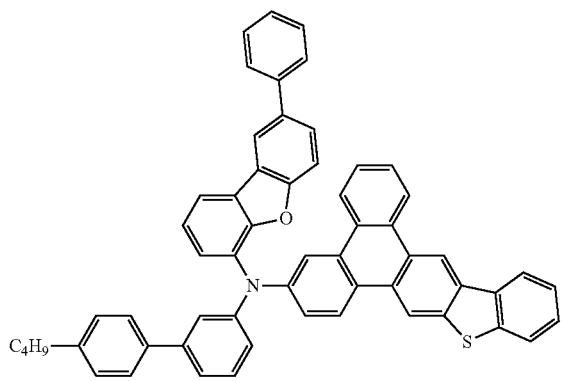
C101
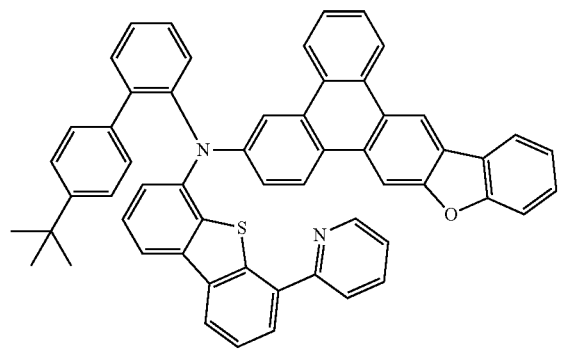
C102
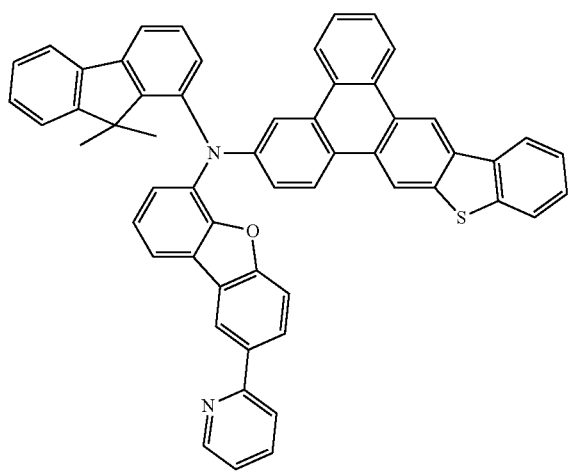
C103
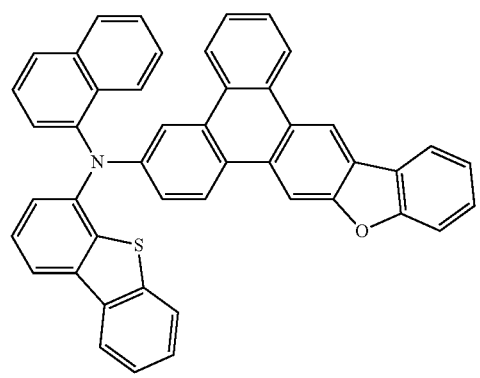

-continued
C104
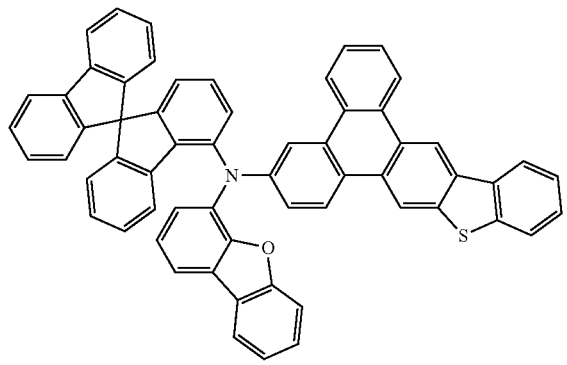
C105
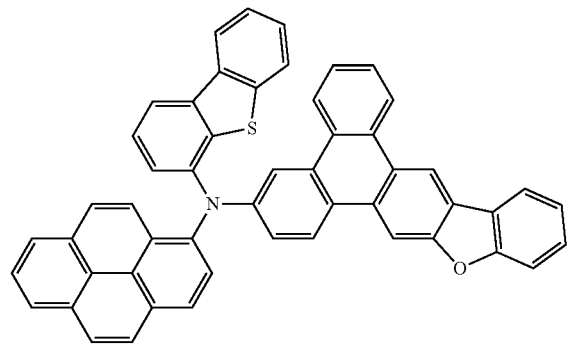
C106
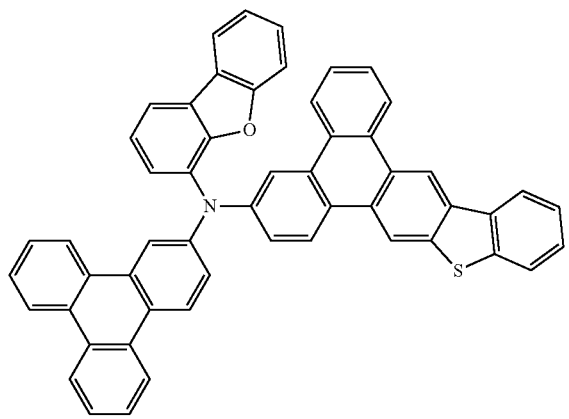
C107
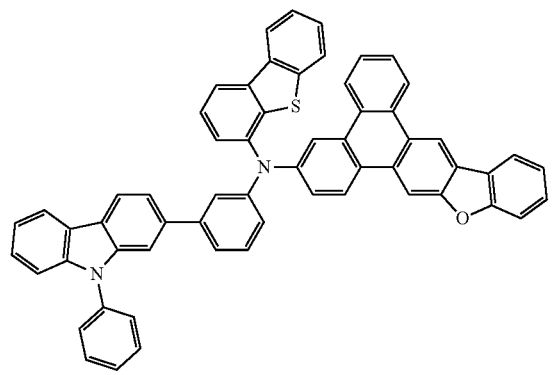
C108
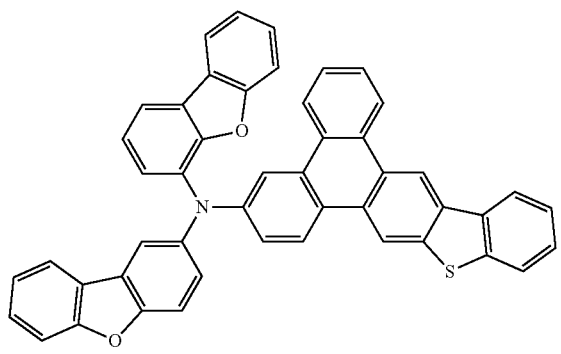
C109
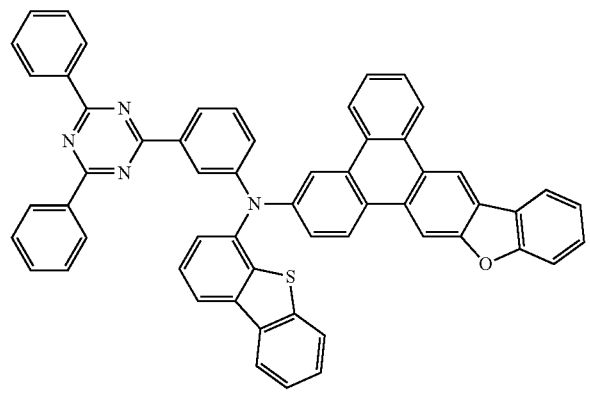

-continued
C110
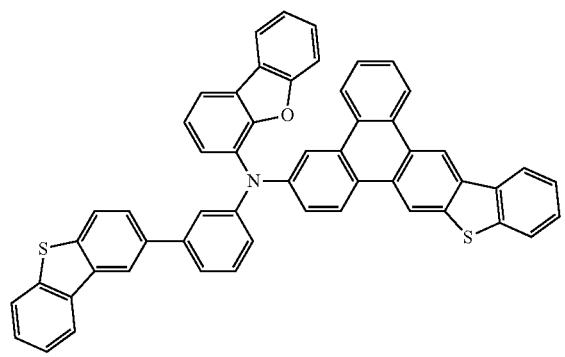
C111
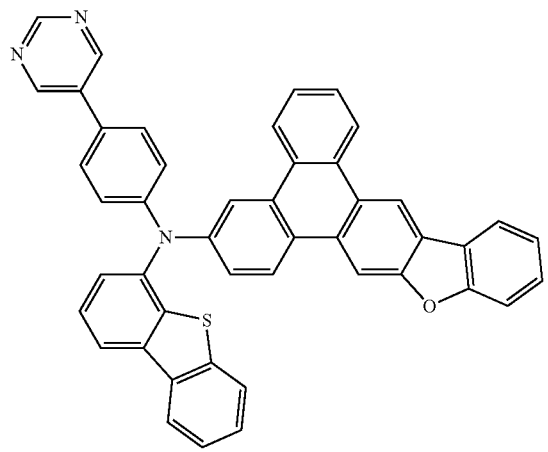
C112
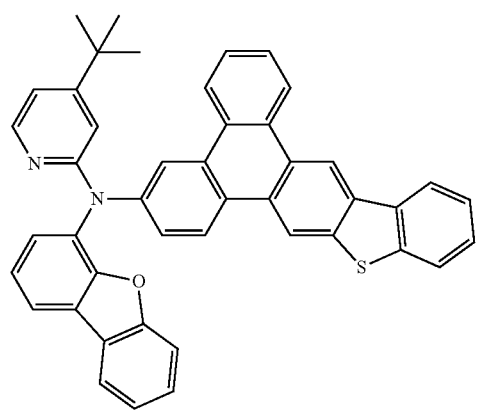
C113
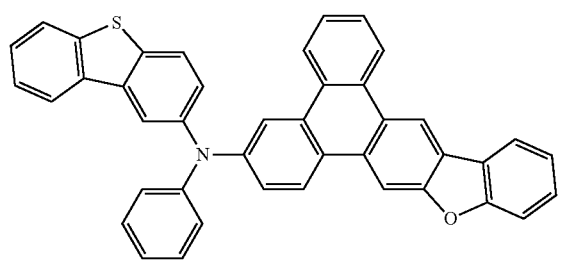
C114
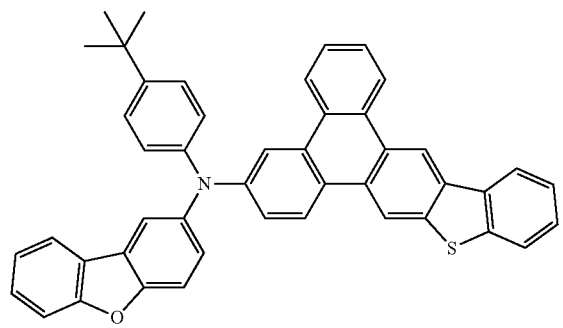
C115
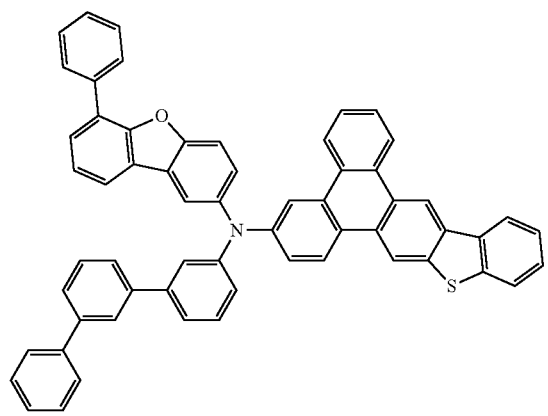

-continued
C116
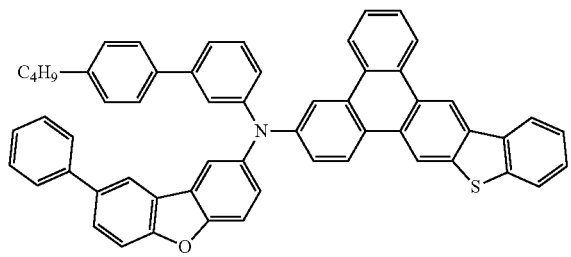
C117
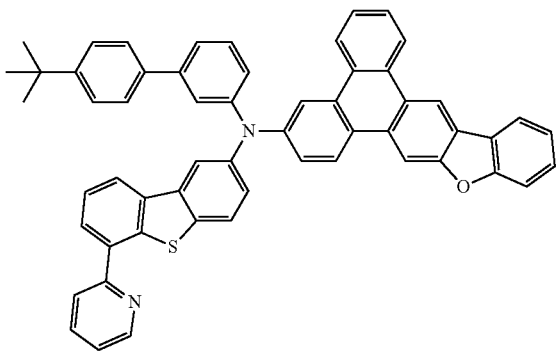
C118
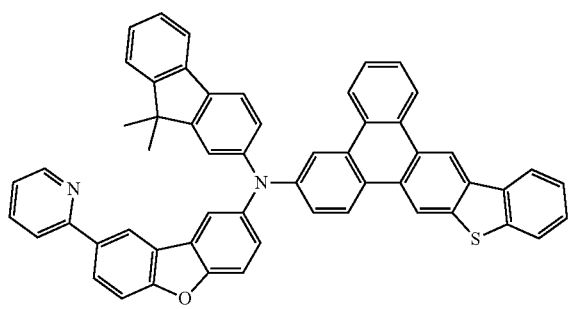
C119
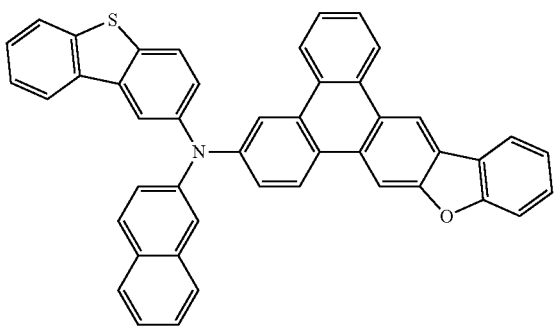
C120
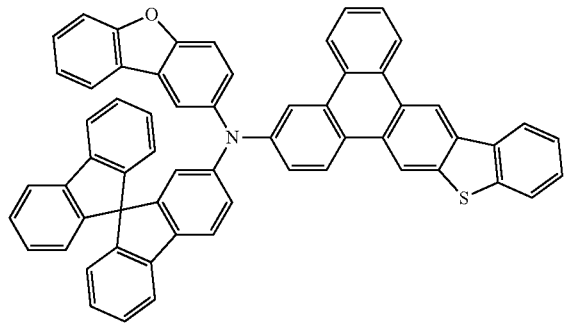
C121
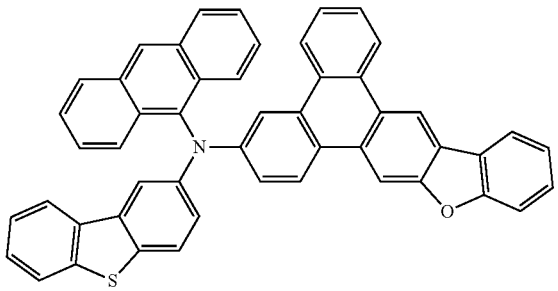
C122
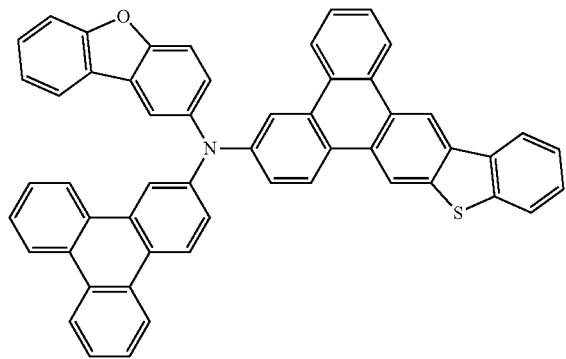
C123
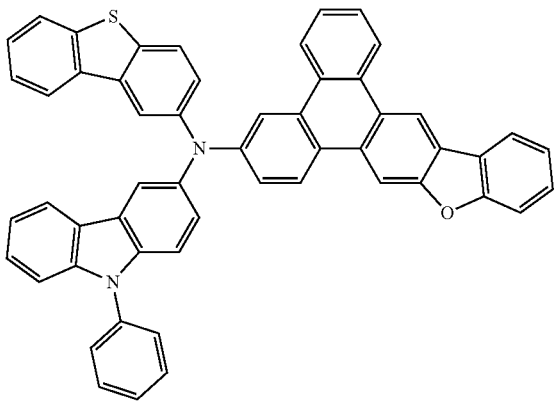

-continued
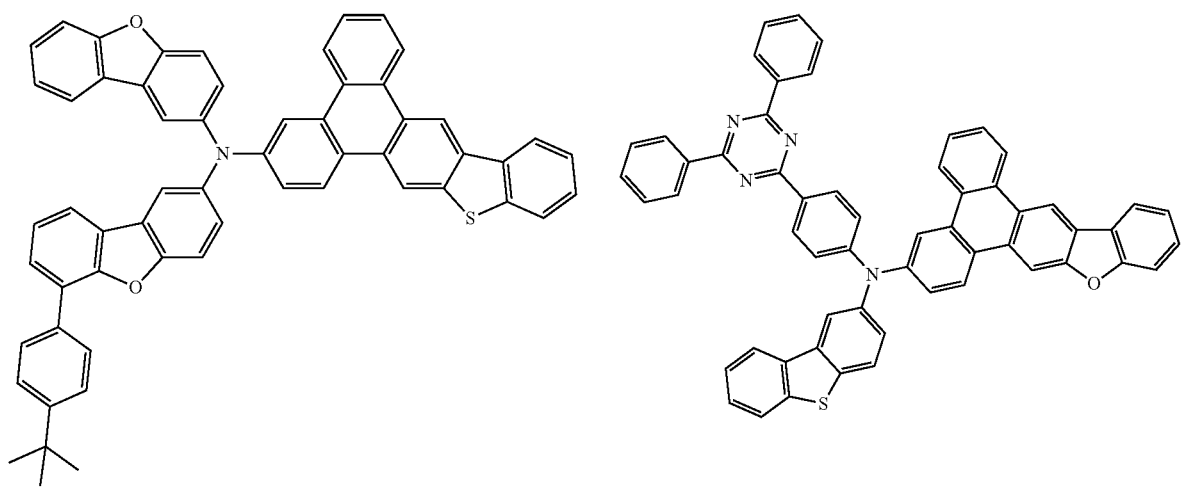
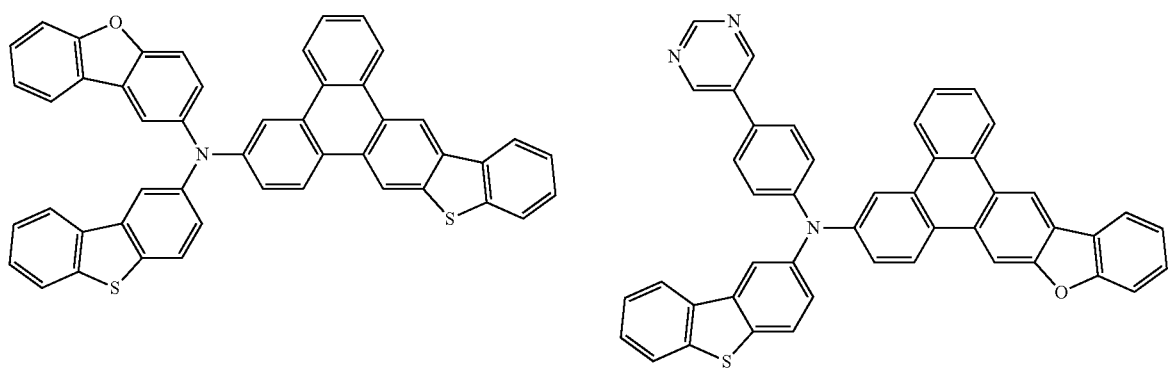
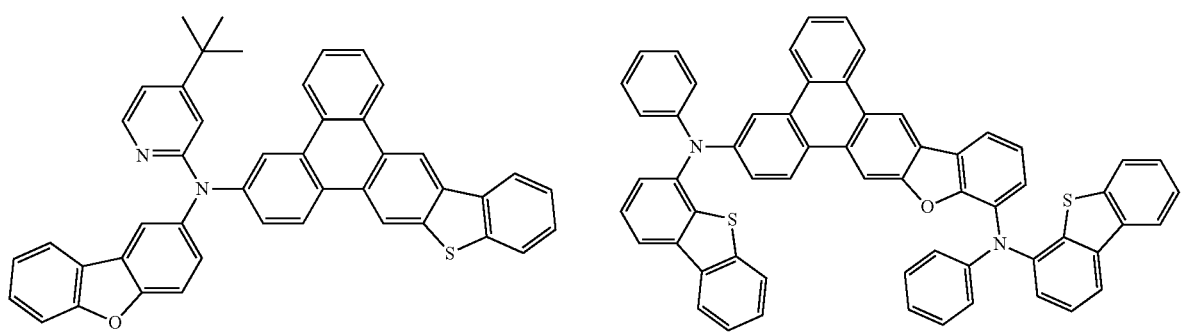

-continued
C130
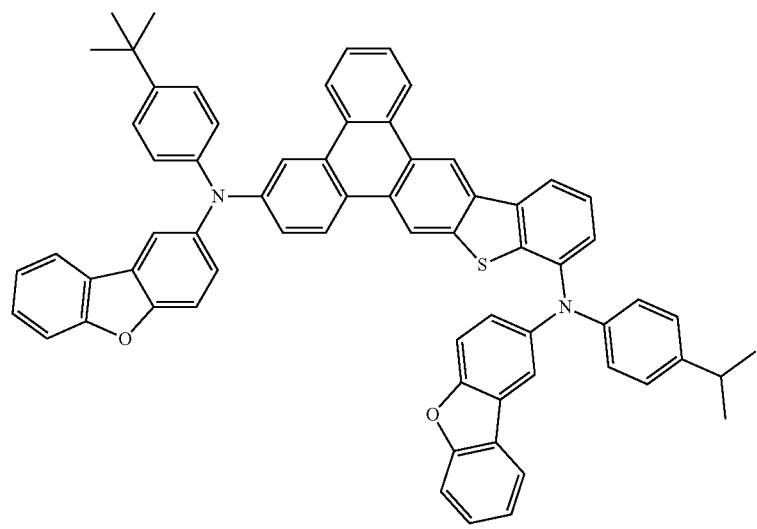
C131
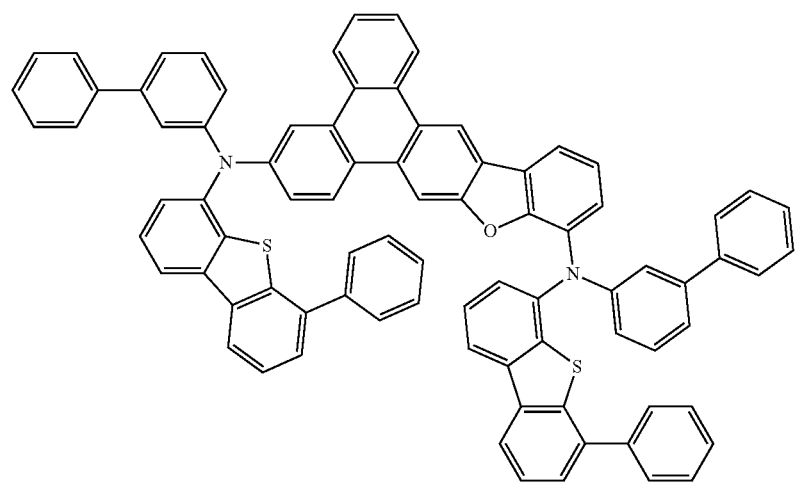
C132
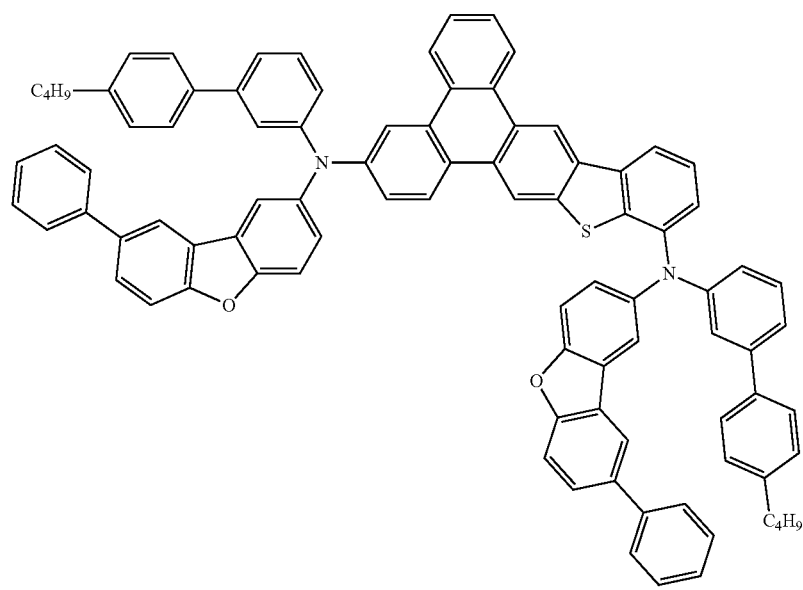

-continued
C133
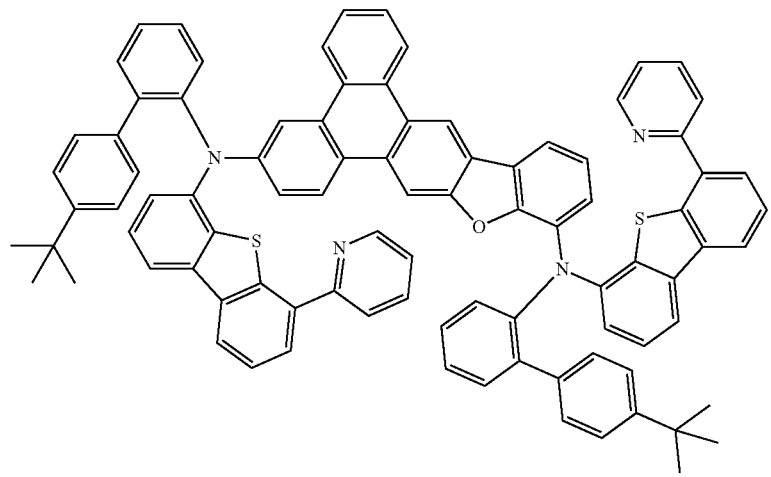
C134
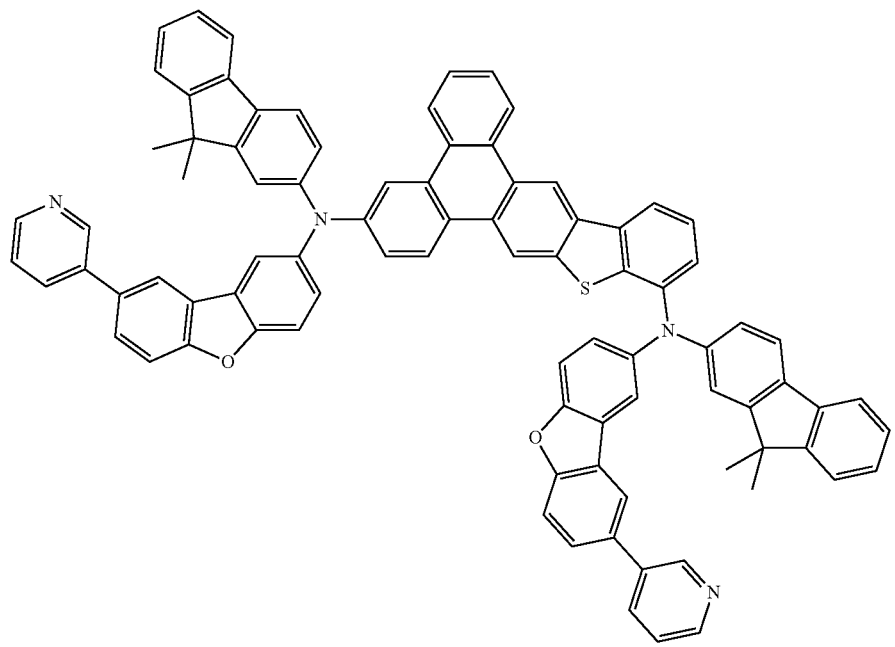
C135
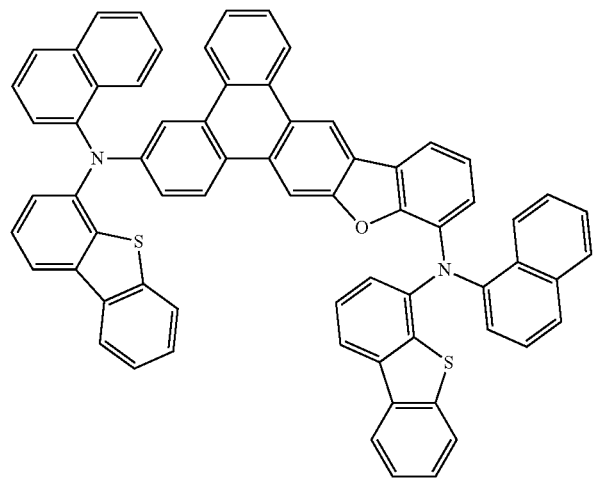

-continued
C136
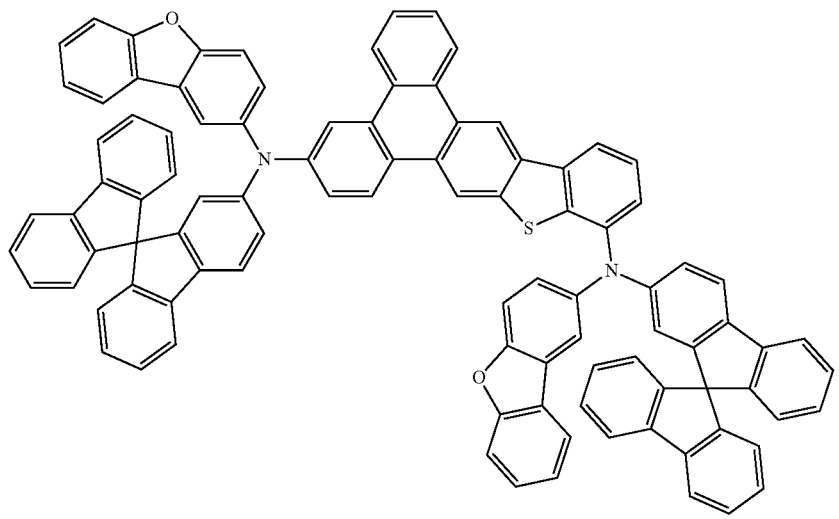
C137
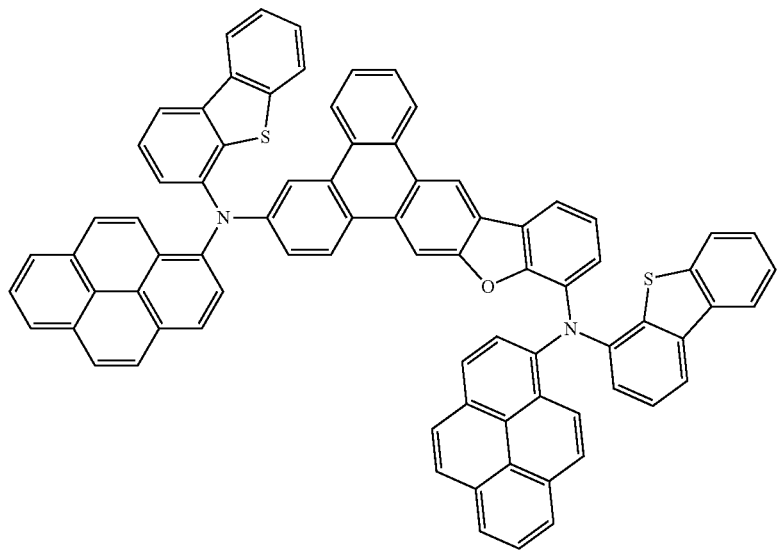
C138
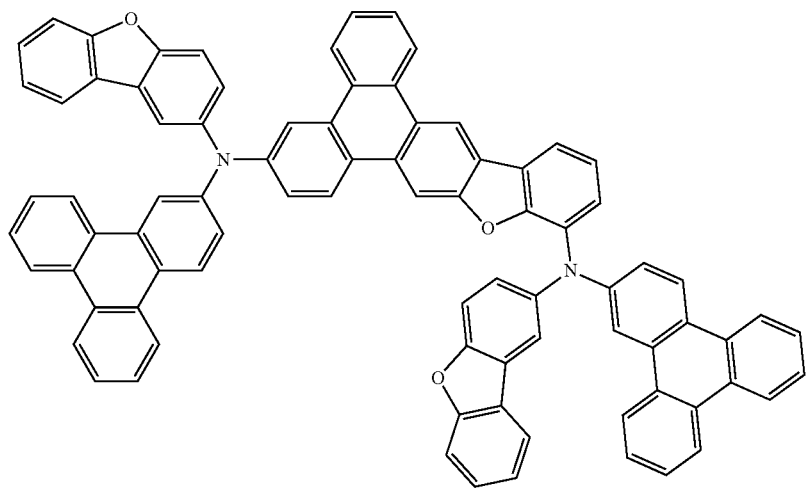

-continued
C139
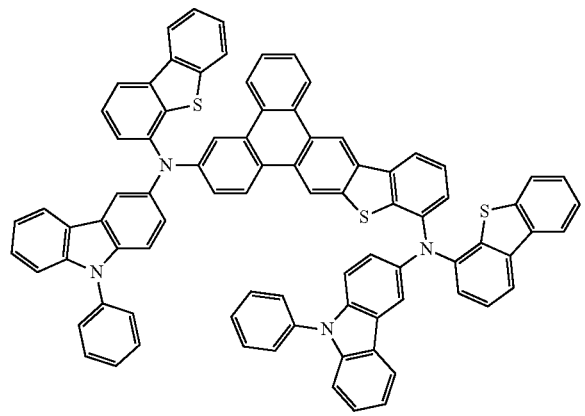
C140
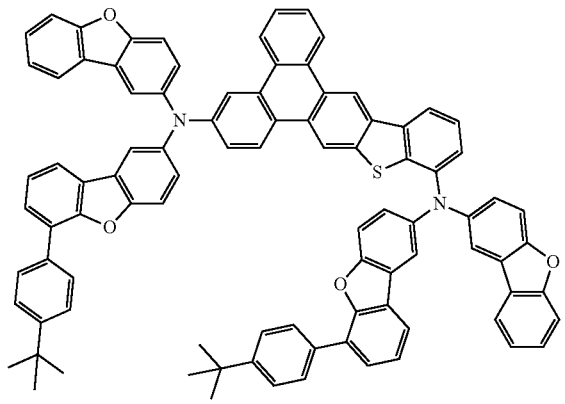
C141
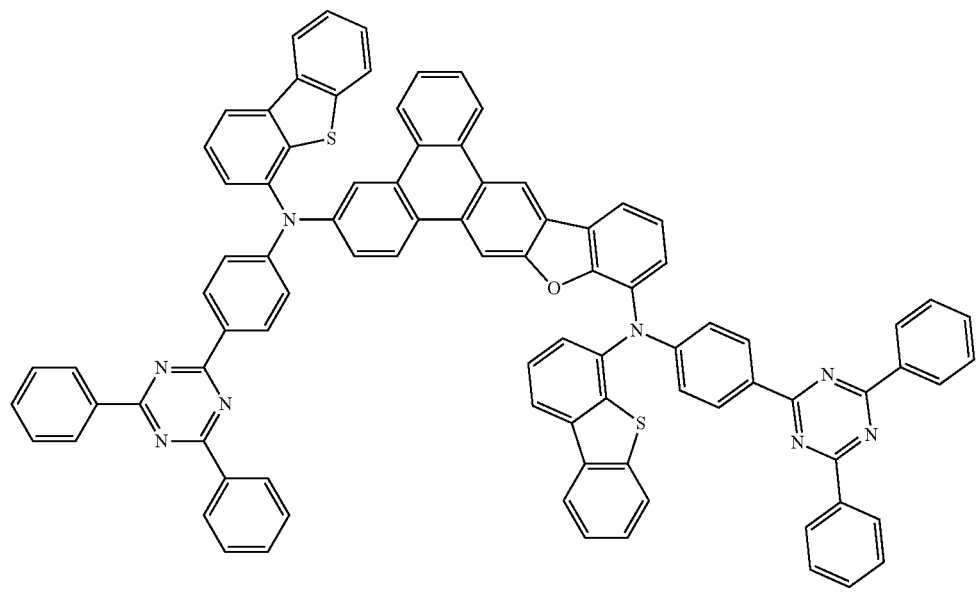
C142
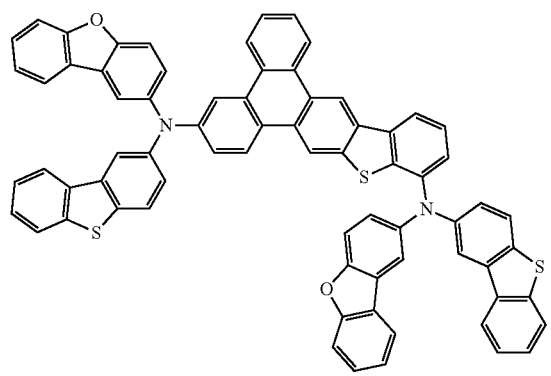
C143
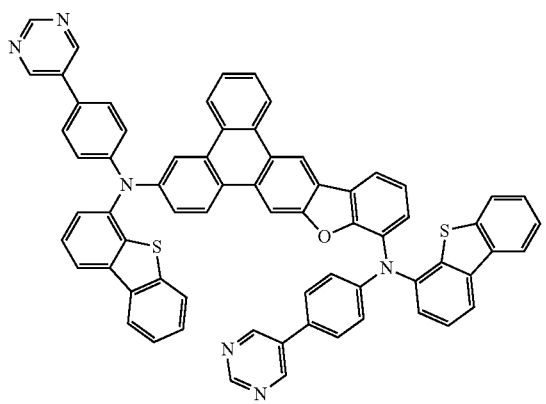

-continued
C144
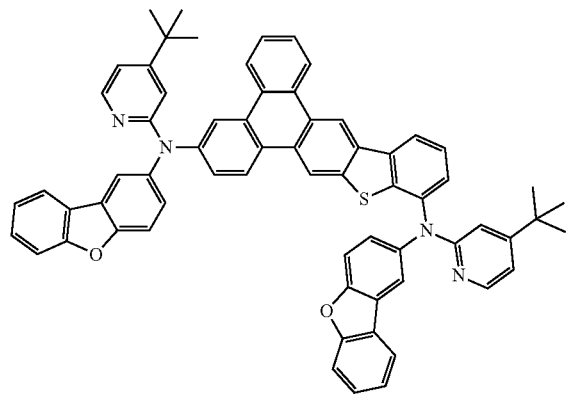
C145
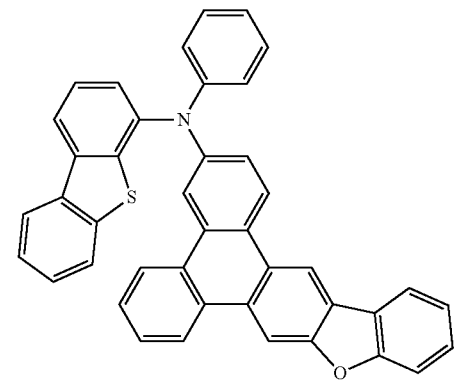
C146
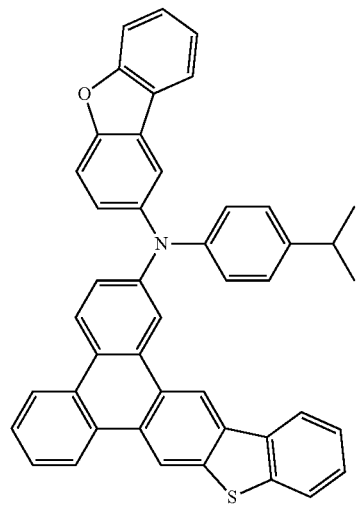
C147
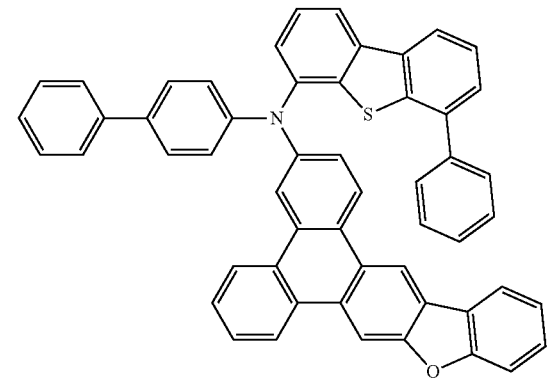
C148
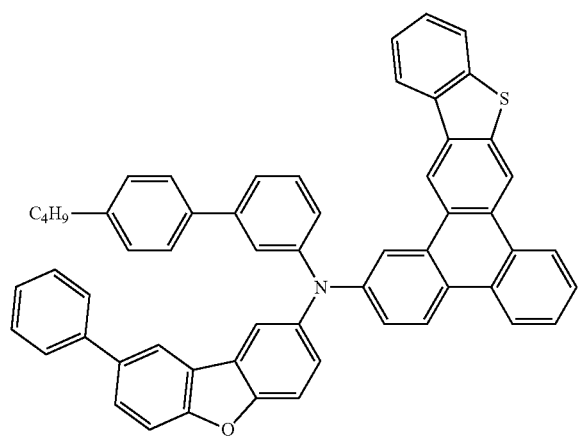
C149
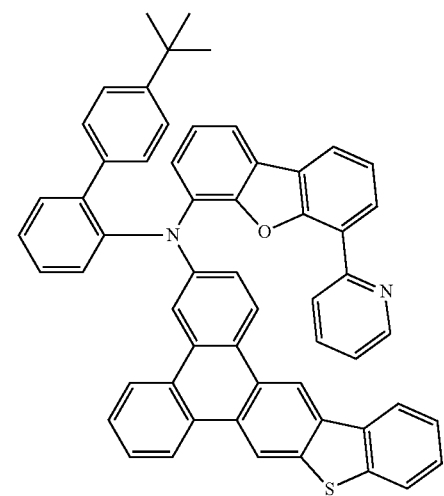

-continued
C150
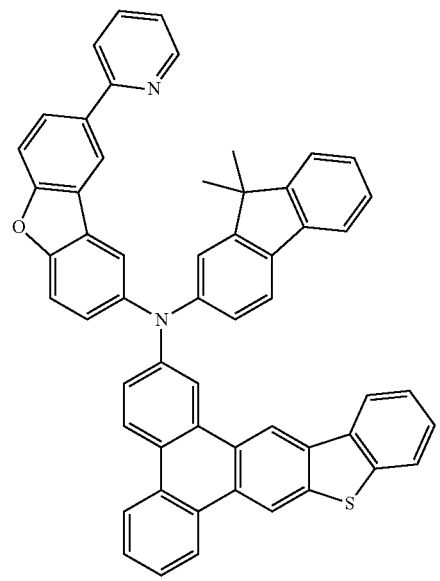
C151
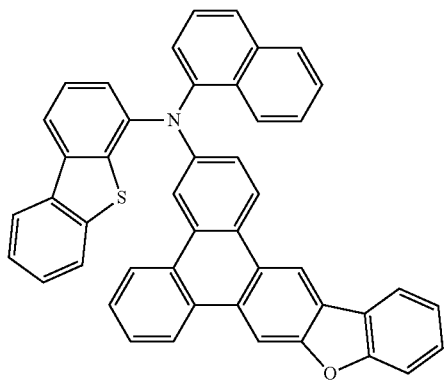
C152
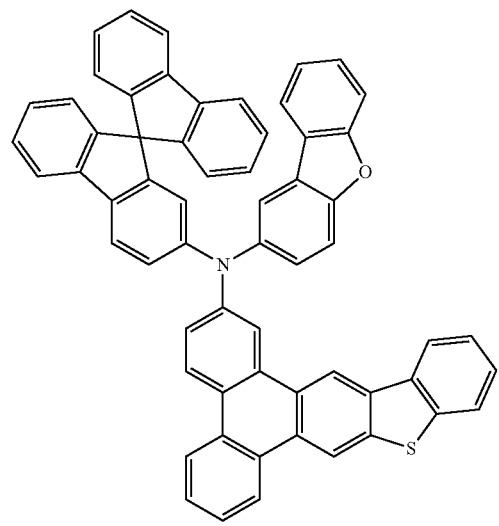
C153
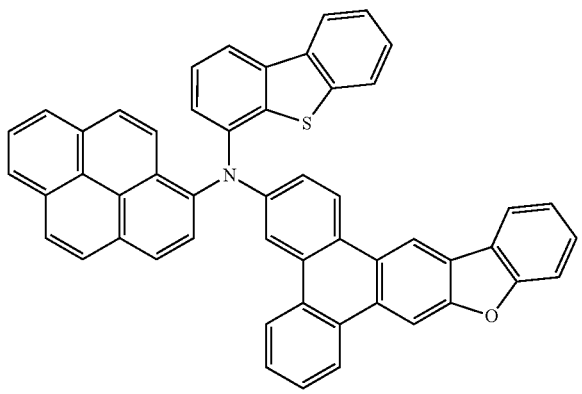
C154
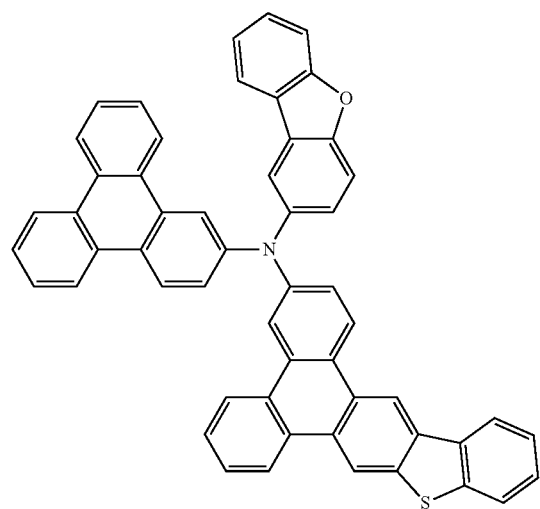
C155
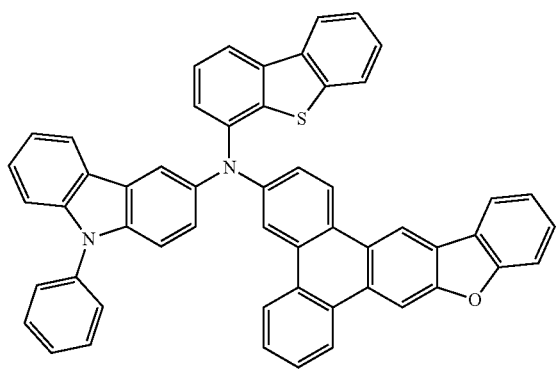

-continued
C156 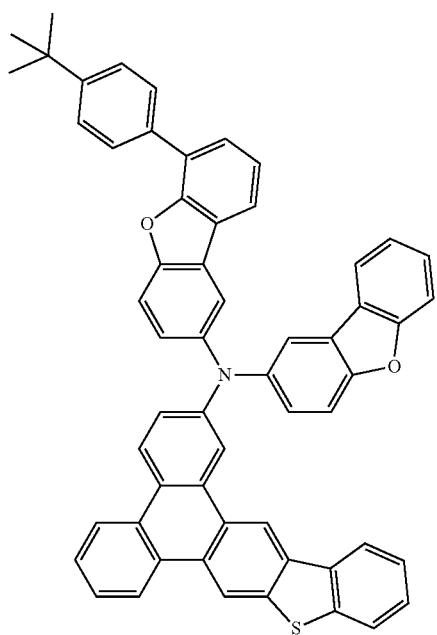 C157 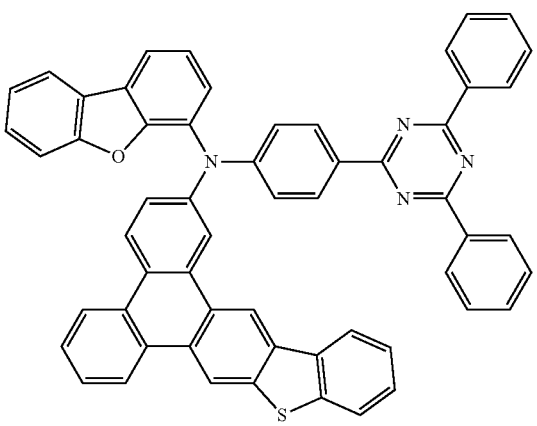
C158 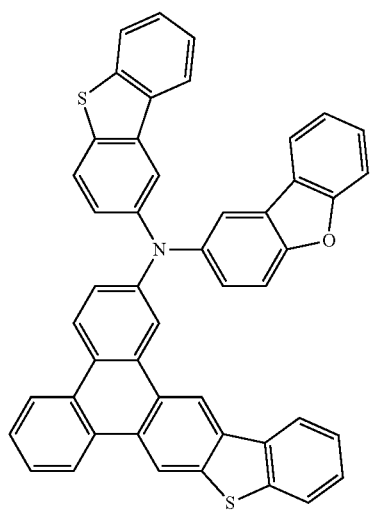 C159 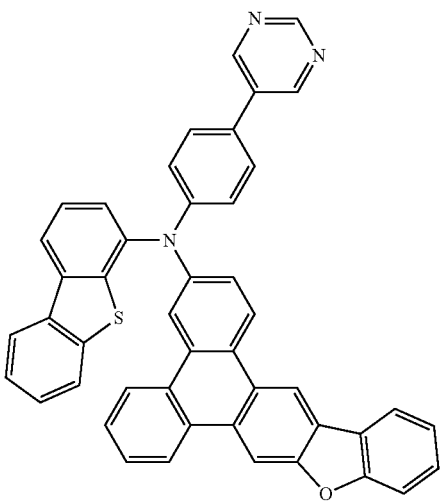
C160 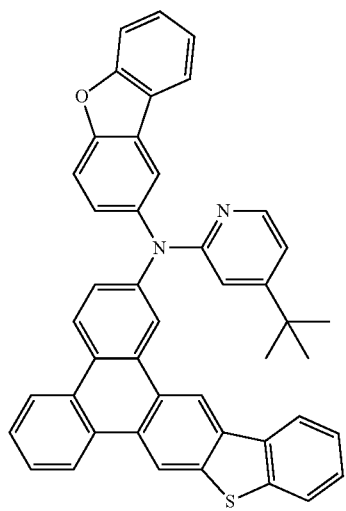 C161 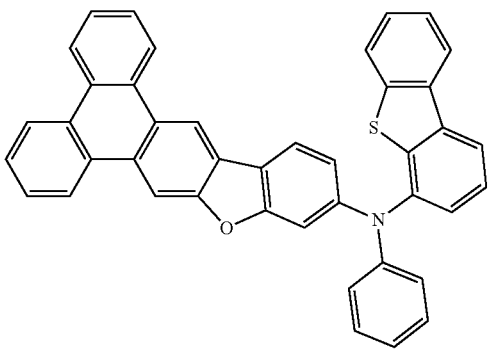

-continued
C162
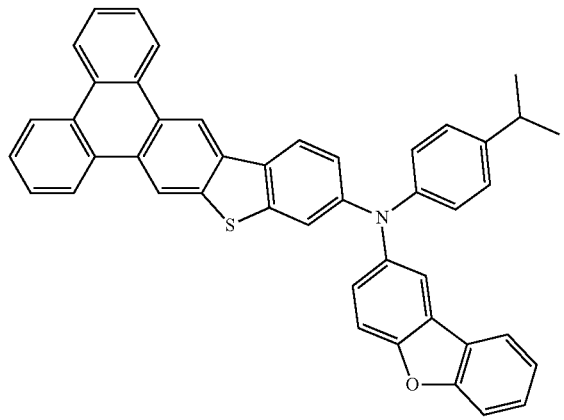
C163
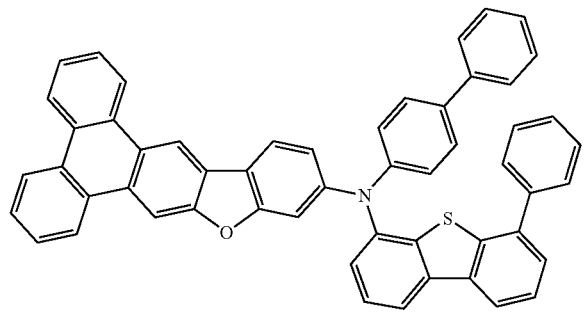
C164
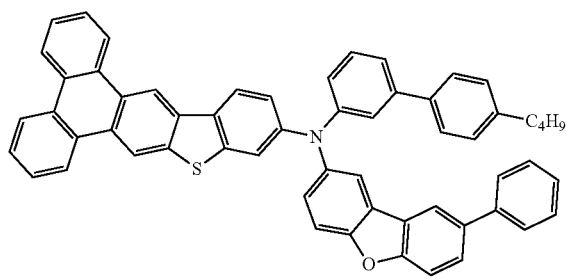
C165
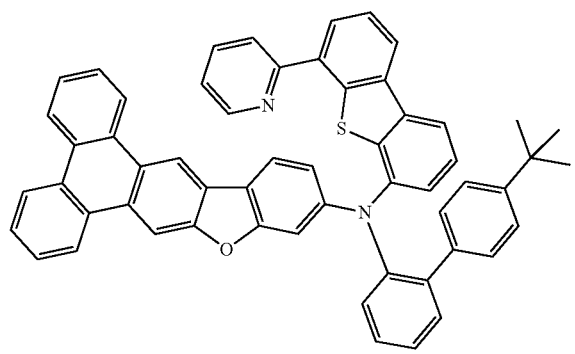
C166
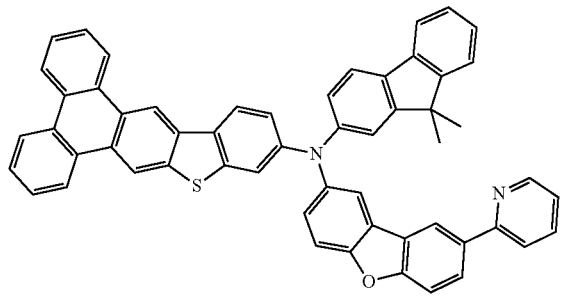
C167
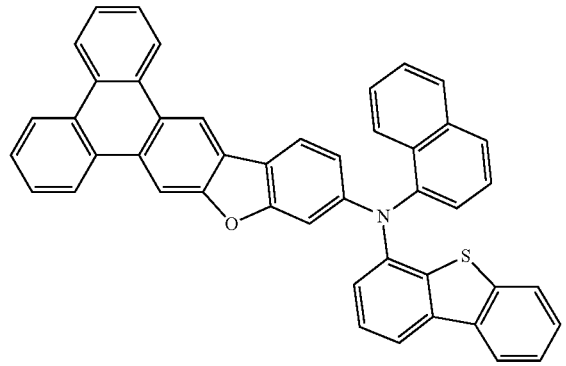
C168
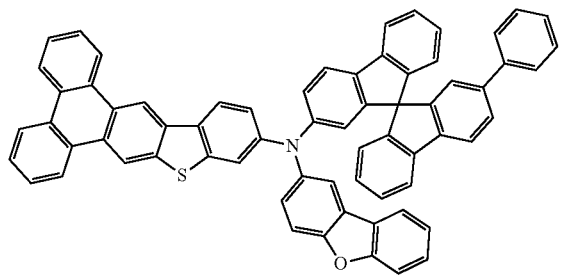
C169
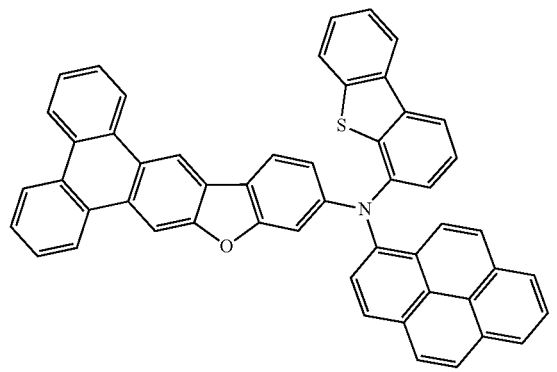

-continued
C170
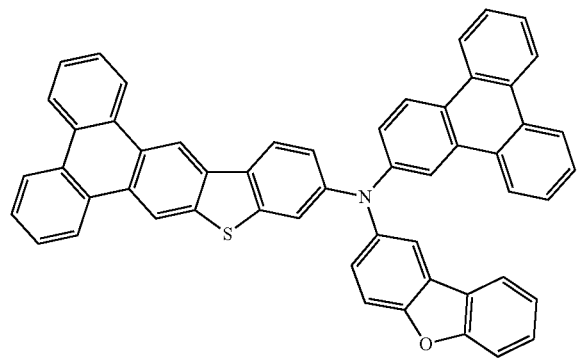
C171
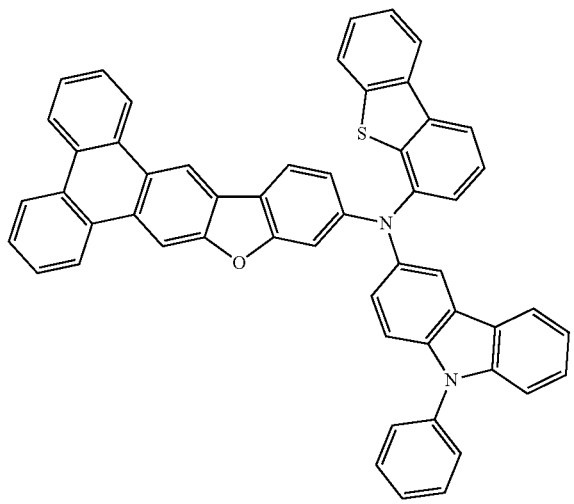
C172
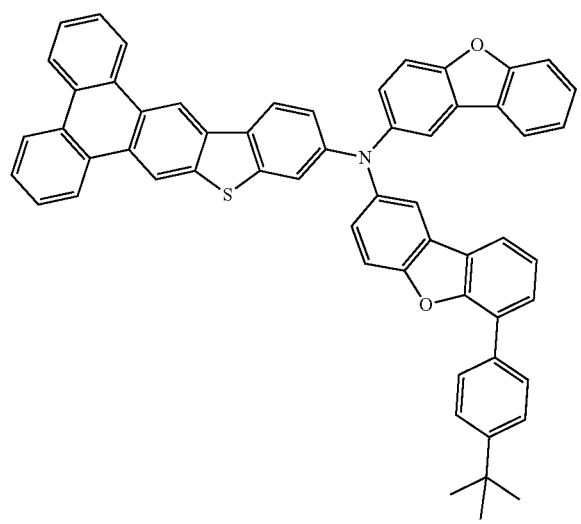
C173
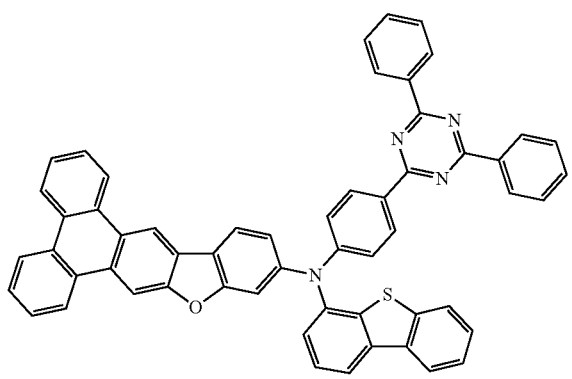
C174
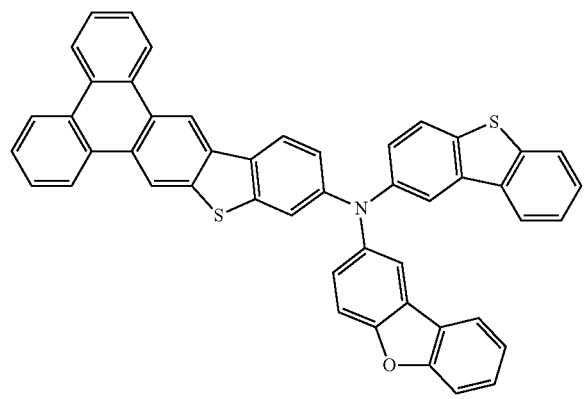
C175
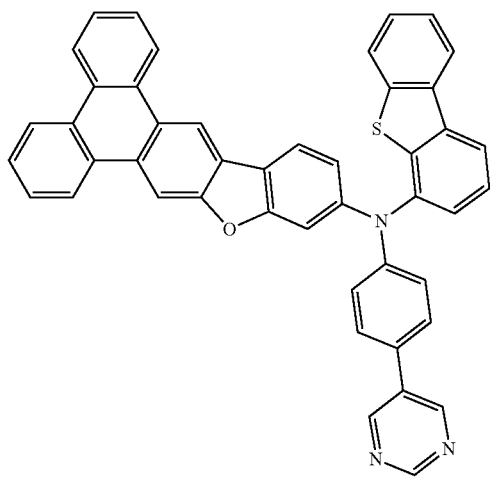

-continued
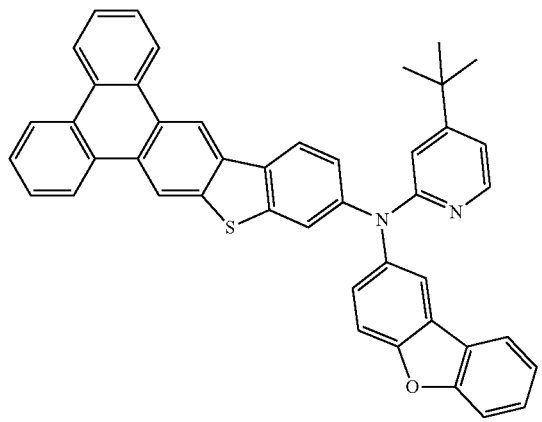
C176
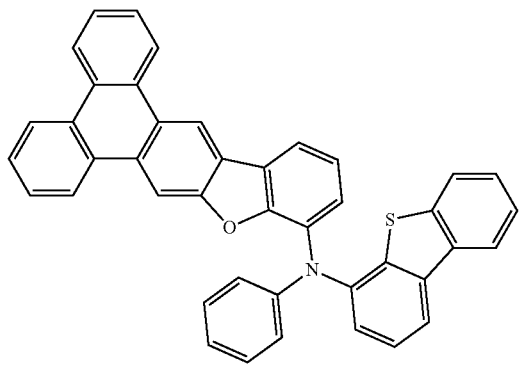
C177
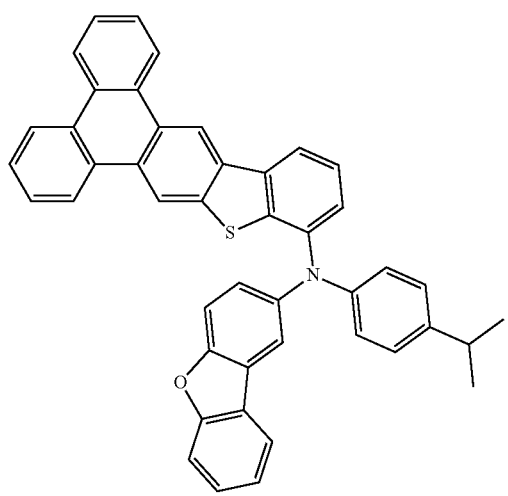
C178
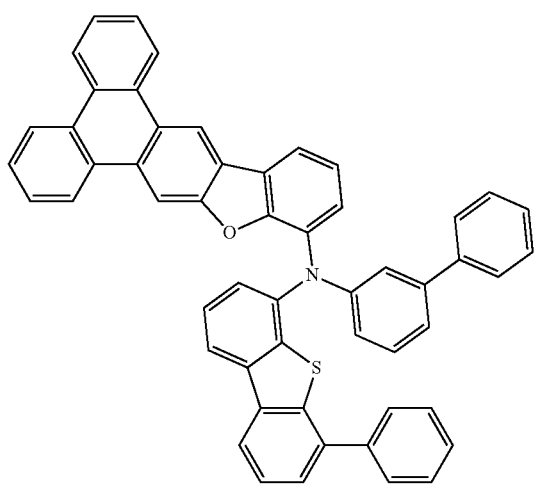
C179
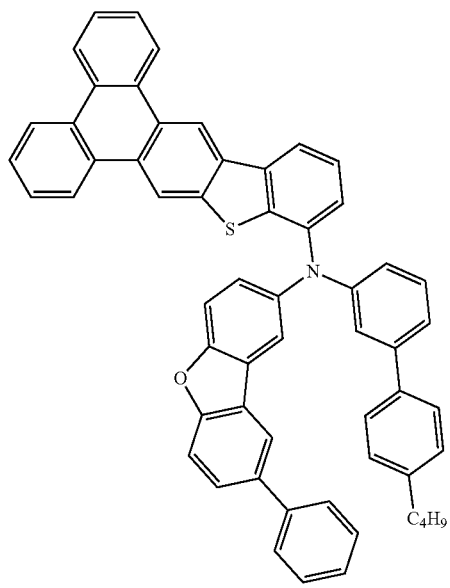
C180
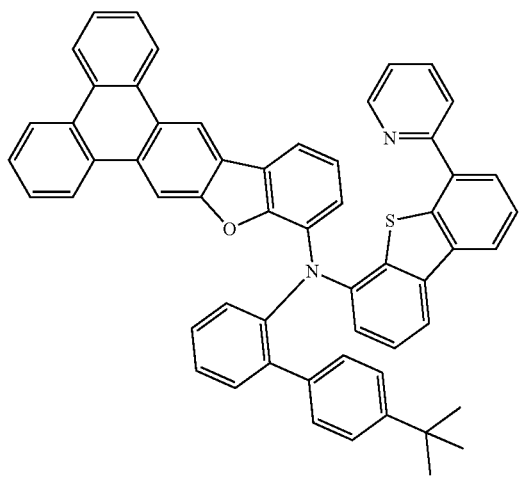
C181

-continued
C182
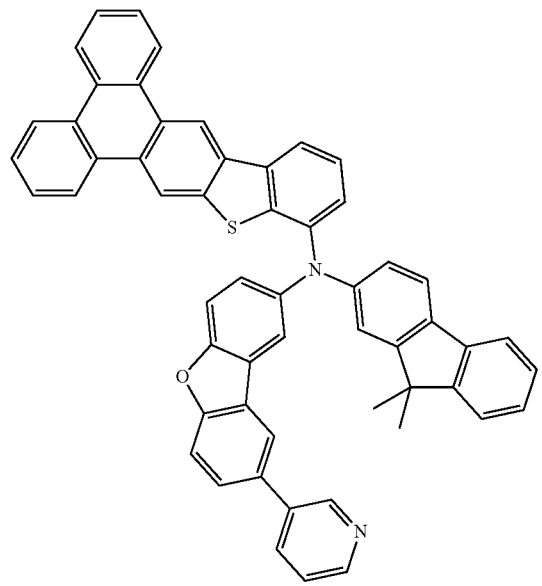
C183
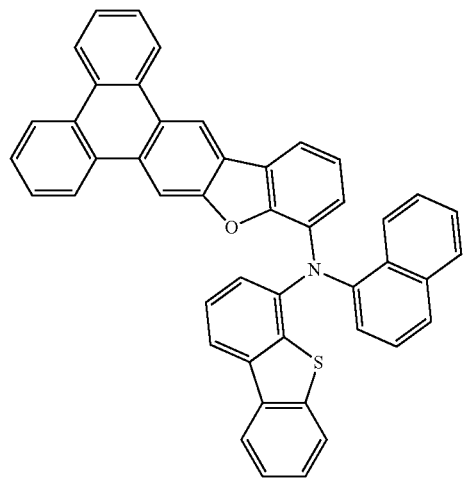
C184
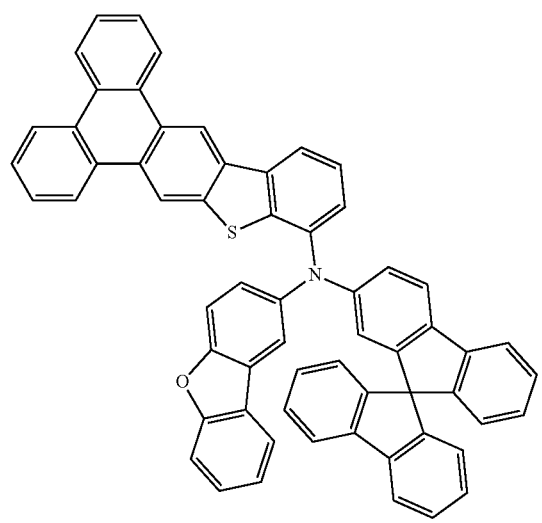
C185

-continued
C186
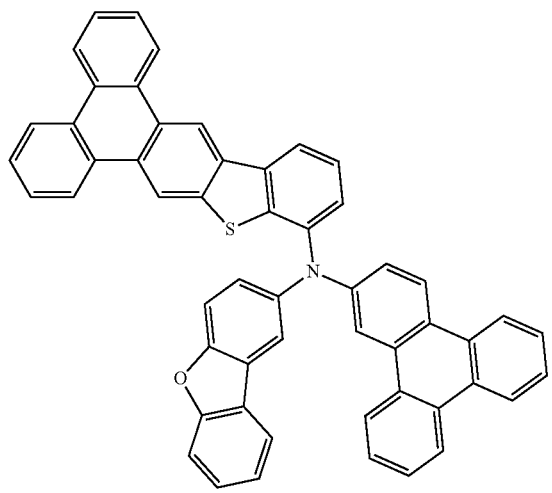
C187
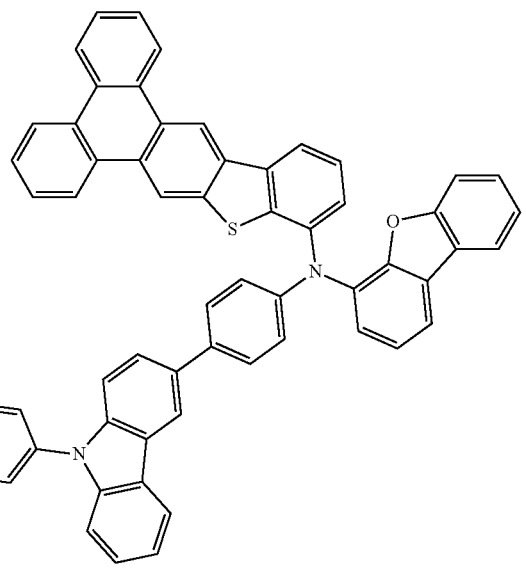
C188
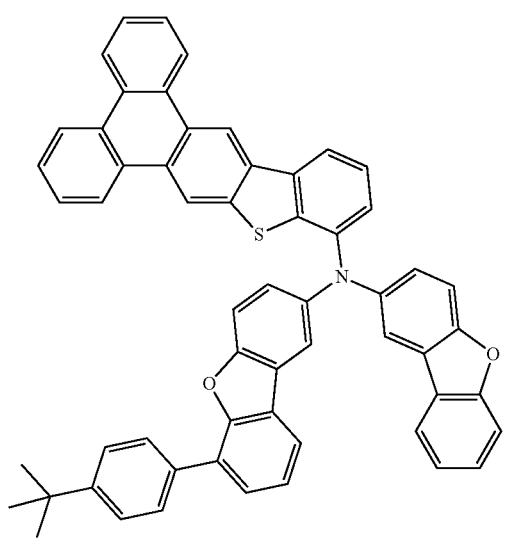
C189
C190
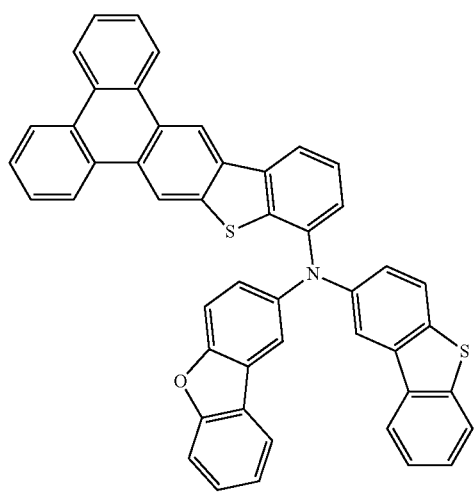
C191
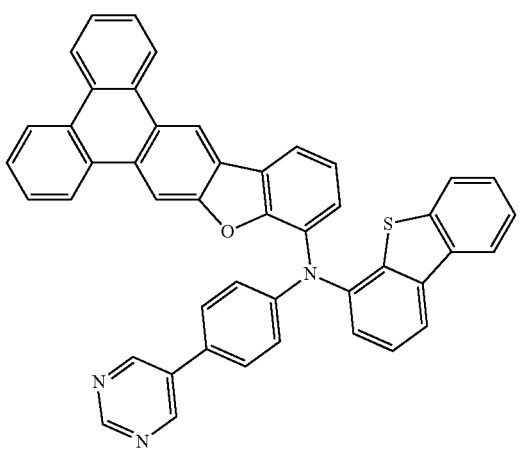

C192

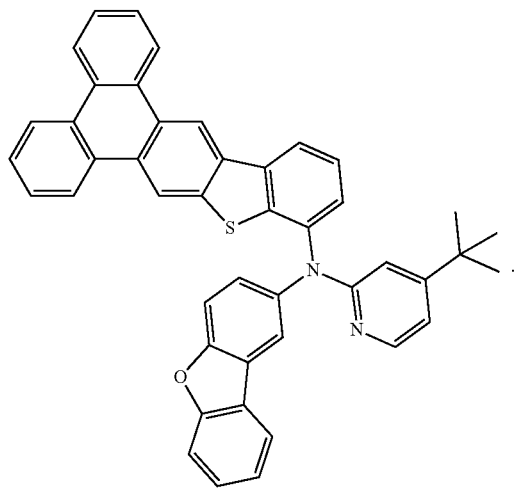

In another embodiment of the present invention, an organic electroluminescence device is disclosed. The organic electroluminescence device comprises a pair of electrodes composed of a cathode and an anode, and a light emitting layer and one or more organic thin film layers between the pair of electrodes. In particular, at least one of the light emitting layer and the organic thin film layer comprises the indenotriphenylene-based amine derivative of formula (1).

In some embodiments, the light emitting layer comprising the indenotriphenylene-based amine derivative of formula (1) is a dopant material. In certain embodiments, the organic thin film layer comprising the indenotriphenylene-based amine derivative of formula (1) is a hole transporting layer. In some embodiments, the organic thin film layer comprising the indenotriphenylene-based amine derivative of formula (1) is an electron blocking layer.

In a further embodiment of the present invention, the organic electroluminescence device is a lighting panel. In other embodiment of the present invention, the organic electroluminescence device is a backlight panel.

Detailed preparation of the organic compounds of the present invention will be clarified by exemplary embodiments below, but the present invention is not limited thereto. EXAMPLES 1 to 16 show the preparation of the organic compounds of the present invention, and EXAMPLE 17 shows the fabrication and test reports of the organic EL devices.

Example 1

Synthesis of C1

Synthesis of Intermediate A

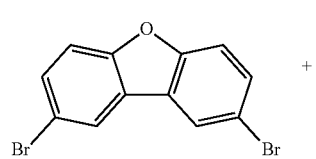

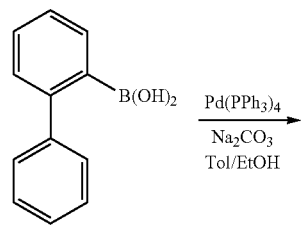

Intermediate A

A mixture of 32.6 g (100 mmol) of 2,8-dibenzofuran, 21.8 g (110 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml of toluene was degassed and placed under nitrogen, and then heated at 100° C. for 12 h. After the reaction finished, the mixture was allowed to cool to room temperature. The organic layer was extracted with ethyl acetate and water, and then dried with anhydrous magnesium sulfate. The solvent was removed and the residue was purified by column chromatography on silica to give Intermediate A (24 g, 60%) as a white solid.

Synthesis of Intermediate B

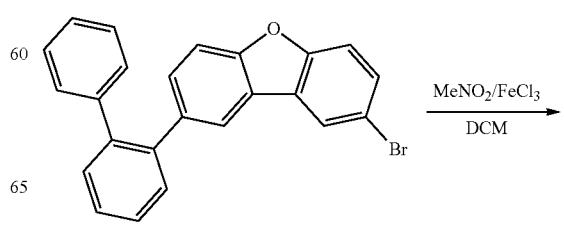

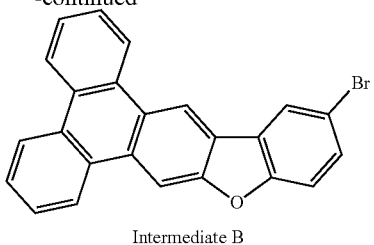

Intermediate B

In a 3000 ml three-necked flask that had been degassed and filled with nitrogen, 24 g (60 mmol) of Intermediate A was dissolved in anhydrous dichloromethane (1500 ml), and then 89.6 g (300 mmol) of Iron(III) chloride and 120 ml of Nitromethane was added. The mixture was stirred for one hour, and then 500 ml of Methanol was added to the mixture. The organic layer was separated and then the solvent was removed in vacuo. The residue was purified by column chromatography on silica (hexane-dichloromethane) to afford a white solid as Intermediate B (10.7 g, 25.3 mmol, 40%).

Synthesis of C1

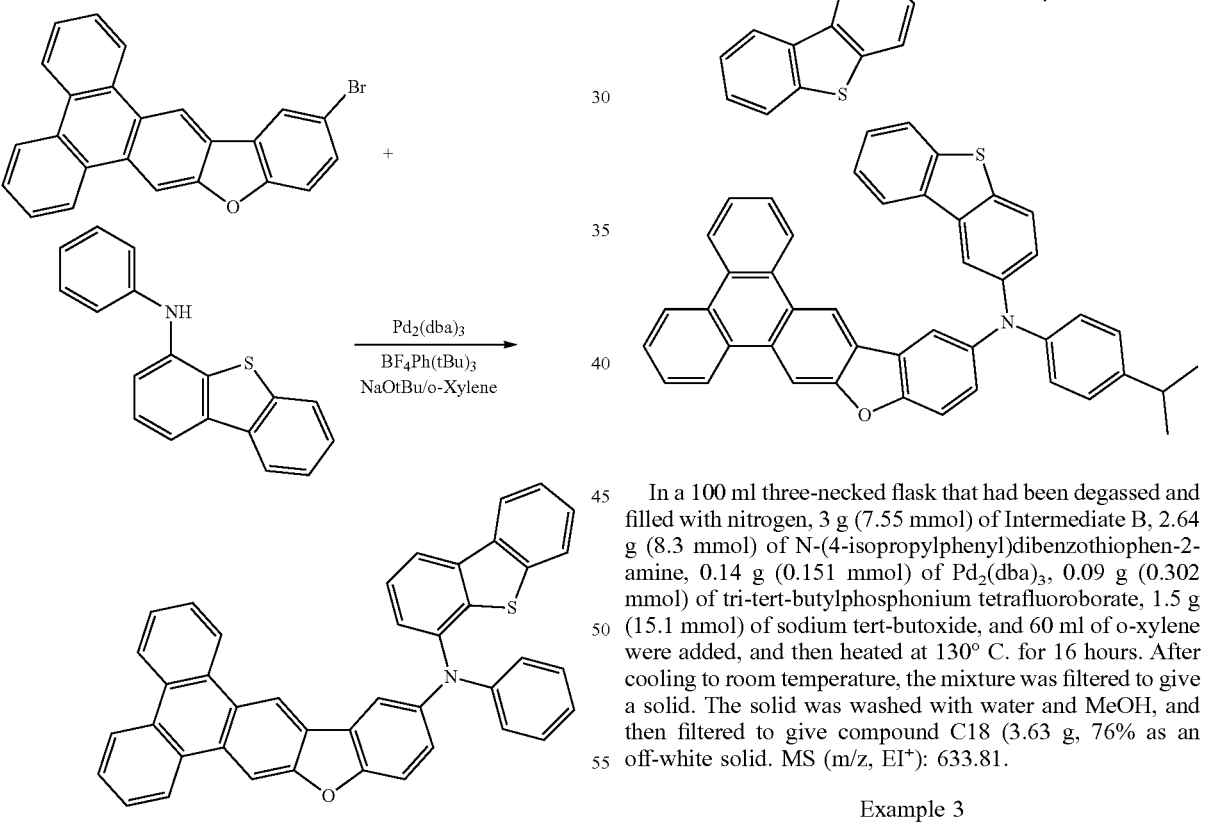

In a 100 ml three-necked flask that had been degassed and filled with nitrogen, 3 g (7.55 mmol) of Intermediate B, 2.3 g (8.3 mmol) of N-phenyldibenzothiophen-4-amine, 0.14 g (0.151 mmol) of $Pd_2(dba)_3$, 0.09 g (0.302 mmol) of tri-tert-butylphosphonium tetrafluoroborate, 1.5 g (15.1 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C1 (3.48 g, 78%) as an off-white solid. MS (m/z, EI+): 591.73.

Example 2

Synthesis of C18
Synthesis of C18

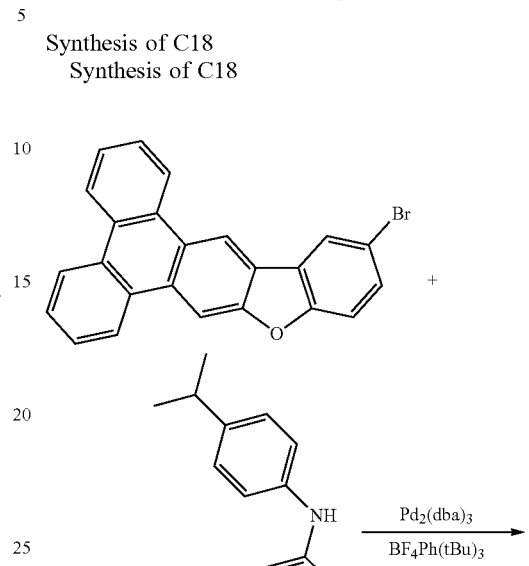

In a 100 ml three-necked flask that had been degassed and filled with nitrogen, 3 g (7.55 mmol) of Intermediate B, 2.64 g (8.3 mmol) of N-(4-isopropylphenyl)dibenzothiophen-2-amine, 0.14 g (0.151 mmol) of $Pd_2(dba)_3$, 0.09 g (0.302 mmol) of tri-tert-butylphosphonium tetrafluoroborate, 1.5 g (15.1 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C18 (3.63 g, 76% as an off-white solid. MS (m/z, EI+): 633.81.

Example 3

Synthesis of C167
Synthesis of Intermediate C

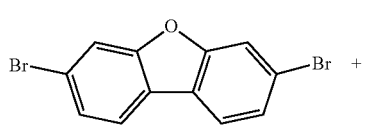

Synthesis of C167

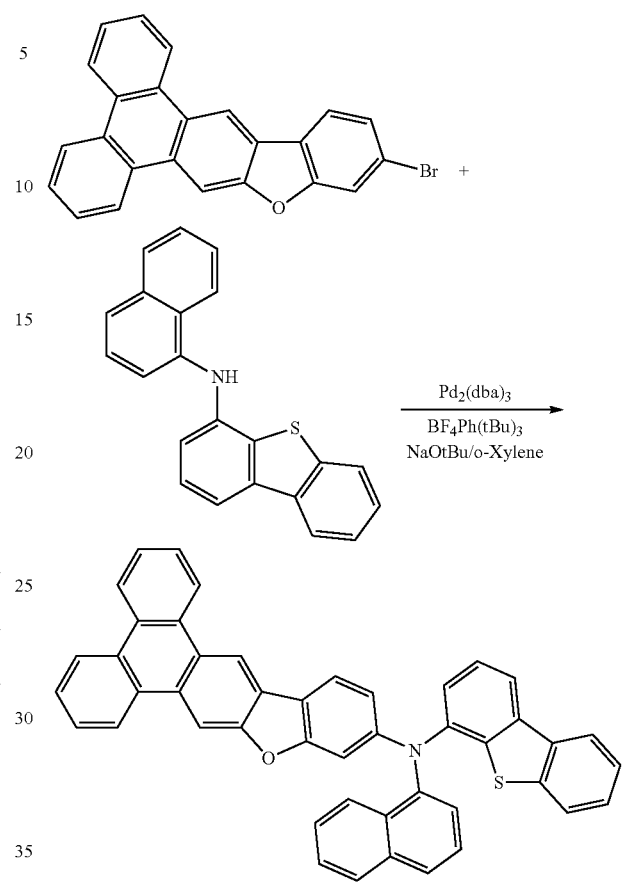

-continued

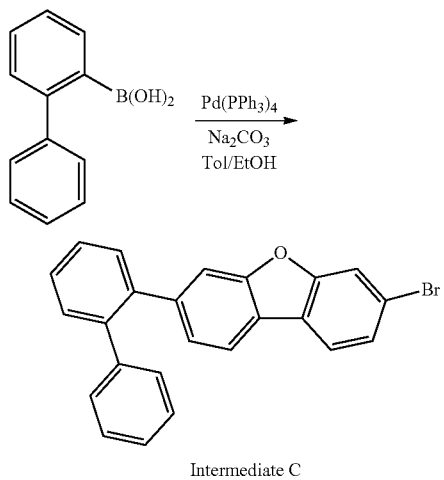

Intermediate C

A mixture of 32.6 g (100 mmol) of 3,7-dibenzofuran, 21.8 g (110 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml of toluene was degassed and placed under nitrogen, and then heated at 100° C. for 12 h. After the reaction finished, the mixture was allowed to cool to room temperature. The organic layer was extracted with ethyl acetate and water, and then dried with anhydrous magnesium sulfate. The solvent was removed and the residue was purified by column chromatography on silica to give Intermediate C (26.8 g, 67%) as a white solid.

Synthesis of Intermediate D

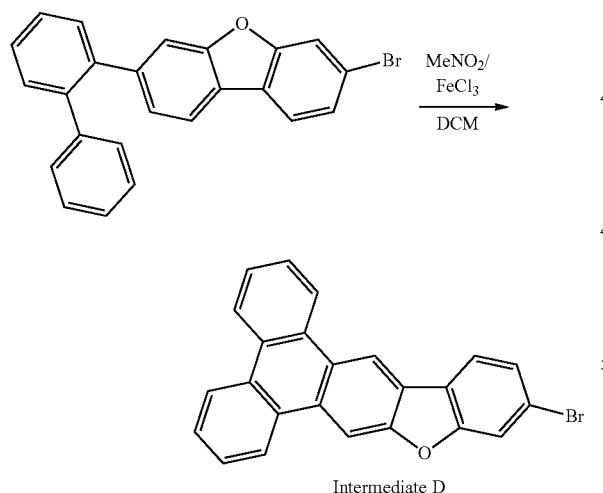

Intermediate D

In a 3000 ml three-necked flask that had been degassed and filled with nitrogen, 24 g (60 mmol) of Intermediate C was dissolved in anhydrous dichloromethane (1500 ml), and then 89.6 g (300 mmol) of Iron(III) chloride and 120 ml of Nitromethane were added. The mixture was stirred for one hour, and then 500 ml of Methanol was added to the mixture. The organic layer was separated and then the solvent was removed in vacuo. The residue was purified by column chromatography on silica (hexane-dichloromethane) to afford a white solid as Intermediate D (12 g, 45%).

In a 100 ml three-necked flask that had been degassed and filled with nitrogen, 3 g (7.55 mmol) of Intermediate D, 2.7 g (8.3 mmol) of N-(naphthalene-1-yl)dibenzothiophen-4-amine, 0.14 g (0.151 mmol) of Pd$_2$(dba)$_3$, 0.09 g (0.302 mmol) of tri-tert-butylphosphonium tetrafluoroborate, 1.5 g (15.1 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C167 (3.58 g, 74%) as an off-white solid. MS (m/z, EI$^+$): 641.79.

Example 4

Synthesis of C170
Synthesis of Intermediate E

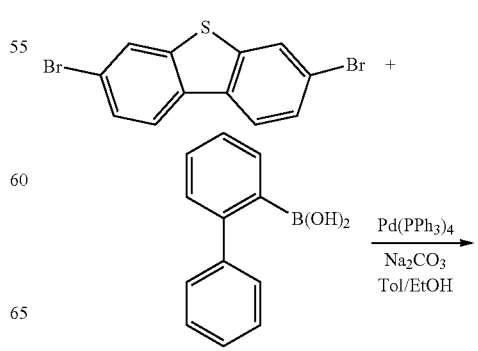

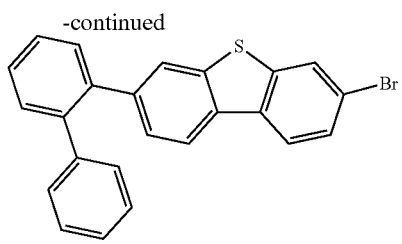

Intermediate E

A mixture of 32.6 g (95.3 mmol) of 3,7-dibromodibenzo[b,d]thiophene, 20.8 g (104.8 mmol) of biphenyl-2-ylboronic acid, 2.31 g (1.9 mmol) of Pd(PPh$_3$)$_4$, 75 ml of 2M Na$_2$CO$_3$, 150 ml of EtOH and 300 ml of toluene was degassed and placed under nitrogen, and then heated at 100° C. for 12 h. After the reaction finished, the mixture was allowed to cool to room temperature. The organic layer was extracted with ethyl acetate and water, and then dried with anhydrous magnesium sulfate. The solvent was removed and the residue was purified by column chromatography on silica to give Intermediate E (26.5 g, 67%) as a white solid.

Synthesis of Intermediate F

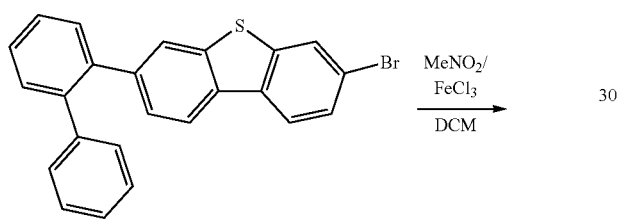

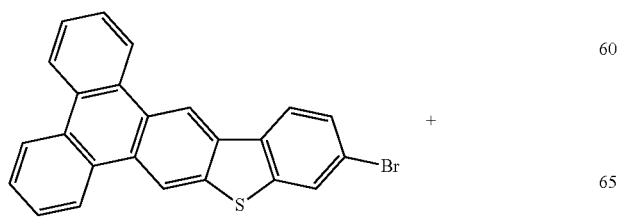

Intermediate F

In a 3000 ml three-necked flask that had been degassed and filled with nitrogen, 24 g (57.7 mmol) of Intermediate E was dissolved in anhydrous dichloromethane (1500 ml), and then 86.3 g (289 mmol) of Iron (III) chloride and 120 ml of Nitromethane were added. The mixture was stirred for one hour, and then 500 ml of Methanol was added to the mixture. The organic layer was separated and then the solvent was removed in vacuo. The residue was purified by column chromatography on silica (hexane-dichloromethane) to afford a white solid as Intermediate F (10.3 g, 43%).

Synthesis of C170

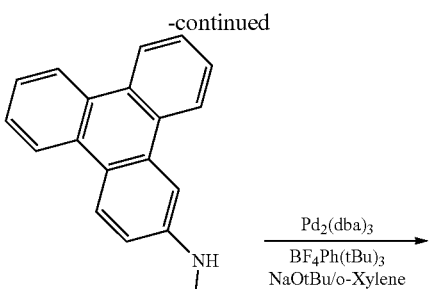

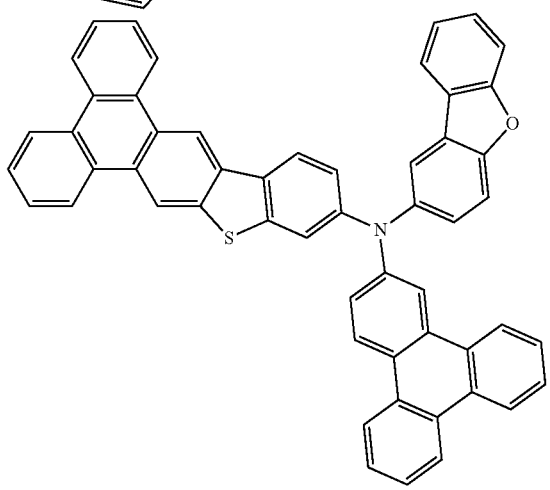

In a 100 ml three-necked flask that had been degassed and filled with nitrogen, 3 g (7.26 mmol) of Intermediate F, 3.3 g (7.99 mmol) of N-(triphenylene-2-yl)dibenzofuran-2-amine, 0.14 g (0.145 mmol) of Pd$_2$(dba)$_3$, 0.09 g (0.29 mmol) of tri-tert-butylphosphonium tetrafluoroborate, 1.4 g (14.25 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C170 (3.87 g, 72%) as an off-white solid. MS (m/z, EI$^+$): 741.91.

Example 5

Synthesis of C184

Synthesis of Intermediate G

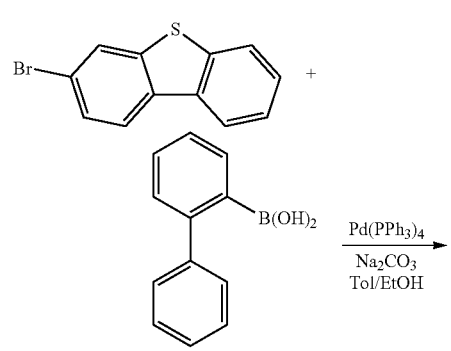

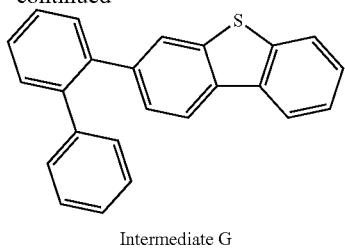

Intermediate G

The same synthesis procedure as in Synthesis of Intermediate E was used, except that 32.6 g of 3-bromodibenzo[b,d]thiophene was used instead of 3,7-dibromodibenzo[b,d]thiophene to obtain the desired Intermediate G (31.26 g, 75%).

Synthesis of Intermediate H

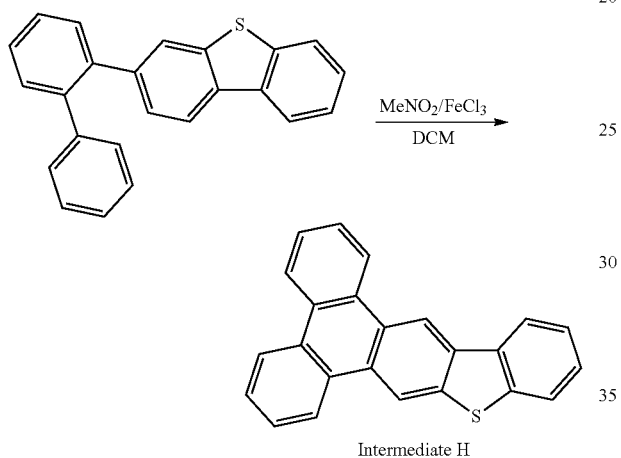

Intermediate H

The same synthesis procedure as in Synthesis of Intermediate F was used, except that 31.26 g of Intermediate G was used instead of Intermediate E to obtain the desired Intermediate H (15.5 g, 50%).

Synthesis of Intermediate I

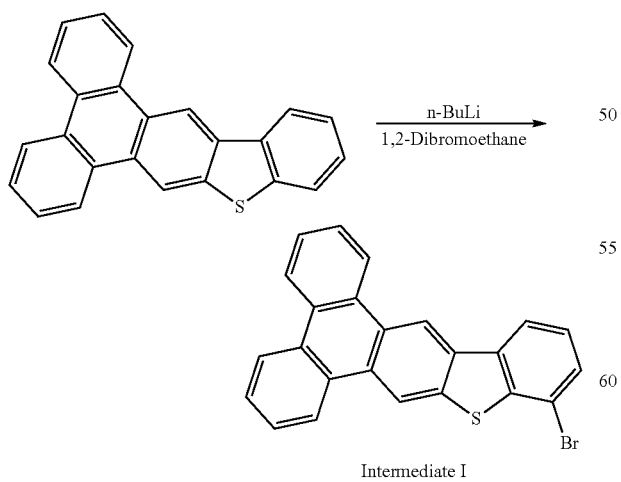

Intermediate I

In a 500 ml three-necked flask that had been degassed and filled with nitrogen, 15 g (44.85 mmol) of Intermediate H and 300 ml of THF were added, and then cooled to −68° C., and 21.5 ml (53.82 mmol) of 2.5M n-BuLi was slowly dripped. After keeping at −68° C. and stirring for 1 hr, 12.63 g (67.27 mmol) of 1,2-Dibromoethane was slowly dripped, and then warmed to room temperature for 16 hrs. Afterwards, 100 ml of $H_2O$ was added to the mixture, and then the organic layer was separated and the solvent was removed in vacuo. The residue was purified by column chromatography on silica (hexane-dichloromethane) to afford a white solid as Intermediate I (14.45 g, 78%).

Synthesis of C184

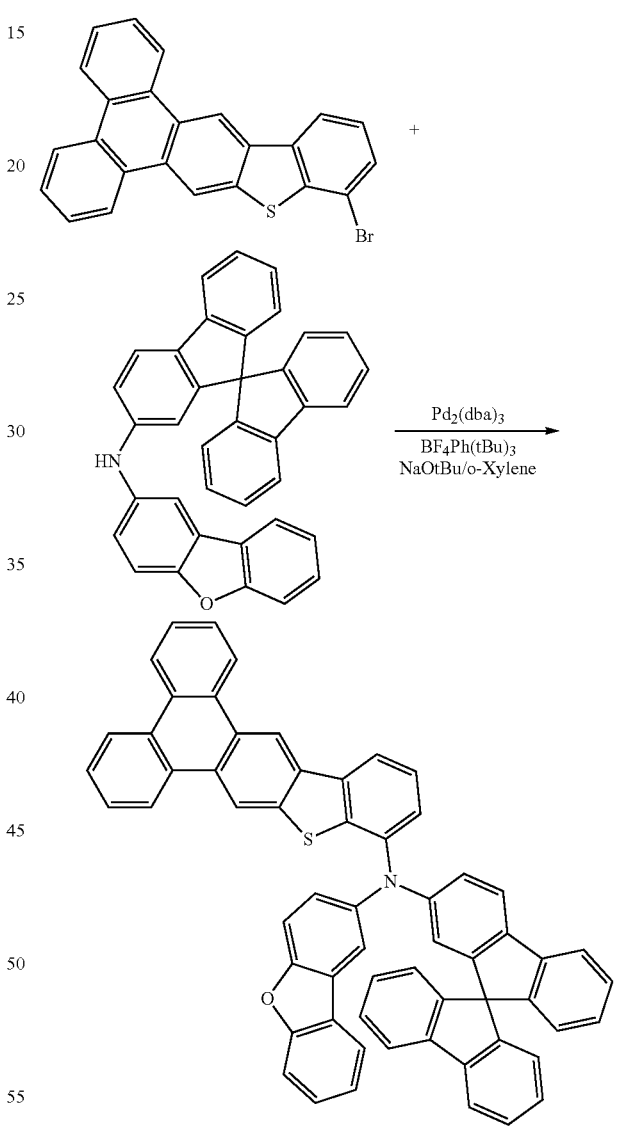

In a 100 ml three-necked flask that had been degassed and filled with nitrogen, 3 g (7.26 mmol) of Intermediate I, 4 g (7.99 mmol) of N-(9,9'''-spirobi[fluoren]-2-yl)dibenzofuran-2-amine, 0.14 g (0.145 mmol) of $Pd_2(dba)_3$, 0.09 g (0.29 mmol) of tri-tert-butylphosphonium tetrafluoroborate, 1.4 g (14.25 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C184 (4.33 g, 72%) as an off-white solid. MS (m/z, EI⁺): 830.02.

Example 6

Synthesis of C187

Synthesis of C187

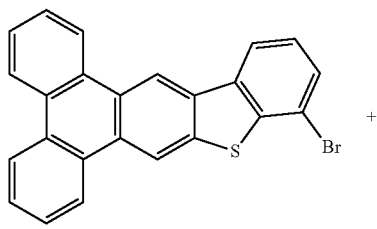

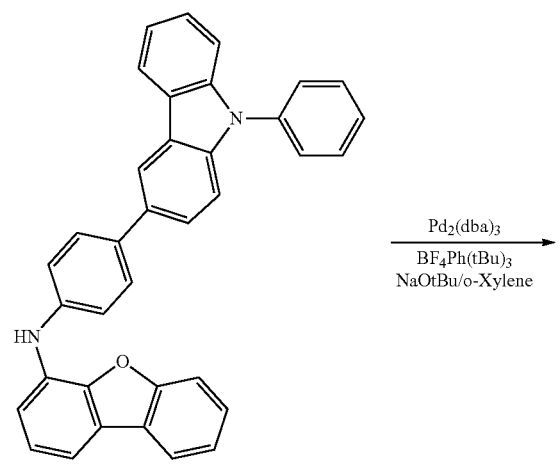

In a 100 ml three-necked flask that had been degassed and filled with nitrogen, 3 g (7.26 mmol) of Intermediate I, 4 g (7.99 mmol) of N-(4-(9-phenyl-9H-carbazol-3-yl)phenyl) dibenzofuran-4-amine, 0.14 g (0.145 mmol) of Pd₂(dba)₃, 0.09 g (0.29 mmol) of tri-tert-butylphosphonium tetrafluoroborate, 1.4 g (14.25 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C187 (4.17 g, 69%) as an off-white solid. MS (m/z, EI⁺): 833.02.

Example 7

Synthesis of C110

Synthesis of Intermediate J

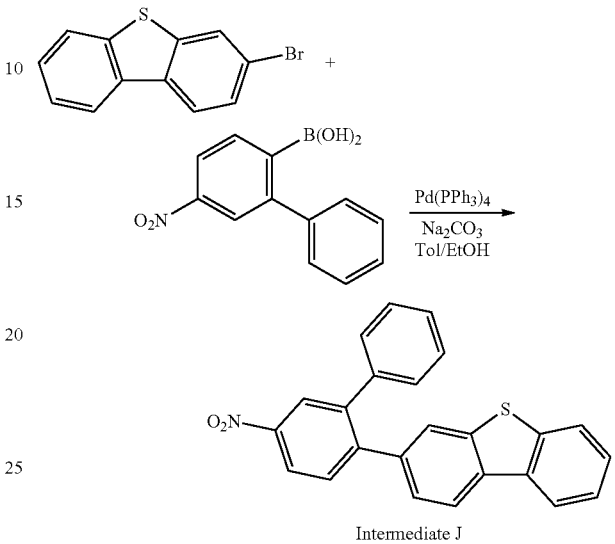

Intermediate J

The same synthesis procedure as in Synthesis of Intermediate G was used, except that 33.12 g of (5-nitro-[1,1'-biphenyl]-2-yl) boronic acid was used instead of biphenyl-2-ylboronic acid to obtain the desired Intermediate J (33 g, 70%).

Synthesis of Intermediate K

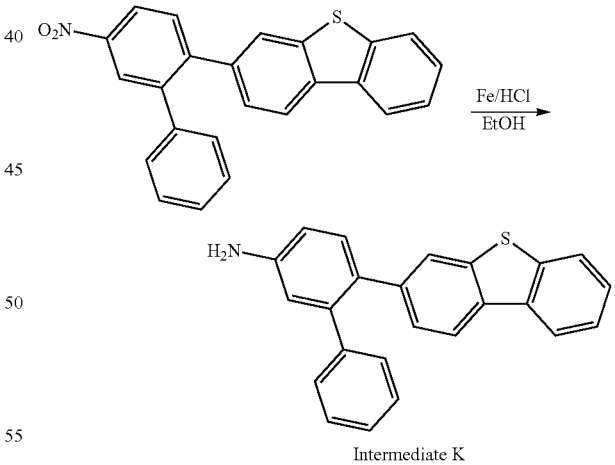

Intermediate K

A mixture of 33 g (86.61 mmol) of Intermediate J, 29 g (519.66 mmol) of iron powder and 33 ml of conc. HCl was refluxed in aqueous ethanol (330 mL of alcohol and 110 mL of water) at 85° C. for 2 h. The reaction mixture was filtered and then the filtrate was extracted with ethyl acetate and water. The organic layer was dried with anhydrous magnesium sulfate and the solvent was evaporated under reduced pressure. The resulting solid was washed with hexane to yield 26.75 g of Intermediate K (88%).

Synthesis of Intermediate L

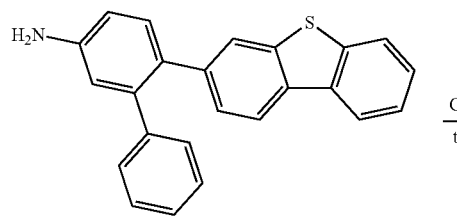

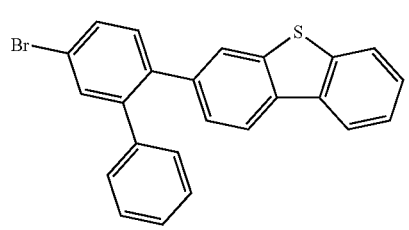

Intermediate L

To a refluxing mixture of 9.41 g (91.32 mmol) of tert-butyl nitrite, 4.26 g (76.1 mmol) of anhydrous copper (II) bromide and 46 mL of anhydrous acetonitrile, 26.75 g (76.1 mmol) of Intermediate K was added slowly over a period of 1 h, giving rise to a reaction with vigorous foaming and evolution of nitrogen gas. After completion of the reaction, the mixture was cooled to room temperature and poured into an aqueous HCl solution. The crude precipitate was purified by column chromatography on silica to give 9.48 g of Intermediate L (25%).

Synthesis of Intermediate M

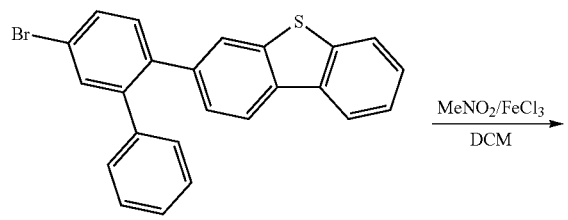

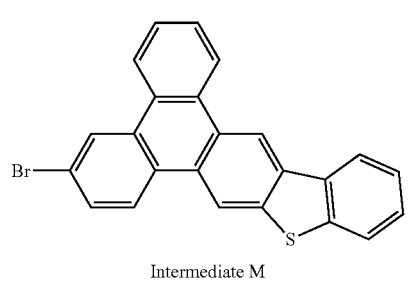

Intermediate M

The same synthesis procedure as in Synthesis of Intermediate H was used, except that 9.48 g of Intermediate L was used instead of Intermediate G to obtain the desired Intermediate M (5.28 g, 56%).

Synthesis of C110

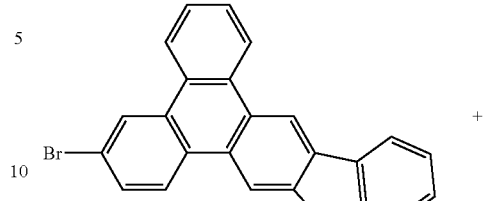

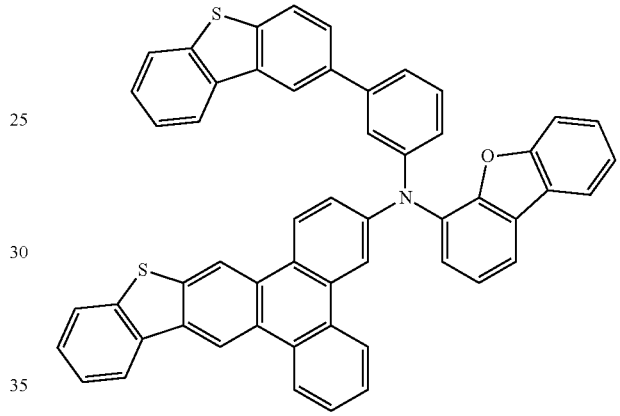

In a 100 ml three-necked flask that had been degassed and filled with nitrogen, 3 g (7.26 mmol) of Intermediate M, 3.52 g (7.99 mmol) of N-(3-(dibenzothiophene-2-yl)phenyl)dibenzofuran-4-amine, 0.14 g (0.145 mmol) of $Pd_2(dba)_3$, 0.09 g (0.29 mmol) of tri-tert-butylphosphonium tetrafluoroborate, 1.4 g (14.25 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C110 (3.42 g, 61%) as an off-white solid. MS (m/z, EI$^-$): 773.97.

Example 8

Synthesis of C115

Synthesis of C115

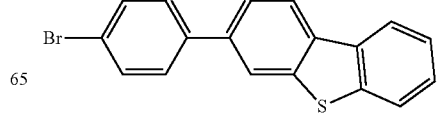

-continued

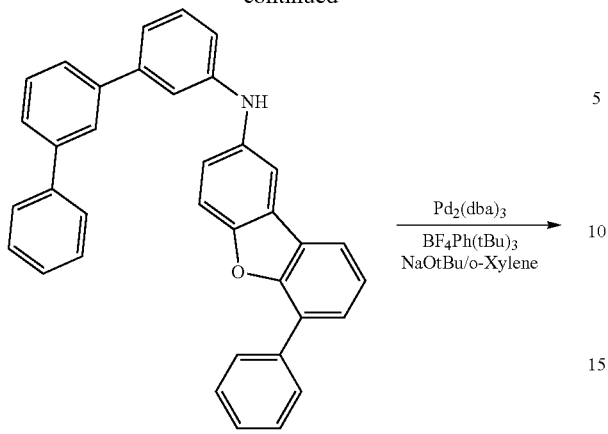

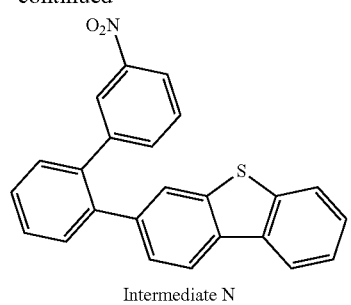

Intermediate N

The same synthesis procedure as in Synthesis of Intermediate J was used, except that 33.12 g of (3'-nitro-[1,1'-biphenyl]-2-yl) boronic acid was used instead of (5-nitro-[1,1'-biphenyl]-2-yl) boronic acid to obtain the desired Intermediate N (33.94 g, 72%).

Synthesis of Intermediate O

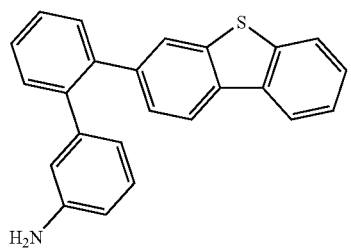

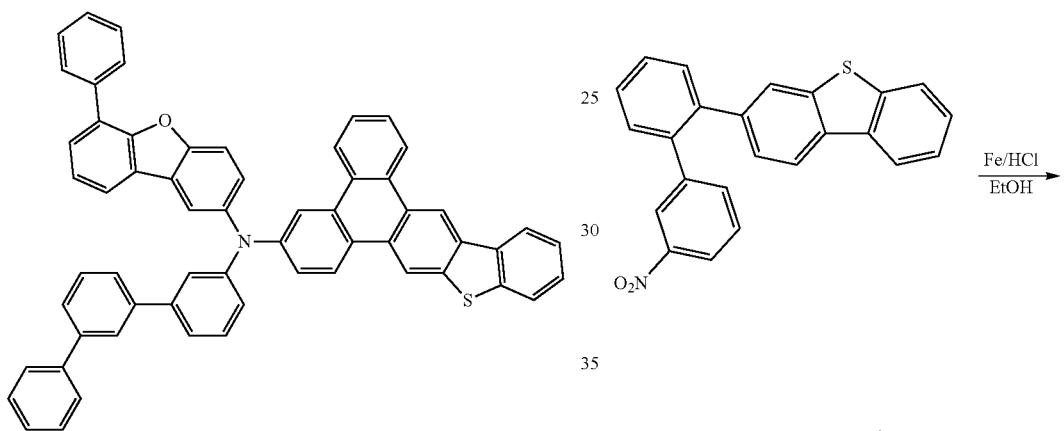

The same synthesis procedure as in Synthesis of C110 was used, except that 3.9 g of N-([1,1':3',1''-terphenyl]-3-yl)-6-phenyldibenzofuran-2-amine was used instead of N-(3-(dibenzothiophene-2-yl)phenyl)dibenzofuran-4-amine to obtain the desired compound C115 (3.69 g, 62%). MS (m/z, EI$^+$): 820.02.

Intermediate O

The same synthesis procedure as in Synthesis of Intermediate K was used, except that 33.94 g of Intermediate N was used instead of Intermediate J to obtain the desired Intermediate O (26.58 g, 85%).

Synthesis of Intermediate P

Example 9

Synthesis of C149

Synthesis of Intermediate N

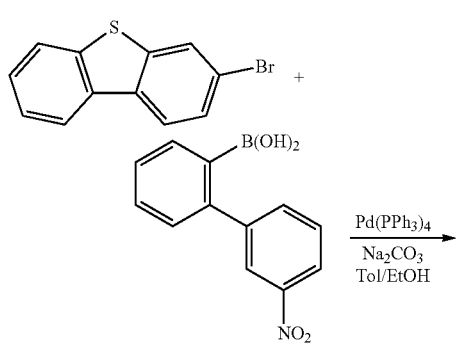

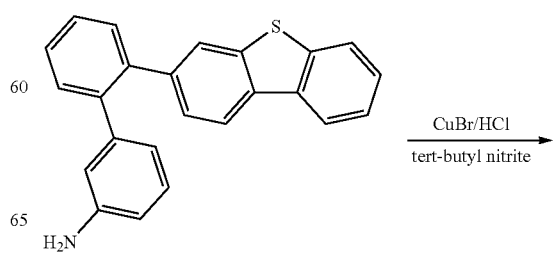

-continued

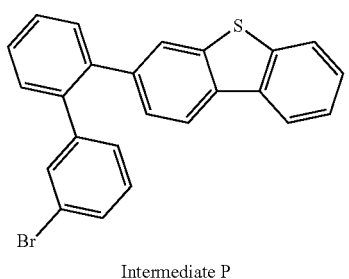
Intermediate P

The same synthesis procedure as in Synthesis of Intermediate L was used, except that 26.58 g of Intermediate O was used instead of Intermediate K to obtain the desired Intermediate P (9.4 g, 30%).

Synthesis of Intermediate Q

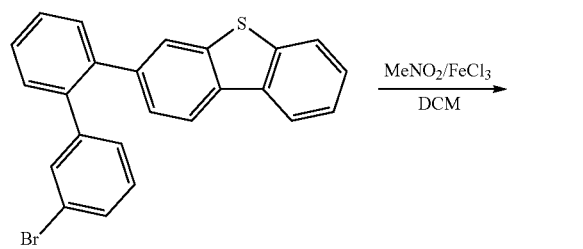

Intermediate Q

The same synthesis procedure as in Synthesis of Intermediate M was used, except that 9.4 g of Intermediate P was used instead of Intermediate L to obtain the desired Intermediate Q (5.61 g, 60%).

Synthesis of C149

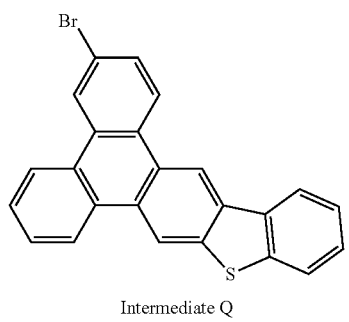

-continued

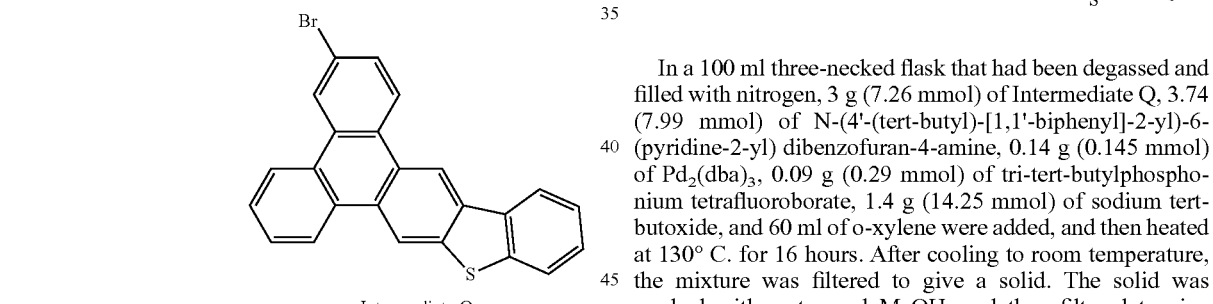

In a 100 ml three-necked flask that had been degassed and filled with nitrogen, 3 g (7.26 mmol) of Intermediate Q, 3.74 (7.99 mmol) of N-(4'-(tert-butyl)-[1,1'-biphenyl]-2-yl)-6-(pyridine-2-yl) dibenzofuran-4-amine, 0.14 g (0.145 mmol) of $Pd_2(dba)_3$, 0.09 g (0.29 mmol) of tri-tert-butylphosphonium tetrafluoroborate, 1.4 g (14.25 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C149 (3.42 g, 61%) as an off-white solid. MS (m/z, EI⁺): 801.02.

Example 10

Synthesis of C154
Synthesis of C154

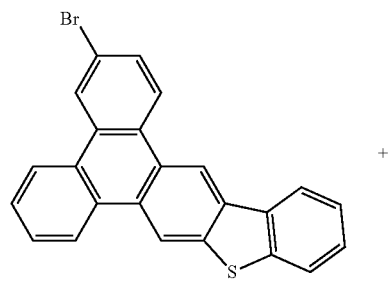 +  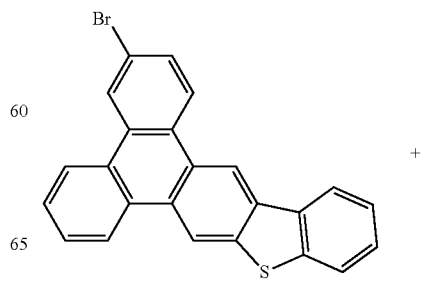 +

117
-continued

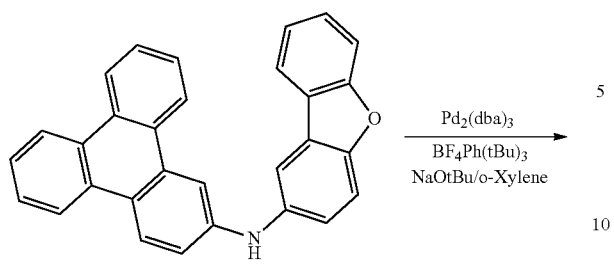

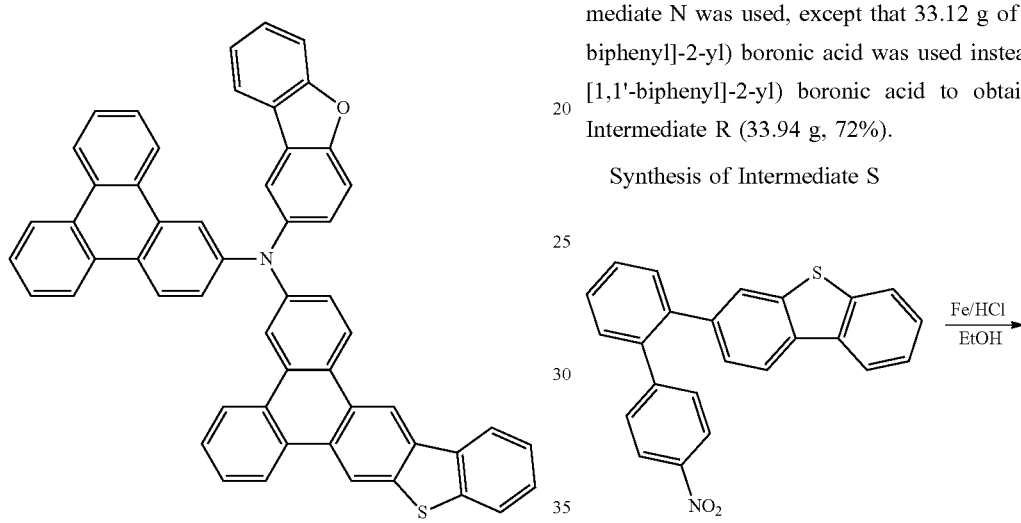

The same synthesis procedure as in Synthesis of C149 was used, except that 3.27 g of N-(triphenylene-2-yl)dibenzofuran-2-amine was used instead of N-(4'-(tert-butyl)-[1,1'-biphenyl]-2-yl)-6-(pyridine-2-yl)dibenzo-furan-4-amine to obtain the desired C154 (3.82 g, 71%). MS (m/z, EI⁺): 741.91.

Example 11

Synthesis of C157

Synthesis of Intermediate R

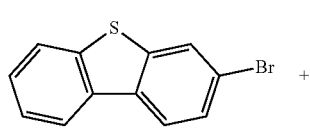

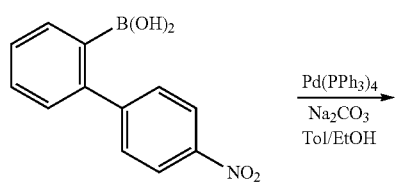

118
-continued

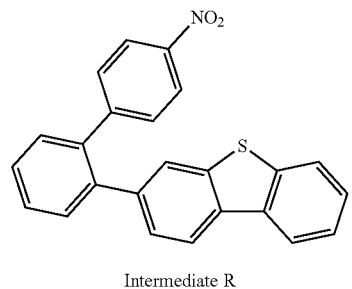

Intermediate R

The same synthesis procedure as in Synthesis of Intermediate N was used, except that 33.12 g of (4'-nitro-[1,1'-biphenyl]-2-yl) boronic acid was used instead of (3'-nitro-[1,1'-biphenyl]-2-yl) boronic acid to obtain the desired Intermediate R (33.94 g, 72%).

Synthesis of Intermediate S

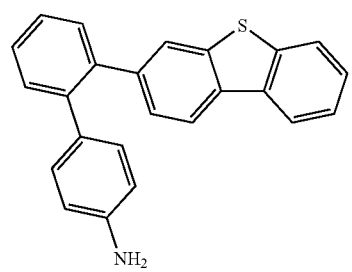

Intermediate S

The same synthesis procedure as in Synthesis of Intermediate O was used, except that 33.94 g of Intermediate R was used instead of Intermediate N to obtain the desired Intermediate S (26.58 g, 85%).

Synthesis of Intermediate T

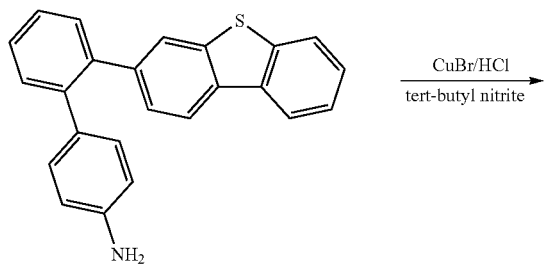

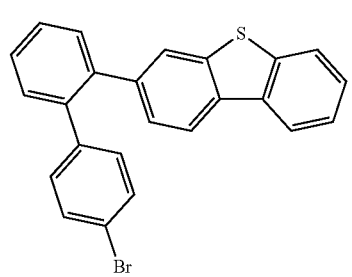

Intermediate T

The same synthesis procedure as in Synthesis of Intermediate P was used, except that 26.58 g of Intermediate S was used instead of Intermediate O to obtain the desired Intermediate T (11 g, 35%).

Synthesis of Intermediate U

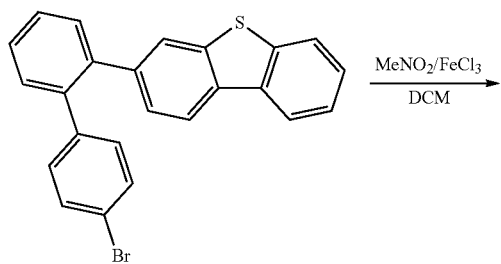

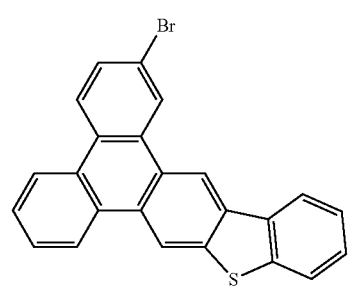

Intermediate U

The same synthesis procedure as in Synthesis of Intermediate Q was used, except that 9.4 g of Intermediate T was used instead of Intermediate P to obtain the desired Intermediate U (5.14 g, 55%).

Synthesis of C157

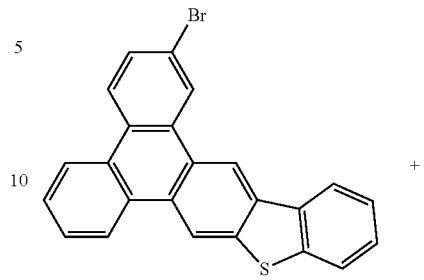

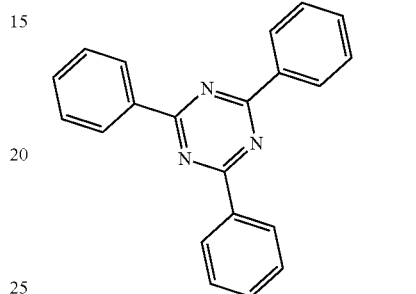

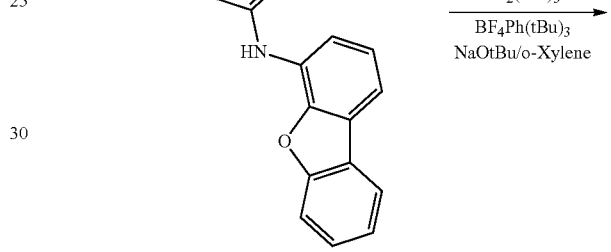

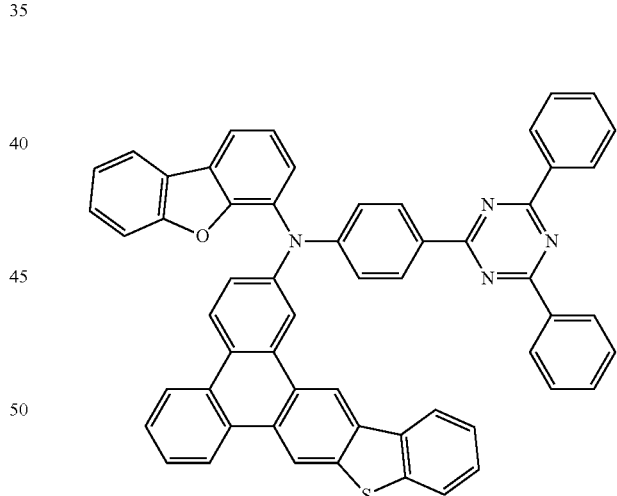

In a 100 ml three-necked flask that had been degassed and filled with nitrogen, 3 g (7.26 mmol) of Intermediate U, 3.91 g (7.99 mmol) of N-(4-(4,6-diphenyl-1,3,5-triazin-2-yl)phenyl)-2-yl)dibenzofuran-4-amine, 0.14 g (0.145 mmol) of Pd$_2$(dba)$_3$, 0.09 g (0.29 mmol) of tri-tert-butylphosphonium tetrafluoroborate, 1.4 g (14.25 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C157 (3.52 g, 59%) as an off-white solid. MS (m/z, EI$^+$): 822.99.

Example 12

Synthesis of C158

Synthesis of C158

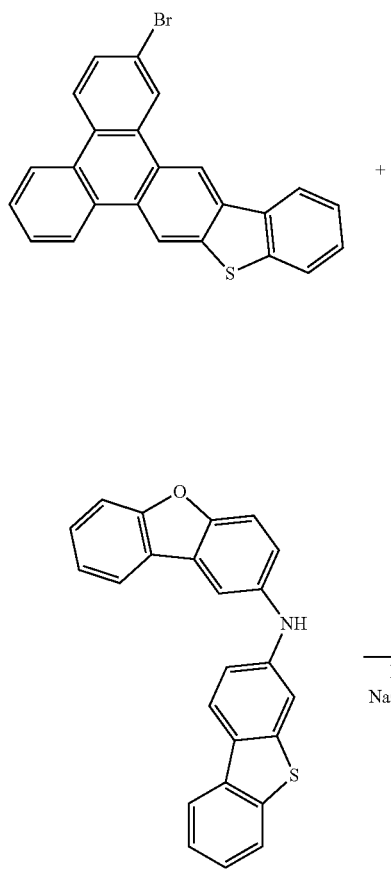

The same synthesis procedure as in Synthesis of C157 was used, except that 2.91 g of N-(dibenzothiophene-3-yl)dibenzofuran-2-amine was used instead of N-(4-(4,6-diphenyl-1,3,5-triazin-2-yl)phenyl)-2-yl)dibenzo-furan-4-amine to obtain the desired compound C158 (3.44 g, 68%). MS (m/z, EI$^+$): 697.87.

Example 13

Synthesis of C38

Synthesis of Intermediate V

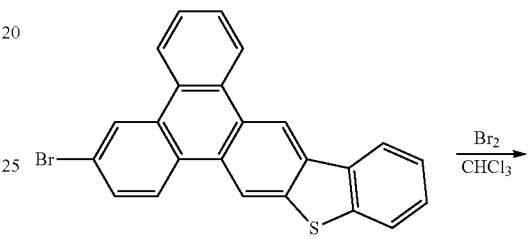

Intermediate V

In a 500 ml three-necked flask that had been degassed and filled with nitrogen, 10 g (24.2 mmol) of Intermediate M and 200 ml of CHCl$_3$ were added, and then allowed to cool at 0-10° C. Afterwards, 4.25 g (26.6 mmol) of Bromine was slowly dripped. After keeping at 0-10° C. and stirring for 1 hr, it was warmed to room temperature for 16 hrs. Subsequently, 100 ml of Na$_2$CO$_3$(aq) was added to the mixture, and then the organic layer was separated and the solvent was removed in vacuo. The residue was purified by column chromatography on silica (hexane-dichloromethane) to afford a white solid as Intermediate V (10.12 g, 85%).

Synthesis of C38
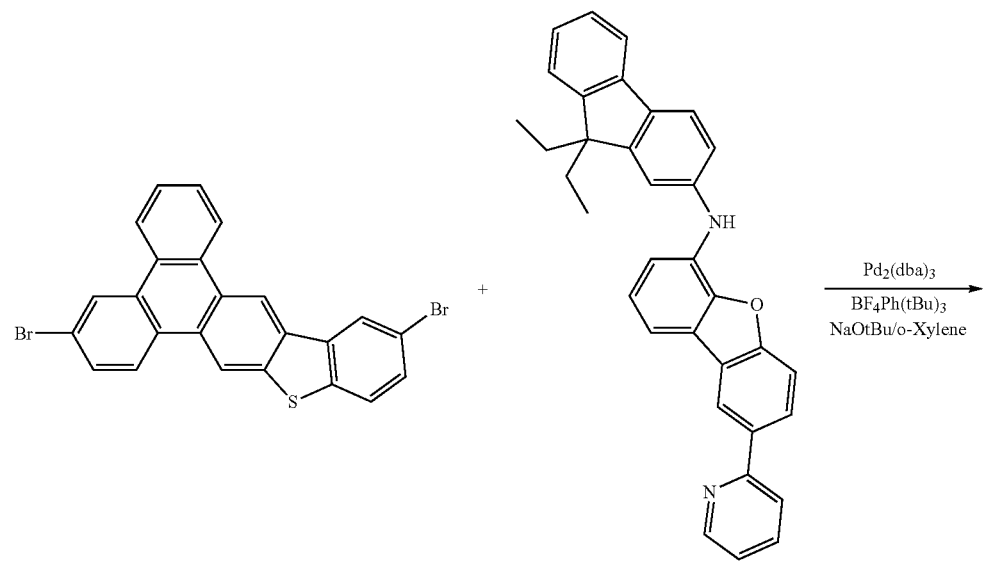
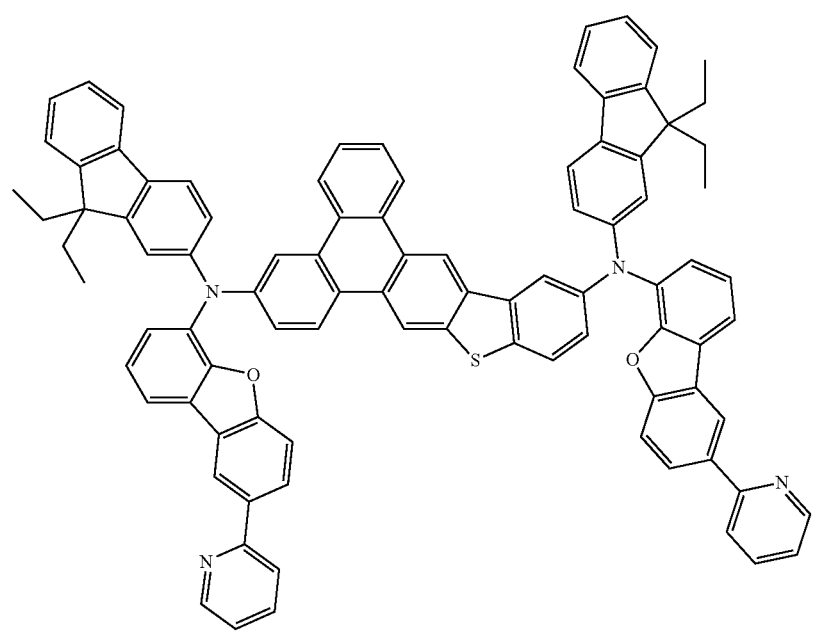

In a 100 ml three-necked flask that had been degassed and filled with nitrogen, 3 g (6.09 mmol) of Intermediate V, 7.32 g (15.23 mmol) of N-(9,9-diethyl-9H-fluoren-2-yl)-8-(pyridine-2-yl)dibenzofuran-4-amine, 0.17 g (0.183 mmol) of $Pd_2(dba)_3$, 0.11 g (0.36 mmol) of tri-tert-butylphosphonium tetrafluoroborate, 2.4 g (24.3 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C38 (5.27 g, 67%) as an off-white solid. MS (m/z, EI+): 1291.63.

Example 14

Synthesis of C51

Synthesis of C51

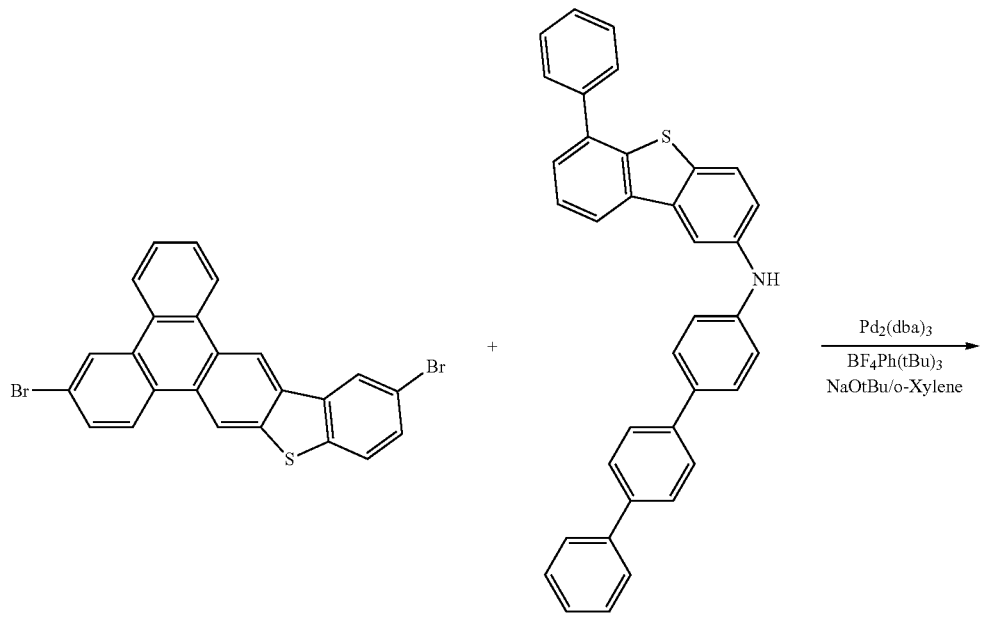

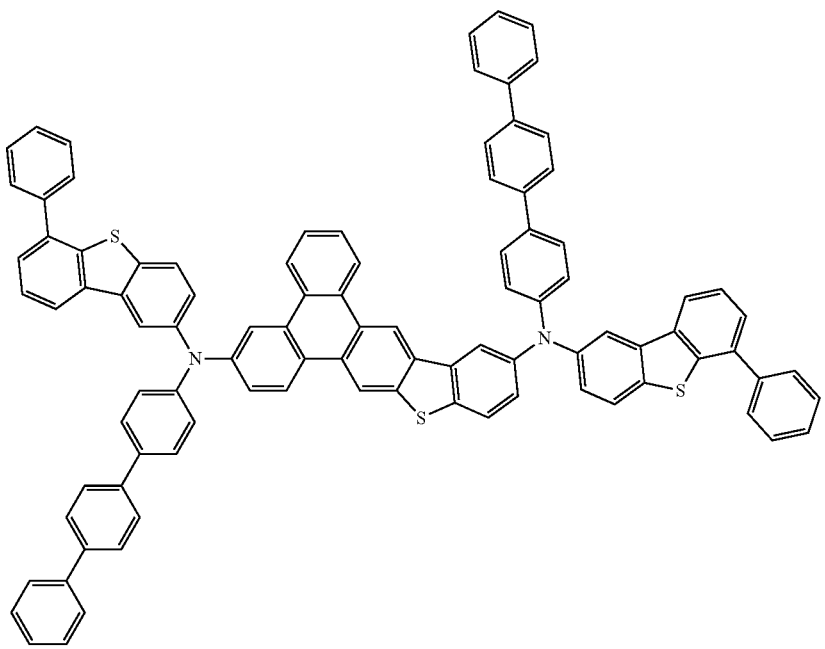

The same synthesis procedure as in Synthesis of C38 was used, except that 7.67 g of N-([1,1':4',1''-terphenyl]-4-yl)-6-phenyl dibenzofuran-2-amine was used instead of N-(9,9-diethyl-9H-fluoren-2-yl)-8-(pyridine-2-yl)dibenzofuran-4-amine to obtain the desired C51 (5.72 g, 71%). MS (m/z, EI$^+$): 1321.67.

Example 15

Synthesis of C139

Synthesis of Intermediate W

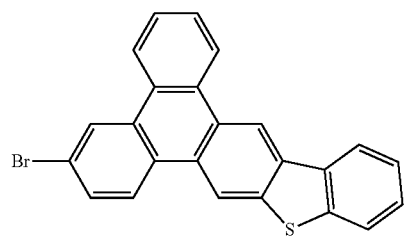

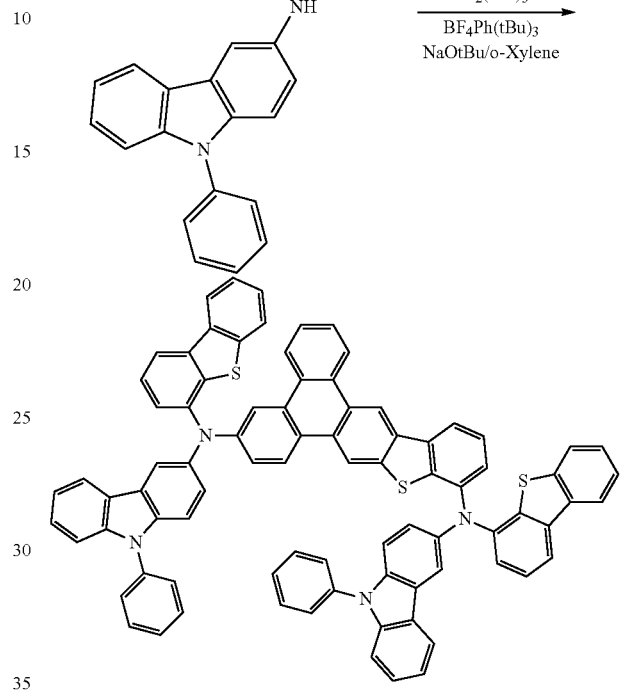

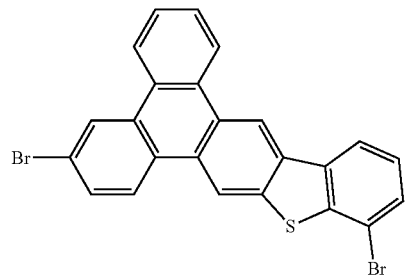

Intermediate W

The same synthesis procedure as in Synthesis of Intermediate I was used, except that 10 g of Intermediate M was used instead of Intermediate H to obtain the desired Intermediate W (7.14 g, 60%).

Synthesis of C139

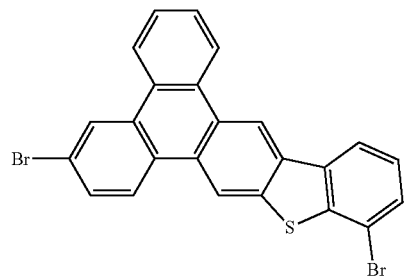

In a 100 ml three-necked flask that had been degassed and filled with nitrogen, 3 g (6.09 mmol) of Intermediate W, 6.71 g (15.23 mmol) of N-(dibenzothiophene-4-yl)-9-phenyl-9H-carbazol-3-amine, 0.17 g (0.183 mmol) of Pd$_2$(dba)$_3$, 0.11 g (0.36 mmol) of tri-tert-butylphosphonium tetrafluoroborate, 2.4 g (24.3 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C139 (5.02 g, 68%) as an off-white solid. MS (m/z, EI$^+$): 1211.53.

Example 16

Synthesis of C142

Synthesis of C142

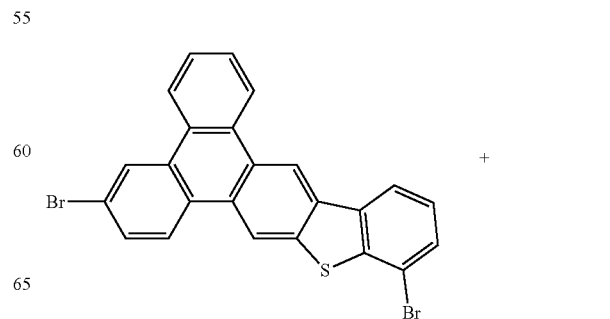

-continued

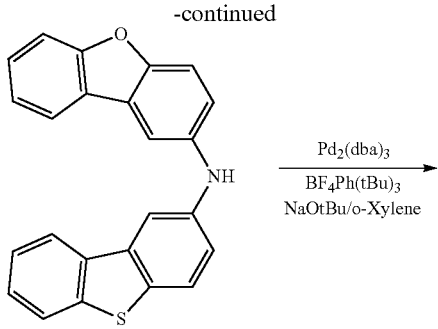

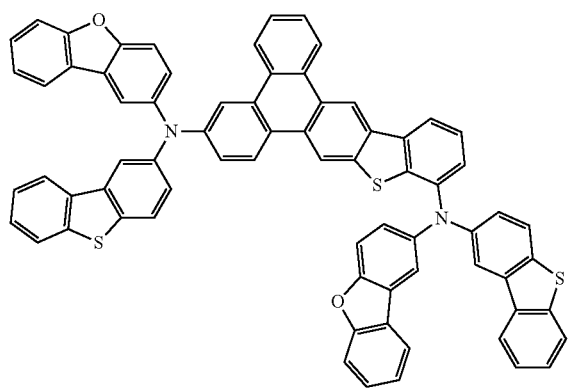

The same synthesis procedure as in Synthesis of C139 was used, except that 5.56 g of N-(dibenzothiophene-2-yl)dibenzofuran-2-amine was used instead of N-(dibenzothiophene-4-yl)-9-phenyl-9H-carbazol-3-amine to obtain the desired C142 (4.01 g, 62%). MS (m/z, EI$^+$): 1061.3.

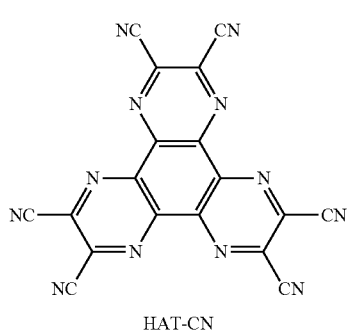

HAT-CN

General Method of Producing Organic EL Device

ITO-coated glasses with 9-12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

The organic layers are applied onto the ITO substrate in order by vapor deposition in a high-vacuum unit ($10^{-7}$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, e.g. a host material doped with a dopant material in the light emitting layer. This is successfully achieved by co-vaporization from two or more sources, which means the iridium complex of the present invention is thermally stable.

Dipyrazino[2,3-f:2,3-]quinoxaline-2,3,6,7,10,11-hexacarbonitrile (HAT-CN) is used to form the hole injection layer, and N,N-bis(naphthalene-1-yl)-N,N-bis(phenyl)-benzidine (NPB) is used to form the hole transporting layer of the organic EL device. N-(biphenyl-4-yl)-9,9-dimethyl-N-(4'-phenyl-biphenyl-4-yl)-9H-fluoren-2-amine (EB2) is used to form the electron blocking layer. HB3 is used as hole blocking material (HBM), and 2-(10,10-dimethyl-10H-indeno [2,1-b]triphenylen-12-yl)-4,6-diphenyl-1,3,5-triazine (ET2) is used as electron transporting material to co-deposit with 8-hydroxyquinolato-lithium (LiQ) in organic EL devices. For fluorescence emitting device, compounds H2 is used as the host material, and (E)-6-(4-(diphenylamino)styryl)-N,N-diphenylnaphthalen-2-amine (D1) is used as the fluorescent dopant. Compound D1 is used as the dopant material. Compounds C1, C18, C167, C170, C184, C187, C110, C115, C149, C154, C157, and C158 are used as the fluorescent dopant materials to compare with D1. Compounds C38, C51, C139 and C142 are used as the electron blocking layer materials to compare with EB2. Compounds C1, C170, C184, C115, C149 and C158 are used as the hole transporting layer materials to compare with NPB. The chemical structures of conventional OLED materials and the exemplary organic compounds of the present invention for producing control and exemplary organic EL devices in this invention are shown as follows:

NPB

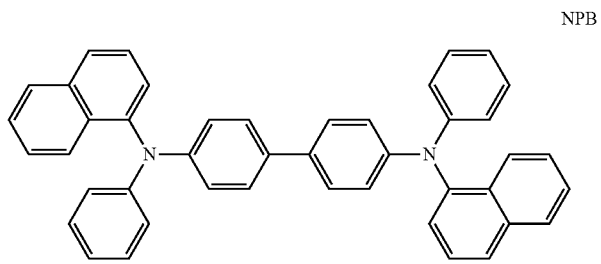

-continued
H2
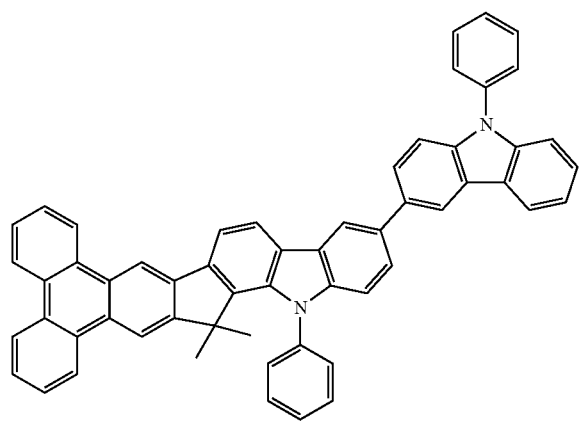
EB2
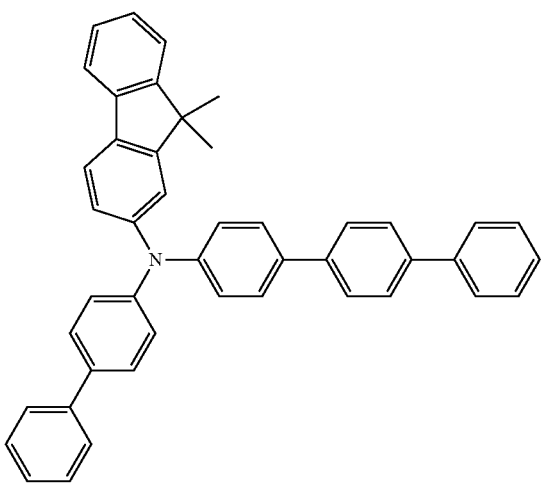
D1
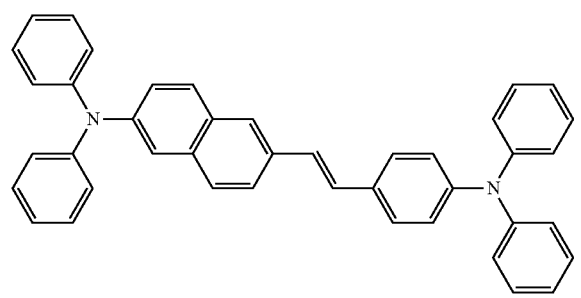
HB3
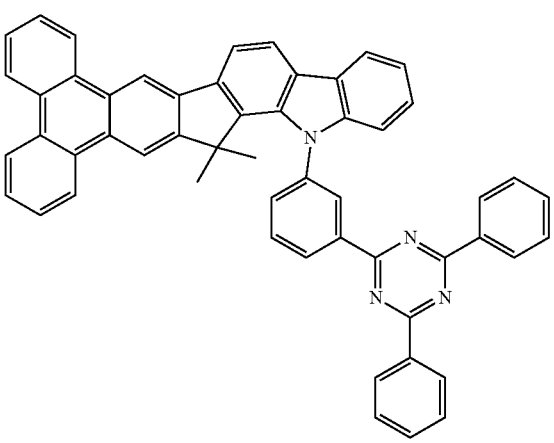
ET2
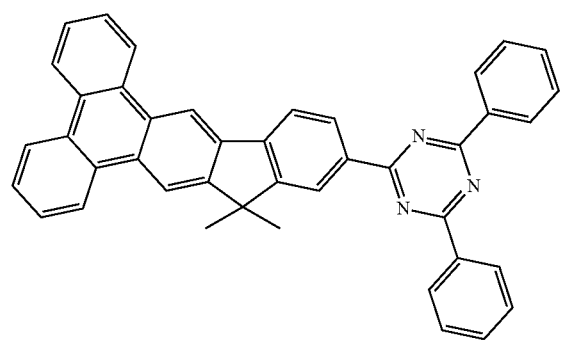
LiQ
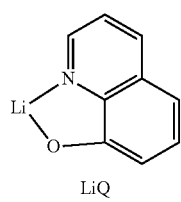

-continued
C1
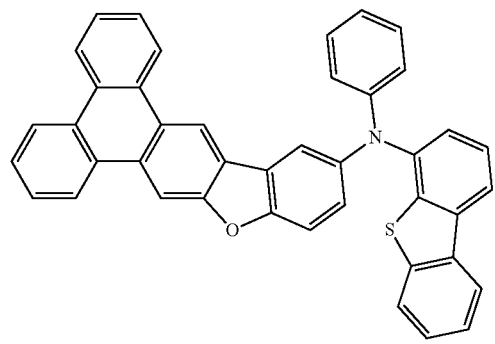
C18
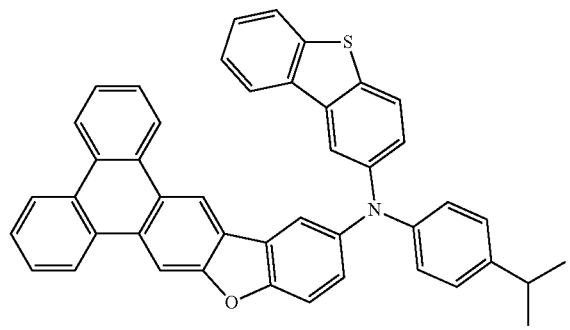
C167
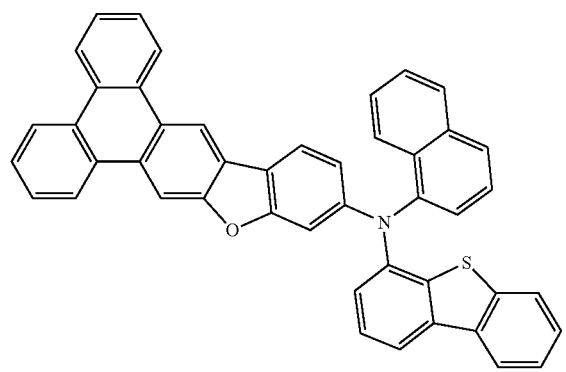
C170
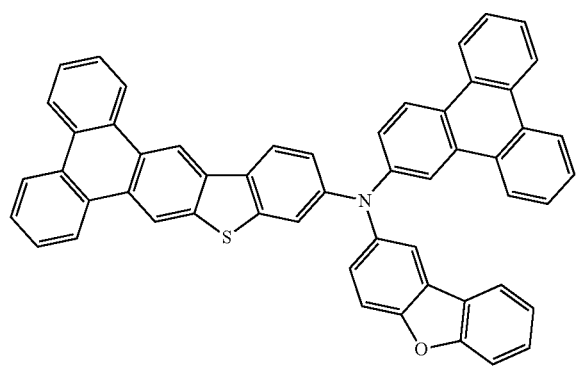
C184
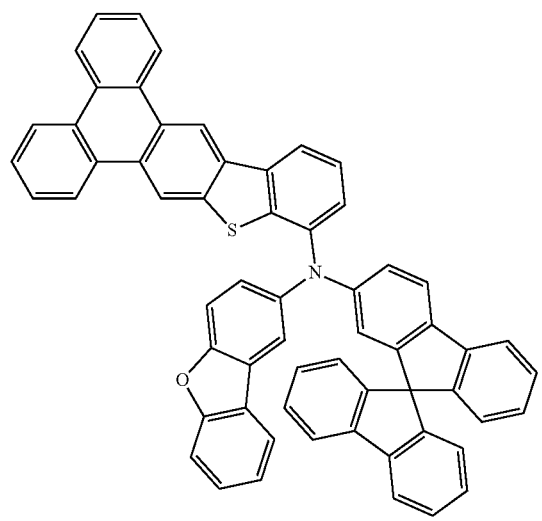
C187
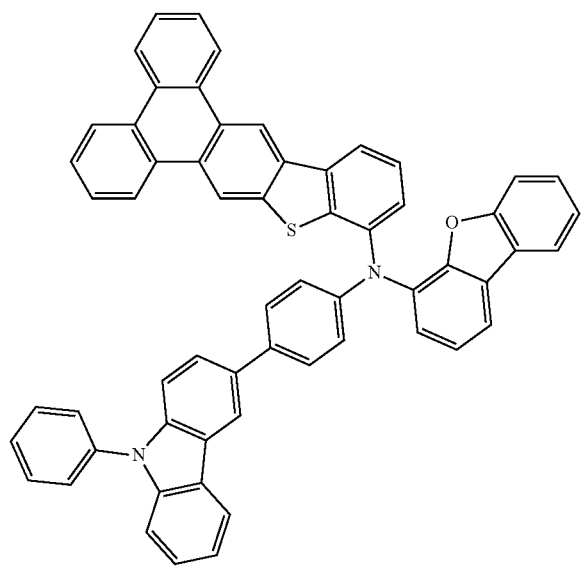

-continued
C110
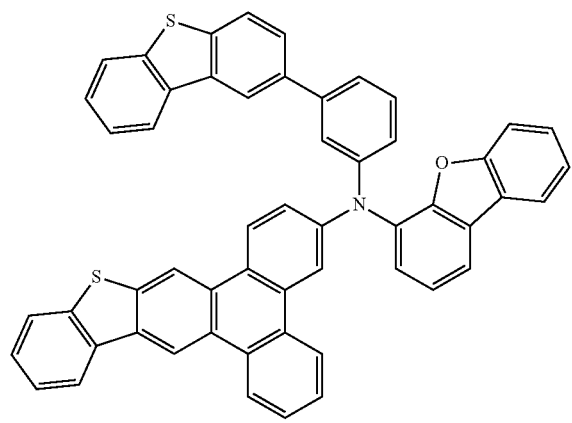
C115
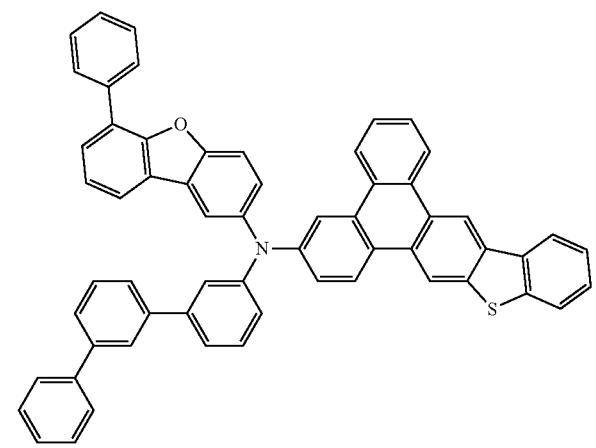
C149
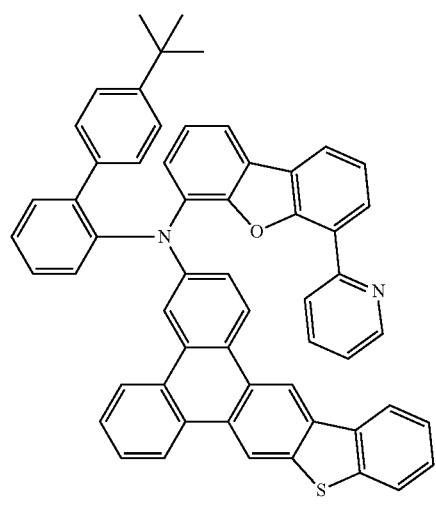
C154
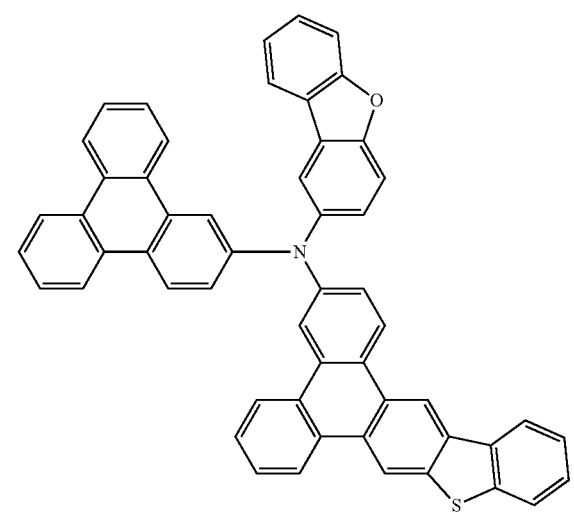
C157
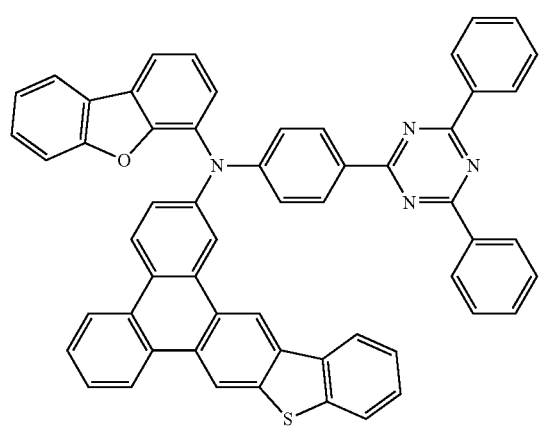
C158
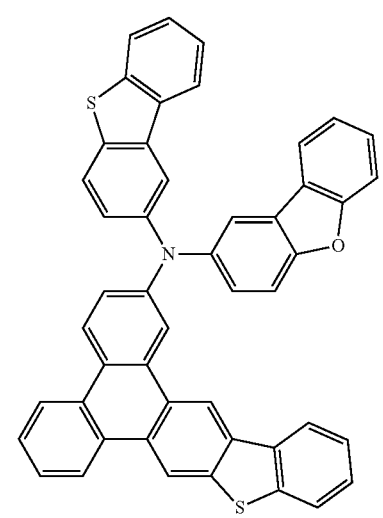

C38
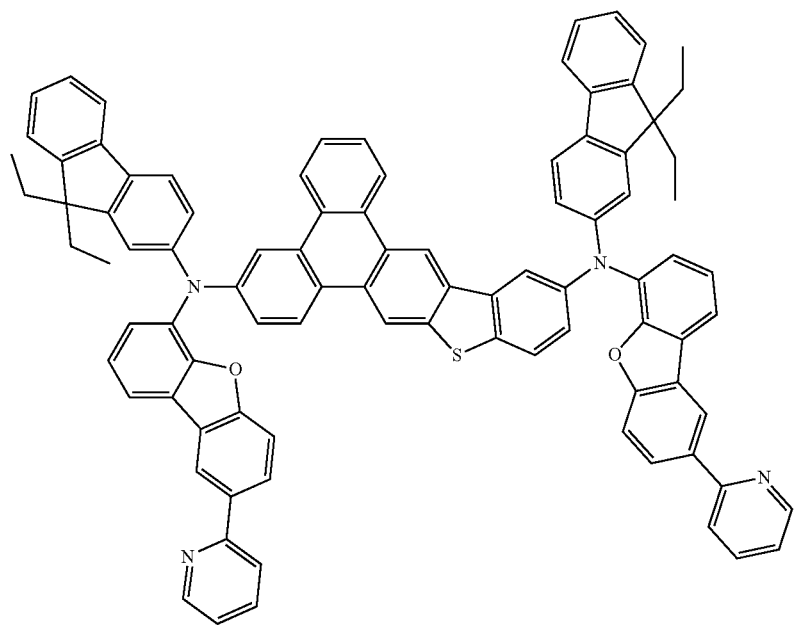
C51
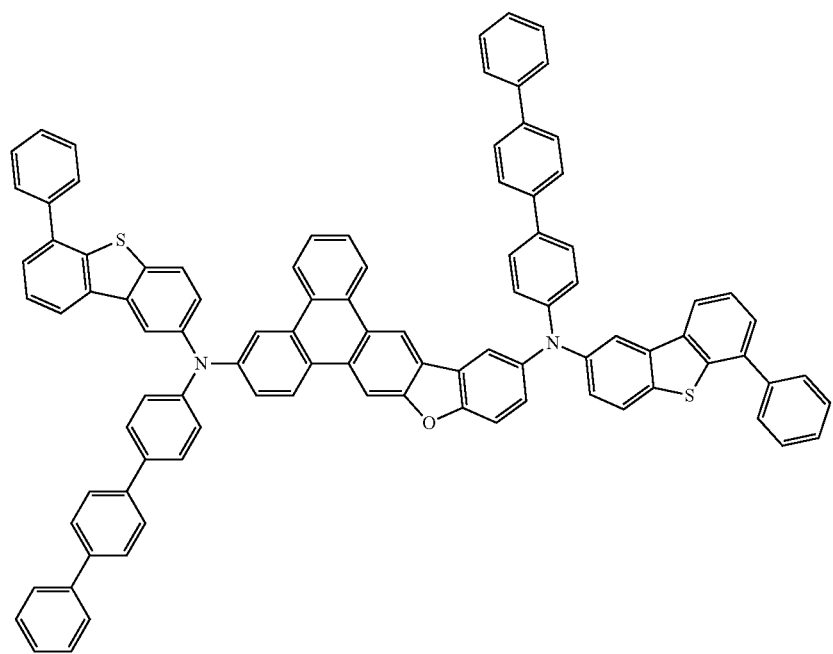

-continued

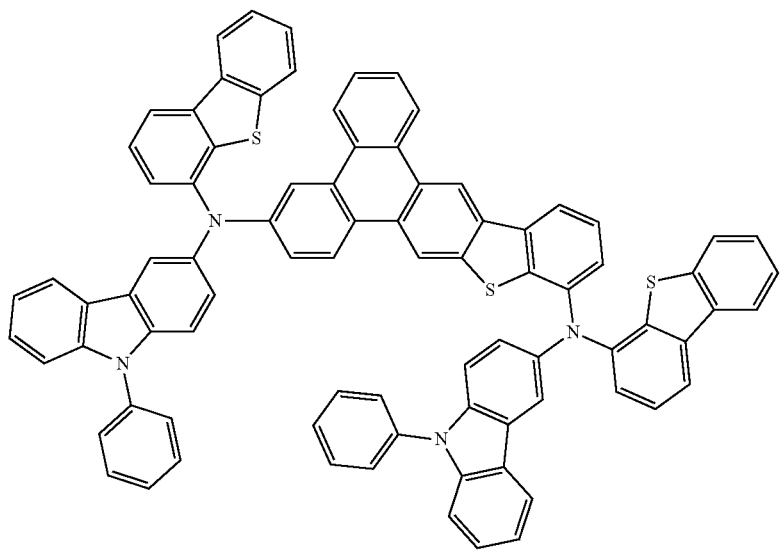

C139

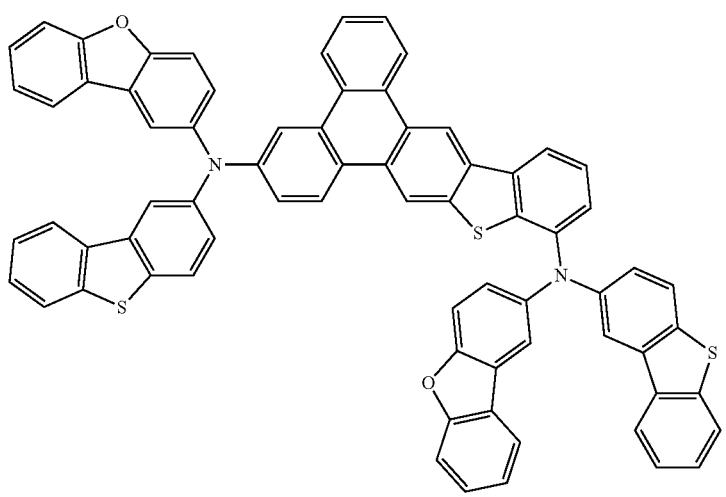

C142

A typical organic EL device consists of low work function metals, such as Al, Mg, Ca, Li and K, as the cathode, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 17

Using a procedure analogous to the above mentioned general method, organic EL devices emitting phosphorescence and having the following device structure (as shown in the FIGURE) were produced: ITO/HAT-CN (20 nm)/NPB (110 nm)/EB2 (5 nm)/H2 doped with 15% phosphorescent dopant (30 nm)/HB3 (10 nm)/ET2 doped with 40% LiQ (35 nm)/LiQ (1 nm)/Al (160 nm). In the device illustrated in the FIGURE, the hole injection layer 20 is deposited onto the transparent electrode 10, the hole transport layer 30 is deposited onto the hole injection layer 20, the electron blocking layer 40 is deposited onto the hole transport layer 30, the phosphorescence emitting layer 50 is deposited onto the electron blocking layer 40, the hole blocking layer 60 is deposited onto the phosphorescence emitting layer 50, the electron transport layer 70 is deposited onto the hole blocking layer 60, the electron injection layer 80 is deposited onto the electron transport layer 70, and the metal electrode 90 is deposited onto the electron injection layer 80. The I-V-B (at 1000 nits) and half-life time test reports of these organic EL devices are summarized in Table 1 below. The half-life time is defined as the time the initial luminance of 1000 $cd/m^2$ has dropped to half.

TABLE 1

| HTL | Dopant | EBL | Voltage (V) | Efficiency (cd/A) | CIE (y) | Half-life time (hour) |
|---|---|---|---|---|---|---|
| NPB | D1 | EB2 | 6 | 5.12 | 0.17 | 310 |
| NPB | C1 | EB2 | 5.2 | 7.5 | 0.16 | 600 |
| NPB | C18 | EB2 | 5.3 | 6.9 | 0.15 | 510 |
| NPB | C167 | EB2 | 5.3 | 7 | 0.16 | 550 |
| NPB | C170 | EB2 | 5.2 | 6.8 | 0.15 | 480 |
| NPB | C184 | EB2 | 5.4 | 6.7 | 0.15 | 420 |
| NPB | C187 | EB2 | 5.5 | 6.9 | 0.16 | 450 |
| NPB | C110 | EB2 | 5.2 | 6.6 | 0.17 | 390 |
| NPB | C115 | EB2 | 5.5 | 6.7 | 0.16 | 480 |
| NPB | C149 | EB2 | 5.3 | 6.8 | 0.15 | 520 |
| NPB | C154 | EB2 | 5.2 | 6.8 | 0.16 | 515 |
| NPB | C157 | EB2 | 5.4 | 6.9 | 0.16 | 505 |
| NPB | C158 | EB2 | 5.1 | 6.6 | 0.15 | 500 |
| NPB | D1 | C38 | 5.2 | 5.8 | 0.17 | 420 |
| NPB | D1 | C51 | 5.3 | 5.9 | 0.17 | 400 |
| NPB | D1 | C139 | 5.4 | 5.6 | 0.17 | 430 |
| NPB | D1 | C142 | 5.2 | 6 | 0.16 | 450 |
| C1 | D1 | EB2 | 5.5 | 6.1 | 0.17 | 470 |
| C170 | D1 | EB2 | 5.4 | 6.2 | 0.16 | 480 |
| C184 | D1 | EB2 | 5.4 | 6.5 | 0.17 | 500 |
| C115 | D1 | EB2 | 5.3 | 6.2 | 0.18 | 490 |
| C149 | D1 | EB2 | 5.2 | 6.2 | 0.17 | 510 |
| C158 | D1 | EB2 | 5.5 | 6.4 | 0.17 | 500 |

In the above test report of organic EL devices (see Table 1), we show that the organic material with formula (1) used as the dopant material, hole transporting material, or electron blocking material for organic EL devices in the present invention displays better performance than the prior art organic EL materials. More specifically, the organic EL devices of the present invention use the organic material with formula (1) as emitting quest material to collocate with emitting host material, such as H2, showing lower power consumption, higher efficiency, and longer half-life time.

To sum up, the present invention discloses an indenotriphenylene-based amine derivative, which can be used as the dopant material, the hole transporting material, or the electron blocking material of the organic EL device. The mentioned indenotriphenylene-based amine derivative is represented by the following formula (1):

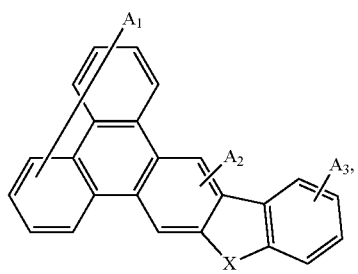

formula (1)

wherein at least one of $A_1$, $A_2$ and $A_3$ exists and represents formula (2) below:

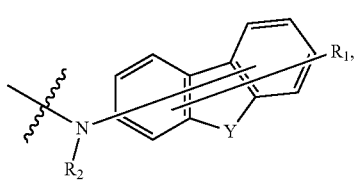

formula (2)

wherein X is a divalent bridge selected from the group consisting of O and S; Y is a divalent bridge selected from the group consisting of O and S; $R_1$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_2$ is a hydrogen atom, a halogen, a substituted or unsubstituted aralkyl group having 5 to 30 ring atoms, a substituted or unsubstituted aryl group having 5 to 30 ring atoms, or a substituted or unsubstituted heteroaryl group having 5 to 30 ring atoms.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An indenotriphenylene-based amine derivative of formula (1):

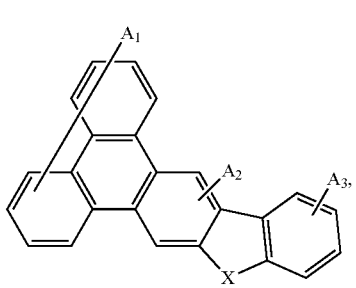

formula (1)

wherein at least one of $A_1$, $A_2$ and $A_3$ exists and represents formula (2) below:

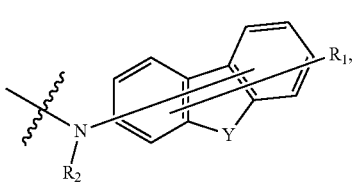

formula (2)

wherein X is a divalent bridge selected from the group consisting of O and S; Y is a divalent bridge selected from the group consisting of O and S; $R_1$ is a hydrogen atom, a halogen, a substituted or unsubstituted aryl group having 5 to 30 ring atoms, a substituted or unsubstituted heteroaryl group having 5 to 30 ring atoms, a substituted or unsubstituted arylamine group having 5 to 30 ring atoms, or a substituted or unsubstituted heteroarylamine group having 5 to 30 ring atoms; and $R_2$ is a hydrogen atom, a halogen, a substituted or unsubstituted aralkyl group having 5 to 30 ring atoms, a substituted or unsubstituted aryl group having 5 to 30 ring atoms, or a substituted or unsubstituted heteroaryl group having 5 to 30 ring atoms.

2. The indenotriphenylene-based amine derivative according to claim 1, wherein the indenotriphenylene-based amine derivative is represented by one of the following formula (3) to formula (22):
formula (3)
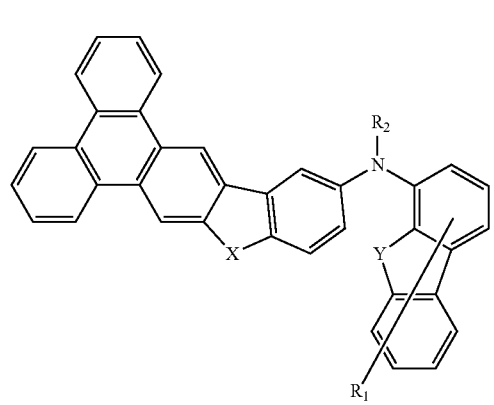
formula (4)
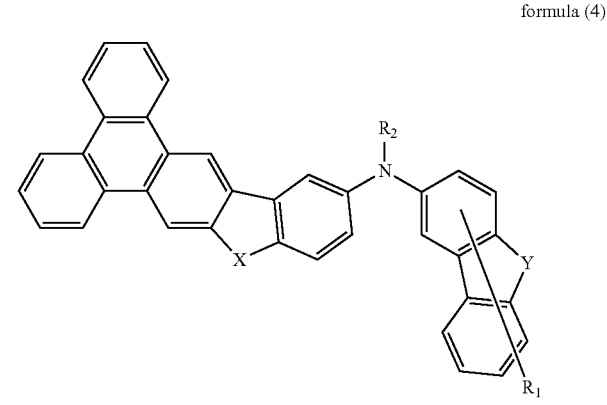
formula (5)
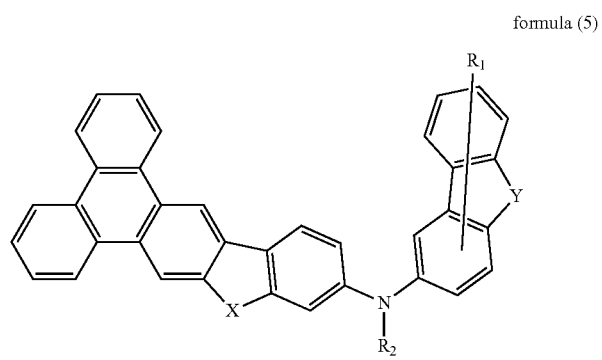
formula (6)
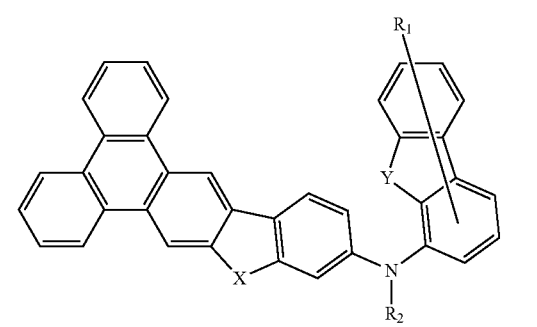
formula (7)
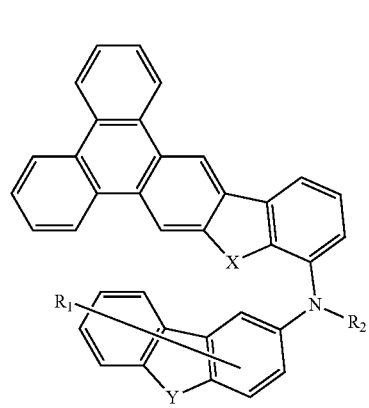
formula (8)
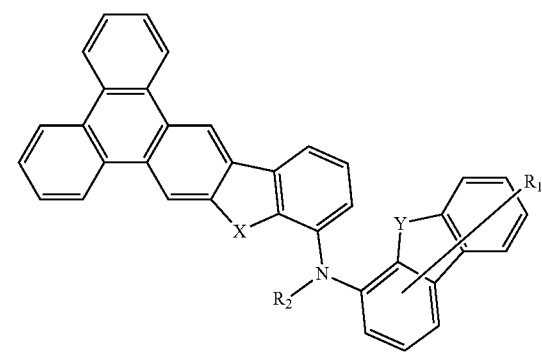

formula (9)
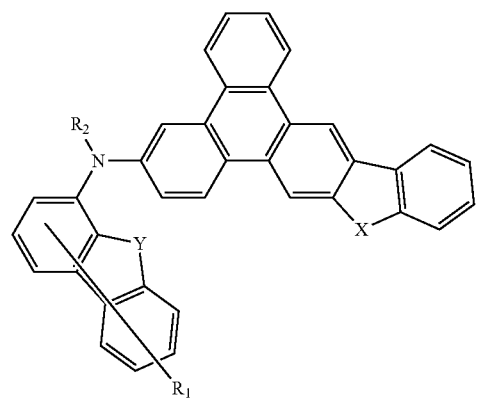
formula (10)
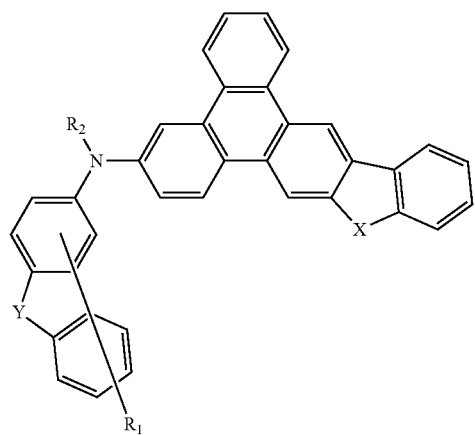
formula (11)
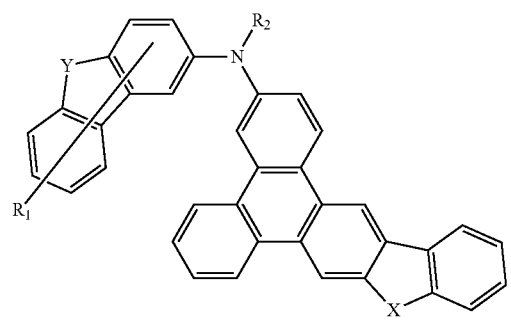
formula (12)
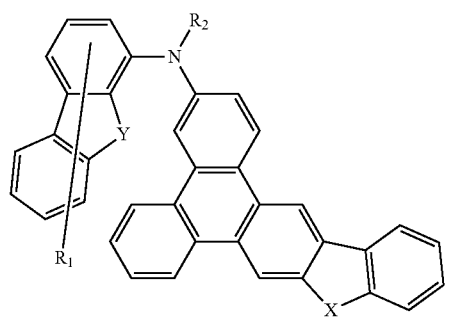
formula (13)
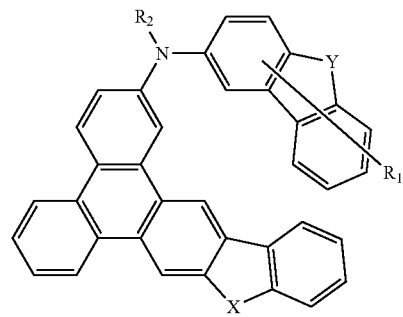
formula (14)
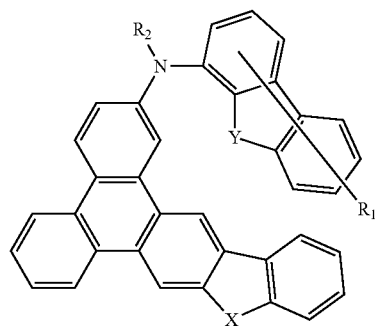
formula (15)
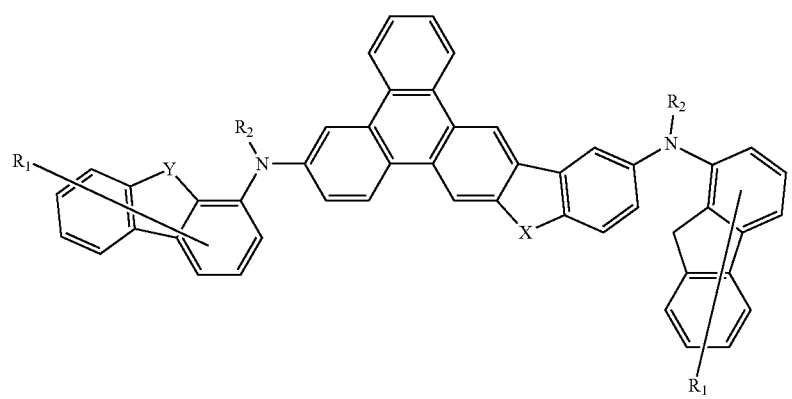

-continued
formula (16)
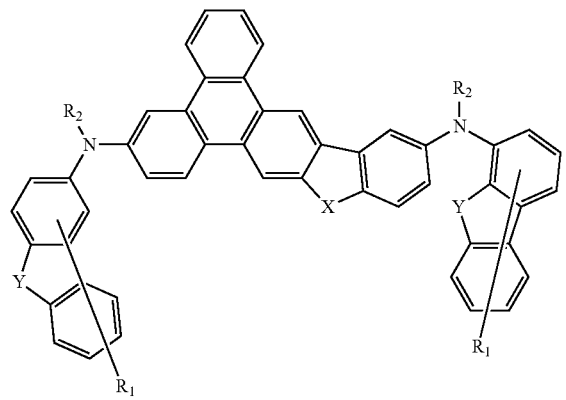
formula (17)
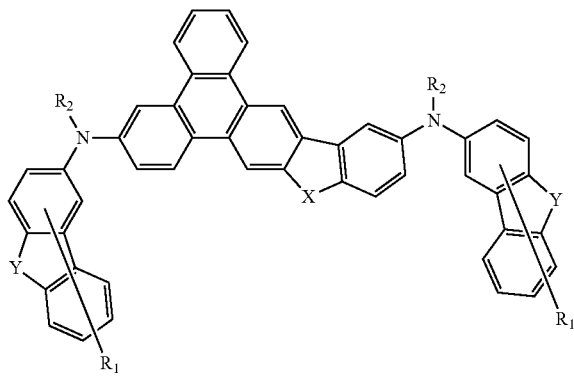
formula (18)
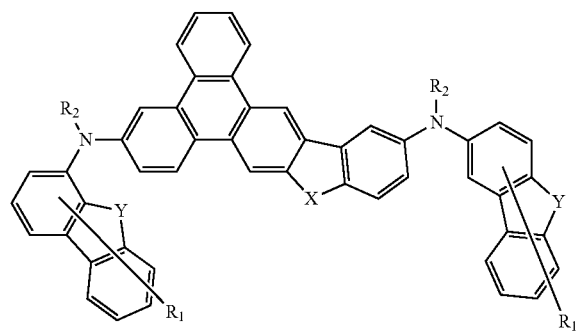
formula (19)
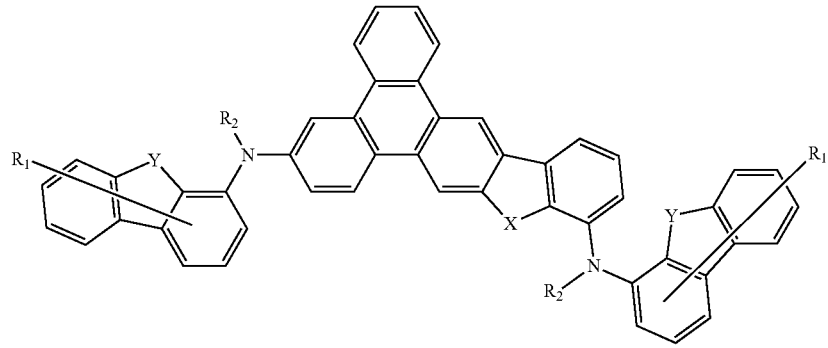
formula (20)
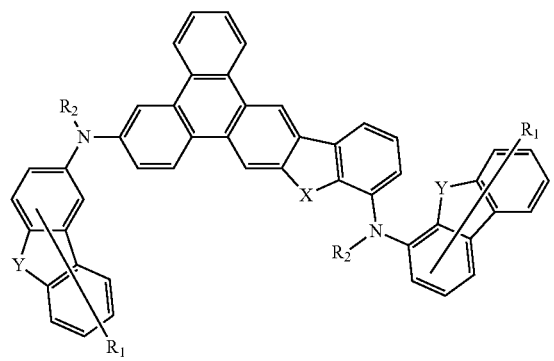
formula (21)
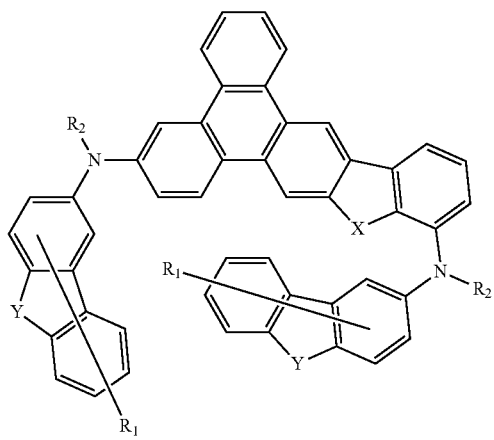

formula (22)

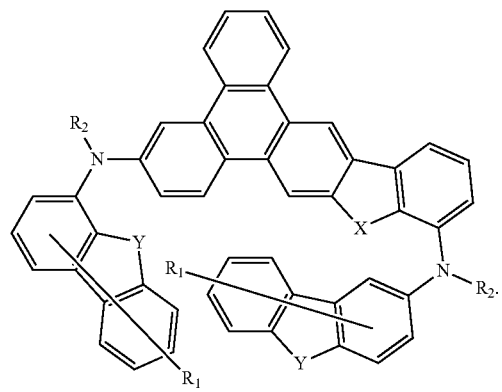

3. The indenotriphenylene-based amine derivative according to claim 1, wherein R₂ is a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, or a substituted or unsubstituted pyridinyl group.

4. The indenotriphenylene-based amine derivative according to claim 1, wherein R₂ represents one of the following substituents:

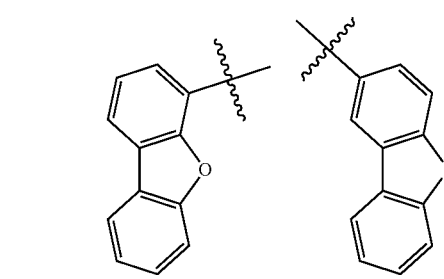

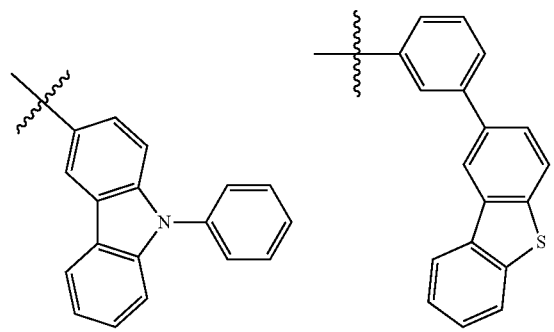

-continued

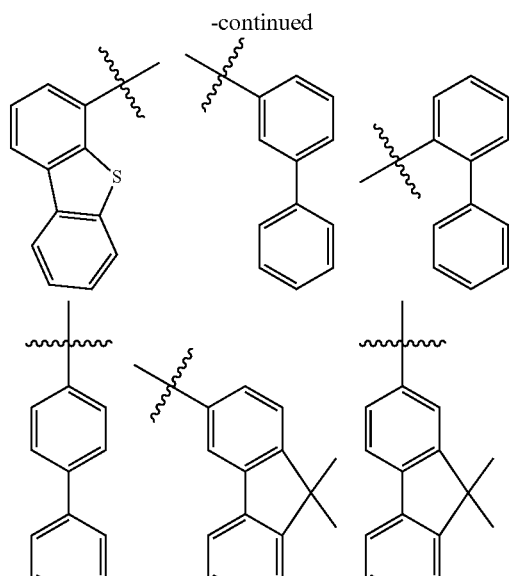

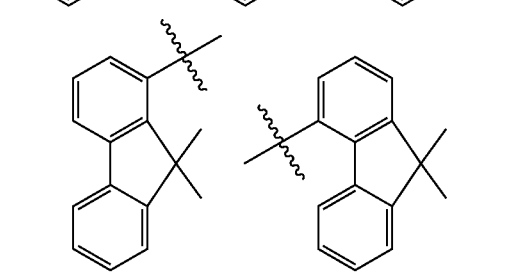

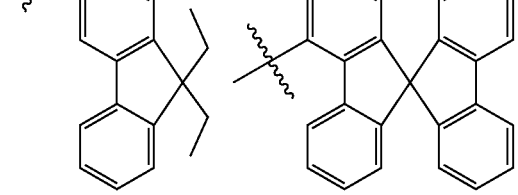

151
-continued
152
-continued
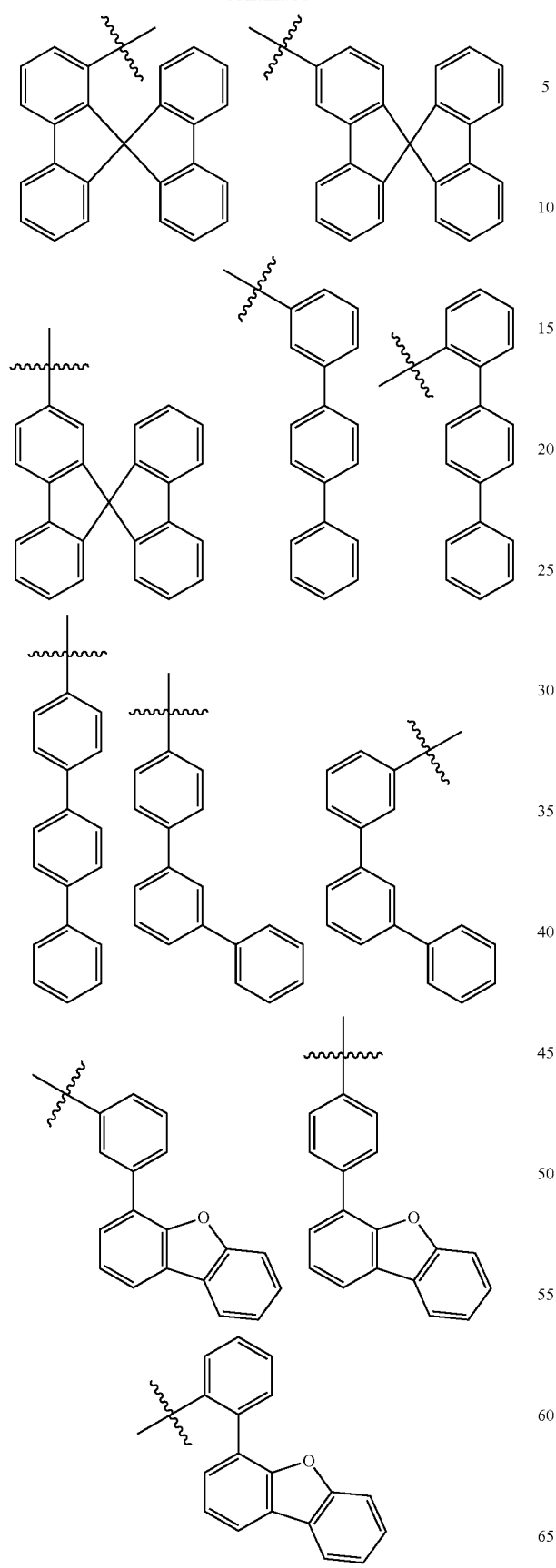
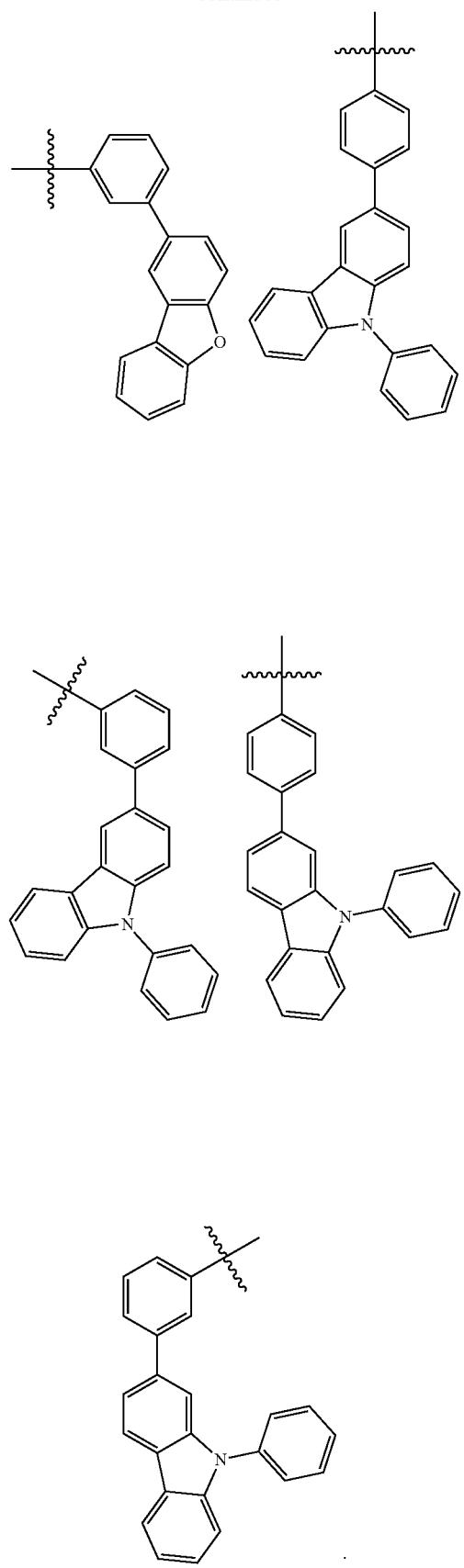

5. The indenotriphenylene-based amine derivative according to claim 1, wherein the indenotriphenylene-based amine derivative is one of the following compounds:
C1
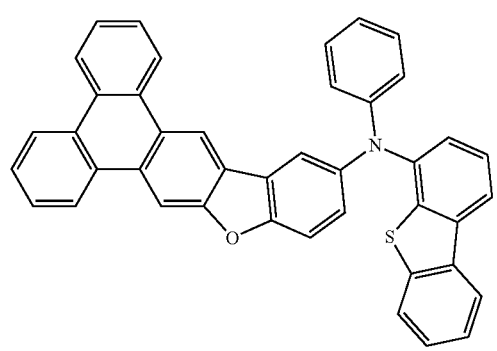
C2
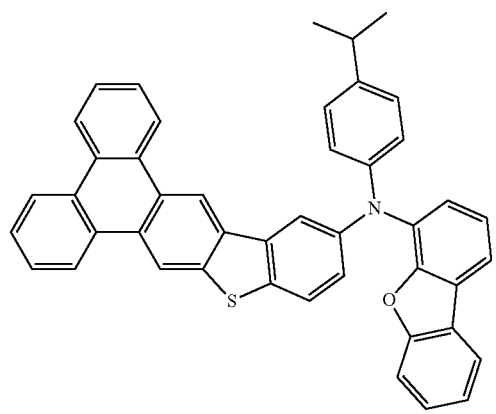
C3
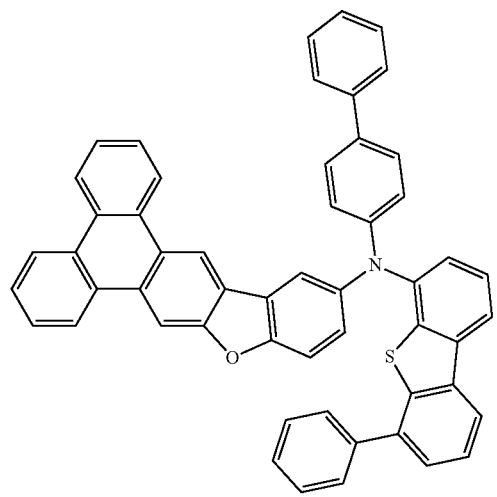
C4
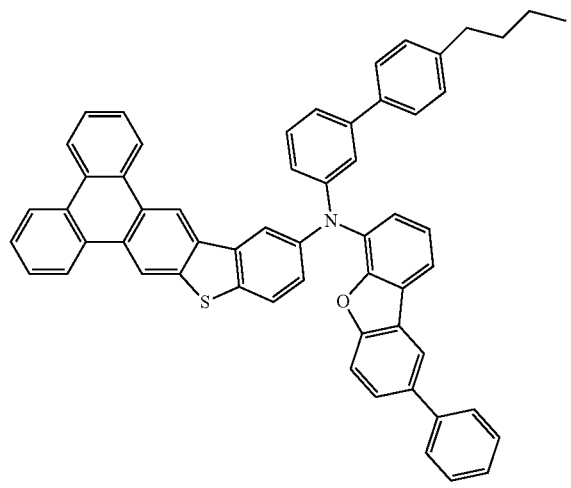
C5
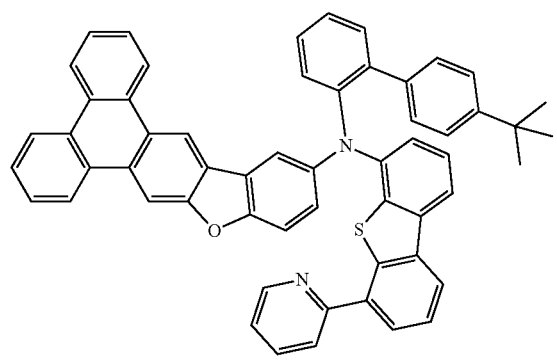
C6
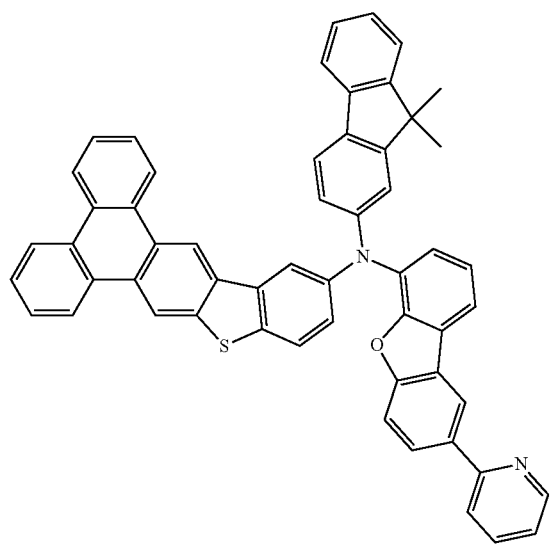

-continued
C7
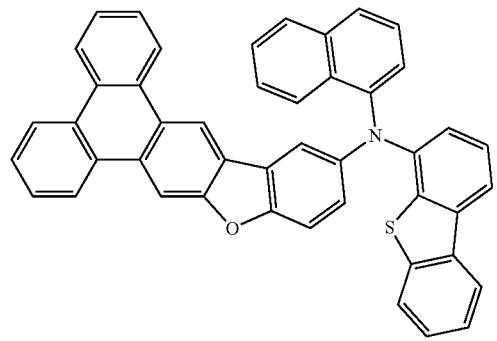
C8
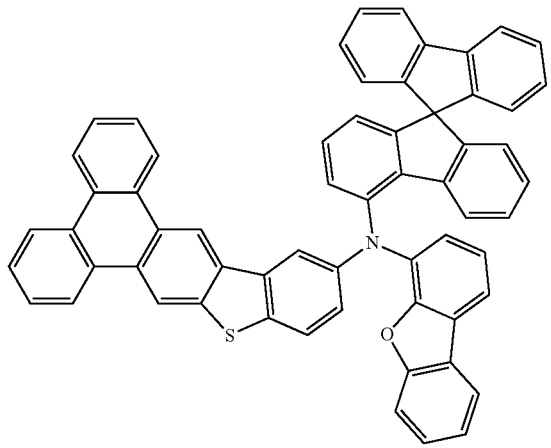
C9
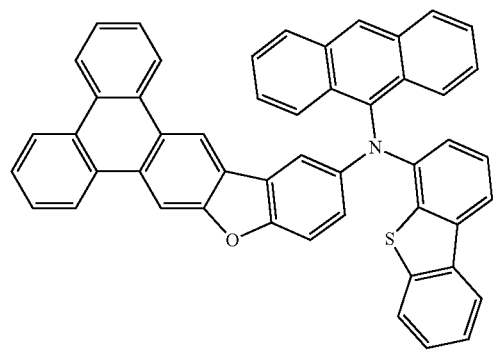
C10
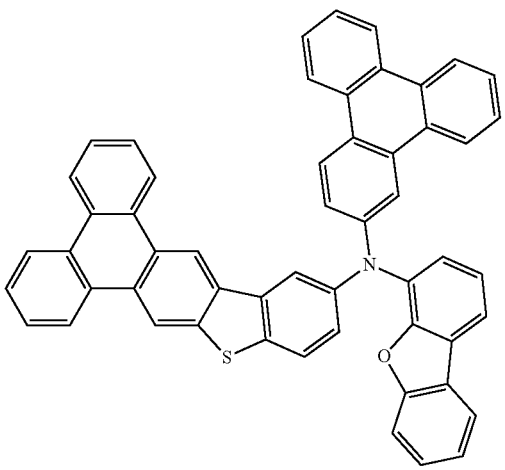
C11
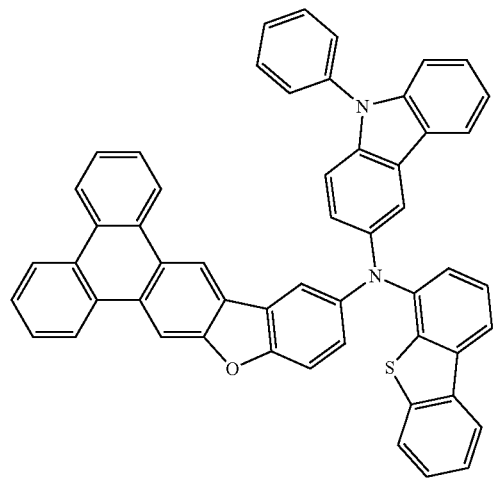
C12
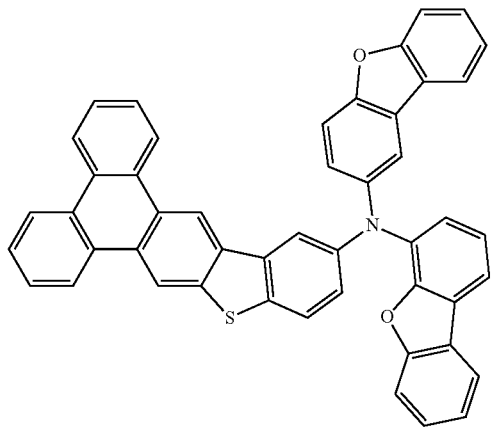

-continued
C13
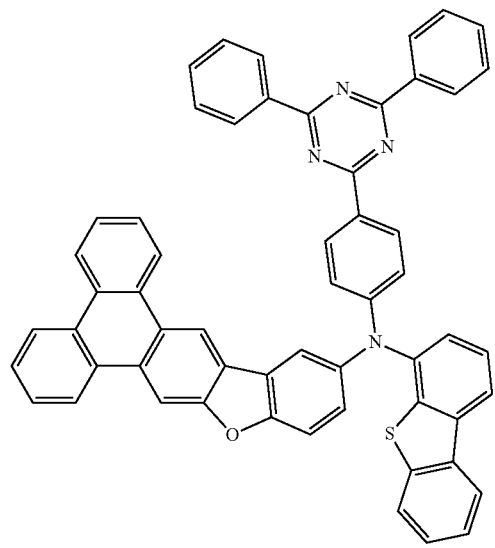
C14
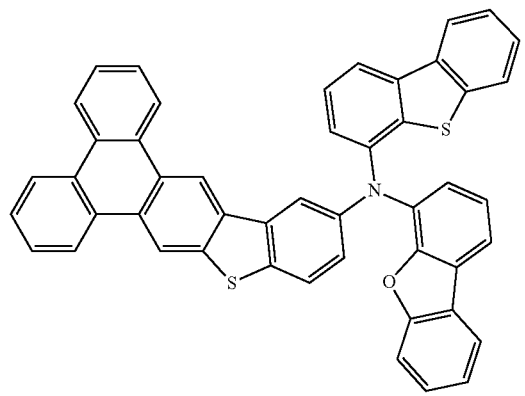
C15
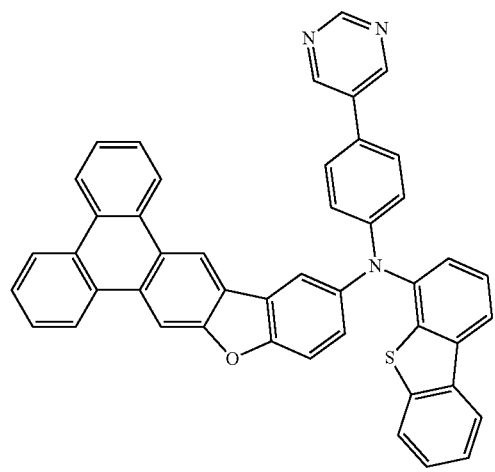
C16
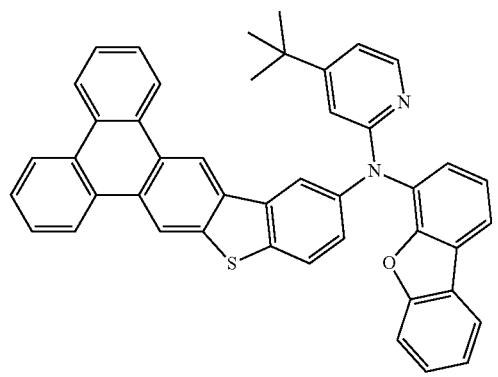
C17
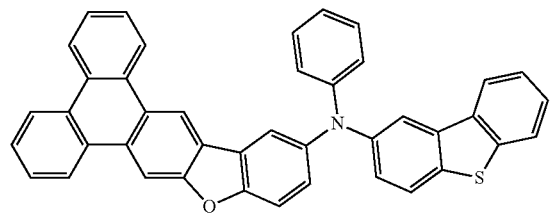
C18
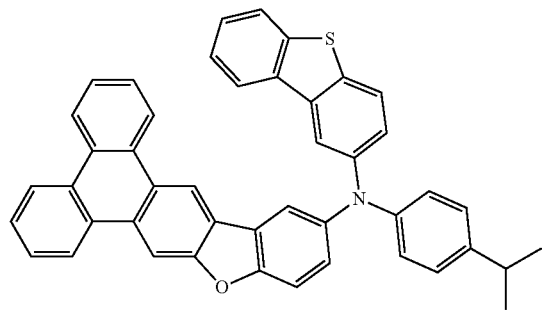

-continued
C19
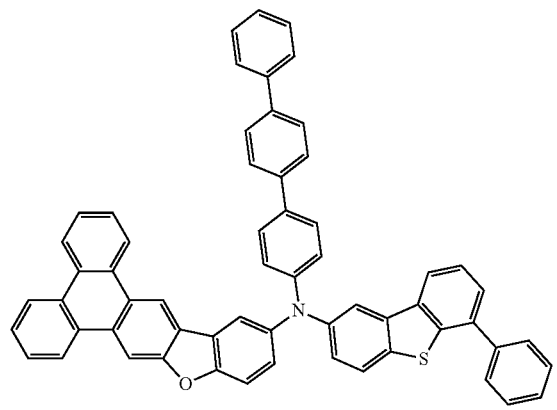
C20
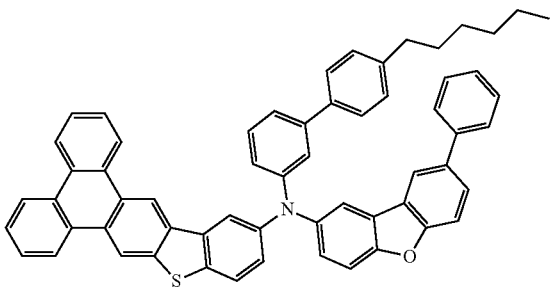
C21
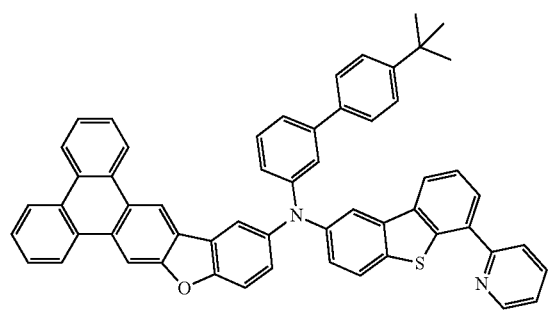
C22
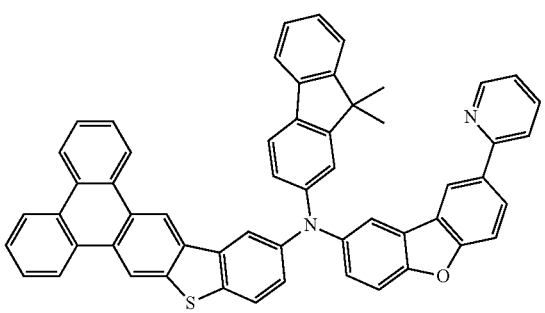
C23
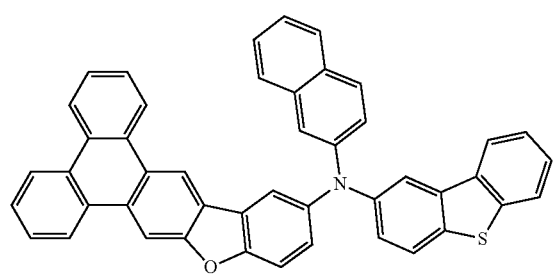
C24
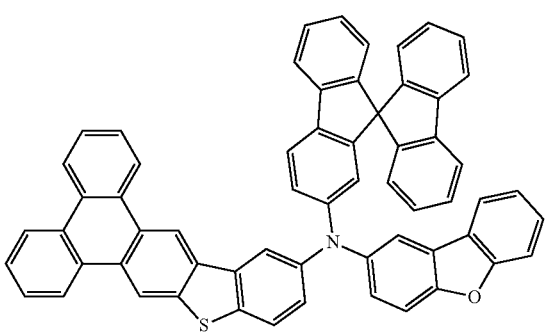
C25
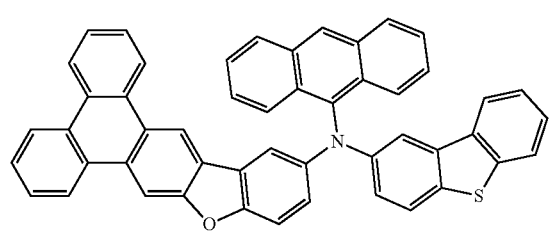
C26
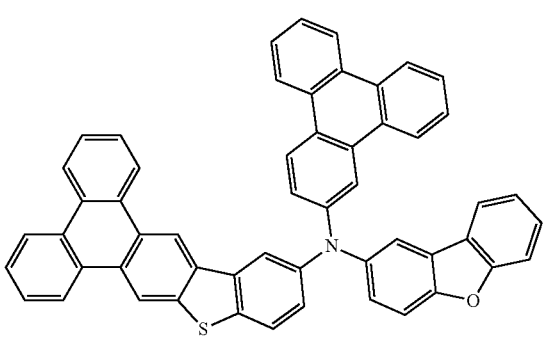

-continued
C27
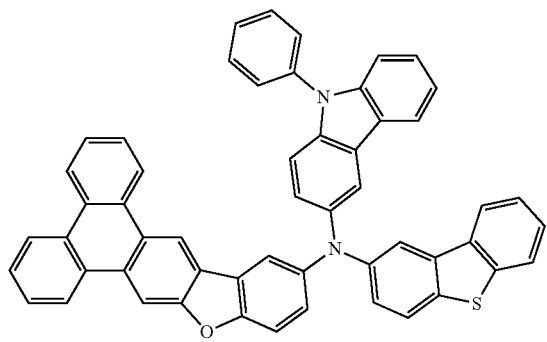
C28
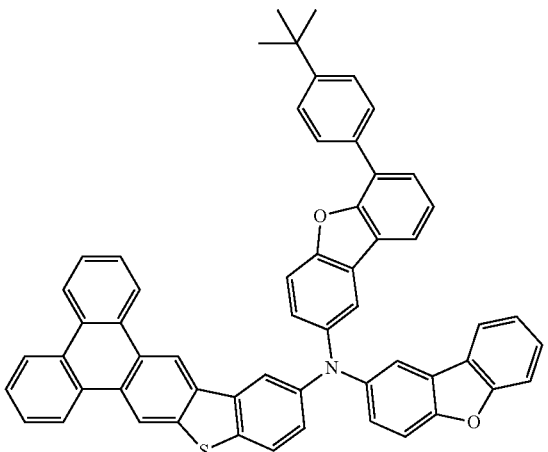
C29
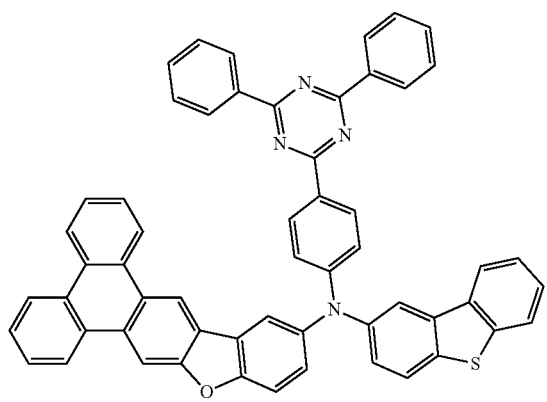
C30
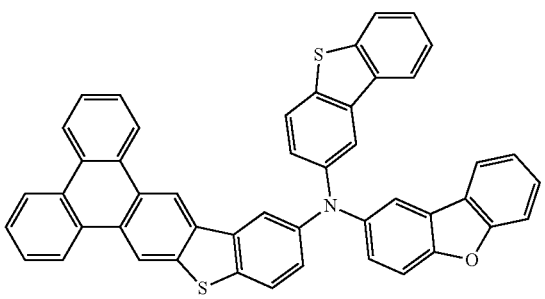
C31
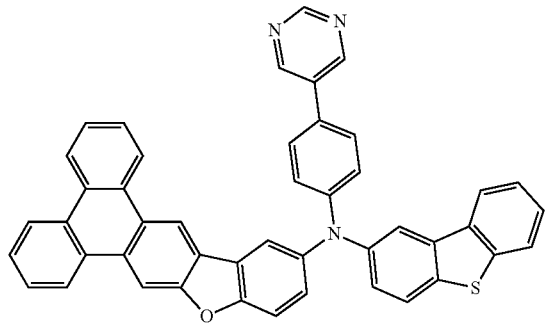
C32
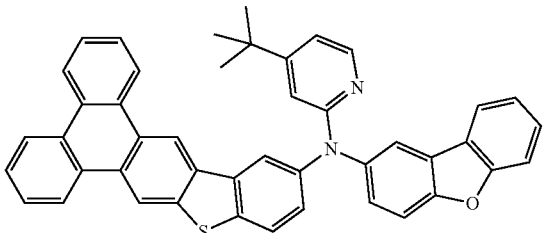
C33
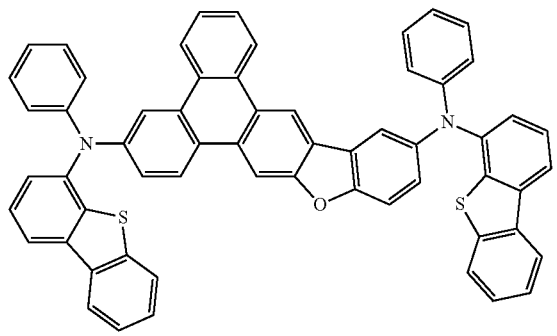
C34
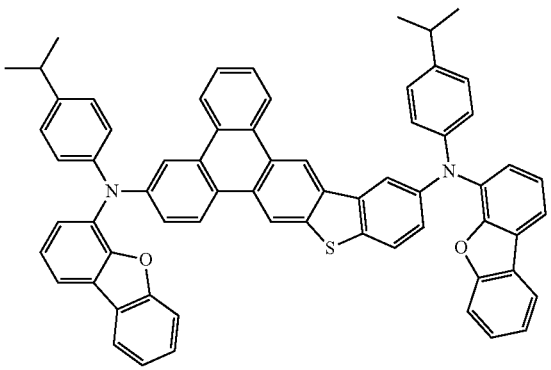

-continued
C35
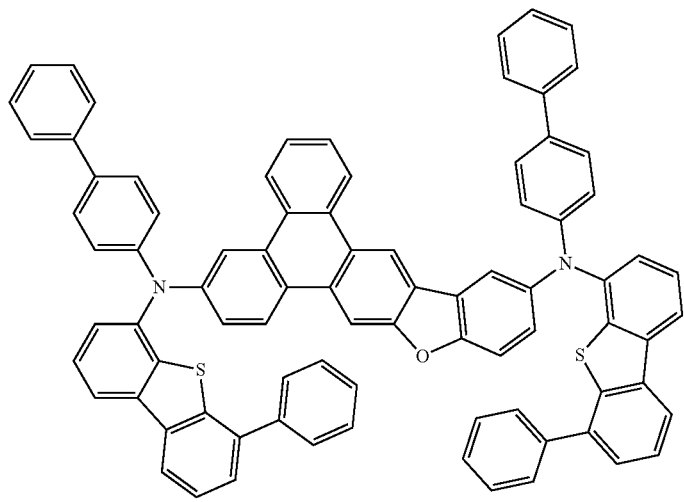
C36
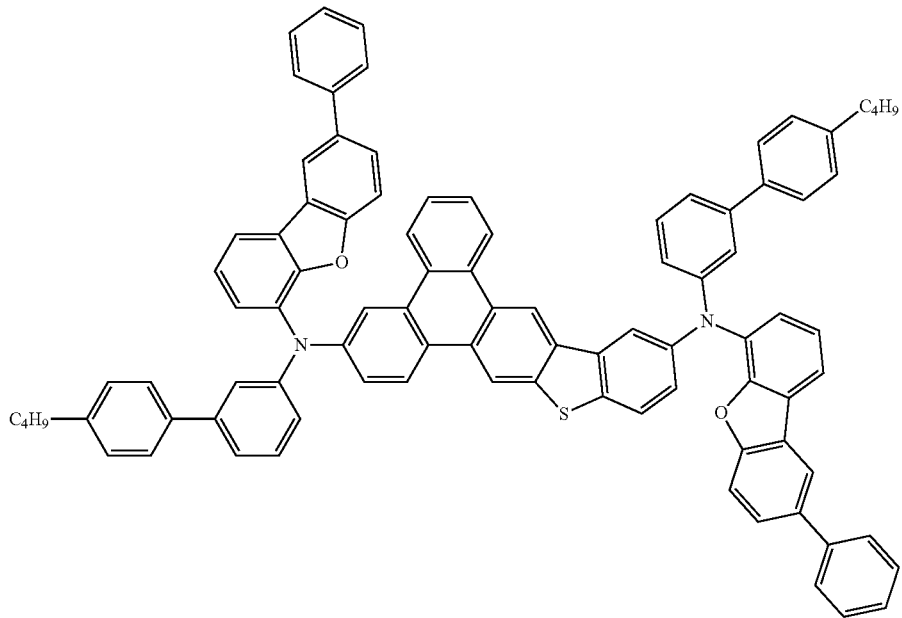
C37
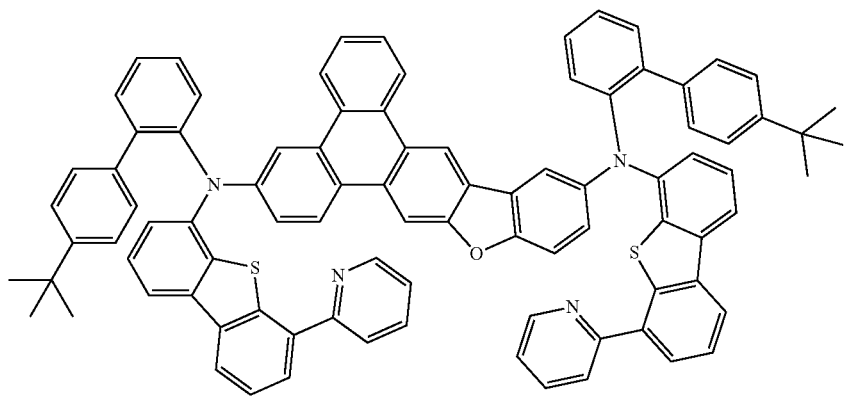

-continued
C38
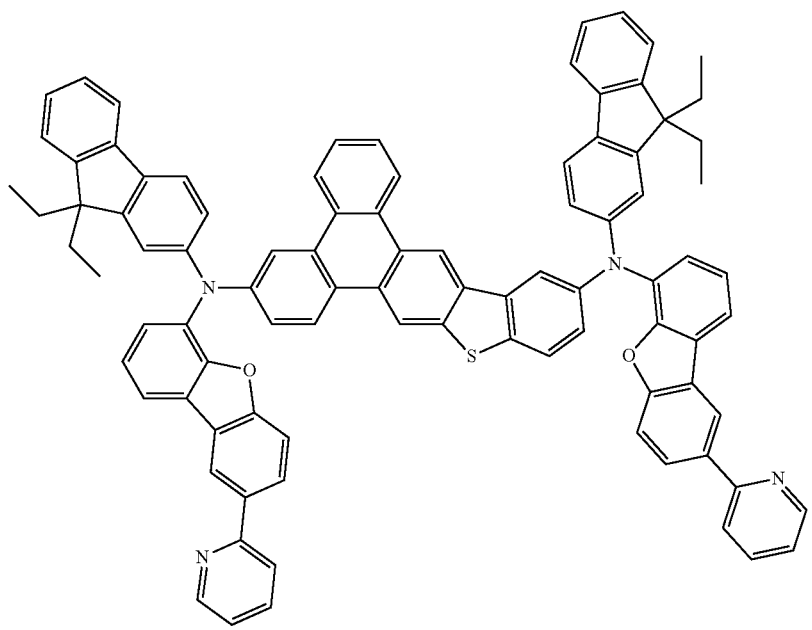
C39
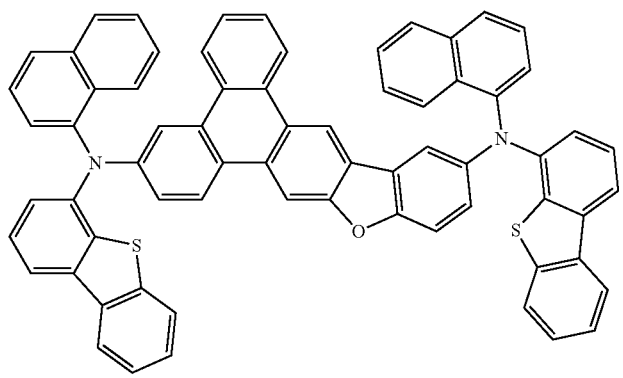
C40
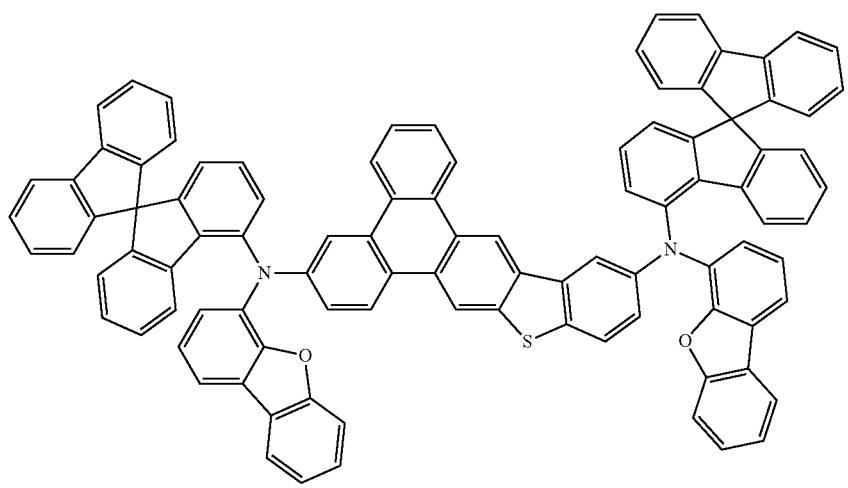

-continued
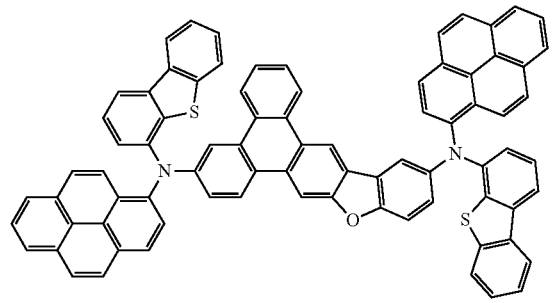
C41
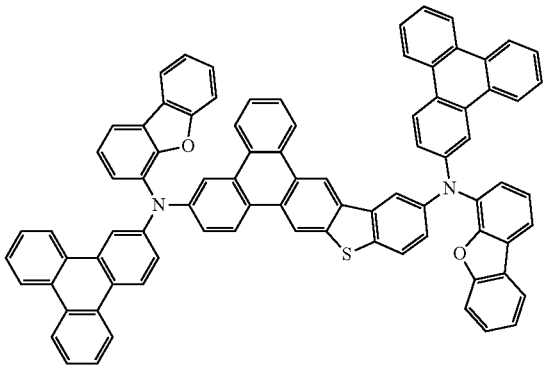
C42
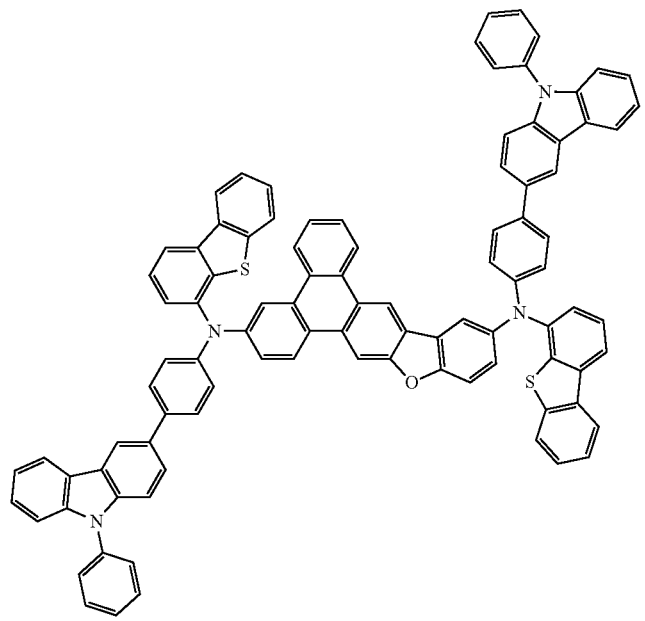
C43
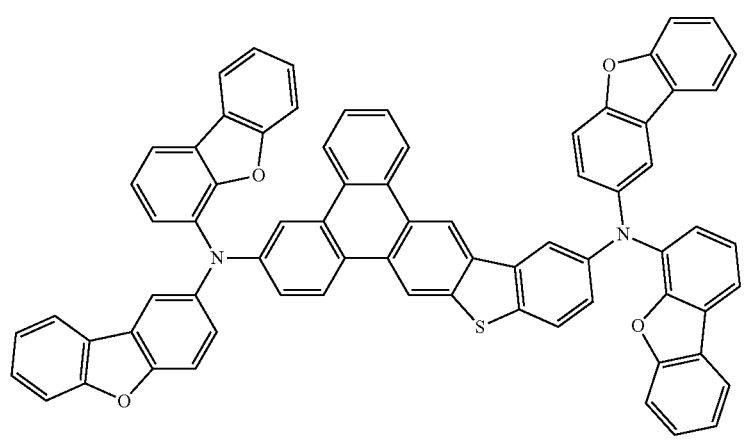
C44

-continued
C45
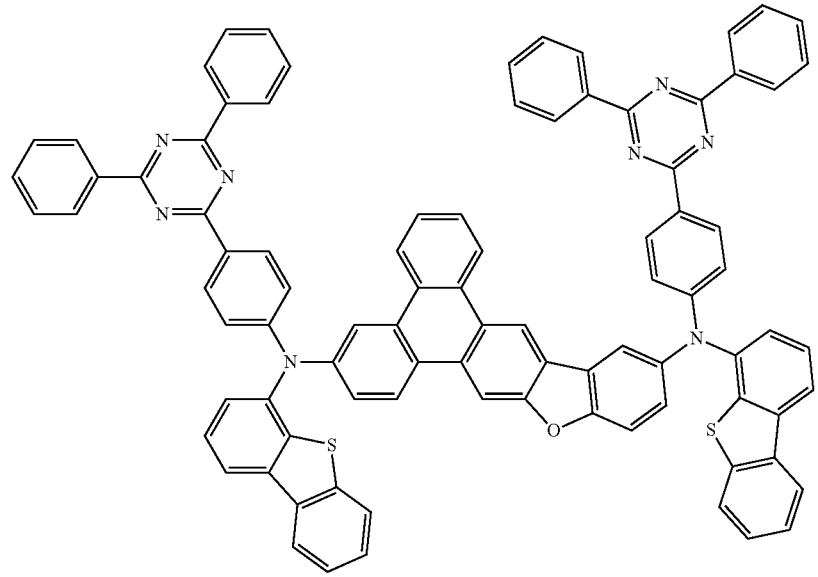
C46
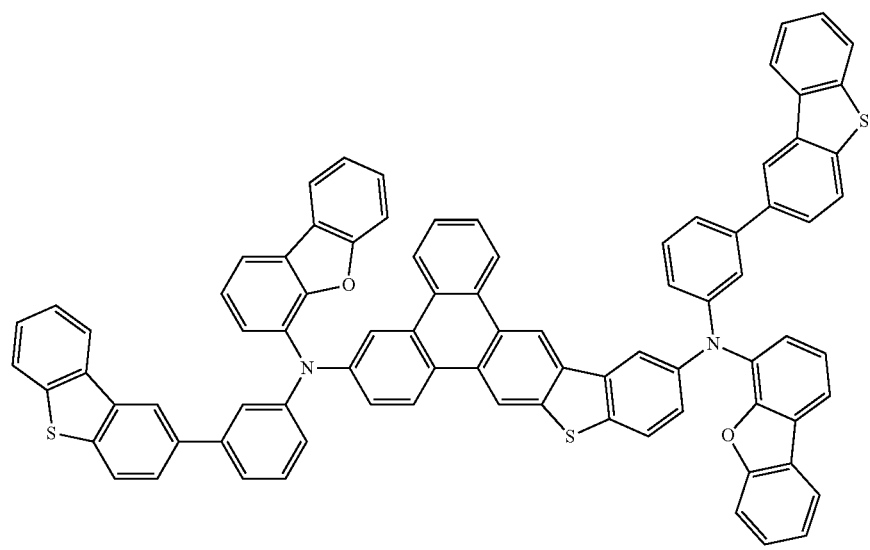
C47 C48
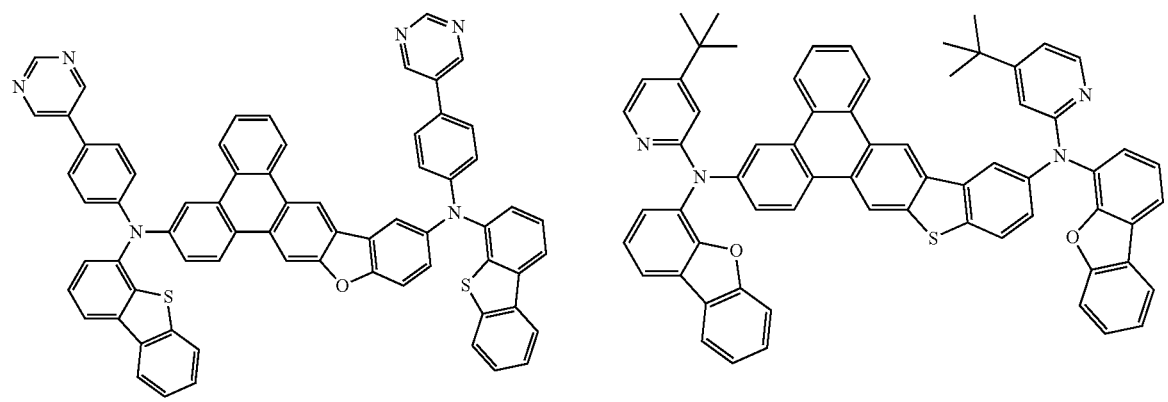

-continued
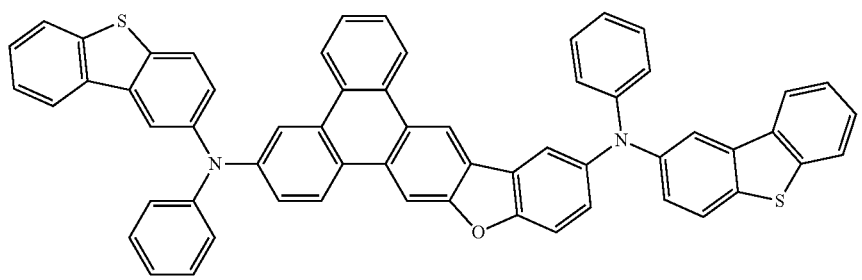
C49
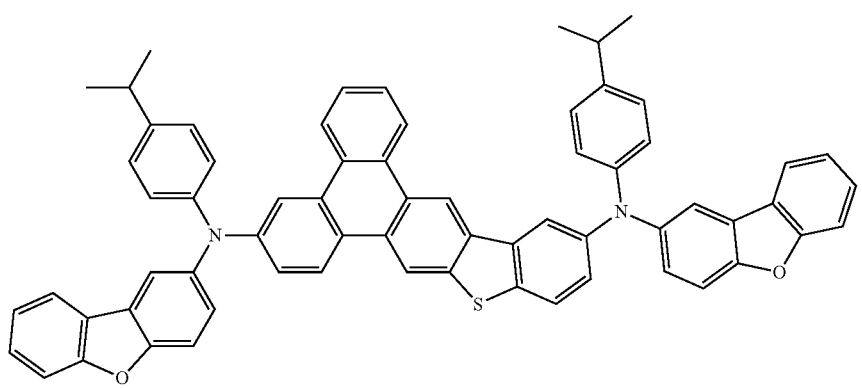
C50
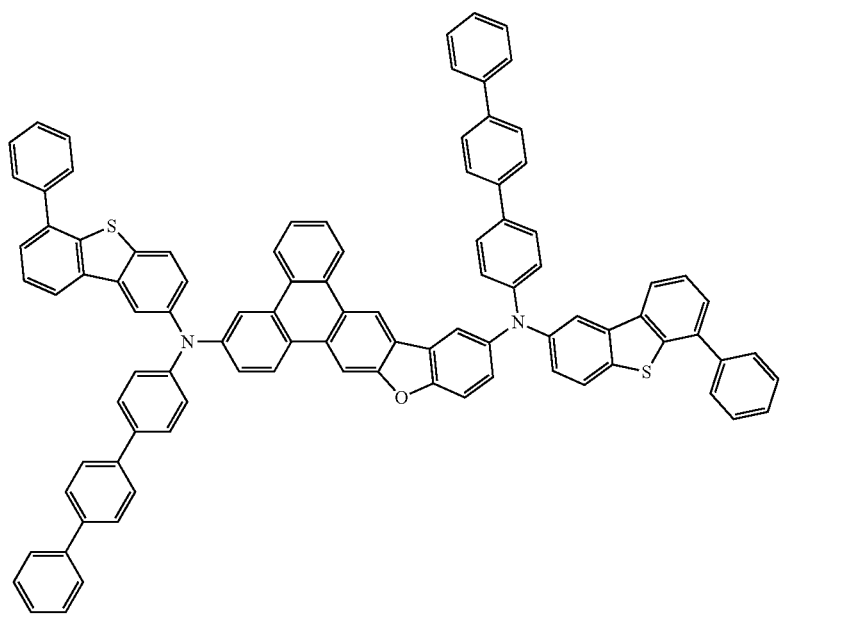
C51

-continued
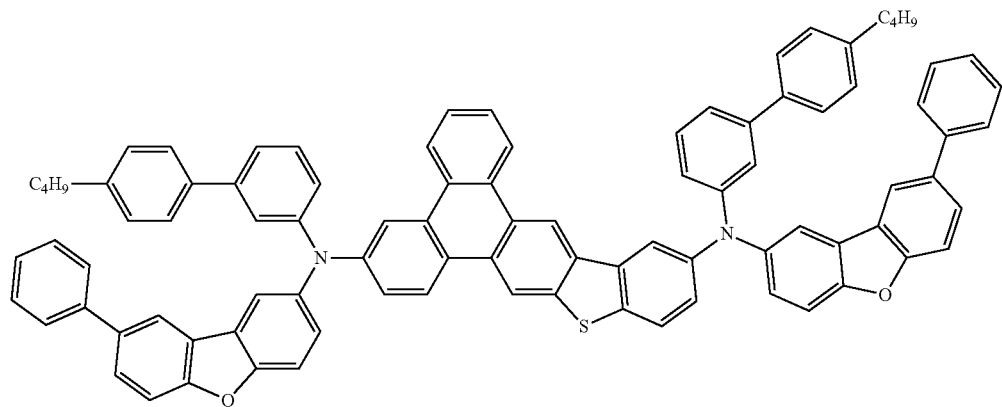
C52
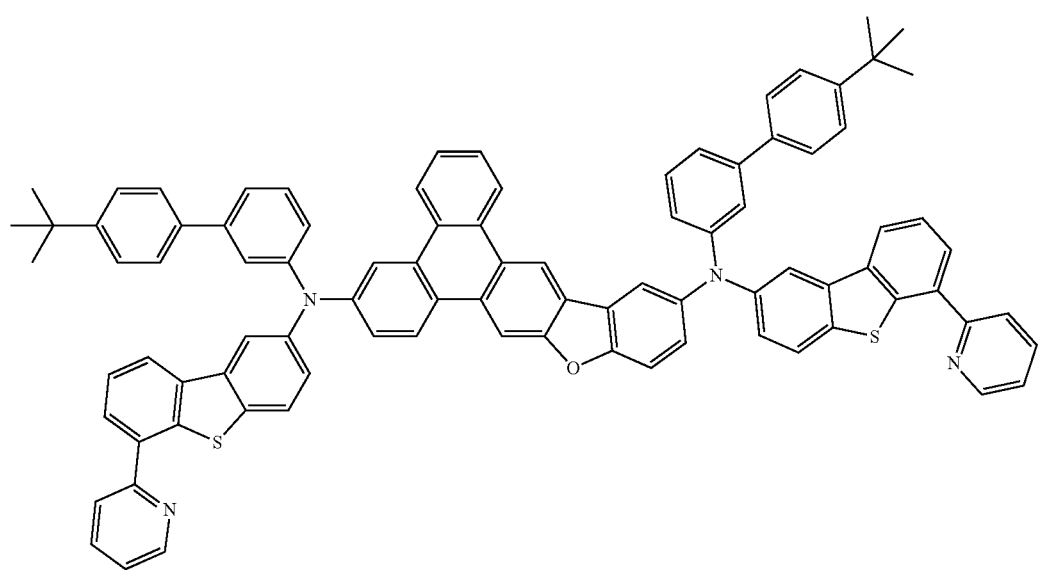
C53
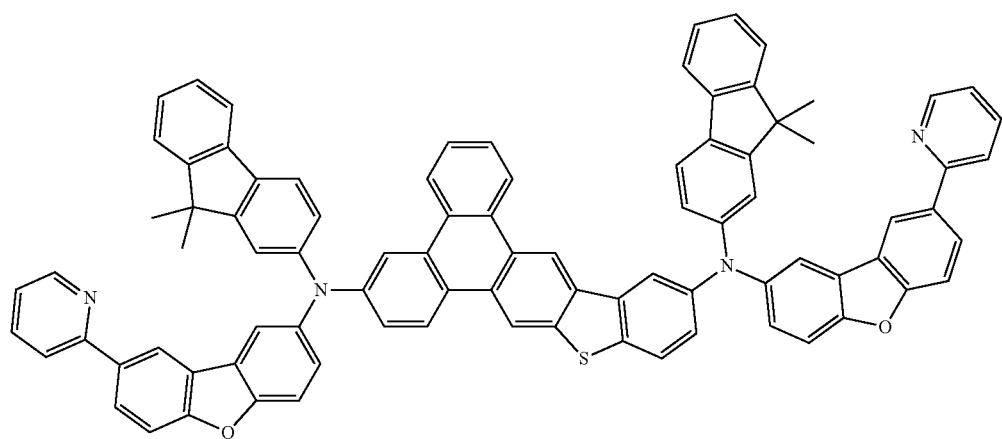
C54

C55
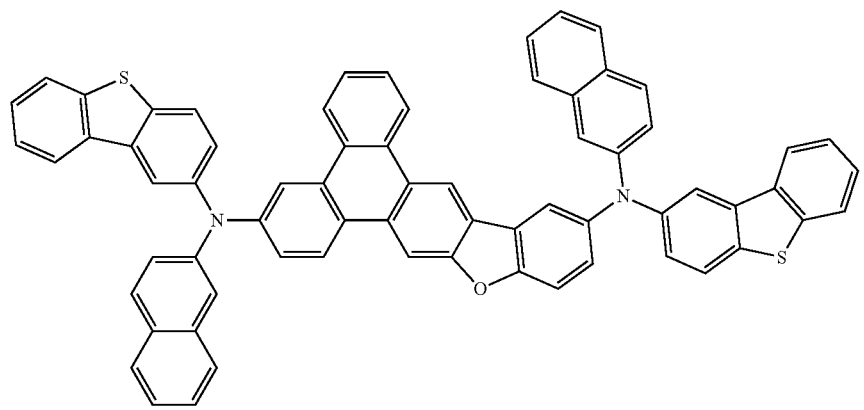
C56
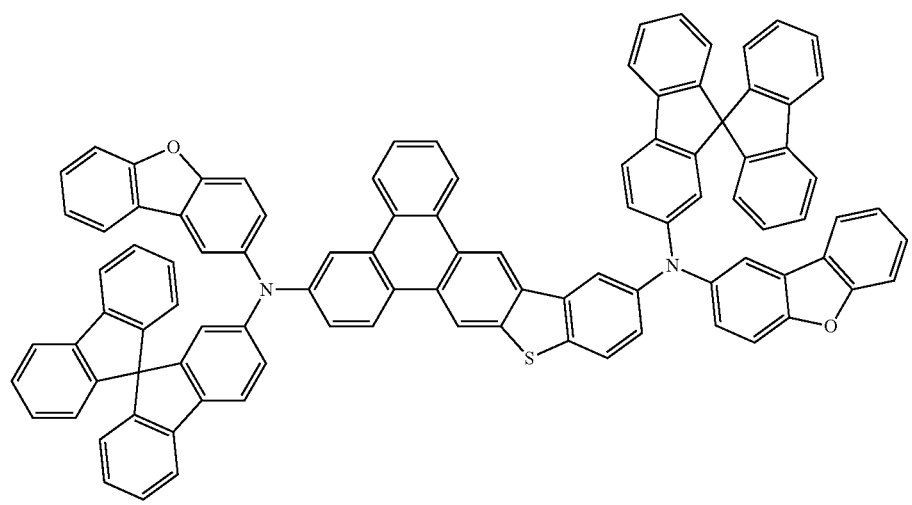
C57
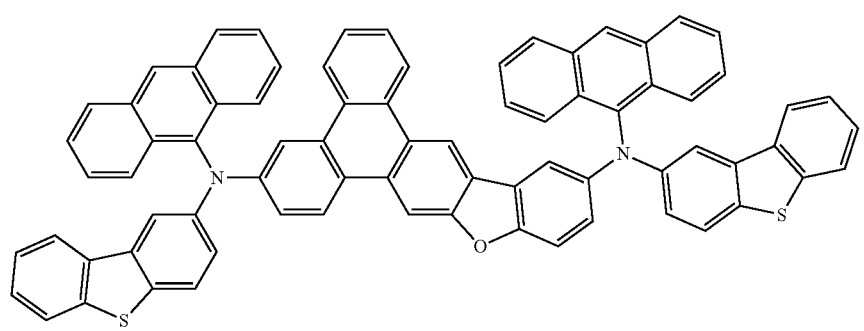

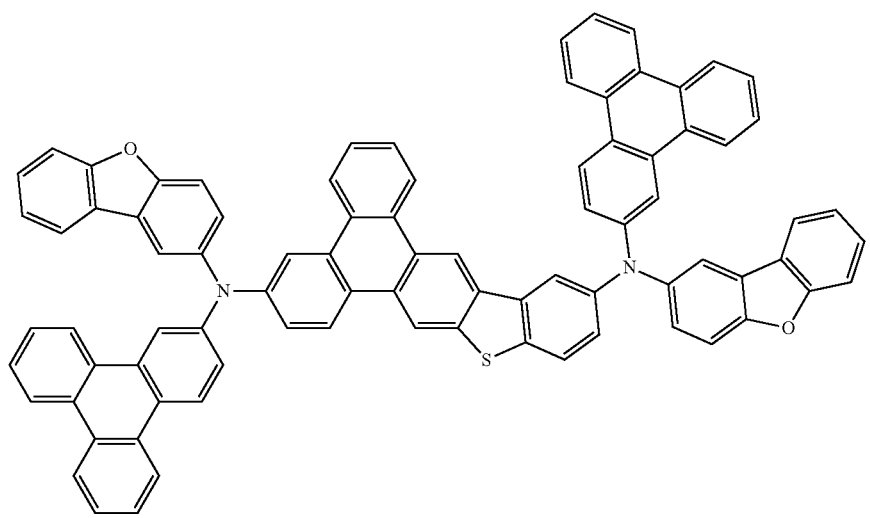
C58
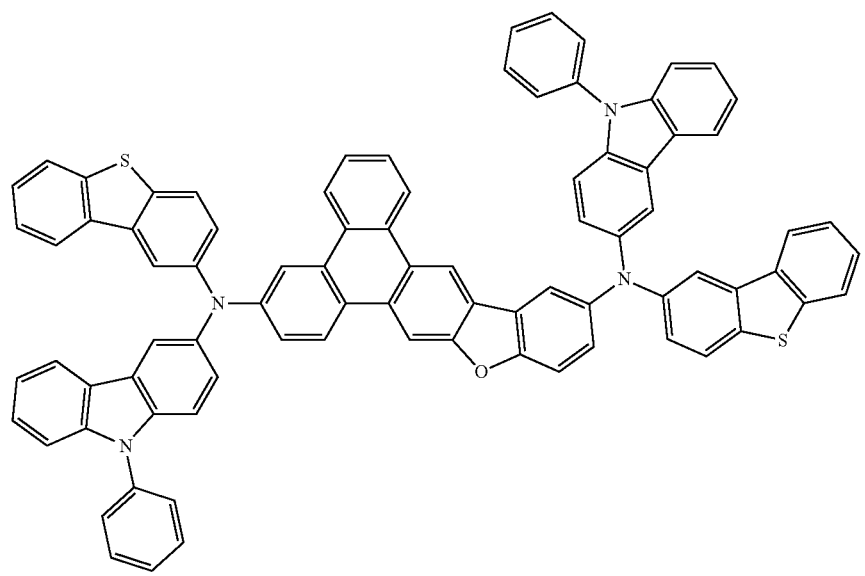
C59

-continued
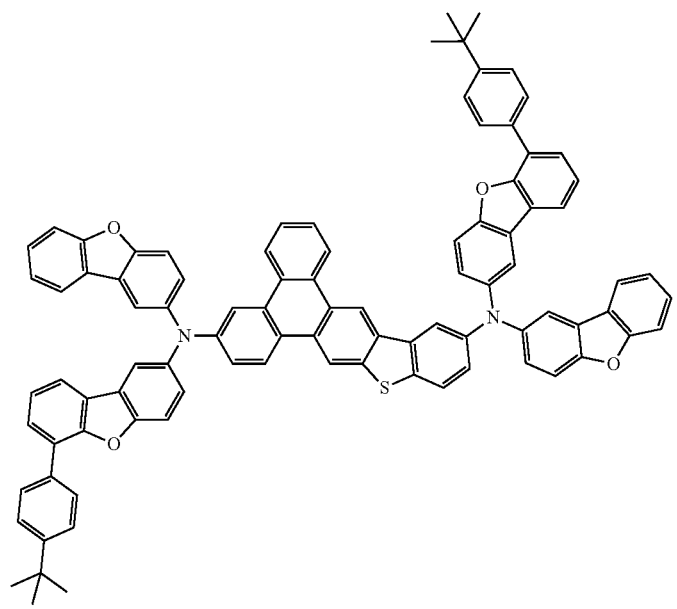
C60
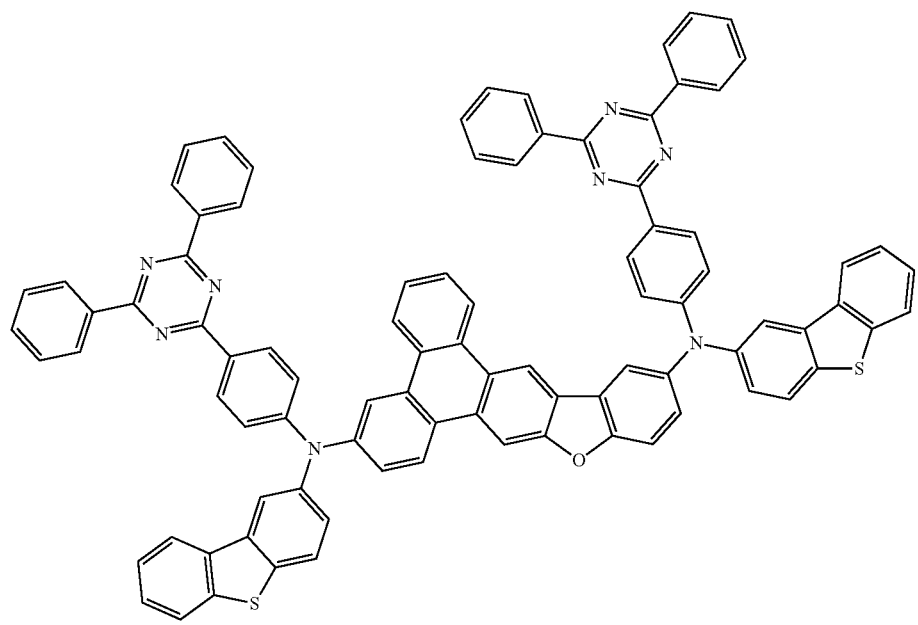
C61
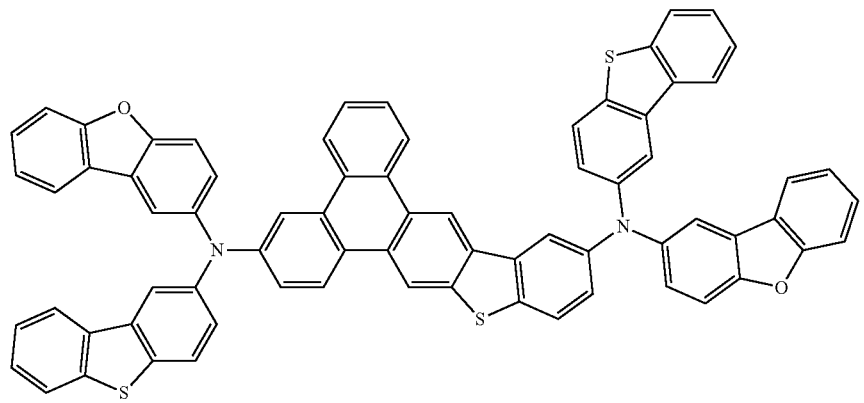
C62

-continued
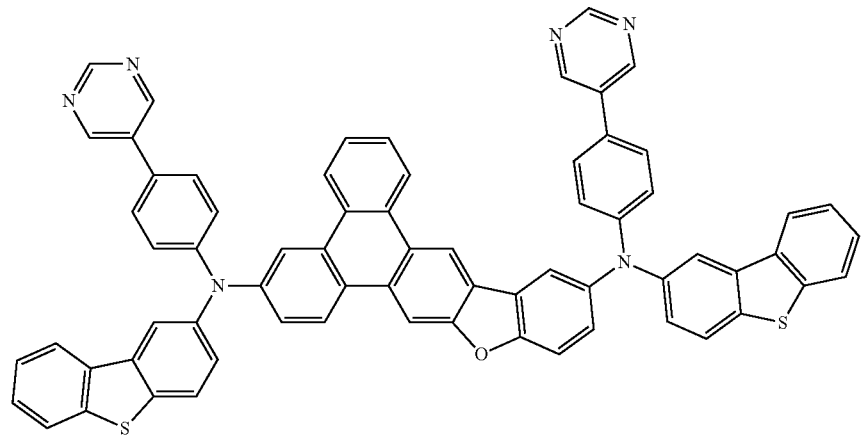
C63
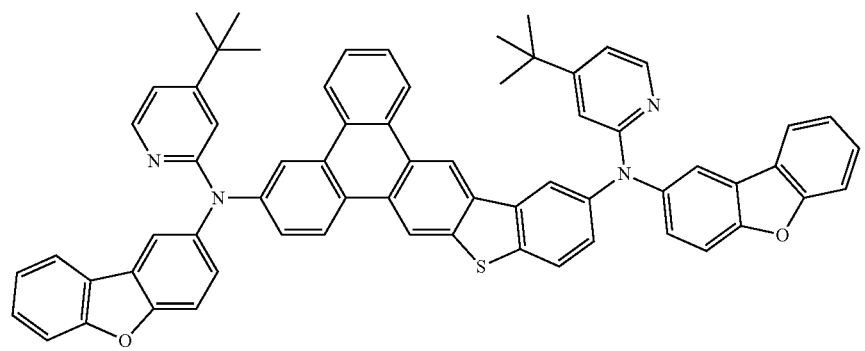
C64
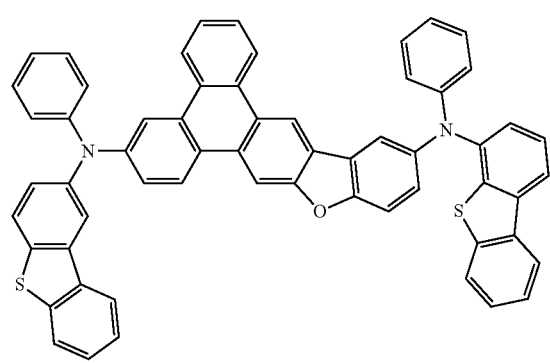
C65
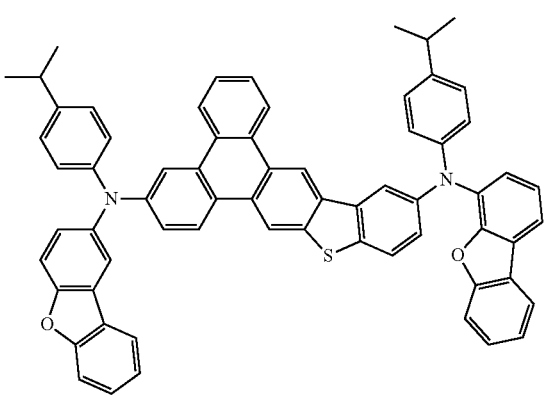
C66

-continued
C67
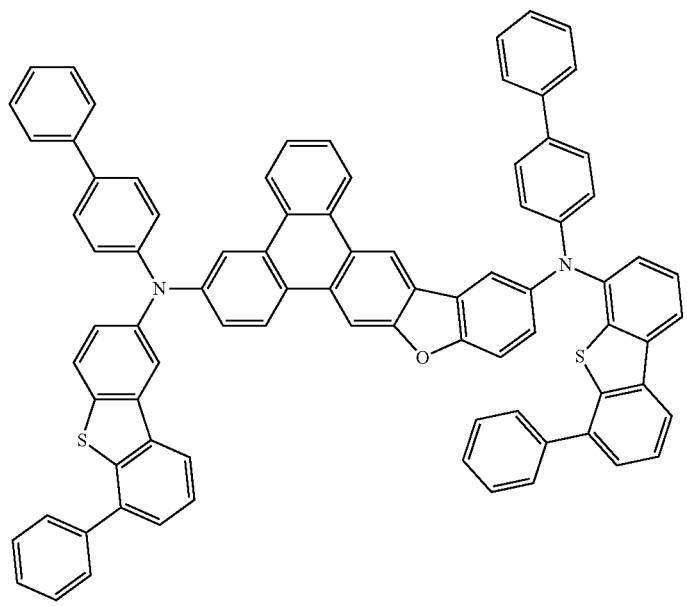
C68
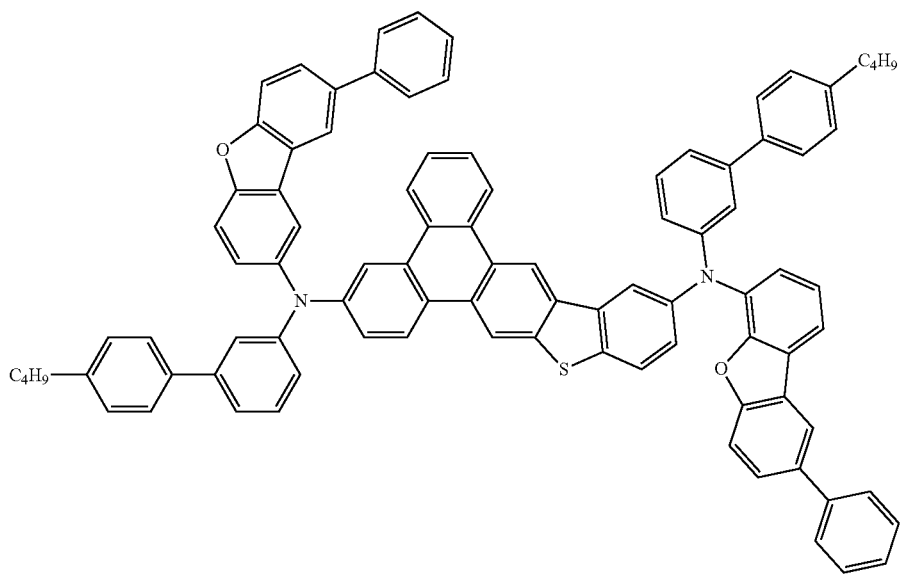

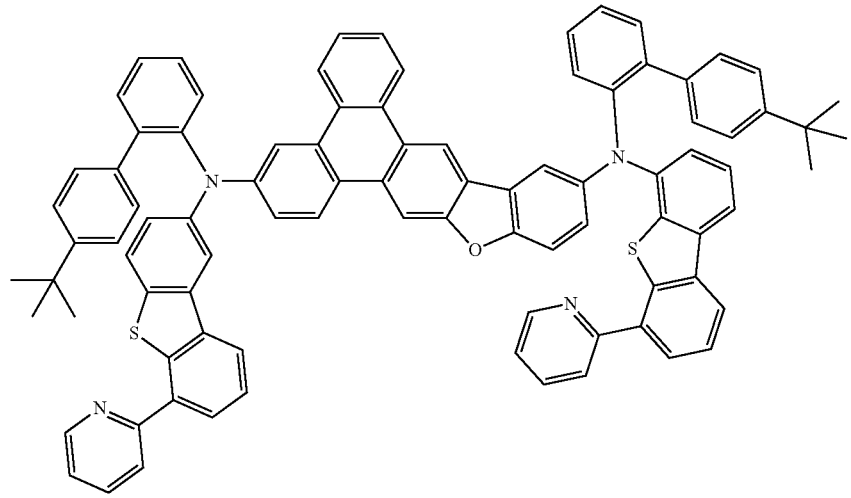
C69
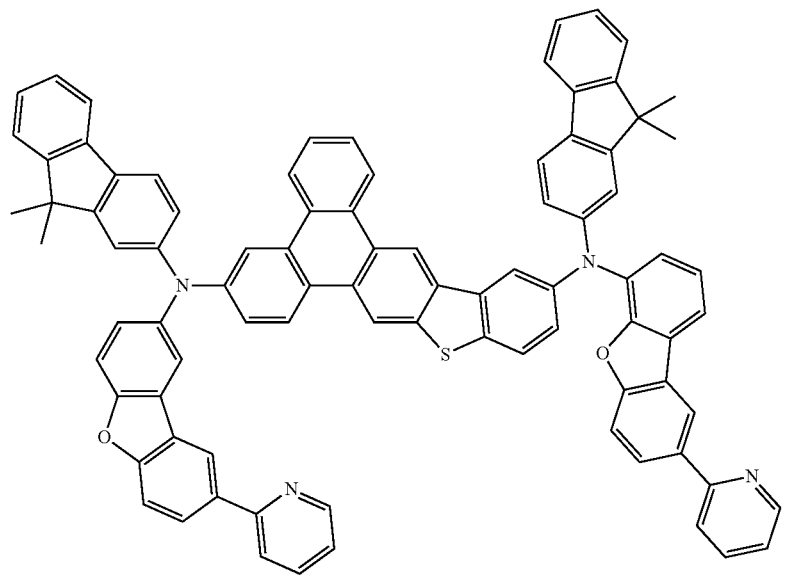
C70
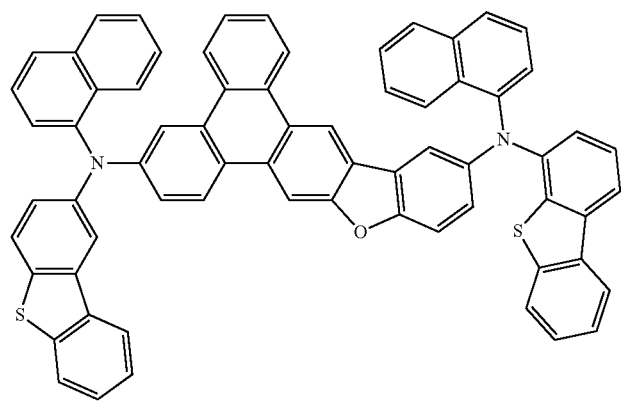
C71

-continued
C72
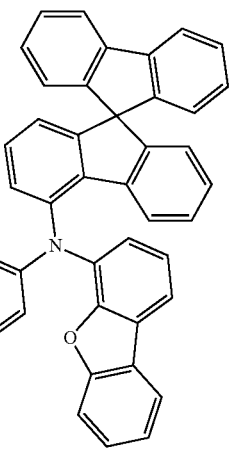
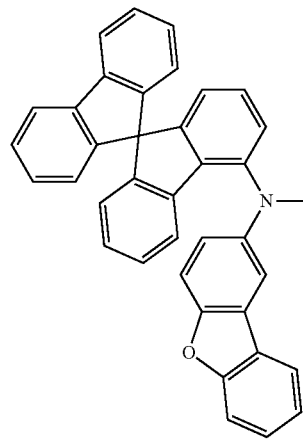
C73
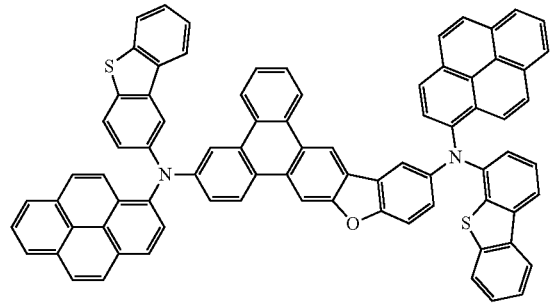
C74
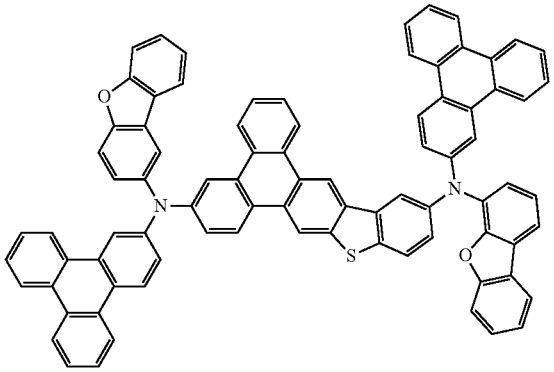
C75
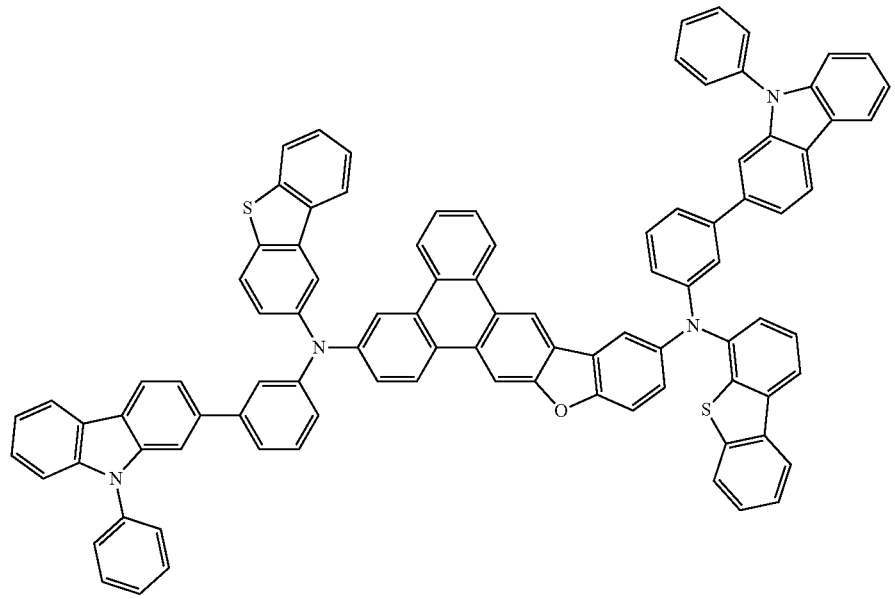

C76
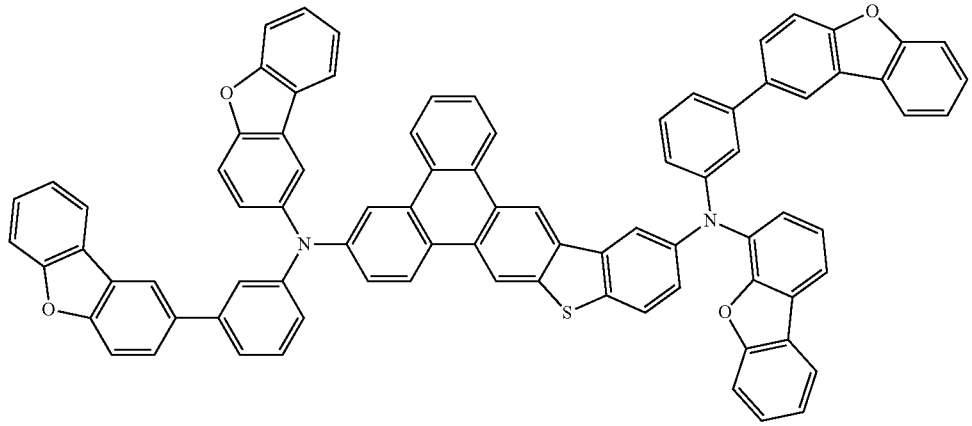
C77
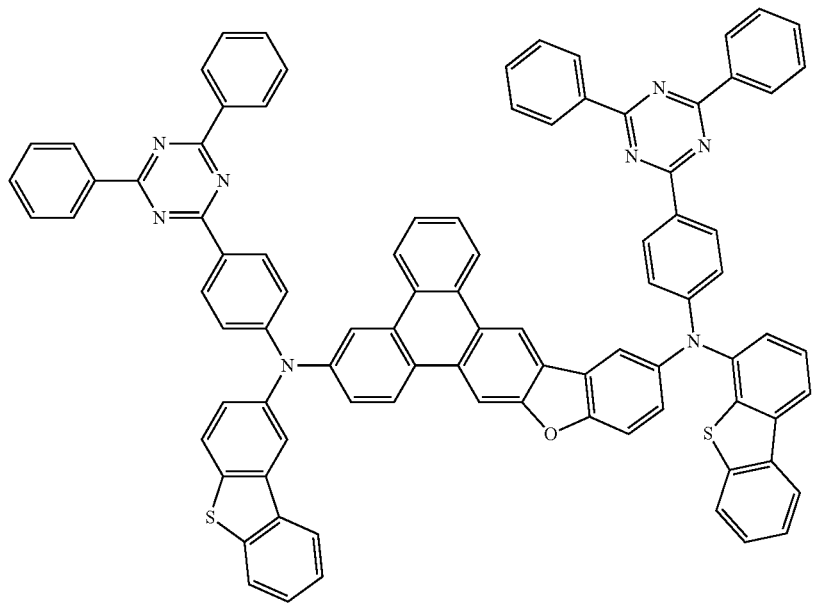
C78
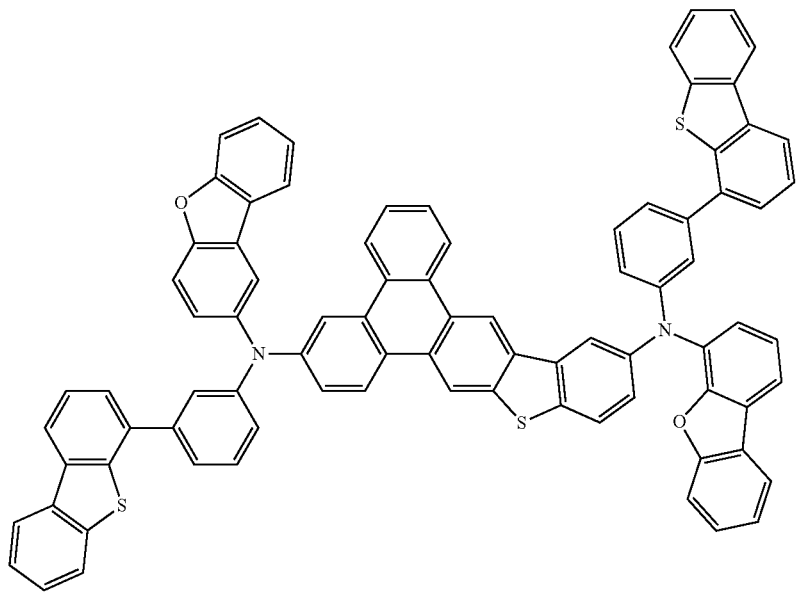

-continued
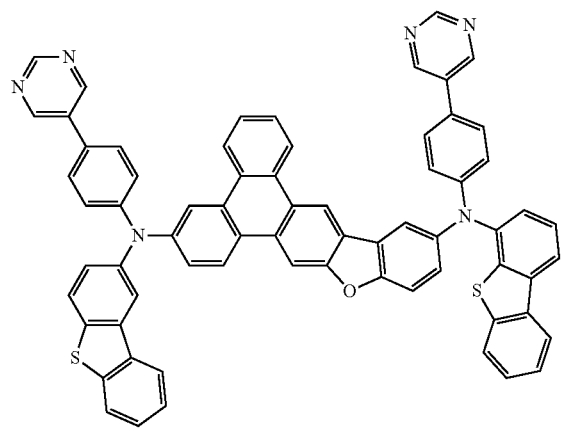
C79
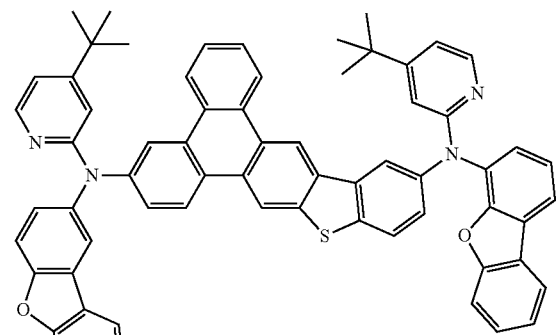
C80
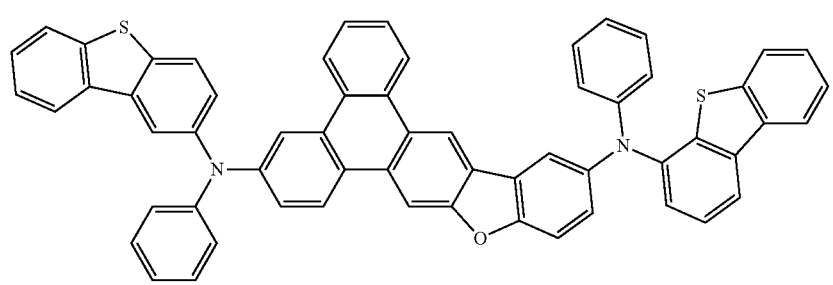
C81
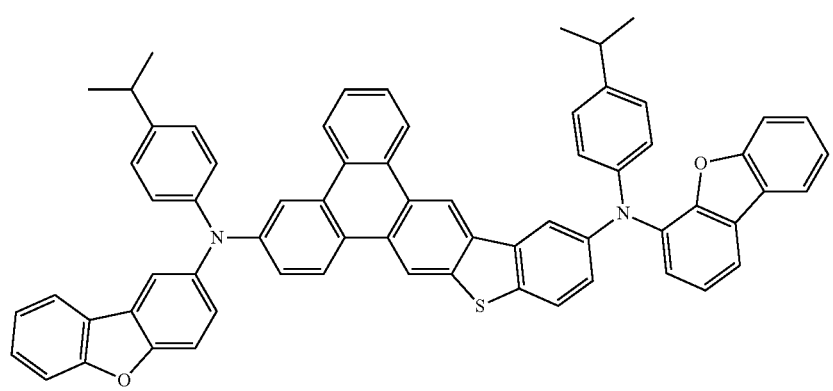
C82
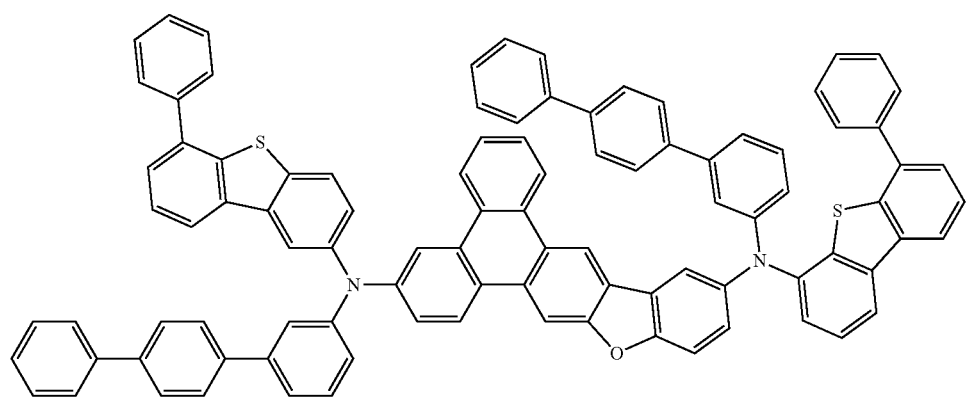
C83

-continued
C84
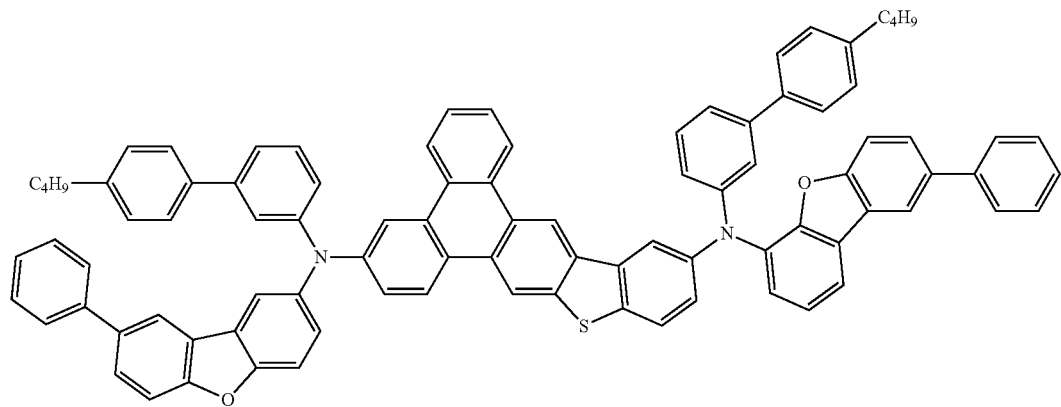
C85
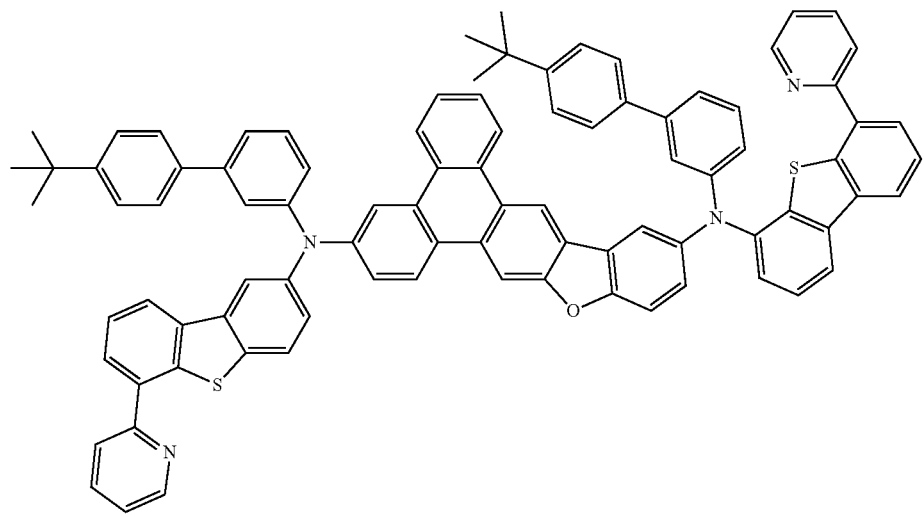
C86
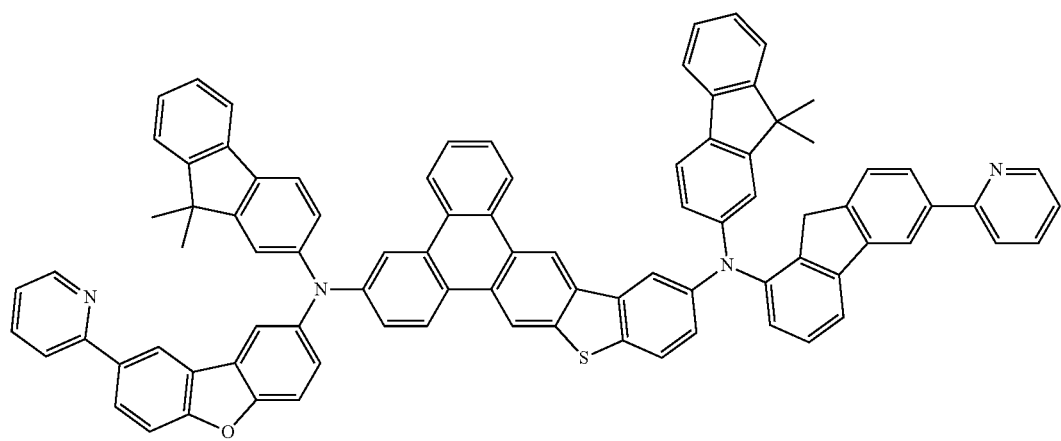

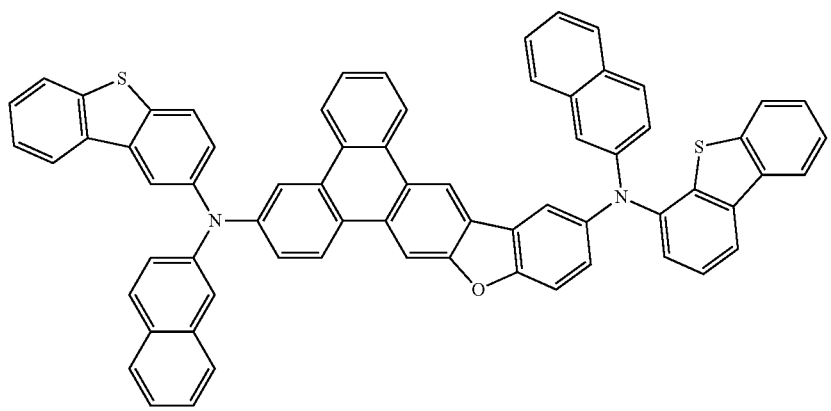
C87
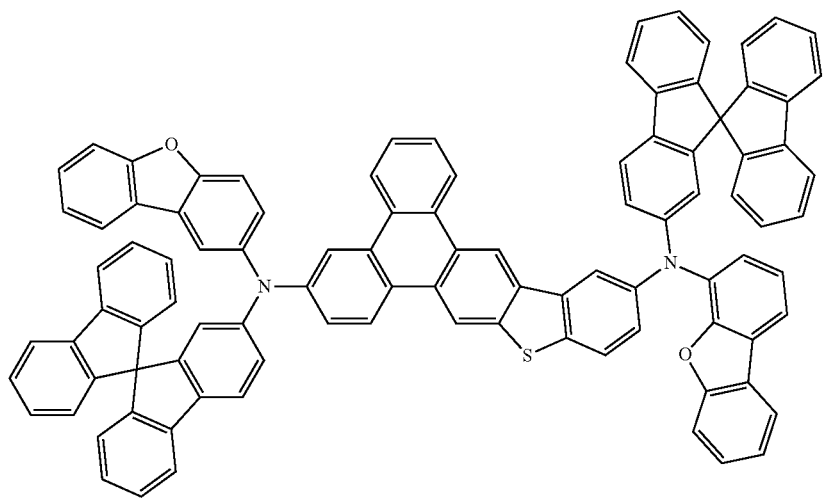
C88
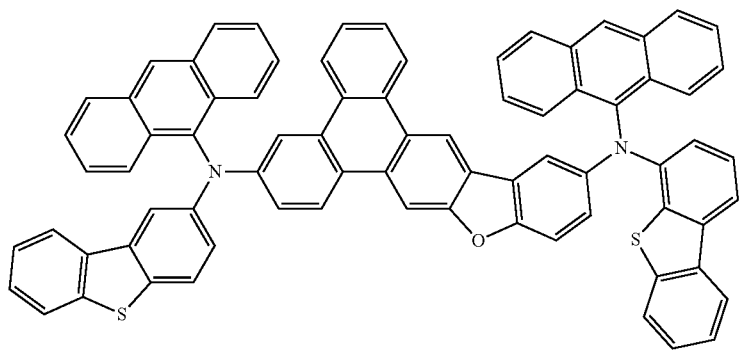
C89

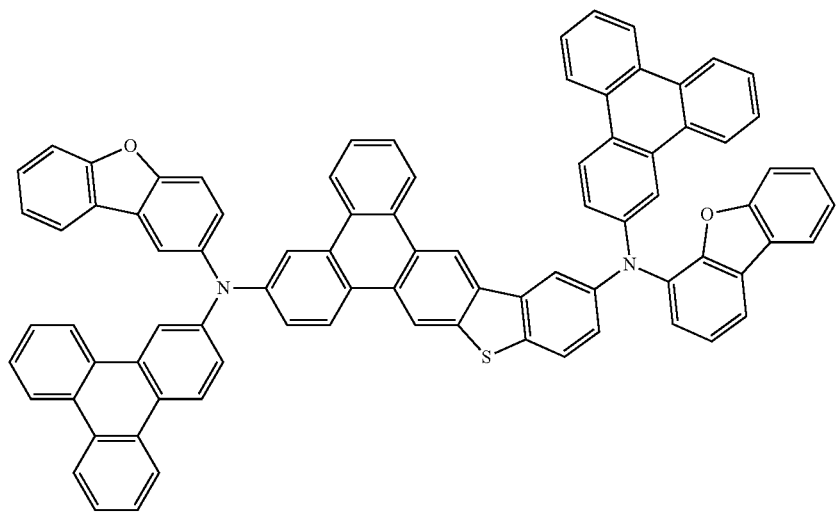
C90
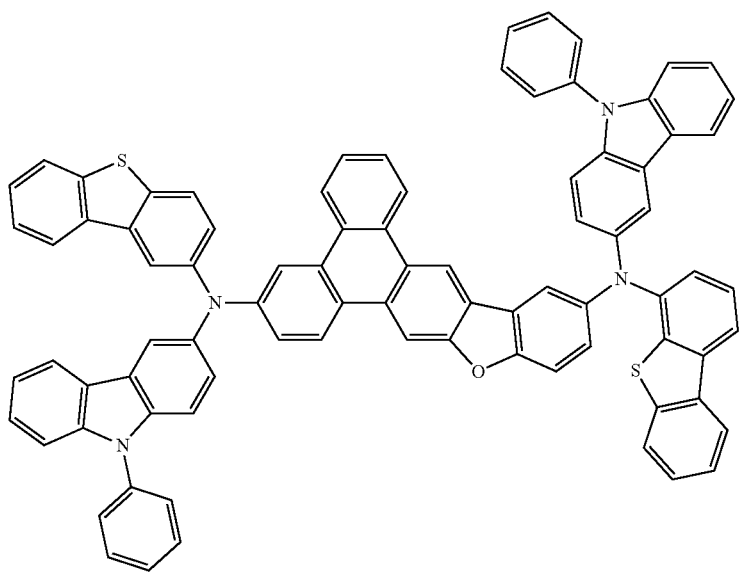
C91

C92
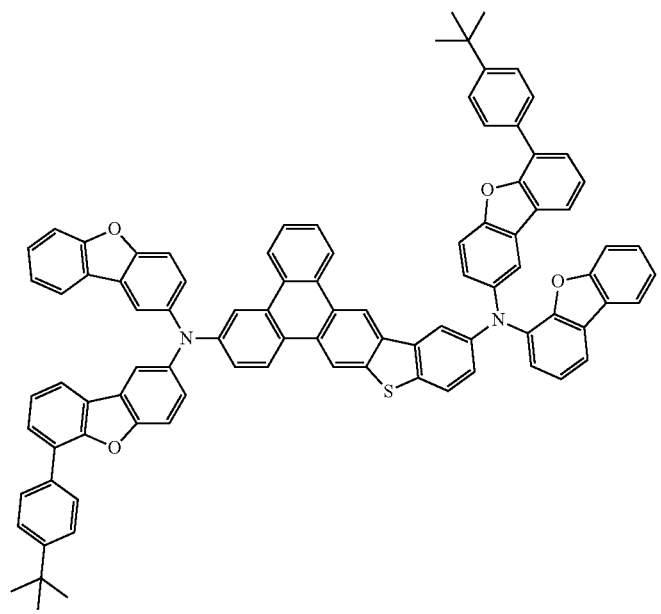
C93
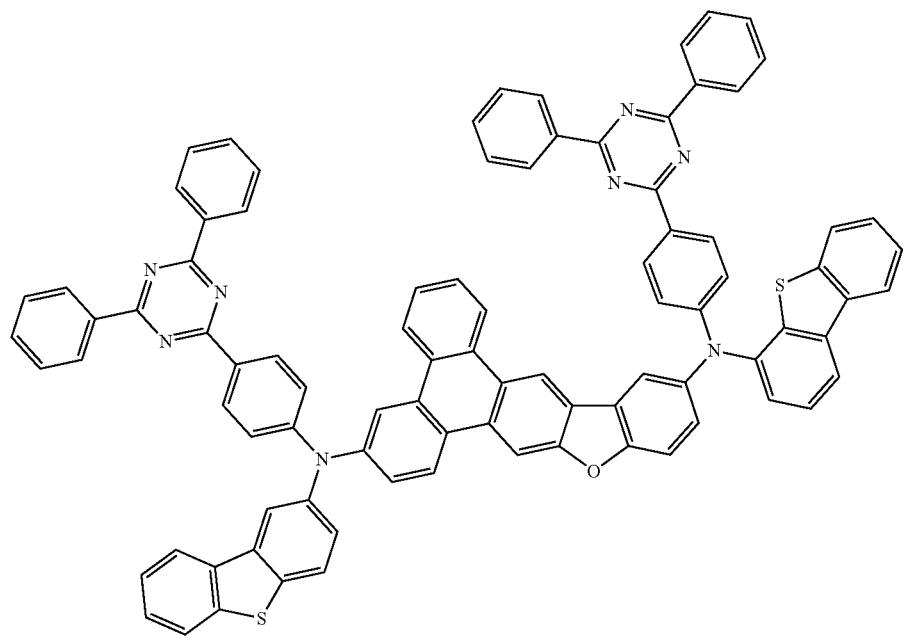
C94
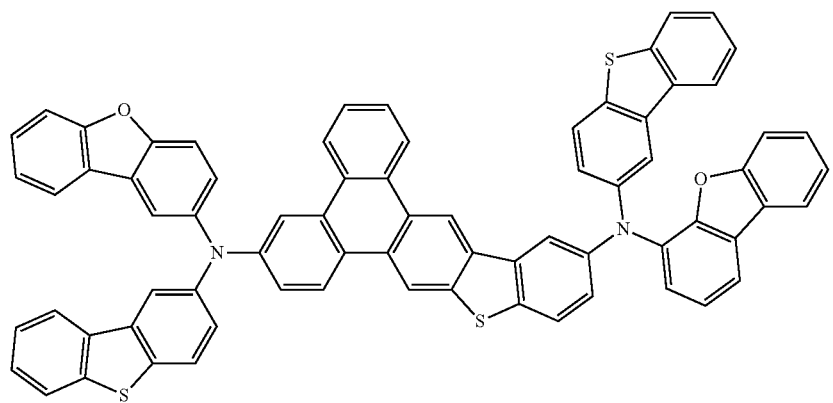

-continued
C95
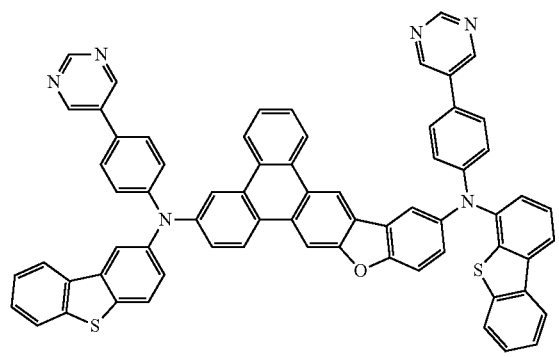
C96
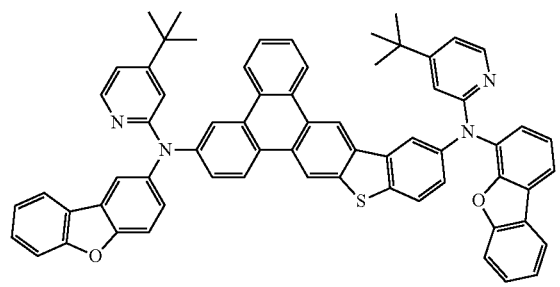
C97
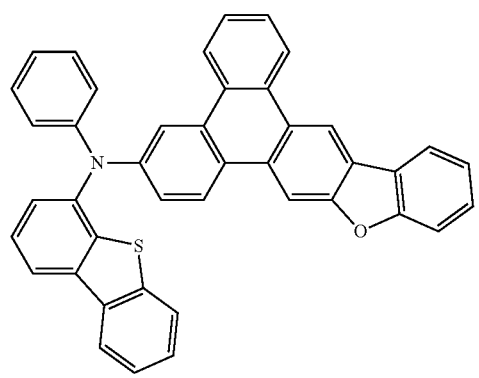
C98
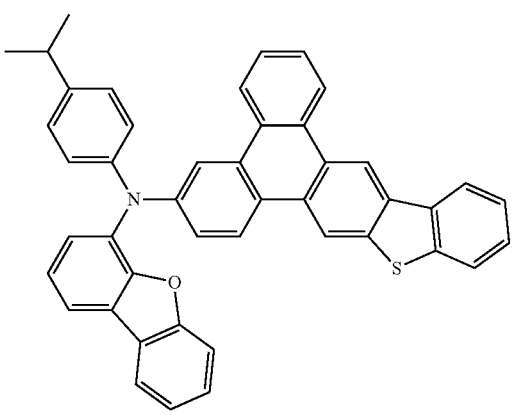
C99
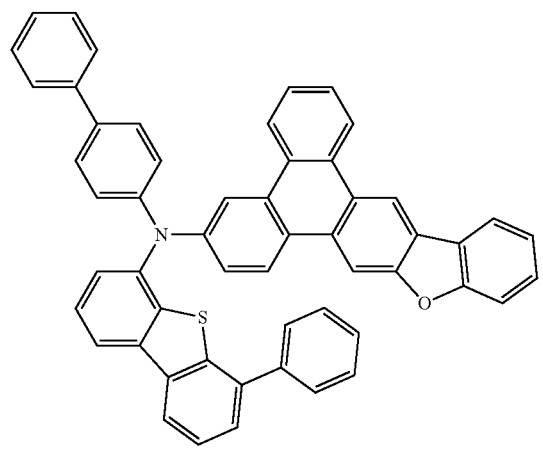
C100
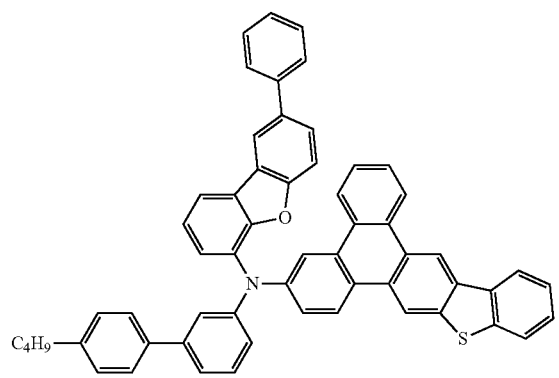

-continued
C101
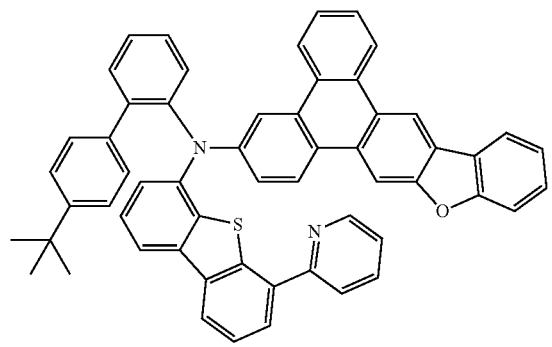
C102
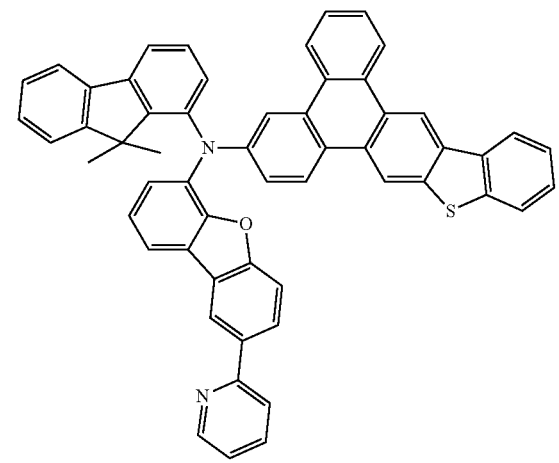
C103
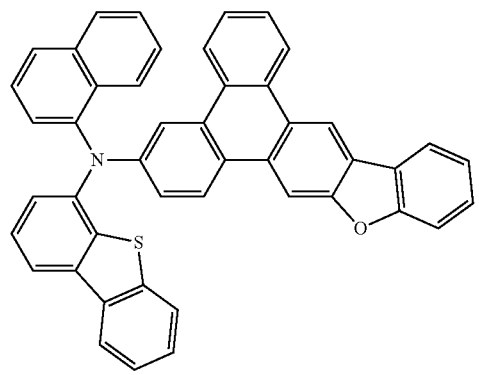
C104
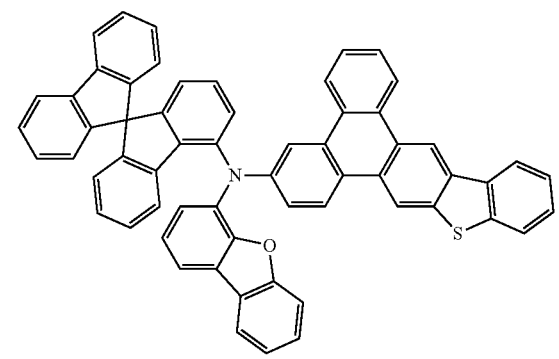
C105
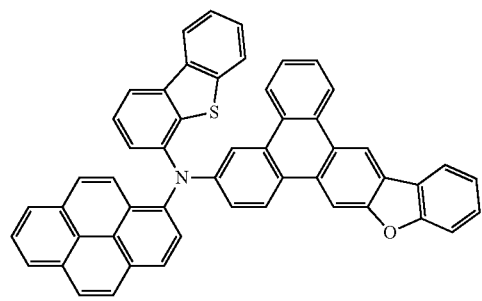
C106
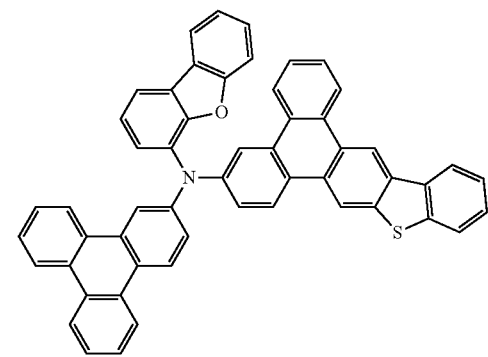
C107
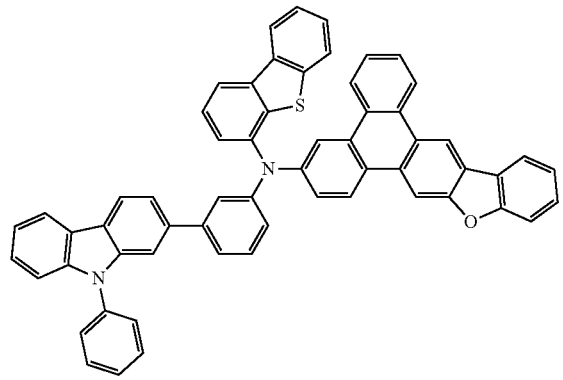
C108
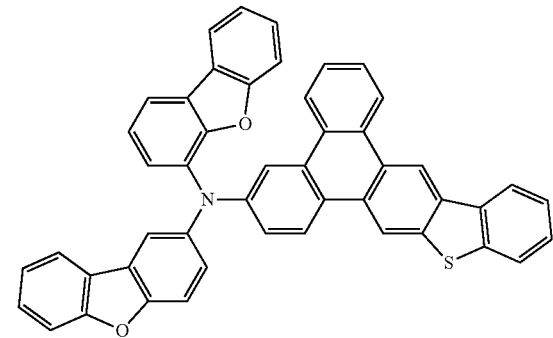

-continued
C109
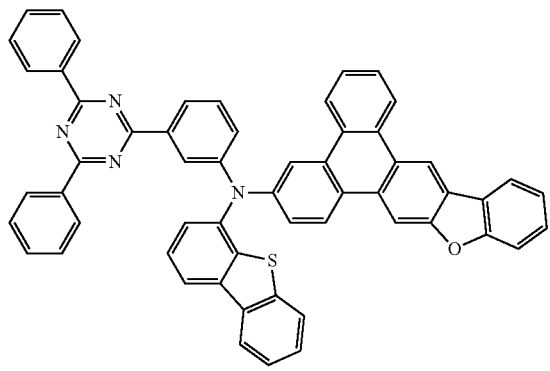
C110
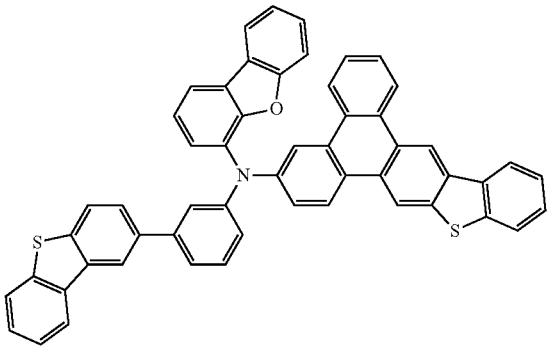
C111
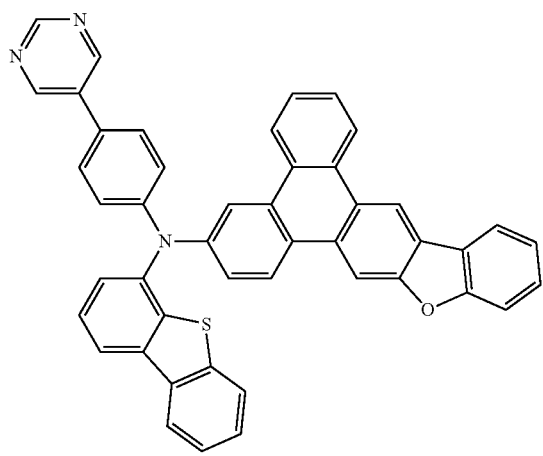
C112
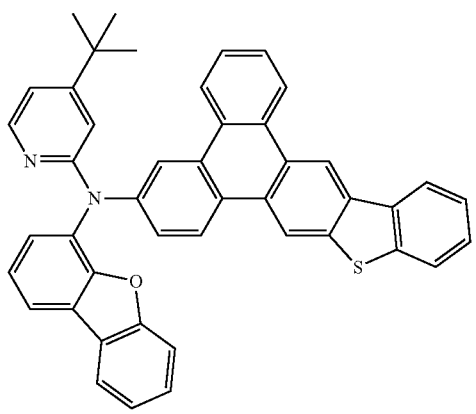
C113
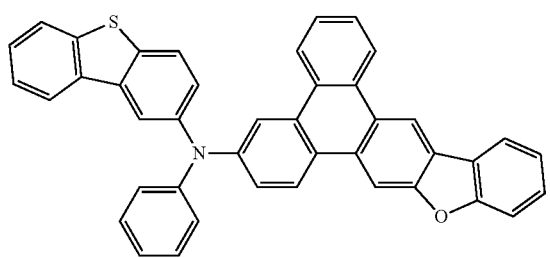
C114
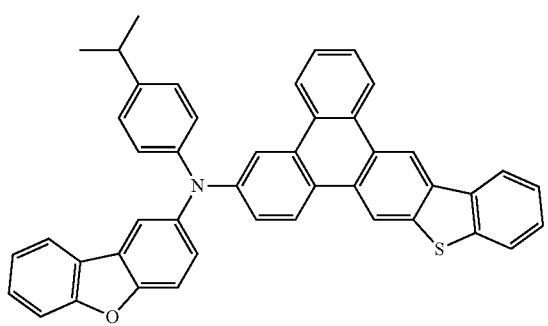
C115
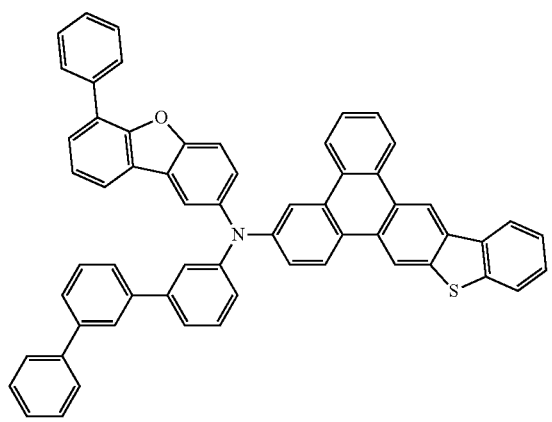
C116
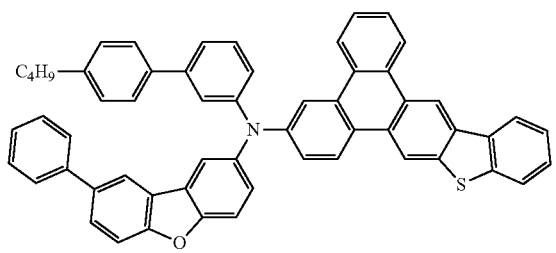

-continued
C117
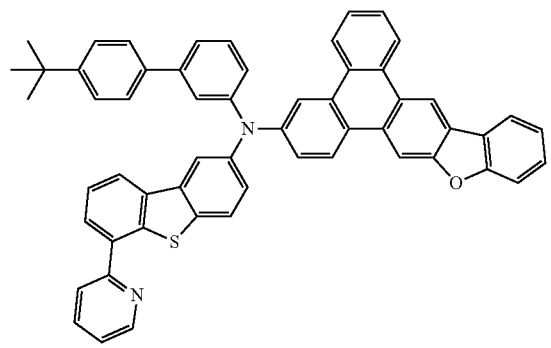
C118
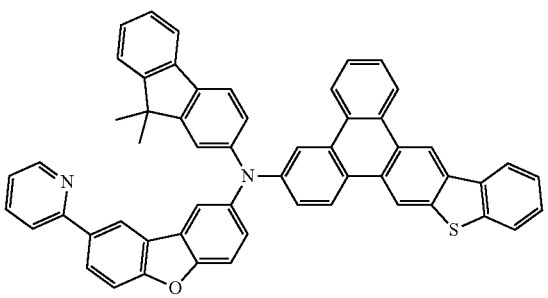
C119
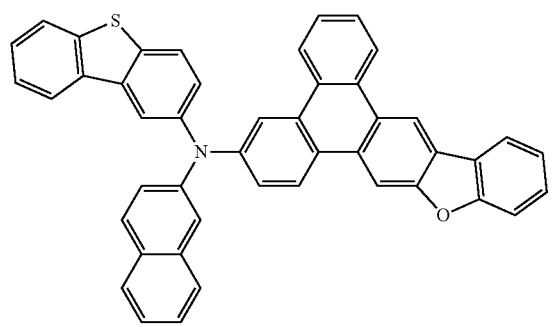
C120
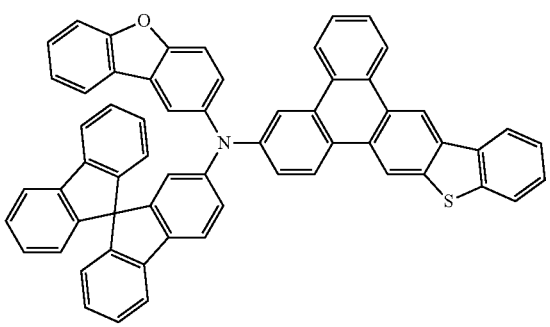
C121
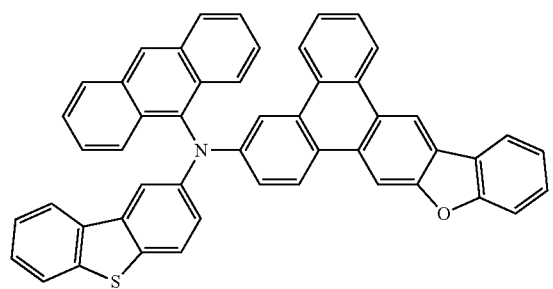
C122
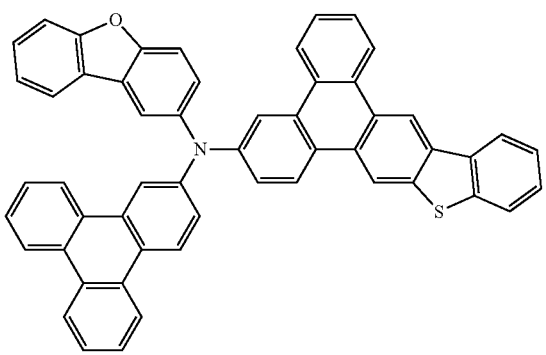
C123
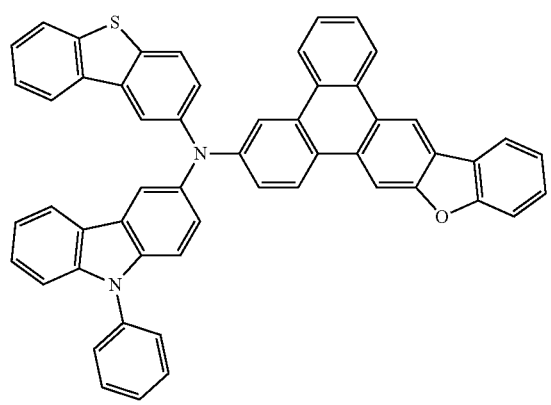
C124
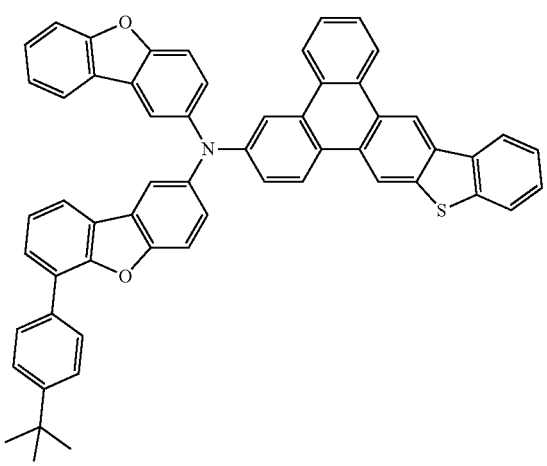

-continued
C125
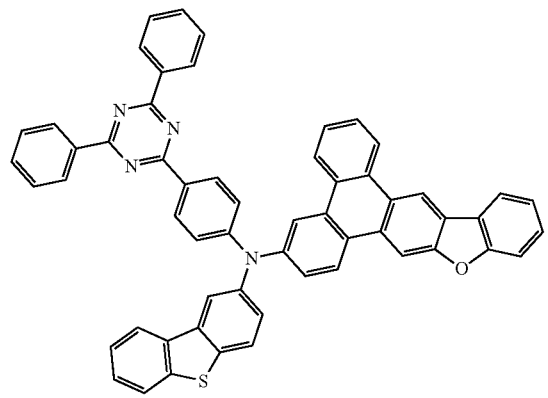
C126
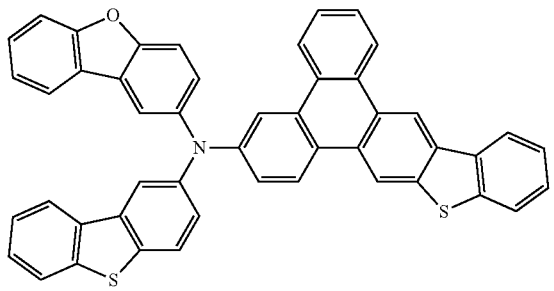
C127
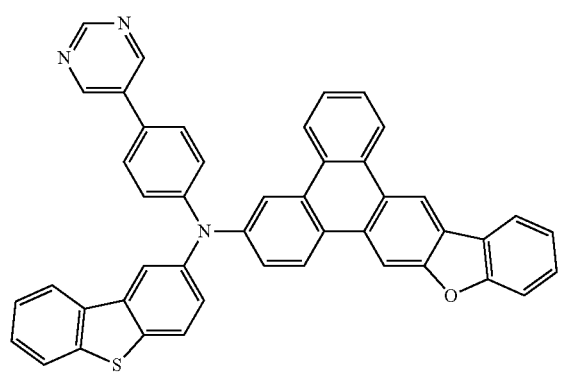
C128
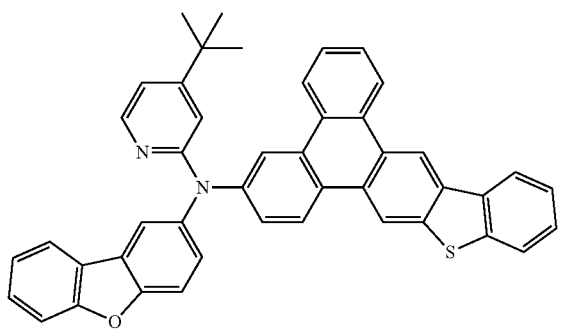
C129
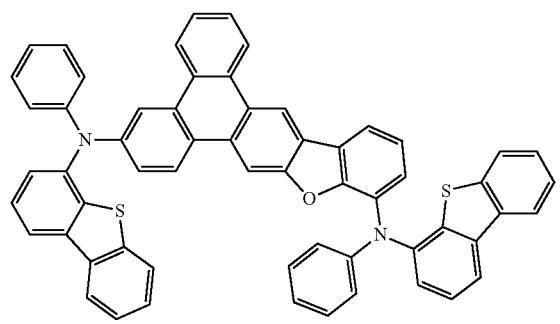
C130
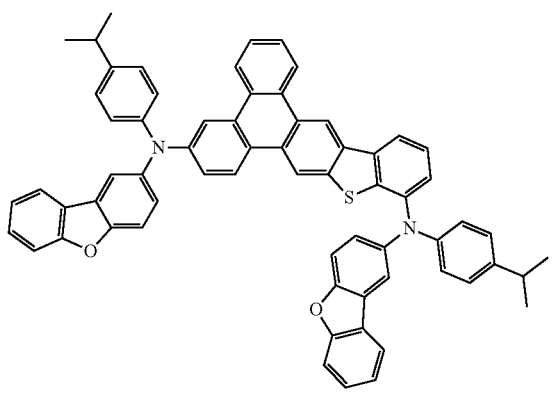

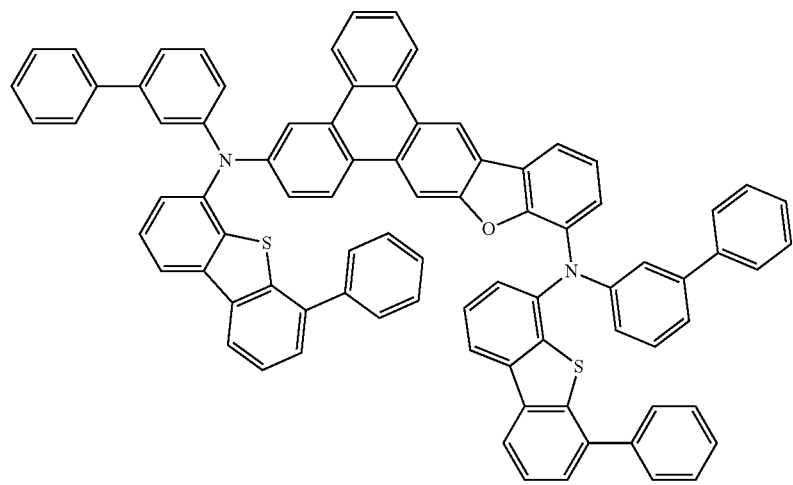
C131
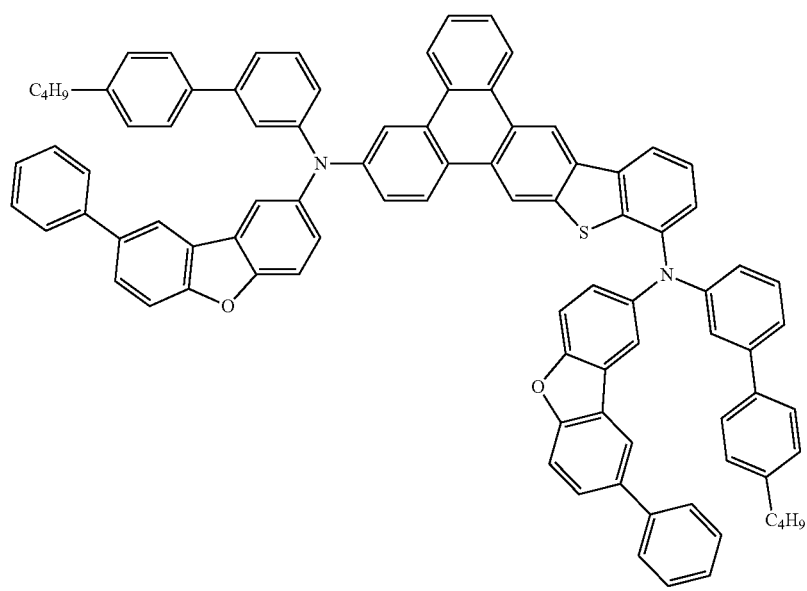
C132
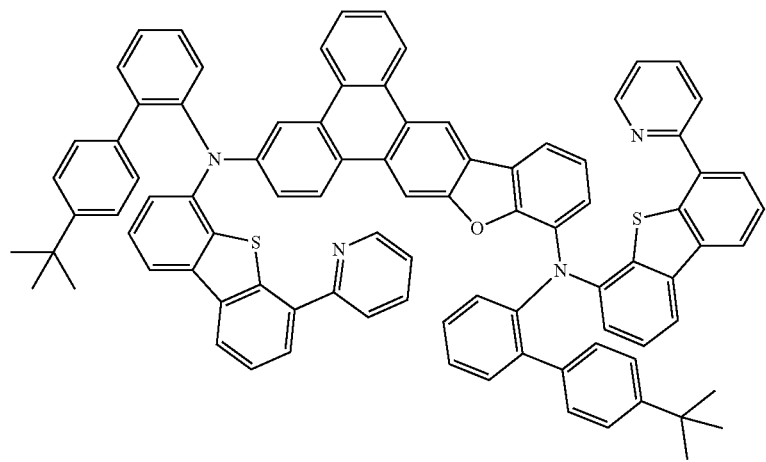
C133

-continued
C134
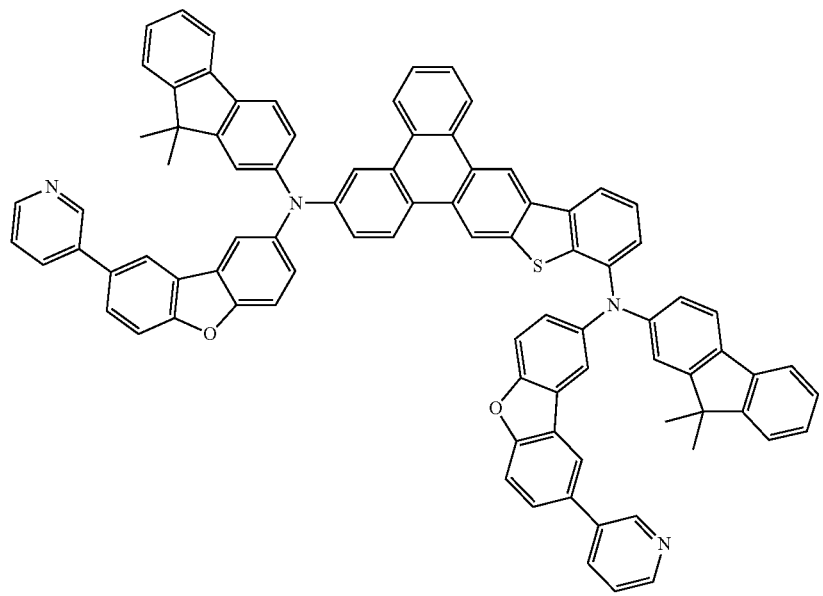
C135
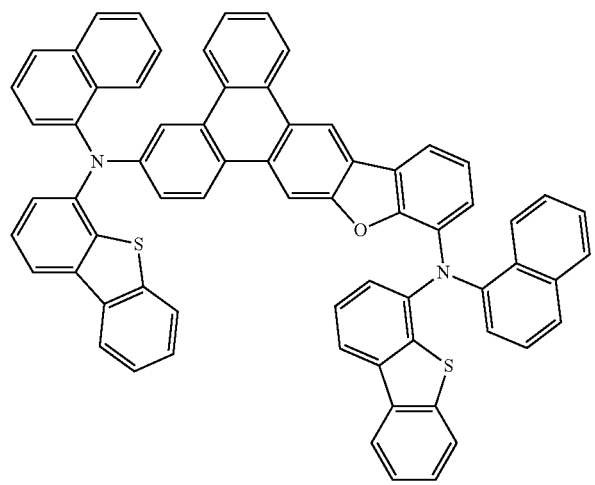
C136
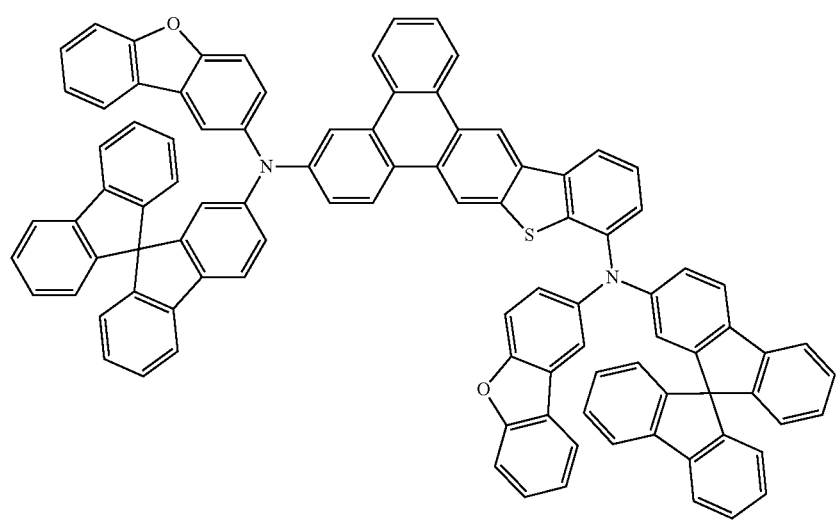

-continued
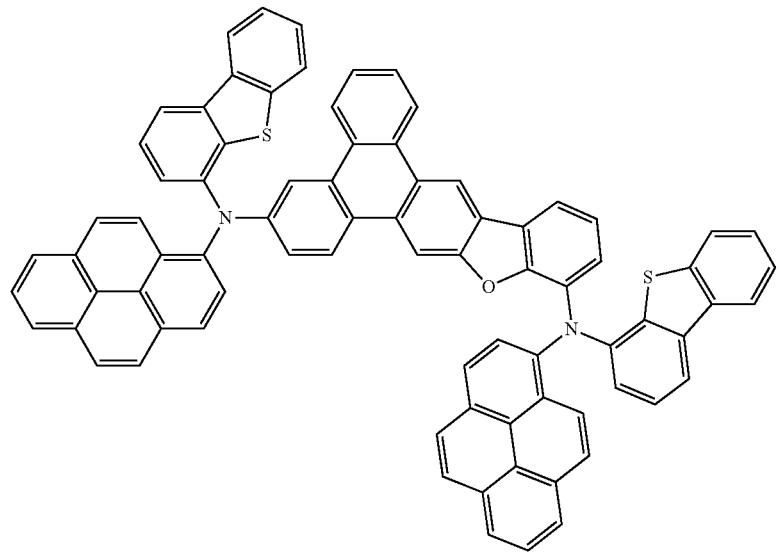
C137
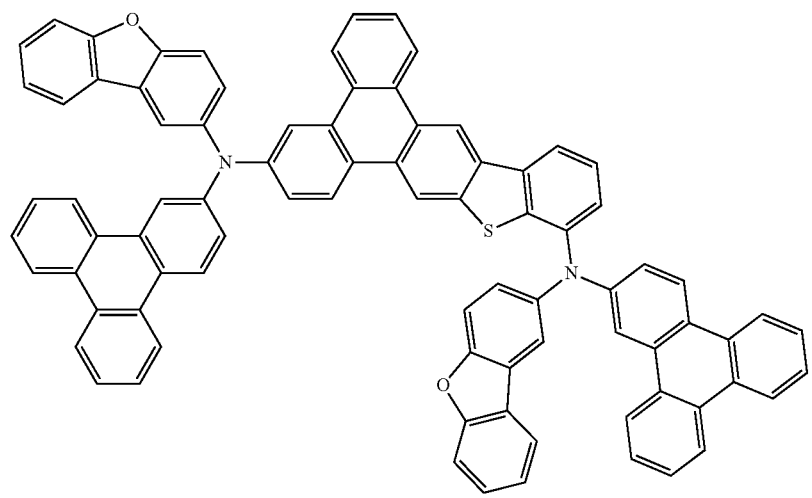
C138
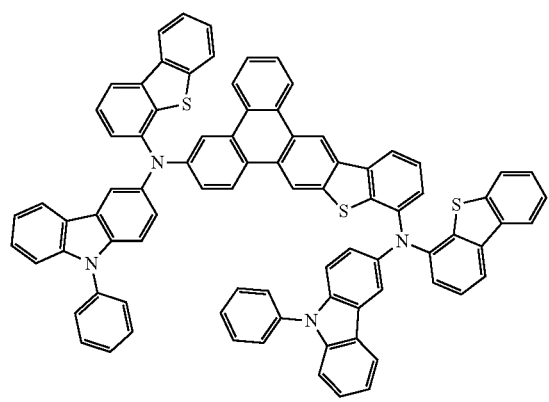
C139
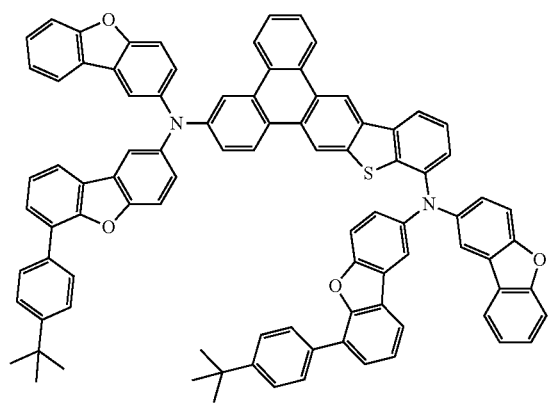
C140

-continued
C141
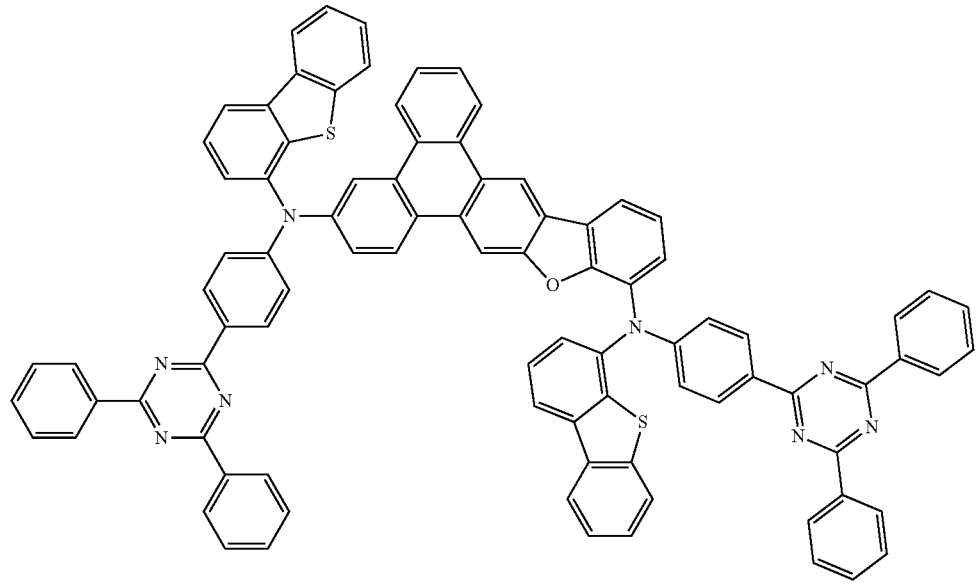
C142 C143
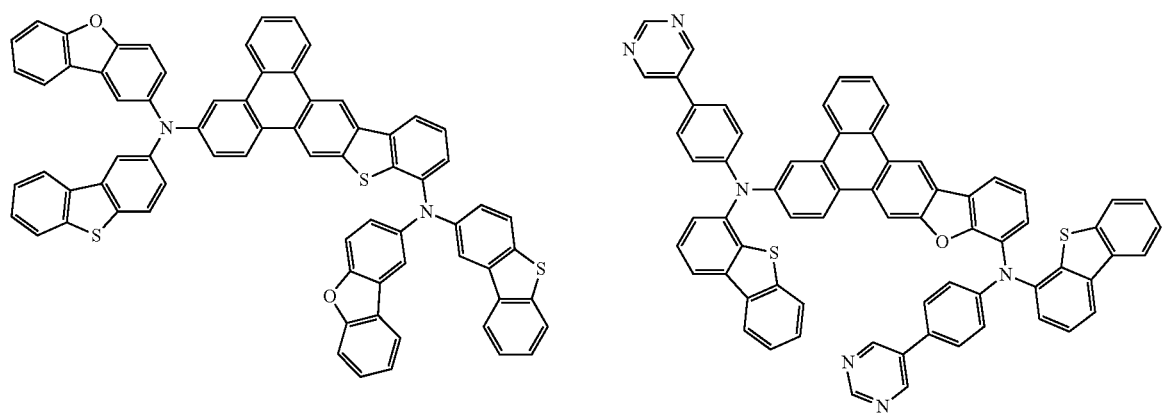
C144 C145
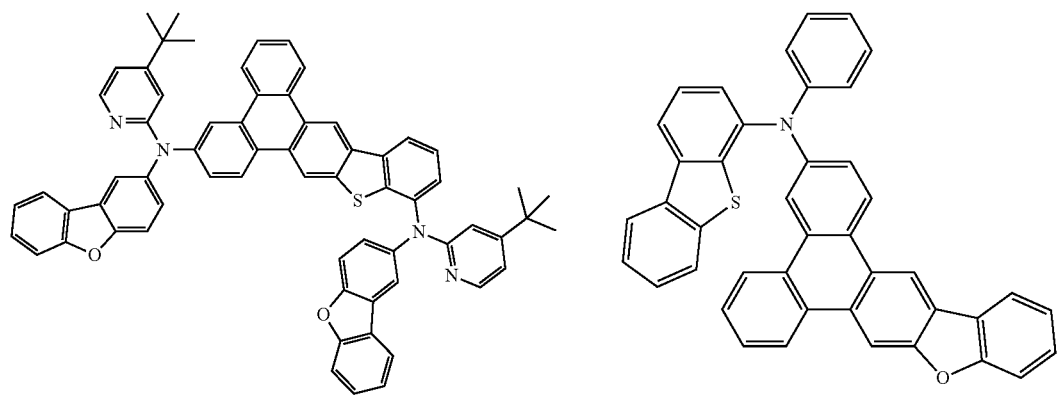

C146 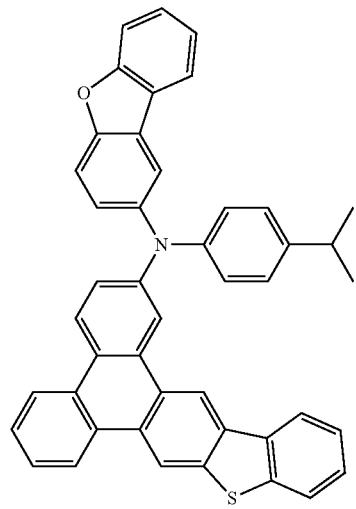
C147 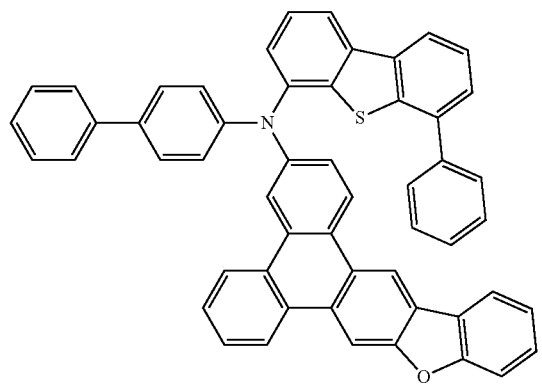
C148 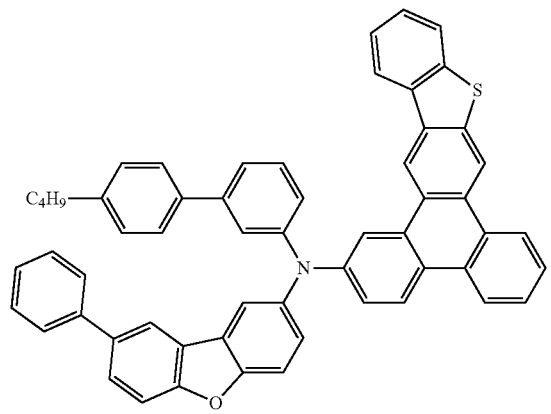
C149 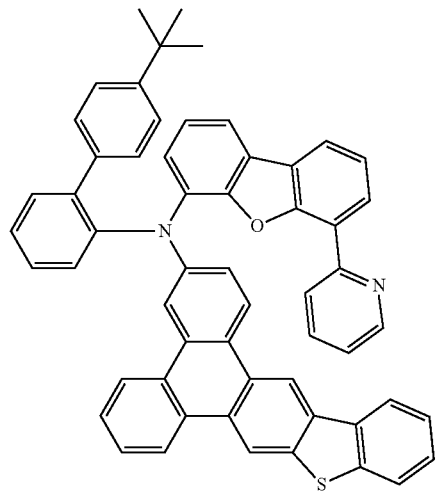
C150 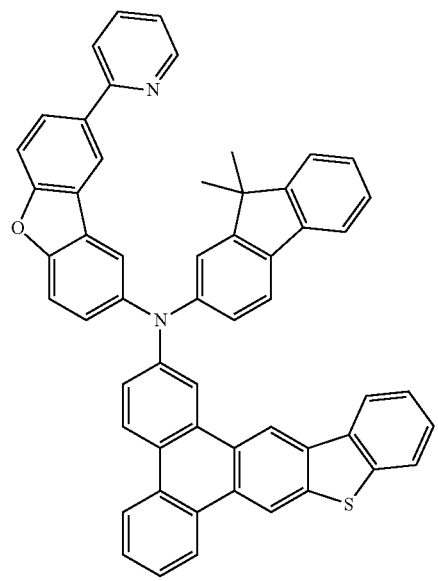
C151 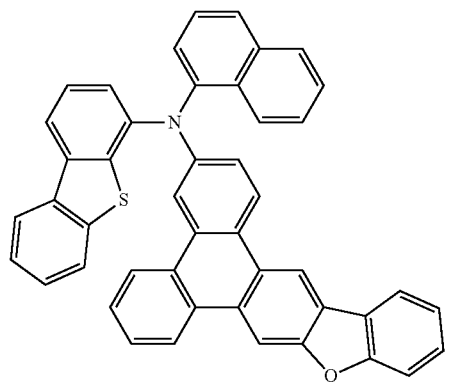

-continued
C152
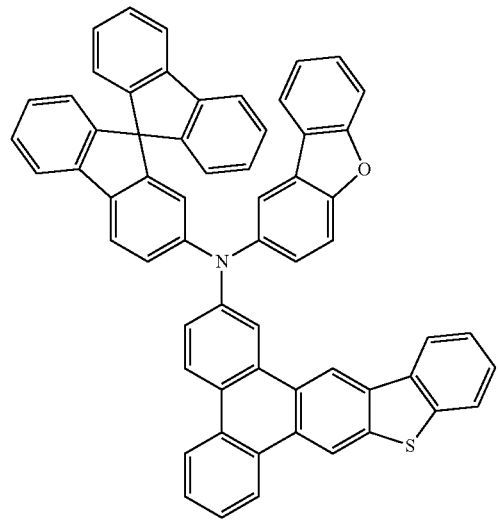
C153
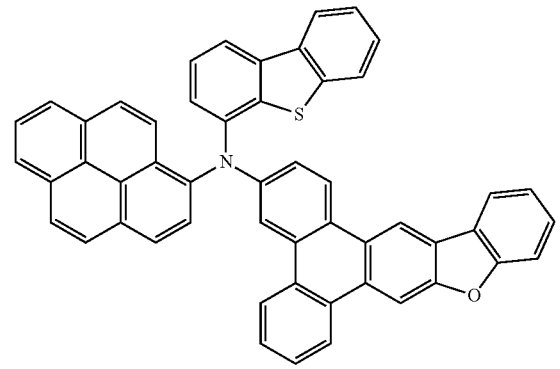
C154
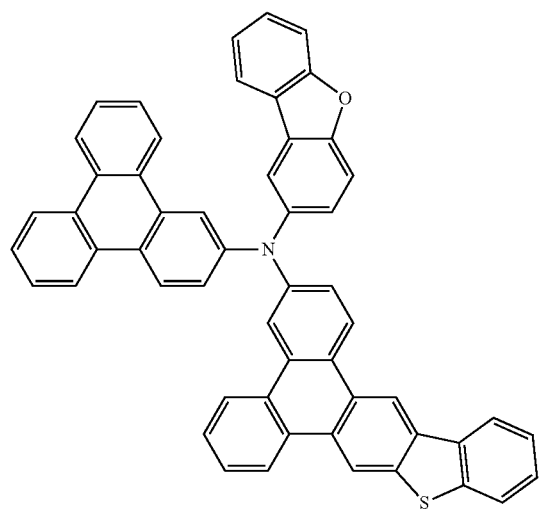
C155
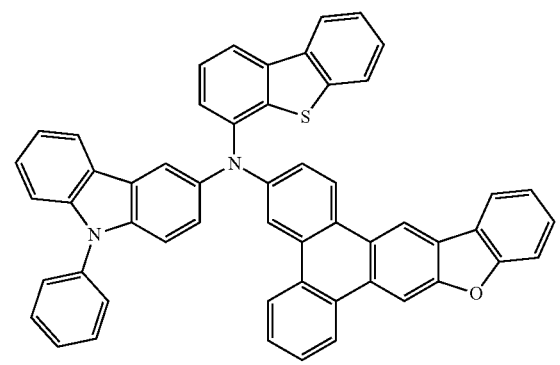

-continued
C156
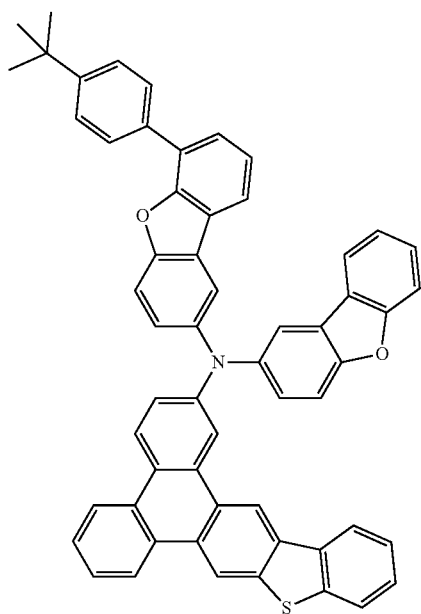
C157
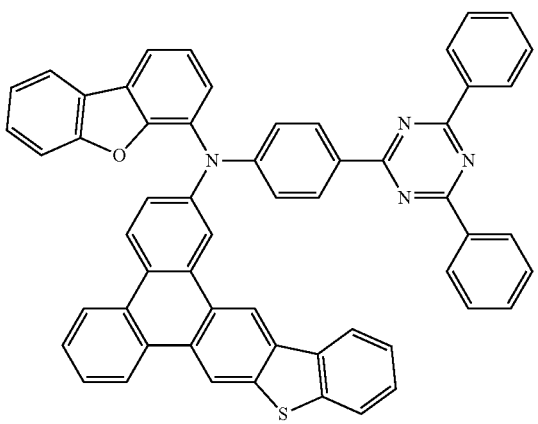
C158
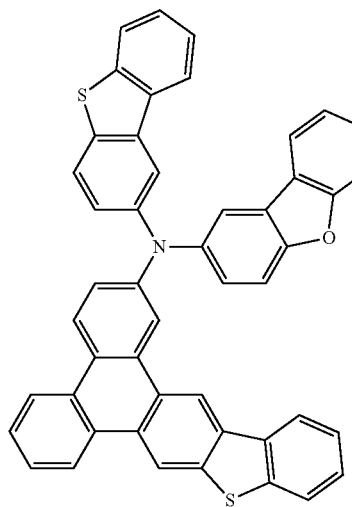
C159
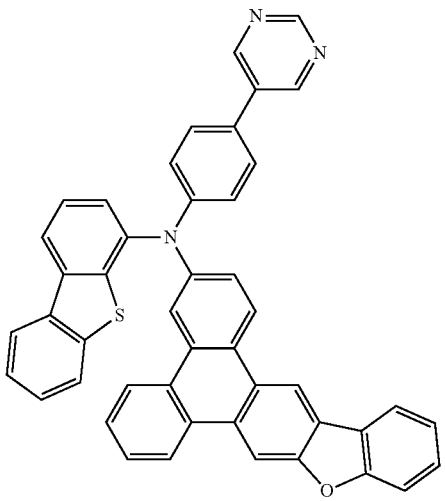
C160
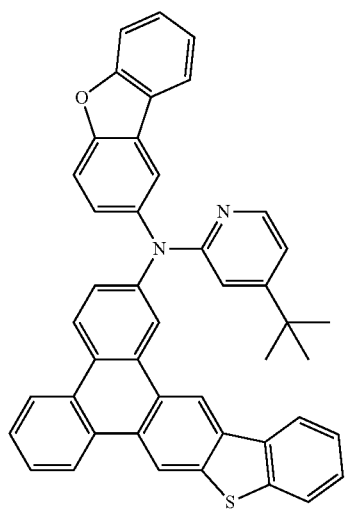
C161
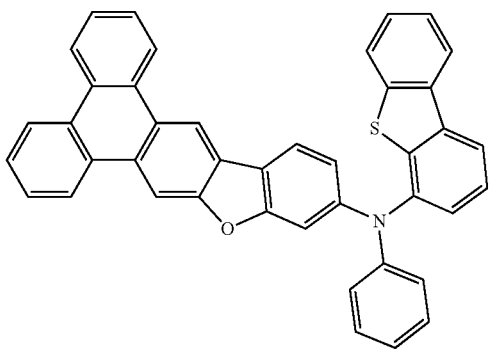

-continued
C162
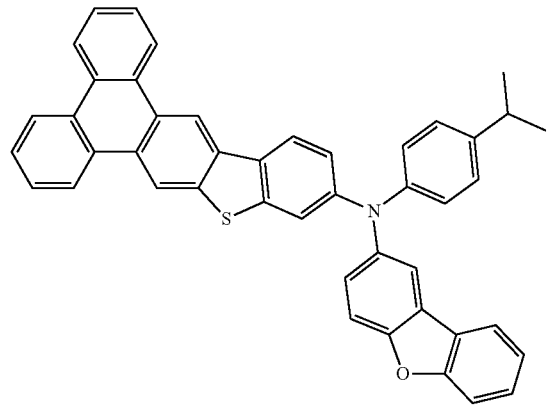
C163
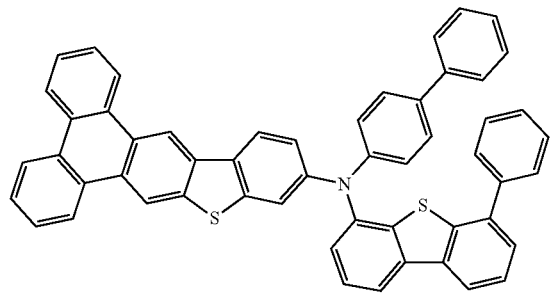
C164
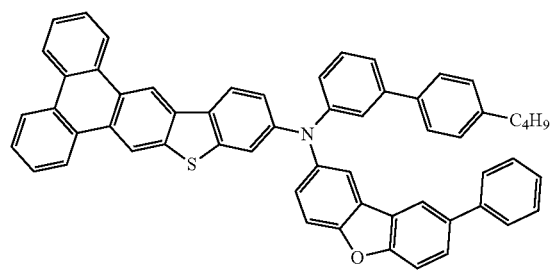
C165
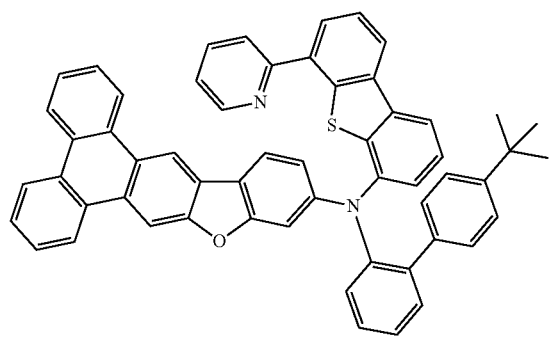
C166
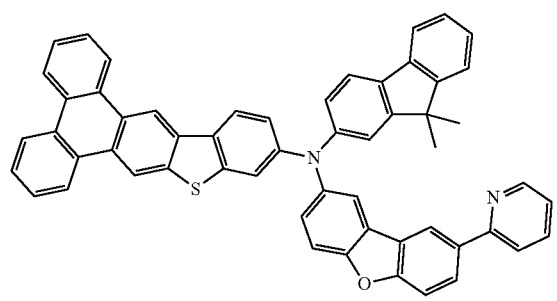
C167
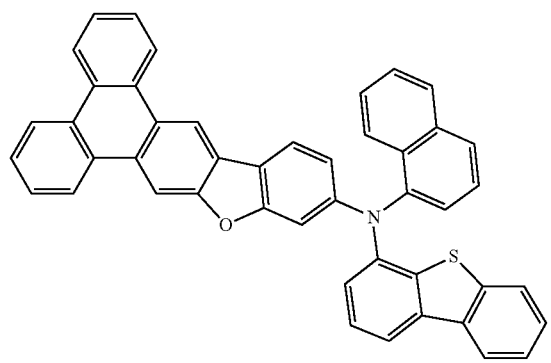
C168
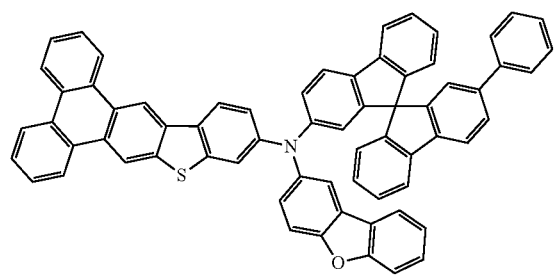
C169
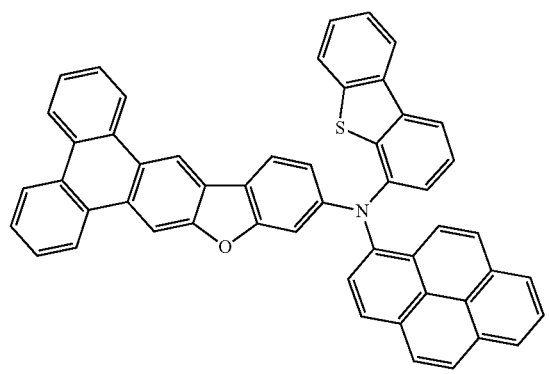

-continued
C170
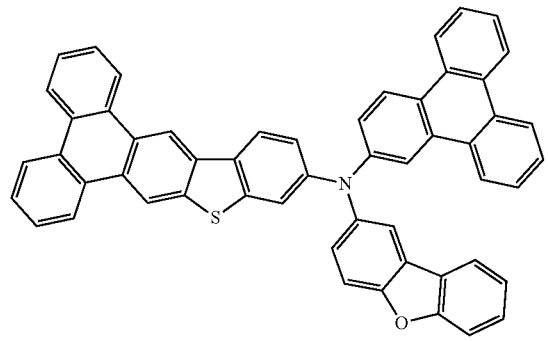
C171
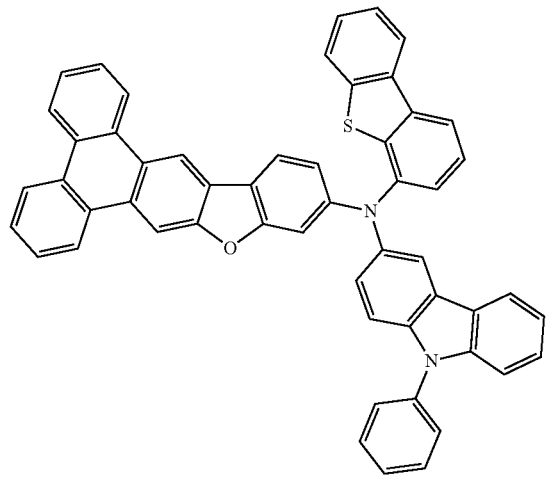
C172
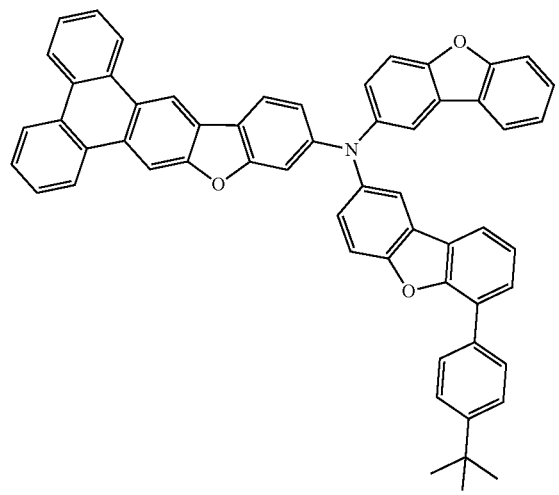
C173
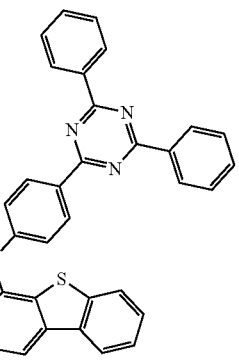
C174
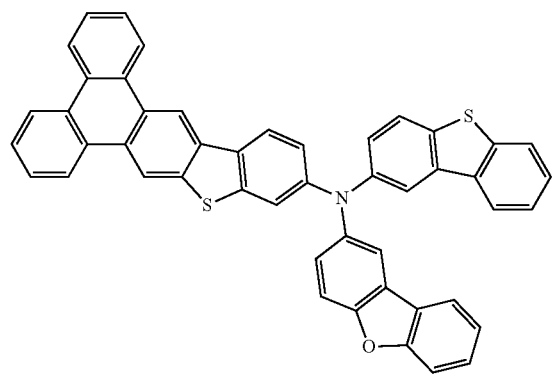
C175
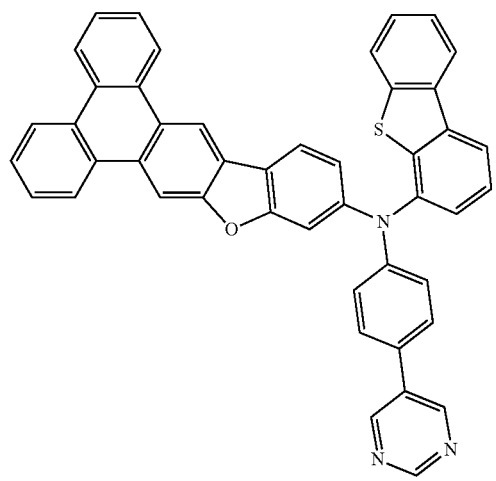

-continued
C176
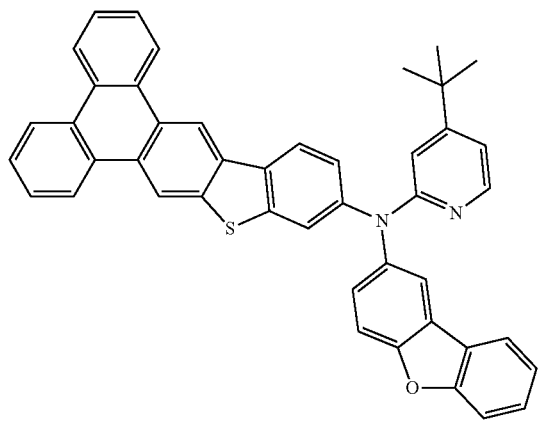
C177
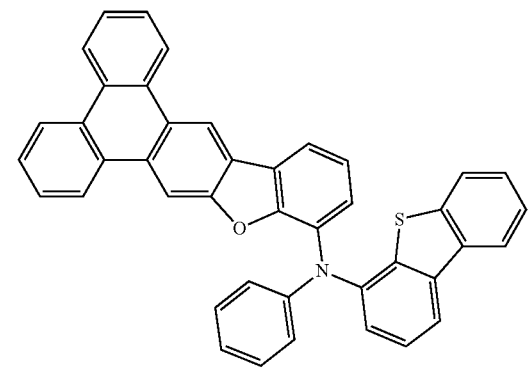
C178
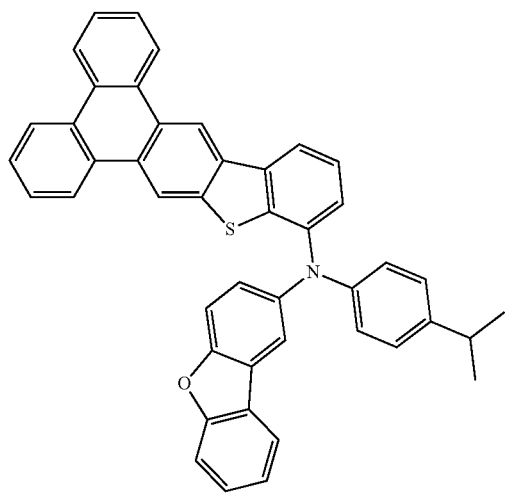
C179
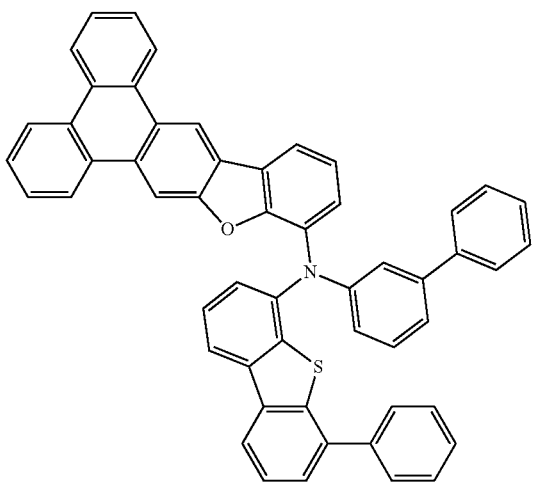
C180
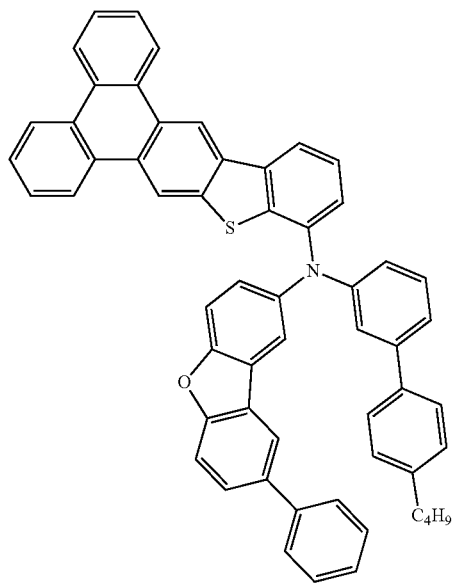
C181
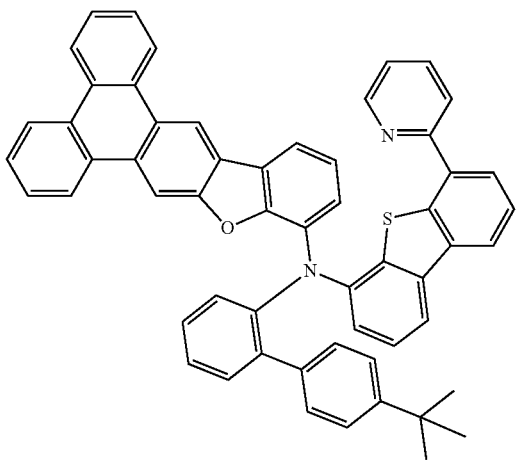

231 232
-continued
C182
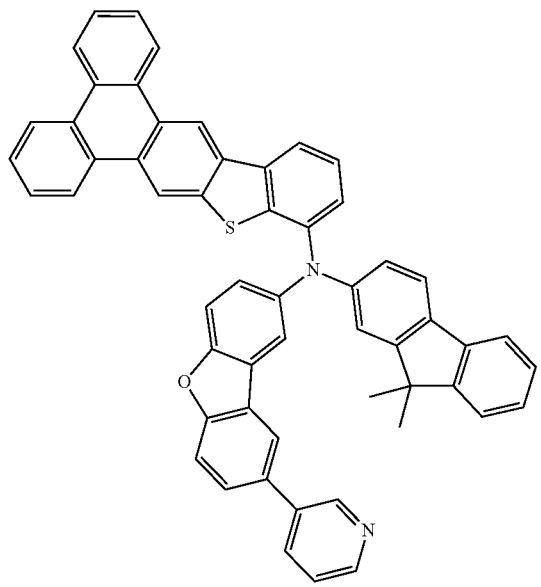
C183
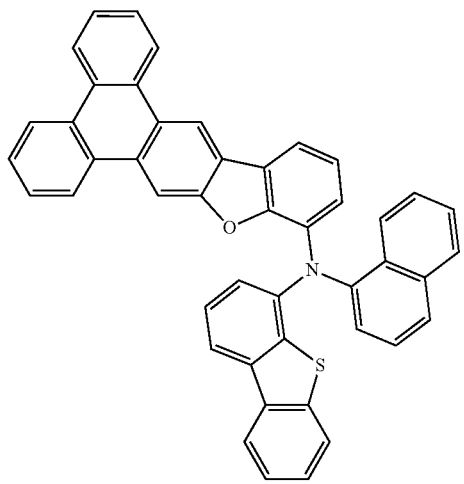
C184
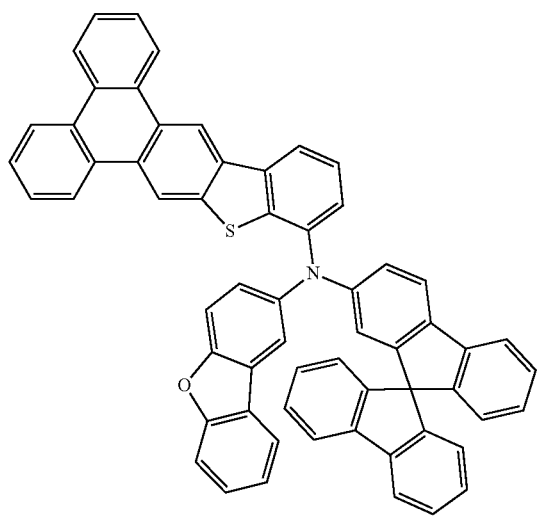
C185
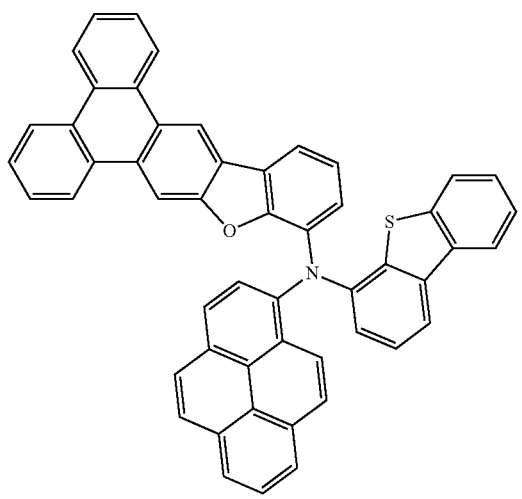
C186
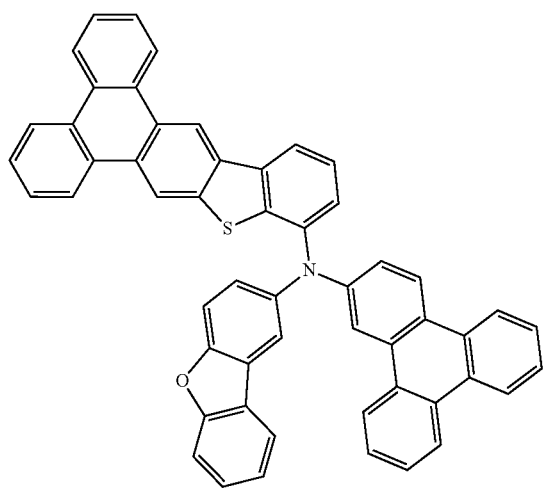
C187
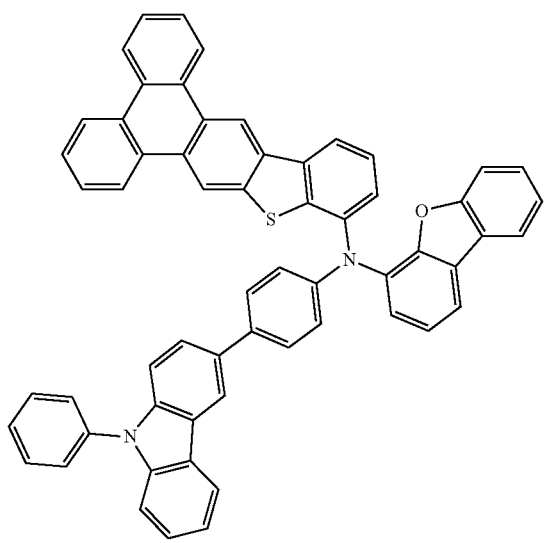

-continued
C188
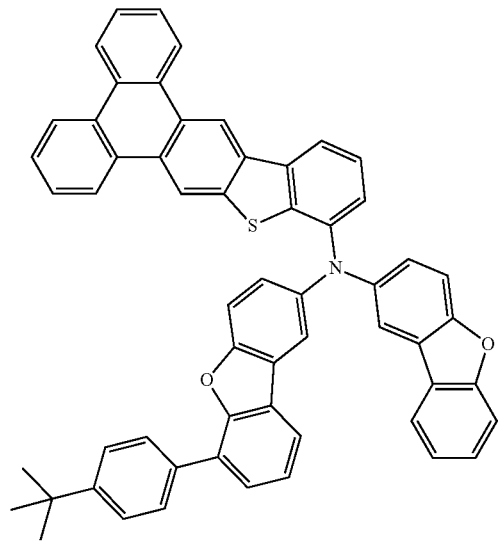
C189
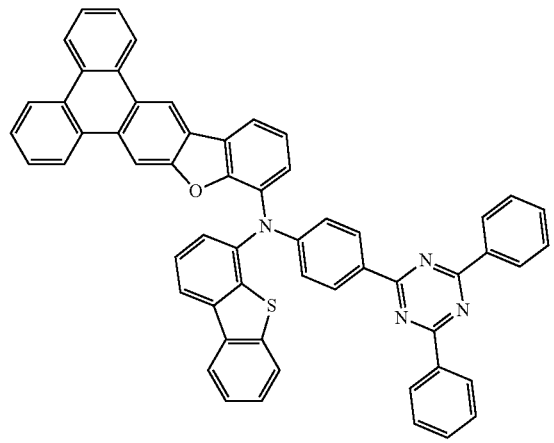
C190
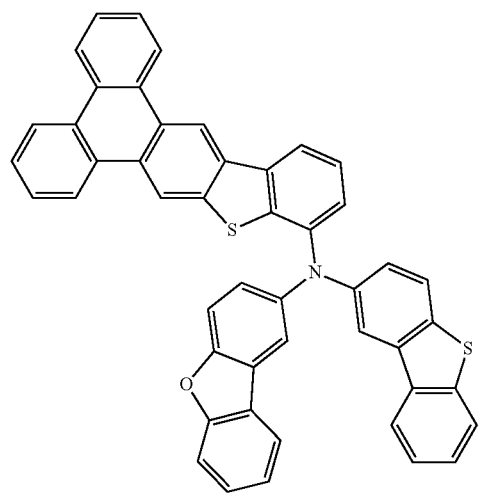
C191
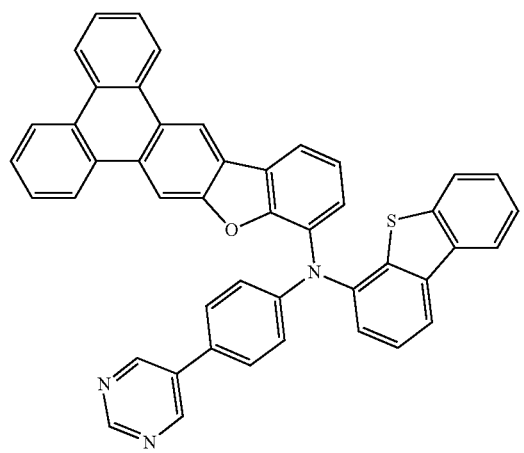
C192
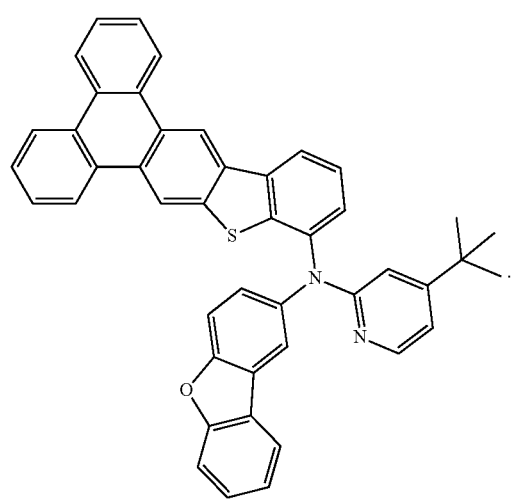

6. An organic electroluminescence device, comprising a pair of electrodes composed of a cathode and an anode, and a light emitting layer and one or more organic thin film layers between the pair of electrodes, wherein at least one of the light emitting layer and the organic thin film layer comprises the indenotriphenylene-based amine derivative of claim 1.

7. The organic electroluminescence device of claim 6, wherein the light emitting layer comprising the indenotriphenylene-based amine derivative of formula (1) is a dopant material.

8. The organic electroluminescence device of claim 6, wherein the organic thin film layer comprising the indenotriphenylene-based amine derivative of formula (1) is a hole transporting layer.

9. The organic electroluminescence device of claim 6, wherein the organic thin film layer comprising the indenotriphenylene-based amine derivative of formula (1) is an electron blocking layer.

10. The organic electroluminescence device of claim 6, wherein the organic electroluminescence device is a lighting panel.

11. The organic electroluminescence device of claim 6, wherein the organic electroluminescence device is a backlight panel.

* * * * *